US011254953B2

(12) United States Patent
Lee

(10) Patent No.: US 11,254,953 B2
(45) Date of Patent: Feb. 22, 2022

(54) COMPOSITIONS AND METHODS FOR ZIKA VIRUS CHARACTERIZATION AND VACCINE DEVELOPMENT

(71) Applicant: Utah State University, Logan, UT (US)

(72) Inventor: Young-Min Lee, Logan, UT (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 16/388,742

(22) Filed: Apr. 18, 2019

(65) Prior Publication Data

US 2019/0323034 A1    Oct. 24, 2019

Related U.S. Application Data

(60) Provisional application No. 62/659,386, filed on Apr. 18, 2018.

(51) Int. Cl.
*C12N 7/00* (2006.01)
*C12N 15/86* (2006.01)
*A61K 39/12* (2006.01)

(52) U.S. Cl.
CPC .............. *C12N 15/86* (2013.01); *A61K 39/12* (2013.01); *C12N 2770/24134* (2013.01); *C12N 2770/24143* (2013.01)

(58) Field of Classification Search
None
See application file for complete search history.

(56) References Cited

U.S. PATENT DOCUMENTS

| 2003/0148325 | A1* | 8/2003 | Sanchez | C12N 15/86 435/6.12 |
| 2003/0186233 | A1* | 10/2003 | Chesnut | C12N 15/66 435/6.18 |
| 2005/0287539 | A1 | 12/2005 | Labourier et al. | |
| 2010/0129406 | A1 | 5/2010 | Lauer et al. | |
| 2013/0267021 | A1* | 10/2013 | Weber | C12N 15/1093 435/320.1 |

(Continued)

FOREIGN PATENT DOCUMENTS

EP        3184118 A1    6/2017
WO    WO-2008027560 A2 *  3/2008    ......... A61K 39/0208

(Continued)

OTHER PUBLICATIONS

Yang et al., "Immunization of Zika virus envelope protein domain III induces specific and neutralizing immune responses against Zika virus," Vaccine 35(33): 4287-4294 (Year: 2017).*

(Continued)

*Primary Examiner* — M Franco G Salvoza

(57) ABSTRACT

The present disclosure relates to compositions and methods for investigating Zika virus (ZIKV) biology and pathogenicity. The present disclosure provides genetically stable viral vectors to produce functional RNA transcripts of ZIKV cDNAs. In particular, the present disclosure provides full-length infectious cDNAs as bacterial artificial chromosomes for spatiotemporally distinct and genetically divergent ZIKVs. The present disclosure also provides methods of generating a genetically engineered attenuated ZIKV using the genetically stable viral vectors described herein.

1 Claim, 51 Drawing Sheets

Specification includes a Sequence Listing.

(56) References Cited

U.S. PATENT DOCUMENTS

| | | | |
|---|---|---|---|
| 2016/0206723 A1* | 7/2016 | Dallmeier | C12N 7/00 |
| 2017/0296646 A1 | 10/2017 | Hernandez et al. | |
| 2018/0016324 A1 | 1/2018 | Kyratsous et al. | |

FOREIGN PATENT DOCUMENTS

| | | |
|---|---|---|
| WO | WO 2016/120412 A1 | 8/2016 |
| WO | WO 2017/192701 A1 | 11/2017 |
| WO | WO 2017/214596 A1 | 12/2017 |
| WO | WO 2019/204654 A1 | 10/2019 |

OTHER PUBLICATIONS

Genbank Accession No. KU501215.1 (Year: 2016).*
Genbank Accession No. KX377337.1 (Year: 2016).*
NCBI Blast Alignment of KX377337.1 and instant SEQ ID No. 6 (Year: 2020).*
Aliota et al., "Characterization of lethal Zika virus infection in AG129 mice," PLoS Negl. Trop. Dis., 2016, 10, e0004682.
Annamalai et al., "Zika Virus Encoding Nonglycosylated Envelope Protein Is Attenuated and Defective in Neuroinvasion," J Virol, Nov. 14, 2017, vol. 91, pp. 1-16.
Atieh et al., "Simple reverse genetics systems for Asian and African Zika viruses," Sci. Rep., 2016, 6, 39384.
Aubry et al., "Flavivirus reverse genetic systems, construction techniques and applications: a historical perspective," Antiviral Res., 2015, 114, 67-85.
Bollati et al., "Structure and functionality in flavivirus NS-proteins: perspectives for drug design," Antiviral Res., 2010, 87, 125-148.
Brinton, "Replication cycle and molecular biology of the West Nile virus," Viruses, 2014, 6, 13-53.
Brown et al., "Extended surface for membrane association in Zika virus NS1 structure," Nat. Struct. Mol. Biol., 2016, 23, 865-867.
Calvet et al., "Detection and sequencing of Zika virus from amniotic fluid of fetuses with microcephaly in Brazil: a case study," Lancet Infect. Dis., 2016, 16, 653-660.
Campos et al., "Zika virus outbreak, Bahia, Brazil," Emerg. Infect. Dis., 2015, 21, 1885-1886.
Cao-Lormeau et al., "Emerging arboviruses in the Pacific," Lancet, 2014, 384, 1571-1572.
Chan et al., "Zika virus infection in dexamethasone-immunosuppressed mice demonstrating disseminated infection with multi-organ involvement including orchitis effectively treated by recombinant type I interferons," EBioMedicine, 2016, 14, 112-122.
Cureton et al., "The length of vesicular stomatitis virus particles dictates a need for actin assembly during clathrin-dependent endocytosis," PLoS Pathog., 2010, 6, e1001127.
Dick et al., "Zika virus. I. Isolations and serological specificity," Trans. R. Soc. Trop. Med. Hyg., 1952, 46, 509-520.
Dowall et al., "A susceptible mouse model for Zika virus infection," PLoS Negl. Trop. Dis., 2016, 10, e0004658.
Duffy et al., "Zika virus outbreak on Yap Island, Federated States of Micronesia," N. Engl. J. Med., 2009, 360, 2536-2543.
Faria et al., "Zika virus in the Americas: early epidemiological and genetic findings," Science, 2016, 352, 345-349.
Fernandes et al., "Experimental Zika virus infection induces spinal cord injury and encephalitis in newborn Swiss mice," Exp. Toxicol. Pathol., 2017, 69, 63-71.
Firth et al., "A conserved predicted pseudoknot in the NS2A-encoding sequence of West Nile and Japanese encephalitis flaviviruses suggests NS1' may derive from ribosomal frameshifting," Virol. J., 2009, 6, 14.
Foy et al., "Probable non-vector-borne transmission of Zika virus, Colorado, USA," Emerg. Infect. Dis., 2011, 17, 880-882.
Frank et al., "Impact of viral and host genetic variations on the outcome of zika virus infection", 2017 American Society for Virology Annual Meeting. Jun. 24, 2017.

Frank et al., "Impact of Viral and Host Genetic Variations on the Outcome of ZIKV Infection". 2017 ADVS Student Research Symposium. Aug. 9, 2017.
Frank, "Development and application of a reverse genetics system for zika virus", Master of Science Thesis, 2018, Utah State University, Logan, UT, USA.
Gebhard et al., "Functional RNA elements in the dengue virus genome," Viruses, 2011, 3, 1739-1756.
GenBank accession No. AB004047 (2000).
GenBank accession No. KX377337 (2016).
Gillespie et al., "The endoplasmic reticulum provides the membrane platform for biogenesis of the flavivirus replication complex," J. Virol., 2010, 84, 10438-10447.
Haddow et al., "Genetic characterization of Zika virus strains: geographic expansion of the Asian lineage," PLoS Negl. Trap. Dis., 2012, 6, e1477.
Harrison, "Viral membrane fusion," Nat. Struct. Mol. Biol., 2008, 15, 690-698.
International Search Report and Written Opinion for PCT/US2019/028190 filed Apr. 19, 2019 and dated Jul. 30, 2019.
Julander et al., "Efficacy of the broad-spectrum antiviral compound BCX4430 against Zika virus in cell culture and in a mouse model," Antiviral Res., 2017, 137, 14-22.
Kaufmann et al., "Molecular mechanisms involved in the early steps of flavivirus cell entry," Microbes Infect., 2011, 13, 1-9.
Kim et al., "A single N-linked glycosylation site in the Japanese encephalitis virus prM protein is critical for cell type-specific prM protein biogenesis, virus particle release, and pathogenicity in mice," J. Virol., 2008, 82, 7846-7862.
Kim et al., "Profiling of viral proteins expressed from the genomic RNA of Japanese encephalitis virus using a panel of 15 region-specific polyclonal rabbit antisera: implications for viral gene expression," PLoS One, 2015, 10, e0124318.
Kostyuchenko et al., "Structure of the thermally stable Zika virus," Nature, 2016, 533, 425-428.
Kyte et al., "A simple method for displaying the hydropathic character of a protein," J. Mol. Biol., 1982, 157:105-132.
Lanciotti et al., "Genetic and serologic properties of Zika virus associated with an epidemic, Yap State, Micronesia, 2007," Emerg. Infect. Dis., 2008, 14, 1232-1239.
Lanciotti et al., "Phylogeny of Zika virus in Western Hemisphere, 2015," Emerg. Infect. Dis., 2016, 22, 933-935.
Larocca et al., "Vaccine protection against Zika virus from Brazil," Nature, 2016, 536, 474-478.
Lazear et al., "A mouse model of Zika virus pathogenesis," Cell Host Microbe, 2016, 19, 720-730.
Lazear et al., "Zika virus: new clinical syndromes and its emergence in the Western Hemisphere," J. Virol., 2016, 90, 4864-4875.
Lecot et al., "Bovine viral diarrhea virus entry is dependent on clathrin-mediated endocytosis," J. Virol., 2005, 79, 10826-10829.
Lessler et al., "Assessing the global threat from Zika virus," Science, 2016, 353, aaf8160.
Li et al., "Zika virus infects neural progenitors in the adult mouse brain and alters proliferation," Cell Stem Cell, 2016, 19, 593-598.
Lindenbach et al., "Flaviviridae," In Fields Virology, 2013, pp. 712-746.
Manangeeswaran et al., "Zika (PRVABC59) infection is associated with T cell infiltration and neurodegeneration in CNS of immunocompetent neonatal C57BL/6 mice," PLoS Pathog., 2016, 12, e1006004.
Marchette et al., "Isolation of Zika virus from Aedes aegypti mosquitoes in Malaysia," Am. J. Trap. Med. Hyg., 1969, 18, 411-415.
Meertens et al., "Axl mediates Zika virus entry in human glial cells and modulates innate immune responses," Cell Rep., 2017, 18, 324-333.
Melian et al., "NS1' of flaviviruses in the Japanese encephalitis virus serogroup is a product of ribosomal frameshifting and plays a role in viral neuroinvasiveness," J. Virol., 2010, 84, 1641-1647.
Methot et al., "What is a pathogen? Toward a process view of host-parasite interactions," Virulence, 2014, 5, 775-785.
Miner et al., "Zika virus infection in mice causes panuveitis with shedding of virus in tears," Cell Rep., 2016, 16, 3208-3218.

(56) References Cited

OTHER PUBLICATIONS

Mlakar et al., "Zika virus associated with microcephaly," N. Engl. J. Med., 2016, 374, 951-958.
Morrison et al., "Animal models of Zika virus infection, pathogenesis, and immunity," J. Virol., 2017, 91, e00009-17.
Musso et al., "Potential sexual transmission of Zika virus," Emerg. Infect. Dis., 2015, 21, 359-361.
Musso et al., "Zika virus," Clin. Microbiol. Rev., 2016, 29, 487-524.
Mutso et al., "Reverse genetic system, genetically stable reporter viruses and packaged subgenmoic replicon based on a Brazilian Zika virus isolate," J Gen Virol, Oct. 12, 2017, vol. 98, pp. 2712-2724.
Panchaud et al., "Emerging role of Zika virus in adverse fetal and neonatal outcomes," Clin. Microbiol. Rev., 2016, 29, 659-694.
Paranjape et al., "Control of dengue virus translation and replication," Curr. Top. Microbiol. Immunol., 2010, 338, 15-34.
Perera-Lecoin et al., "Flavivirus entry receptors: an update," Viruses, 2014, 6, 69-88.
Petersen et al., "Zika virus," N. Engl. J. Med., 2016, 374, 1552-1563.
Pierson et al., "Degrees of maturity: the complex structure and biology of flaviviruses," Curr. Opin. Virol., 2012, 2, 168-175.
Pierson et al., "Flaviviruses: braking the entering," Curr. Opin. Virol., 2013, 3, 3-12.
Prasad et al., "Structure of the immature Zika virus at 9 A resolution," Nat. Struct. Mol. Biol., 2017, 24, 184-186.
Roby et al., "Post-translational regulation and modifications of flavivirus structural proteins," J. Gen. Virol., 2015, 96, 1551-1569.
Rossi et al., "Characterization of a novel murine model to study Zika virus," Am. J. Trop. Med. Hyg., 2016, 94, 1362-1369.
Schwarz et al., "Rescue of the 1947 Zika virus prototype strain with a cytomegalovirus promoter-driven cDNA clone," mSphere, 2016, 1, e00246-16.
Setoh et al., "De novo generation and characterization of new Zika virus isolate using sequence data from a microcephaly case," mSphere, 2017, 2, e00190-17.
Shan et al., "An infectious cDNA clone of Zika virus to study viral virulence, mosquito transmission, and antiviral inhibitors," Cell Host Microbe, 2016, 19, 891-900.
Shizuya et al., "Cloning and stable maintenance of 300-kilobase-pair fragments of human DNA in *Escherichia coli* using an F-factor-based vector," Proc. Natl. Acad. Sci. USA, 1992, 89, 8794-8797.
Sirohi et al., "The 3.8 A resolution cryo-EM structure of Zika virus," Science, 2016, 352, 467-470.
Smit et al., "Flavivirus cell entry and membrane fusion," Viruses, 2011, 3, 160-171.
Smith et al., "Neuropathogenesis of Zika virus in a highly susceptible immunocompetent mouse model after antibody blockade of type I interferon," PLoS Negl. Trop. Dis., 2017, 11, e0005296.
Song et al., "Zika virus: history, epidemiology, transmission, and clinical presentation," J. Neuroimmunol., 2017, 308, 50-64.
Stobart et al., "RNA virus reverse genetics and vaccine design," Viruses, 2014, 6, 2531-2550.
Tsetsarkin et al., "A full-length infectious cDNA clone of Zika virus from the 2015 epidemic in Brazil as a genetic platform for studies of virus-host interactions and vaccine development," mBio, 2016, 7, e01114-16.
Wang et al., "Complete nucleotide sequence of two generations of a bacterial artificial chromosome cloning vector," Biotechniques, Dec. 1, 1997, vol. 23, pp. 992-994.
Wang et al., "From mosquitos to humans: genetic evolution of Zika virus," Cell Host Microbe, 2016, 19, 561-565.
Weaver et al., "Zika virus: history, emergence, biology, and prospects for control," Antiviral Res., 2016, 130, 69-80.
Weger-Lucarelli et al., "Development and characterization of recombinant virus generated from a New World Zika virus infectious clone," J. Virol., 2017, 91, e01765-16.
Welsch et al., "Composition and three-dimensional architecture of the dengue virus replication and assembly sites," Cell Host Microbe, 2009, 5, 365-375.
Widman et al., "A reverse genetics platform that spans the Zika virus family tree," mBio, 2017, 8, e02014-16.
Xu et al., "Contribution of intertwined loop to membrane association revealed by Zika virus full-length NS1 structure," EMBO J., 2016, 35, 2170-2178.
Ye et al., "A single nucleotide mutation in NS2A of Japanese encephalitis-live vaccine virus (SA14-14-2) ablates NS1' formation and contributes to attenuation," J. Gen. Virol., 2012, 93, 1959-1964.
Yun et al., "3' cis-acting elements that contribute to the competence and efficiency of Japanese encephalitis virus genome replication: functional importance of sequence duplications, deletions, and substitutions," J. Virol., 2009, 83, 7909-7930.
Yun et al., "A molecularly cloned, live-attenuated Japanese encephalitis vaccine SA14-14-2 virus: a conserved single amino acid in the ij hairpin of the viral E glycoprotein determines neurovirulence in mice," PLoS Pathog., 2014, 10, e1004290.
Yun et al., "Bacterial artificial chromosomes: a functional genomics tool for the study of positive-strand RNA viruses," J. Vis. Exp., 2015, 106, e53164.
Yun et al., "Comparison of the live-attenuated Japanese encephalitis vaccine SA14-14-2 strain with its pre-attenuated virulent parent SAM strain: similarities and differences in vitro and in vivo," J. Gen. Virol., 2016, 97, 2575-2591.
Yun et al., "Complete genome sequences of three historically important, spatiotemporally distinct, and genetically divergent strains of Zika virus: MR-766, P6-740, and PRVABC-59," Genome Announc., 2016, 4, e00800-16.
Yun et al., "Development and application of a reverse genetics system for Japanese encephalitis virus," J. Virol., 2003, 77, 6450-6465.
Yun et al., "Functional genomics and immunologic tools: the impact of viral and host genetic variations on the outcome of zika virus infection", Viruses, Aug. 11, 2018, 28 pages.
Yun et al., "Molecular characterization of the full-length genome of the Japanese encephalitis viral strain K87P39," Virus Res., 2003, 96, 129-140.
Yun et al., "Zika virus: an emerging flavivirus," J. Microbiol., 2017, 55, 204-219.
Zanluca et al., "First report of autochthonous transmission of Zika virus in Brazil," Mem. Inst. Oswaldo Cruz, 2015, 110, 569-572.
Zmurko et al., "The viral polymerase inhibitor 7-deaza-2'-C-methyladenosine is a potent inhibitor of in vitro Zika virus replication and delays disease progression in a robust mouse infection model," PLoS Negl. Trop. Dis., 2016, 10, e0004695.

\* cited by examiner

| Strain | vgRNA (nt) | 5'NCR (nt) | ORF (nt) | 3'NCR (nt) |
|---|---|---|---|---|
| MR-766 | 10,807 | 106 | 10,272 | 429 |
| P6-740 | 10,807 | 107 | 10,272 | 428 |
| PRVABC-59 | 10,807 | 107 | 10,272 | 428 |

FIG. 8A

| Strain pair | nt sequence identity (%) | aa sequence identity (%) |
|---|---|---|
| MR-766 vs. P6-740 | 90.4 | 97.4 |
| MR-766 vs. PRVABC-59 | 89.1 | 96.8 |
| P6-740 vs. PRVABC-59 | 95.6 | 98.8 |

| Antigen GST fusion protein | Region fused to the C-terminus of GST | | | Antiserum | Dilution |
|---|---|---|---|---|---|
| | Fusion protein | Genome (nt) | Protein (aa) | | |
| pGex (pGex-4T-1) | GST | — | — | — | — |
| pGex-jC | GST-jC | 96-404 | 1-103 | α-jC | 1:3000 |
| pGex-jPr | GST-jPr | 477-752 | 1-92 | α-jPr | 1:4000 |
| pGex-jM | GST-jM | 753-884 | 93-136 | α-jM | 1:1000 |
| pGex-jE N-term | GST-jE N-term | 978-1325 | 1-116 | α-jE N-term | 1:4000 |
| pGex-jE C-term | GST-jE C-term | 1587-1892 | 204-305 | α-jE C-term | 1:100 |
| pGex-jNS1 N-term | GST-jNS1 N-term | 2478-2975 | 1-166 | α-jNS1 N-term | 1:3000 |
| pGex-jNS1 C-term | GST-jNS1 C-term | 3174-3533 | 233-352 | α-jNS1 C-term | 1:1000 |
| pGex-jNS1 FS | GST-jNS1 FS | 3560-3688 | 362-404 | α-jNS1 FS | 1:1000 |
| pGex-jNS3 N-term | GST-jNS3 N-term | 4608-5504 | 1-299 | α-jNS3 N-term | 1:1000 |
| pGex-jNS3 C-term | GST-jNS3 C-term | 5505-6464 | 300-619 | α-jNS3 C-term | 1:1000 |
| pGex-jNS4A | GST-jNS4A | 6465-6629 | 1-55 | α-jNS4A | 1:1000 |
| pGex-jNS4B | GST-jNS4B | 7377-7556 | 156-215 | α-jNS4B | 1:500 |
| pGex-jNS5 N-term | GST-jNS5 N-term | 7677-9017 | 1-447 | α-jNS5 N-term | 1:1000 |
| pGex-jNS5 C-term | GST-jNS5 C-term | 9018-10391 | 448-905 | α-jNS5 C-term | 1:1000 |

| Antigen Synthetic peptide | | | | Antiserum | Dilution |
|---|---|---|---|---|---|
| jNS2B | KLH-DMWLERAADISW (SEQ ID NO: 45) | — | 51-62 | α-jNS2B | 1:1000 |

FIG. 14

| Antigen GST fusion protein | | Fusion protein | Region fused to the C-terminus of GST | | | Predicted MW (kD) | Antiserum | Dilution |
|---|---|---|---|---|---|---|---|---|
| | | | Genome (nt) | Protein (aa) | | | | |
| pGex (pGex-4T-1) | | GST | — | — | | 28 | — | — |
| pGex-zC | zC | GST-zC | 297-419 | 64-104 | | 32 | α-zC | 1:100 |
| pGex-zM | zM | GST-zM | 753-848 | 94-125 | | 31 | α-zM | 1:1000 |
| pGex-zE | zE | GST-zE | 1416-1538 | 147-187 | | 31 | α-zE | 1:250 |
| pGex-zNS4A | zNS4A | GST-zNS4A | 6465-6617 | 1-51 | | 32 | α-zNS4A | 1:1000 |
| pGex-zNS4B | zNS4B | GST-zNS4B | 7374-7526 | 154-204 | | 32 | α-zNS4B | 1:1000 |

| Antigen Synthetic peptide | | | | | | | Antiserum | Dilution |
|---|---|---|---|---|---|---|---|---|
| zNS1 (SEQ ID NO: 46) | KLH-NPMRGPQRLPVPVNELPH | | — | 95-113 | | — | α-zNS1 | 1:1000 |
| zNS2B | KLH-SGDFSLVEDDGPPMREIL | | — | 81-99 | | — | α-zNS2B | 1:100 |

(SEQ ID NO: 47)

| | RNA infectivity (PFU/µg) |
|---|---|
| pBac/P6-740 | $7.5 \pm 3.8 \times 10^5$ |
| pBac/P6-740/NS5H713Y ($C^{9804}U$, $His^{713} \to Tyr$) | $8.0 \pm 2.5 \times 10$ |

FIG. 19A

| Oligonucleotide | Sequence (5' to 3') | Position | Direction |
|---|---|---|---|
| Z1RT | GCTATTGGGTTCATGCCACAGATGGTCATCA (SEQ ID NO: 10) | 4531–4561 | Reverse |
| Z1F | tatgttttaaacAGTTGTTGATCGTGTGAATCAGACTGCGA (SEQ ID NO: 11) | 1–30 | Forward |
| Z1R | tatgcgcgccAGGACCACCTTGAGTATGATCTCTCTCATG (SEQ ID NO: 12) | 4502–4531 | Reverse |
| Z2RT | ATTGTCATTGTCAATGTCAGTCACCACTA (SEQ ID NO: 13) | 7369–7399 | Reverse |
| Z2F | tatgttttaaacTCATTGTTGGAGGAATGTCCTGGTTCTCA (SEQ ID NO: 14) | 2340–2369 | Forward |
| Z2R | tatgcgcgccTCAATGTCAGTCACCACTATTCCATCCACA (SEQ ID NO: 15) | 7358–7387 | Reverse |
| Z3RT | CTCCAGTTCAGGCCCCAGATTGAAGGGTGGG (SEQ ID NO: 16) | 10603–10634 | Reverse |
| Z3F | tatgttttaaacGGAAGTCCCAGAGAGAGCCTGGAGCTCAGG (SEQ ID NO: 17) | 5627–5656 | Forward |
| Z3R | tatgcgcgccAAGGGGTGGGAAGGTCGCCACCTTCTTTTC (SEQ ID NO: 18) | 10583–10612 | Reverse |
| S123-5sp1F | Ctaggatcctaattaacctgcagggggctgtta (SEQ ID NO: 19) | 1–11 | Forward |
| S123-5sp1R | GATCAACAACTctatagtgtccctaaatc (SEQ ID NO: 20) | 1–21 | Reverse |
| S1-5sp2F | ggacactatagAGTTGTTGATCGTGTGAGTC (SEQ ID NO: 21) | 860–884 | Forward |
| S1-5sp2R | tatccgcggTAGCGCAAACCCGGGGTTCCTGAAT (SEQ ID NO: 22) | 10191–10215 | Reverse |
| S1-3roF | tatccgcggGGAAAAAGGGAGGACTTATGGTGTG (SEQ ID NO: 23) | 10785–10807 | Forward |
| S1-3roR | agggcgccgtatgtcgcgttcgtacgttctagAGAAACCATGGATTTCCCACACC (SEQ ID NO: 24) | 1–21 | Reverse |
| S23-5sp2F | ggacactatagAGTTGTTGATCGTGTGAATC (SEQ ID NO: 25) | 859–883 | Forward |
| S23-5sp2R | tatccgcggAACGCAAAGCCAGGGTTCCTGAATA (SEQ ID NO: 26) | 10190–10214 | Reverse |
| S23-3roF | tatccgcggGGGAAAAAGGGAAGACTTATGGTGT (SEQ ID NO: 27) | 10784–10807 | Forward |
| S23-3roR | agggcgccgtatgtcgccttcgtacgttctagAGACCCATGGATTTCCCACACCG (SEQ ID NO: 28) | | Reverse |
| ZikaC-F | tttgaattcGGTCTCATCAATAGATGGGGT (SEQ ID NO: 29) | 297–317 | Forward |
| ZikaC-R | tttctcgagctattaTCGTCTCTTCTTCTCCTTCCT (SEQ ID NO: 30) | 399–419 | Reverse |
| ZikaM-F | tttgaattcGCTGTGACGCTCCCCTCCCAT (SEQ ID NO: 31) | 753–773 | Forward |
| ZikaM-R | tttctcgagctattaGACTTCAATCAAGTGCTTTGT (SEQ ID NO: 32) | 828–848 | Reverse |
| ZikaE-F | tttgaattcCAGCACAGTGGGATGATCGTT (SEQ ID NO: 33) | 1416–1436 | Forward |
| ZikaE-R | tttctcgagctattaTCCTAGGCTTCCAAAACCCCC (SEQ ID NO: 34) | 1518–1538 | Reverse |
| ZikaNS4A-F | tttgaattcGGAGCGGGCTTTTGGAGTGATG (SEQ ID NO: 35) | 6465–6485 | Forward |
| ZikaNS4A-R | tttctcgagctattaGGTCTCCGGCAATTGGGCGC (SEQ ID NO: 36) | 6597–6617 | Reverse |
| ZikaNS4B-F | tttgaattcGTGACTGACATTGACACAATG (SEQ ID NO: 37) | 7374–7394 | Forward |
| ZikaNS4B-R | tttctcgagctattaGAAGTTGCGGCGTGATCAG (SEQ ID NO: 38) | 7506–7526 | Reverse |
| ZikaF | GAAGTGGAAGTCCCAGAGAG (SEQ ID NO: 39) | 5622–5641 | Forward |
| ZikaR | TGCTGAGCTGTATGACCCG (SEQ ID NO: 40) | 5757–5775 | Reverse |
| ZikaProbe | FAM-TGGAGCTCAGGCTTTGATTGGGTGAC-BHQ1 (SEQ ID NO: 41) | 5646–5671 | Forward |
| VeroF | AGCGGGAAATCGTGCGTGAC (SEQ ID NO: 42) | 624–643 | Forward |
| VeroR | CAATGGTGATGACCTGGCCA (SEQ ID NO: 43) | 742–761 | Reverse |
| VeroProbe | HEX-CACGGCGGCTTCTAGCTCCTCCC-BHQ2 (SEQ ID NO: 44) | 694–716 | Forward |

FIG. 21

| Organism | Cell | Tissue | Growth medium | Culture condition | Source (catalog number) |
|---|---|---|---|---|---|
| Human | HEK | Embryo, kidney | MEM supplemented with 10% FBS, 2 mM L-glutamine, 0.1 mM NEAA, 1.0 mM SP, and PS | 37°C, 5% $CO_2$ | ATCC (CRL-1573) |
| Human | Huh-7 | Liver | DMEM supplemented with 10% FBS, 0.1 mM NEAA, and PS | 37°C, 5% $CO_2$ | Charles M. Rice, RU |
| Human | SH-SY5Y | Bone marrow | A 1:1 mixture of MEM and Ham's F-12 nutrient medium supplemented with 10% FBS, 0.1 mM NEAA, and PS | 37°C, 5% $CO_2$ | ATCC (CRL-2266) |
| Mouse | MEF | Embryo (C57BL/6), fibroblast | DMEM supplemented with 10% FBS and PS | 37°C, 5% $CO_2$ | ATCC (SCRC-1008) |
| Mouse | NIH/3T3 | Embryo (NIH/Swiss), fibroblast | DMEM supplemented with 10% FBS and PS | 37°C, 5% $CO_2$ | ATCC (CRL-1658) |
| Mouse | NSC-34 | Motor neuron-like hybrid | DMEM (without SP) supplemented with 10% FBS and PS | 37°C, 5% $CO_2$ | Cedarlane (CLU140) |
| Monkey | Vero | Kidney | α-MEM supplemented with 10% FBS and PS | 37°C, 5% $CO_2$ | ATCC (WHO-Vero) |
| Cow | BT | Turbinate | DMEM (without SP) supplemented with 10% HS and PS | 37°C, 5% $CO_2$ | ATCC (CRL-1390) |
| Cow | MDBK | Kidney | DMEM (without SP) supplemented with 10% HS and PS | 37°C, 5% $CO_2$ | ATCC (CCL-22) |
| Pig | ST | Testis | α-MEM supplemented with 10% FBS and PS | 37°C, 5% $CO_2$ | ATCC (CRL-1746) |
| Sheep | SFF-6 | Fetus, fibroblast | DMEM supplemented with 15% FBS and PS | 37°C, 5% $CO_2$ | Irina A. Polejaeva, USU |
| Goat | GFF-4 | Fetus, fibroblast | DMEM supplemented with 15% FBS and PS | 37°C, 5% $CO_2$ | Irina A. Polejaeva, USU |
| Horse | NBL-6 | Skin, dermis | EMEM supplemented with 10% FBS and PS | 37°C, 5% $CO_2$ | ATCC (CCL-57) |
| Dog | MDCK | Kidney | MEM supplemented with EBSS, 10% FBS, 0.1 mM NEAA, 1.0 mM SP, and PS | 37°C, 5% $CO_2$ | ATCC (CCL-34) |
| Cat | CRFK | Kidney, cortex | MEM supplemented with EBSS, 10% HS, 0.1 mM NEAA, 1.0 mM SP, and PS | 37°C, 5% $CO_2$ | ATCC (CCL-94) |
| Chicken | CEF | Embryo, fibroblast | DMEM supplemented with 10% FBS and PS | 37°C, 5% $CO_2$ | Sung-June Byun, KNIAS |
| Mosquito | C6/36 | Larva (*Aedes albopictus*) | MEM supplemented with EBSS, 10% FBS, 2 mM L-glutamine, 0.1 mM NEAA, 1.0 mM SP, and PS | 28°C, 5% $CO_2$ | ATCC (CRL-1660) |

FIG. 22

SEQUENCE LISTING

<160> NUMBER OF SEQ ID NOS: 68

<210> SEQ ID NO 1
<211> LENGTH: 18571
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gagttgttga | tctgtgtgag | tcagactgcg | acagttcgag | tctgaagcga | gagctaacaa | 60 |
| cagtatcaac | aggtttaatt | tggatttgga | aacgagagtt | tctggtcatg | aaaaacccaa | 120 |
| agaagaaatc | cggaggattc | cggattgtca | atatgctaaa | acgcggagta | gcccgtgtaa | 180 |
| accccttggg | aggtttgaag | aggttgccag | ccggacttct | gctgggtcat | ggacccatca | 240 |
| gaatggtttt | ggcgatacta | gccttttga | gatttacagc | aatcaagcca | tcactgggcc | 300 |
| ttatcaacag | atggggttcc | gtggggaaaa | aagaggctat | ggaataata | aagaagttca | 360 |
| agaaagatct | tgctgccatg | ttgagaataa | tcaatgctag | gaaagagagg | aagagacgtg | 420 |
| gcgcagacac | cagcatcgga | atcattggcc | tcctgctgac | tacagccatg | gcagcagaga | 480 |
| tcactagacg | cgggagtgca | tactacatgt | acttggatag | gagcgatgcc | gggaaggcca | 540 |
| tttcgtttgc | taccacattg | ggagtgaaca | agtgccacgt | acagatcatg | gacctcgggc | 600 |
| acatgtgtga | cgccaccatg | agttatgagt | gccctatgct | ggatgaggga | gtggaaccag | 660 |
| atgatgtcga | ttgctggtgc | aacacgacat | caacttgggt | tgtgtacgga | acctgtcatc | 720 |
| gcaaaaaagg | tgaggcacgg | cgatctagaa | gagccgtgac | gctcccttct | cactctacaa | 780 |
| ggaagttgca | aacgcggtcg | cagacctggt | tagaatcaag | agaatacacg | aagcacttga | 840 |
| tcaaggttga | aaactggata | ttcaggaacc | ccgggtttgc | gctagtggcc | gttgccattg | 900 |
| cctggctttt | gggaagctcg | acgagccaaa | aagtcatata | cttggtcatg | atactgctga | 960 |
| ttgccccggc | atacagtatc | aggtgcattg | gagtcagcaa | tagagacttc | gtggagggca | 1020 |
| tgtcaggtgg | gacctgggtt | gatgttgtct | tggaacatgg | aggctgcgtt | accgtgatgg | 1080 |
| cacaggacaa | gccaacagtt | gacatagagt | tggtcacgac | gacggttagt | aacatggccg | 1140 |
| aggtaagatc | ctattgctac | gaggcatcga | tatcggacat | ggcttcggac | agtcgttgcc | 1200 |
| caacacaagg | tgaagcctac | cttgacaagc | aatcagacac | tcaatatgtc | tgcaaaagaa | 1260 |
| cattagtgga | cagaggttgg | ggaaacggtt | gtggactttt | tggcaaaggg | agcttggtga | 1320 |
| catgtgccaa | gtttacgtgt | tctaagaaga | tgaccgggaa | gagcattcaa | ccggaaaatc | 1380 |
| tggagtatcg | gataatgcta | tcagtgcatg | gctcccagca | tagcgggatg | attgtcaatg | 1440 |
| atacaggata | tgaaactgac | gaaaatagag | cgaaagtcga | ggttacgcct | aattcaccaa | 1500 |

```
gagcggaagc aaccttggga ggctttggaa gcttaggact tgactgtgaa ccaaggacag    1560
gtcttgactt ttcagatctg tattacctga ccatgaacaa taagcattgg ttggtgcaca    1620
aagagtggtt tcatgacatc ccattgcctt ggcatgctgg ggcagacacc ggaactccac    1680
actggaacaa caaagaggca ttggtagaat tcaaggatgc ccacgccaag aggcaaaccg    1740
tcgtcgttct ggggagccag gaaggagccg ttcacacggc tctcgctgga gctctagagg    1800
ctgagatgga tggtgcaaag ggaaagctgt tctctggcca tttgaaatgc cgcctaaaaa    1860
tggacaagct tagattgaag ggcgtgtcat attccttgtg cactgcggca ttcacattca    1920
ccaaggtccc agctgaaaca ctgcatgaaa cagtcacagt ggaggtgcag tatgcaggga    1980
cagatggacc ctgcaagatc ccagtccaga tggcggtgga catgcagacc ctgaccccag    2040
ttggaaggct gataaccgcc aacccgtga ttactgaaag cactgagaac tcaaagatga    2100
tgttggagct tgacccacca tttggggatt cttacattgt cataggagtt ggggacaaga    2160
aaatcaccca ccactggcat aggagtggta gcaccatcgg aaaggcattt gaggccactg    2220
tgagaggcgc caagagaatg gcagtcctgg gggatacagc ctgggacttc ggatcagtcg    2280
ggggtgtgtt caactcactg gtaagggca ttcaccagat ttttggagca gccttcaaat    2340
cactgtttgg aggaatgtcc tggttctcac agatcctcat aggcacgctg ctagtgtggt    2400 taggttttgaa cacaaagaat ggatctatct ccctcacatg cttggccctg ggggagtga    2460 tgatcttcct ctccacggct gtttctgctg acgtggggtg ctcagtggac ttctcaaaaa    2520
aggaaacgag atgtgcacg ggggtattca tctataatga tgttgaagcc tgagggacc    2580 ggtacaagta ccatcctgac tcccccgca gattggcagc agcagtcaag caggcctggg    2640
aagaggggat ctgtgggatc tcatccgttt caagaatgga aaacatcatg tggaaatcag    2700
tagaagggga gctcaatgct atcctagagg agaatggagt tcaactgaca gttgttgtgg    2760
gatctgtaaa aaaccccatg tggagaggtc acaaagatt gccagtgcct gtgaatgagc    2820
tgccccatgg ctggaaagcc tgggggaaat cgtattttgt tagggcggca aagaccaaca    2880
acagttttgt tgtcgacggt gacacactga aggaatgtcc gcttgagcac agagcatgga    2940
atagttttct tgtggaggat cacgggtttg gagtcttcca caccagtgtc tggcttaagg    3000
tcagagaaga ttactcatta gaatgtgacc cagccgtcat aggaacagct gttaagggaa    3060
gggaagccgc gcacagtgat ctgggctatt ggattgaaag tgaaaagaat gacacatgga    3120
ggctgaagag ggcccacctg attgagatga aaacatgtga atggccaaag tctcacacat    3180 tgtgacaga tggagtagaa gaaagtgatc ttatcatacc caagtcttta gctggtccac    3240
tcagccacca caacaccaga gagggttaca gaacccaagt gaaagggcca tggcacagtg    3300
aagagcttga aatccggttt gaggaatgtc caggcaccaa ggtttacgtg gaggagacat    3360
gcggaactag aggaccatct ctgagatcaa ctactgcaag tggaagggtc attgaggaat    3420
ggtgctgtag ggaatgcaca atgccccac tatcgtttcg agcaaaagac ggctgctggt    3480
atggaatgga gataaggccc aggaaagaac cagagagcaa cttagtgagg tcaatggtga    3540
cagcggggtc aaccgatcat atggaccact ctctcttgg agtgcttgtg attctactca    3600
tggtgcagga ggggttgaag aagagaatga ccacaaagat catcatgagc acatcaatgg    3660
cagtgctggt agtcatgatc ttgggaggat tttcaatgag tgacctggcc aagcttgtga    3720
tcctgatggg tgctactttc gcagaaatga acactggagg agatgtagct cacttggcat    3780
tggtagcggc atttaaagtc agaccagcct tgctggtctc cttcatttc agagccaatt    3840
```

```
ggacacccccg tgagagcatg ctgctagccc tggcttcgtg tcttctgcaa actgcgatct    3900
ctgctcttga aggtgacttg atggtcctca ttaatggatt tgctttggcc tggttggcaa    3960
ttcgagcaat ggccgtgcca cgcactgaca acatcgctct accaatcttg gctgctctaa    4020
caccactagc tcgaggcaca ctgctcgtgg catggagagc gggcctggct acttgtggag    4080
ggatcatgct cctctccctg aaagggaaag gtagtgtgaa gaagaacctg ccatttgtca    4140
tggccctggg attgacagct gtgagggtag tagaccctat taatgtggta ggactactgt    4200
tactcacaag gagtgggaag cggagctggc ccctagtga agttctcaca gccgttggcc    4260
tgatatgtgc actggccgga gggttttgcca aggcagacat tgagatggct ggacccatgg    4320
ctgcagtagg cttgctaatt gtcagctatg tggtctcggg aaagagtgtg gacatgtaca    4380
ttgaaagagc aggtgacatc acatgggaaa aggacgcgga agtcactgga aacagtcctc    4440
ggcttgacgt ggcactggat gagagtggtg atttctcctt ggtagaggaa gatggtccac    4500
ccatgagaga gatcatactc aaggtggtcc tgatggccat ctgtggcatg aacccaatag    4560
ctataccttt tgctgcagga gcgtggtatg tgtatgtgaa gactgggaaa aggagtggcg    4620
ccctctggga cgtgcctgct cccaaagaag tgaagaaagg agagaccaca gatggagtgt    4680
acagagtgat gactcgcaga ctgctaggtt caacacaggt tggagtggga gtcatgcaag    4740
agggagtctt ccacaccatg tggcacgtta caaaggagc cgcactgagg agcggtgagg    4800
gaagacttga tccatactgg ggggatgtca agcaggactt ggtgtcatac tgtgggcctt    4860
ggaagttgga tgcagcttgg gatggactca gcgaggtaca gcttttggcc gtacctcccg    4920
gagagagggc cagaaacatt cagaccctgc ctggaatatt caagacaaag gacggggaca    4980
tcggagcagt tgctctggac taccctgcag ggacctcagg atctccgatc ctagacaaat    5040
gtggaagagt gataggactc tatggcaatg gggttgtgat caagaatgga agctatgtta    5100
gtgctataac ccagggaaag agggaggagg agactccggt tgaatgtttc gaaccctcga    5160
tgctgaagaa gaagcagtta actgtcttgg atctgcatcc aggagccgga aaaaccagga    5220
gagttcttcc tgaaatagtc cgtgaagcca taaaaaagag actccggaca gtgatcttgg    5280
caccaactag ggttgtcgct gctgagatgg aggaggcctt gagaggactt ccggtgcgtt    5340
acatgacaac agcagtcaac gtcacccatt ctgggacaga aatcgttgat tgatgtgcc     5400 atgccacttt cacttcacgc ttactacaac ccatcagagt ccctaattac aatctctaca    5460
tcatggatga agcccacttc acagacccct caagtatagc tgcaagagga tacatatcaa    5520
caagggttga aatgggcgag gcggctgcca tttttatgac tgccacacca ccaggaaccc    5580
gtgatgcgtt tcctgactct aactcaccaa tcatggacac agaagtggaa gtcccagaga    5640
gagcctggag ctcaggcttt gattgggtga cagaccattc tgggaaaaca gtttggttcg    5700
ttccaagcgt gagaaacgga aatgaaatcg cagcctgtct gacaaaggct ggaaagcggg    5760
tcatacagct cagcaggaag acttttgaga cagaatttca gaaaacaaaa aatcaagagt    5820
gggactttgt cataacaact gacatctcag agatgggcgc caacttcaag gctgaccggg    5880
tcatagactc taggagatgc ctaaaaccag tcatacttga tggtgagaga gtcatcttgg    5940
ctgggcccat gcctgtcacg catgctagtg ctgctcagag gagaggacgt ataggcagga    6000
accctaacaa acctggagat gagtacatgt atggaggtgg gtgtgcagag actgatgaag    6060
gccatgcaca ctggcttgaa gcaagaatgc ttcttgacaa catctacctc caggatggcc    6120
tcatagcctc gctctatcgg cctgaggccg ataaggtagc cgccattgag ggagagttta    6180
agctgaggac agagcaaagg aagaccttcg tggaactcat gaagagagga gaccttcccg    6240
```

```
tctggctagc ctatcaggtt gcatctgccg gaataactta cacagacaga agatggtgct    6300
ttgatggcac aaccaacaac accataatgg aagacagcgt accagcagag gtgtggacaa    6360
agtatggaga gaagagagtg ctcaaaccga gatggatgga tgctagggtc tgttcagacc    6420
atgcggccct gaagtcgttc aaagaattcg ccgctggaaa aagaggagcg gctttgggag    6480
taatggaggc cctgggaaca ctgccaggac acatgacaga gaggtttcag gaagccattg    6540
acaacctcgc cgtgctcatg cgagcagaga ctggaagcag gccttataag gcagcggcag    6600
cccaactgcc ggagaccta gagaccatta tgctcttagg tttgctggga acagtttcac    6660
tggggatctt cttcgtcttg atgcggaata agggcatcgg gaagatgggc tttggaatgg    6720
taacccttgg ggccagtgca tggctcatgt ggctttcgga aattgaacca gccagaattg    6780
catgtgtcct cattgttgtg tttttattac tggtggtgct catacccgag ccagagaagc    6840
aaagatctcc ccaagataac cagatggcaa ttatcatcat ggtggcagtg ggccttctag    6900
gtttgataac tgcaaacgaa cttggatggc tggaaagaac aaaaaatgac atagctcatc    6960
taatgggaag gagagaagaa ggagcaacca tgggattctc aatggacatt gatctgcggc    7020
cagcctccgc ctgggctatc tatgccgcat tgacaactct catcacccca gctgtccaac    7080
atgcggtaac cacttcatac aacaactact ccttaatggc gatggccaca caagctggag    7140
tgctgtttgg catgggcaaa gggatgccat tttatgcatg gaccttggaa gtcccgctgc    7200
taatgatggg ttgctattca caattaacac ccctgactct gatagtagct atcattctgc    7260
ttgtggcgca ctacatgtac ttgatcccag gcctacaagc ggcagcagcg cgtgctgccc    7320
agaaaaggac agcagctggc atcatgaaga atcccgttgt ggatggaata gtggtaactg    7380
acattgacac aatgacaata gaccccccagg tggagaagaa gatgggacaa gtgttactca    7440
tagcagtagc catctccagt gctgtgctgc tgcggaccgc ctggggatgg ggggaggctg    7500
gagctctgat cacagcagcg acctccacct tgtgggaagg ctctccaaac aaatactgga    7560
actcctctac agccacctca ctgtgcaaca tcttcagagg aagctatctg gcaggagctt    7620
cccttatcta tacagtgacg agaaacgctg gcctggttaa gagacgtgga ggtgggacgg    7680
gagagactct gggagagaag tggaaagctc gtctgaatca gatgtcggcc ctggagttct    7740
actcttataa aaagtcaggt atcactgaag tgtgtagaga ggaggctcgc cgtgccctca    7800
aggatggagt ggcacagga ggacatgccg tatcccgggg aagtgcaaag ctcagatggt    7860
tggtggagag aggatatctg cagccctatg ggaaggttgt tgacctcgga tgtggcagag    7920
ggggctggag ctattatgcc gccaccatcc gcaaagtgca ggaggtgaga ggatacacaa    7980
agggaggtcc cggtcatgaa gaacccatgc tggtgcaaag ctatgggtgg aacatagttc    8040
gtctcaagag tggagtggac gtcttccaca tggcggctga gccgtgtgac actctgctgt    8100
gtgacatagg tgagtcatca tctagtcctg aagtggaaga gacacgaaca ctcagagtgc    8160
tctctatggt gggggactgg cttgaaaaaa gaccaggggc cttctgtata aaggtgctgt    8220
gcccatacac cagcactatg atggaaacca tggagcgact gcaacgtagg catggggag    8280 gattagtcag agtgccattg tctcgcaact ccacacatga gatgtactgg gtctctgggg    8340
caaagagcaa catcataaaa agtgtgtcca ccacaagtca gctcctcctg gggcgcatgt    8400
atggccccag gaggccagtg aaatatgagg aggatgtgaa cctcggctcg ggtacgcgag    8460
ctgtggcaag ctgtgctgag gctcctaaca tgaaaatcat cggcaggcgc attgagagaa    8520
tccgcaatga acatgcagaa acatggtttc ttgatgaaaa ccacccatac aggacatggg    8580
```

```
cctaccatgg gagctacgaa gcccccacgc aaggatcagc gtcttccctc gtgaacgggg   8640
ttgttagact cctgtcaaag ccttgggacg tggtgactgg agttacagga atagccatga   8700
ctgacaccac accatacggc aacaaagag tcttcaaaga aaagtggac accagggtgc     8760 cagatcccca agaaggcact cgccaggtaa tgaacatagt ctcttcctgg ctgtggaagg   8820
agctggggaa acgcaagcgg ccacgcgtct gcaccaaaga agagtttatc aacaaggtgc   8880
gcagcaatgc agcactggga gcaatatttg aagaggaaaa agaatggaag acggctgtgg   8940
aagctgtgaa tgatccaagg ttttgggccc tagtggatag ggagagagaa caccacctga   9000
gaggagagtg tcacagctgt gtgtacaaca tgatgggaaa aagagaaaag aagcaaggag   9060
agttcgggaa agcaaaaggt agccgcgcca tctggtacat gtggttggga gccagattct   9120
tggagtttga agcccttgga ttcttgaacg aggaccattg gatgggaaga gaaaactcag   9180
gaggtggagt cgaagggtta ggattgcaaa gacttggata cattctagaa gaaatgaatc   9240
gggcaccagg aggaaagatg tacgcagatg acactgctgg ctgggacacc cgcattagta   9300
agtttgatct ggagaatgaa gctctgatta ccaaccaaat ggaggaaggg cacagaactc   9360
tggcgttggc cgtgattaaa tacacatacc aaaacaaagt ggtgaaggtt ctcagaccag   9420
ctgaaggagg aaaaacagtt atggacatca tttcaagaca agaccagaga gggagtggac   9480
aagttgtcac ttatgctctc aacacattca ccaacttggt ggtgcagctt atccggaaca   9540
tggaagctga ggaagtgtta gagatgcaag acttatggtt gttgaggaag ccagagaaag   9600
tgaccagatg gttgcagagc aatggatggg atagactcaa acgaatggcg gtcagtggag   9660
atgactgcgt tgtgaagcca atcgatgata ggtttgcaca tgccctcagg ttcttgaatg   9720
acatgggaaa agttaggaaa gacacacagg agtggaaacc ctcgactgga tggagcaatt   9780
gggaagaagt cccgttctgc tcccaccact tcaacaagct gtacctcaag gatgggagat   9840
ccattgtggt cccttgccgc caccaagatg aactgattgg ccgagctcgc gtctcaccag   9900
gggcaggatg gagcatccgg gagactgcct gtcttgcaaa atcatatgcg cagatgtggc   9960 agctcctta tttccacaga agagaccttc gactgatggc taatgccatt gctcggctg   10020 tgccagttga ctgggtacca actggagaaa ccacctggtc aatccatgga aagggagaat   10080
ggatgaccac tgaggacatg ctcatggtgt ggaatagagt gtggattgag agaacgacc    10140 atatggagga caagactcct gtaacaaaat ggacagacat tccctatcta ggaaaaaggg   10200
aggacttatg gtgtggatcc cttataggc acagaccccg caccacttgg ctgaaaaca    10260 tcaaagacac agtcaacatg gtgcgcagga tcataggtga tgaagaaaag tacatggact   10320
atctatccac ccaagtccgc tacttgggtg aggaagggtc cacacccgga gtgttgtaag   10380
caccaatttt agtgttgtca ggcctgctag tcagccacag tttggggaaa gctgtgcagc   10440 ctgtaaccc cccaggagaa gctgggaaac caagctcata gtcaggccga aacgccatg    10500 gcacggaaga agccatgctg cctgtgagcc cctcagagga cactgagtca aaaaccccca   10560
cgcgcttgga agcgcaggat gggaaaagaa ggtggcgacc ttccccaccc ttcaatctgg   10620
ggcctgaact ggagactagc tgtgaatctc cagcagaggg actagtggtt agaggagacc   10680
ccccggaaaa cgcaaaacag catattgacg ctgggaaaga ccagagactc catgagtttc   10740
caccacgctg gccgccaggc acagatcgcc gaacagcggc ggccggtgtg gggaaatcca   10800
tggtttctct agaacgtacg gaacgcgaca tacgcggccg ccctgcaggc atgccctcgt   10860
ccacgtggca tctcgagacc tttattccaa ggcgtcgaac cactgacgac tacccgtac    10920 tcagggctta agccatccaa cgaactcacc actgttgcta cccccctcat tatgctagtc   10980
```

```
ctactaaggg catggctagc ctcttttcgg ccttcgctga gagggatttg ttccctaggc    11040
ctaattatta ttttttaattg cccaatacgt atacgagtgc cttttctaat tctcgtatac   11100
tatagtgagt cgtattatct agccgcccgg gccgtcgacc aattctcatg tttgacagct    11160
tatcatcgaa tttctgccat tcatccgctt attatcactt attcaggcgt agcaaccagg    11220
cgtttaaggg caccaataac tgccttaaaa aaattacgcc ccgccctgcc actcatcgca    11280
gtactgttgt aattcattaa gcattctgcc gacatgaaag ccatcacaaa cggcatgatg    11340
aacctgaatc gccagcggca tcagcacctt gtcgccttgc gtataatatt tgcccatggt    11400
gaaaacgggg gcgaagaagt tgtccatatt ggccacgttt aaatcaaaac tggtgaaact    11460
cacccaggga ttggctgaga cgaaaaacat attctcaata aacccttag ggaaataggc     11520 caggttttca ccgtaacacg ccacatcttg cgaatatatg tgtagaaact gccgaaatc     11580 gtcgtggtat tcactccaga gcgatgaaaa cgtttcagtt tgctcatgga aacggtgta    11640 acaaggtga acactatccc atatcaccag ctcaccgtct ttcattgcca tacgaattc     11700 cggatgagca ttcatcaggc gggcaagaat gtgaataaag gccggataaa acttgtgctt    11760 attttttcttt acggtctttta aaaaggccgt aatatccagc tgaacggtct ggttataggt    11820
acattgagca actgactgaa atgcctcaaa atgttcttta cgatgccatt gggatatatc    11880
aacggtggta tatccagtga ttttttttctc cattttagct tccttagctc ctgaaaatct    11940
cgataactca aaaaatacgc ccggtagtga tcttatttca ttatggtgaa agttggaacc    12000
tcttacgtgc cgatcaacgt ctcattttcg ccaaaagttg gcccaggggct tcccggtatc    12060 aacagggaca ccaggattta tttattctgc gaagtgatct tccgtcacag gtatttattc    12120
gcgataagct catggagcgg cgtaaccgtc gcacaggaag acagagaaa gcgcggatct    12180 gggaagtgac ggacagaacg gtcaggacct ggattgggga ggcggttgcc gccgctgctg    12240
ctgacggtgt gacgttctct gttccggtca caccacatac gttccgccat tcctatgcga    12300
tgcacatgct gtatgccggt ataccgctga agttctgca aagcctgatg ggacataagt    12360
ccatcagttc aacggaagtc tacacgaagg ttttttgcgct ggatgtggct gcccggcacc    12420
gggtgcagtt tgcgatgccg gagtctgatg cggttgcgat gctgaaacaa ttatcctgag    12480
aataaatgcc ttggcctttta tatggaaatg tggaactgag tggatatgct gttttttgtct    12540 gttaaacaga gaagctggct gttatccact gagaagcgaa cgaaacagtc gggaaaatct    12600
cccattatcg tagagatccg cattattaat ctcaggagcc tgtgtagcgt ttataggaag    12660
tagtgttctg tcatgatgcc tgcaagcggt aacgaaaacg atttgaatat gccttcagga    12720
acaatagaaa tcttcgtgcg gtgttacgtt gaagtggagc ggattatgtc agcaatggac    12780
agaacaacct aatgaacaca gaaccatgat gtggtctgtc cttttacagc cagtagtgct    12840
cgccgcagtc gagcgacagg gcgaagccct cgagtgagcg aggaagcacc agggaacagc    12900
acttatatat tctgcttaca cacgatgcct gaaaaaactt cccttggggt tatccactta    12960
tccacgggga tatttttata attattttttt ttatagtttt tagatcttct tttttagagc    13020
gccttgtagg cctttatcca tgctggttct agagaaggtg ttgtgacaaa ttgcccttc    13080 agtgtgacaa atcaccctca aatgacagtc ctgtctgtga caaattgccc ttaaccctgt    13140
gacaaattgc cctcagaaga agctgttttt tcacaaagtt atccctgctt attgactctt    13200
ttttatttag tgtgacaatc taaaaaacttg tcacacttca catggatctg tcatggcgga    13260
aacagcggtt atcaatcaca agaaacgtaa aaatagcccg cgaatcgtcc agtcaaacga    13320
```

```
cctcactgag gcggcatata gtctctcccg ggatcaaaaa cgtatgctgt atctgttcgt   13380
tgaccagatc agaaaatctg atggcaccct acaggaacat gacggtatct gcgagatcca   13440
tgttgctaaa tatgctgaaa tattcggatt gacctctgcg gaagccagta aggatatacg   13500
gcaggcattg aagagtttcg cggggaagga agtggttttt tatcgccctg aagaggatgc   13560
cggcgatgaa aaaggctatg aatcttttcc ttggtttatc aaacgtgcgc acagtccatc   13620
cagagggctt tacagtgtac atatcaaccc atatctcatt cccttcttta tcggttaca    13680 gaaccggttt acgcagtttc ggcttagtga aacaaaagaa atcaccaatc cgtatgccat   13740
gcgtttatac gaatccctgt gtcagtatcg taagccggat ggctcaggca tcgtctctct   13800
gaaaatcgac tggatcatag agcgttacca gctgcctcaa agttaccagc gtatgcctga   13860
cttccgccgc cgcttcctgc aggtctgtgt taatgagatc aacagcagaa ctccaatgcg   13920
cctctcatac attgagaaaa agaaaggccg ccagacgact catatcgtat tttccttccg   13980
cgatatcact tccatgacga caggatagtc tgagggttat ctgtcacaga tttgaggtg    14040 gttcgtcaca tttgttctga cctactgagg gtaatttgtc acagttttgc tgtttccttc   14100
agcctgcatg gattttctca tactttttga actgtaattt ttaaggaagc caaatttgag   14160
ggcagtttgt cacagttgat ttccttctct ttcccttcgt catgtgacct gatatcgggg   14220
gttagttcgt catcattgat gagggttgat tatcacagtt tattactctg aattggctat   14280
ccgcgtgtgt acctctacct ggagttttc ccacggtgga tatttcttct tgcgctgagc    14340
gtaagagcta tctgacagaa cagttcttct ttgcttcctc gccagttcgc tcgctatgct   14400
cggttacacg gctgcggcga gcgctagtga taataagtga ctgaggtatg tgctcttctt   14460
atctcctttt gtagtgttgc tcttatttta aacaactttg cggttttttg atgactttgc   14520
gattttgttg ttgctttgca gtaaattgca agatttaata aaaaaacgca aagcaatgat   14580
taaaggatgt tcagaatgaa actcatggaa acacttaacc agtgcataaa cgctggtcat   14640
gaaatgacga aggctatcgc cattgcacag tttaatgatg acagcccgga agcgaggaaa   14700
ataacccggc gctggagaat aggtgaagca gcggatttag ttggggtttc ttctcaggct   14760
atcagagatg ccgagaaagc agggcgacta ccgcacccgg atatggaaat tcgaggacgg   14820
gttgagcaac gtgttggtta tacaattgaa caaattaatc atatgcgtga tgtgttttggt  14880 acgcgattgc gacgtgctga agacgtattt ccaccggtga tcggggttgc tgcccataaa   14940
ggtggcgttt acaaaacctc agtttctgtt catcttgctc aggatctggc tctgaagggg   15000
ctacgtgttt tgctcgtgga aggtaacgac ccccagggaa cagcctcaat gtatcacgga   15060
tgggtaccag atcttcatat tcatgcagaa gacactctcc tgcctttcta tcttggggaa   15120
aaggacgatg tcacttatgc aataaagccc acttgctggc cggggcttga cattattcct   15180
tcctgtctgg ctctgcaccg tattgaaact gagttaatgg gcaaatttga tgaaggtaaa   15240
ctgcccaccg atccacacct gatgctccga ctggccattg aaactgttgc tcatgactat   15300
gatgtcatag ttattgacag cgcgcctaac ctgggtatcg gcacgattaa tgtcgtatgt   15360
gctgctgatg tgctgattgt tcccacgcct gctgagttgt ttgactacac ctccgcactg   15420 cagttttcg atatgcttcg tgatctgctc aagaacgttg atcttaaagg gttcgagcct   15480
gatgtacgta ttttgcttac caaatacagc aatagtaatg gctctcagtc cccgtggatg   15540
gaggagcaaa ttcgggatgc ctggggaagc atggttctaa aaaatgttgt acgtgaaacg   15600
gatgaagttg gtaaaggtca gatccggatg agaactgttt ttgaacaggc cattgatcaa   15660
cgctcttcaa ctggtgcctg gagaaatgct ctttctattt gggaacctgt ctgcaatgaa   15720
```

```
attttcgatc gtctgattaa accacgctgg gagattagat aatgaagcgt gcgcctgtta    15780
ttccaaaaca tacgctcaat actcaaccgg ttgaagatac ttcgttatcg acaccagctg    15840
ccccgatggt ggattcgtta attgcgcgcg taggagtaat ggctcgcggt aatgccatta    15900 cttgcctgt atgtggtcgg gatgtgaagt ttactcttga agtgctccgg ggtgatagtg     15960
ttgagaagac ctctcgggta tggtcaggta atgaacgtga ccaggagctg cttactgagg    16020
acgcactgga tgatctcatc ccttctttc tactgactgg tcaacagaca ccggcgttcg     16080
gtcgaagagt atctggtgtc atagaaattg ccgatgggag tcgccgtcgt aaagctgctg    16140
cacttaccga aagtgattat cgtgttctgg ttggcgagct ggatgatgag cagatggctg    16200
cattatccag attgggtaac gattatcgcc caacaagtgc ttatgaacgt ggtcagcgtt    16260
atgcaagccg attgcagaat gaatttgctg gaaatatttc tgcgctggct gatgcggaaa    16320
atatttcacg taagattatt acccgctgta tcaacaccgc caaattgcct aaatcagttg    16380
ttgctctttt ttctcacccc ggtgaactat ctgcccggtc aggtgatgca cttcaaaaag    16440
cctttacaga taaagaggaa ttacttaagc agcaggcatc taaccttcat gagcagaaaa    16500
aagctggggt gatatttgaa gctgaagaag ttatcactct tttaacttct gtgcttaaaa    16560
cgtcatctgc atcaagaact agtttaagct cacgacatca gtttgctcct ggagcgacag    16620
tattgtataa gggcgataaa atggtgctta acctggacag gtctcgtgtt ccaactgagt    16680
gtatagagaa aattgaggcc attcttaagg aacttgaaaa gccagcaccc tgatgcgacc    16740
acgttttagt ctacgtttat ctgtctttac ttaatgtcct ttgttacagg ccagaaaagca   16800 taactggcct gaatattctc tctgggccca ctgttccact tgtatcgtcg gtctgataat    16860
cagactggga ccacggtccc actcgtatcg tcggtctgat tattagtctg ggaccacggt    16920
cccactcgta tcgtcggtct gattattagt ctggaccac ggtcccactc gtatcgtcgg     16980
tctgataatc agactgggac cacggtccca ctcgtatcgt cggtctgatt attagtctgg    17040
gaccatggtc ccactcgtat cgtcggtctg attattagtc tgggaccacg gtcccactcg    17100
tatcgtcggt ctgattatta gtctggaacc acggtcccac tcgtatcgtc ggtctgatta    17160
ttagtctggg accacggtcc cactcgtatc gtcggtctga ttattagtct gggaccacga    17220
tcccactcgt gttgtcggtc tgattatcgg tctgggacca cggtcccact tgtattgtcg    17280
atcagactat cagcgtgaga ctacgattcc atcaatgcct gtcaagggca agtattgaca    17340
tgtcgtcgta acctgtagaa cggagtaacc tcggtgtgcg gttgtatgcc tgctgtggat    17400
tgctgctgtg tcctgcttat ccacaacatt ttgcgcacgg ttatgtggac aaaatacctg    17460
gttacccagg ccgtgccggc acgttaaccg ggctgcatcc gatgcaagtg tgtcgctgtc    17520
gacgagctcg cgagctcgga catgaggttg ccccgtattc agtgtcgctg atttgtattg    17580
tctgaagttg ttttacgtt aagttgatgc agatcaatta atacgatacc tgcgtcataa     17640
ttgattattt gacgtggttt gatggcctcc acgcacgttg tgatatgtag atgataatca    17700
ttatcacttt acgggtcctt tccggtgatc cgacaggtta cggggcggcg acctcgcggg    17760
ttttcgctat ttatgaaaat tttccggttt aaggcgtttc cgttcttctt cgtcataact    17820
taatgttttt atttaaaata ccctctgaaa agaaaggaaa cgacaggtgc tgaaagcgag    17880 cttttttggcc tctgtcgttt cctttctctg tttttgtccg tggaatgaac aatggaagtc    17940
cgagctcatc gctaataact tcgtatagca tacattatac gaagttatat tcgatgcggc    18000
gctgaggtct gcctcgtgaa gaaggtgttg ctgactcata ccaggcctga atcgccccat    18060
```

| | |
|---|---|
| catccagcca gaaagtgagg gagccacggt tgatgagagc tttgttgtag gtggaccagt | 18120 |
| tggtgatttt gaacttttgc tttgccacgg aacggtctgc gttgtcggga agatgcgtga | 18180 |
| tctgatcctt caactcagca aaagttcgat ttattcaaca aagccacgtg tctcaaaatc | 18240 |
| tctgatgtta cattgcacaa gataaaaata tatcatcatg aacaataaaa ctgtctgctt | 18300 |
| acataaacag taatacaagg ggtgttatga gccatattca acgggaaacg tcttgctcga | 18360 |
| cgatgataag ctgtcaaaca tgagaattgg gtcgtcaata tgctaaaacg cggcataccc | 18420 |
| cgcgtattcc cactagttaa ttaacctgca gggggctgtt agaggtcttc cctagtccaa | 18480 |
| ctatagcgta tggacatatt gtcgttagaa cgcggctaca attaatacat aaccttatgt | 18540 |
| atcatacaca tacgatttag gggacactat a | 18571 |

<210> SEQ ID NO 2
<211> LENGTH: 18571
<212> TYPE: DNA
<213> ORGANISM: Artificial Sequence
<220> FEATURE:
<223> OTHER INFORMATION: Synthetic

<400> SEQUENCE: 2

| | |
|---|---|
| gagttgttga tctgtgtgaa tcagactgcg acagttcgag tttgaagcga aagctagcaa | 60 |
| cagtatcaac aggtttttatt ttggatttgg aaacgagagt ttctggtcat gaaaaaccca | 120 |
| aaaaagaaat ccggaggatt ccggattgtc aatatgctaa aacgcggagt agcccgtgtg | 180 |
| agccccttg ggggcttgaa gaggctacca gctggacttc tgctgggtca tggacccatc | 240 |
| aggatggtct tggcgatact agccttcttg agattcacgg caatcaagcc atcactgggt | 300 |
| ctcatcaata gatggggttc cgtggggaaa aagaggcta tggaaataat aagaagttc | 360 |
| aagaaagatc tggctgccat gctgagaata atcaatgcta ggaaggagaa gagagacgt | 420 |
| ggcgcagaca ccagtgtcgg aattgttggc ctcctgctga ccacagccat ggcagtggag | 480 |
| gtcaccagac gtgggagtgc atactatatg tacttagaca gaagcgatgc tgggaaggcc | 540 |
| atatctttc aaccacact ggggtgaat aagtgttaca tacagatcat ggatcttgga | 600 |
| cacatgtgtg atgccacaat gagctatgaa tgccctatgt tggatgaggg ggtagaacca | 660 |
| gatgacgtcg attgctggtg caacacgaca tcgacttggg ttgtgtacgg aacctgccat | 720 |
| cacaaaaaag gtgaggcacg gagatctaga agagctgtga cgctcccctc tcattccact | 780 |
| aggaagctgc aaacgcggtc gcagacctgg ttggaatcaa gagaatacac aaagcacttg | 840 |
| atcagagtcg aaaattggat attcaggaac cctggctttg cgttggcagc agctgccatt | 900 |
| gcttggcttt tgggaagctc aacgagccaa aaagtcatat acttggtcat gatactgttg | 960 |
| attgccccgg catacagtat caggtgcata ggagtcagca atagggattt tgtggaaggt | 1020 |
| atgtcaggtg ggacctgggt tgatgttgtc ttggaacatg gaggttgtgt taccgtaatg | 1080 |
| gcacaggaca agccaactgt tgatatagag ttggtcacaa caacggttag caacatggcg | 1140 |
| gaggtaagat cctactgcta cgaggcatca atatcggaca tggcttcgga cagccgctgc | 1200 |
| ccaacacaag gtgaagccta ccttgacaag cagtcagaca ctcaatatgt ttgcaaaaga | 1260 |
| acgttagtgg acagaggttg gggaaatgga tgtggactct ttggcaaagg gagcctggtg | 1320 |
| acatgcgcca gtttgcatg ctccaagaaa atgactggga agagcatcca gccagagaac | 1380 |
| ctggagtacc ggataatgct gtcagttcat ggctcccagc acagtgggat gattgttaat | 1440 |
| gacataggac atgaaactga tgagaataga gcgaaggttg agataacgcc caattccacca | 1500 |
| agagccgaag ccaccctggg aggttttgga agcctaggac ttgattgtga accgaggaca | 1560 |

```
ggccttgact tttcagattt gtattacttg actatgaata caagcattg gttggtgcac    1620 aaggagtggt tccatgacat tccactacct tggcatgctg gggcagacac cggaactcca    1680
cattggaaca acaaagaagc attggtagag ttcaaggacg cacatgccaa aaggcaaact    1740
gtcgtggttc tagggagtca agaaggagcc gttcacacgg ctcttgctgg agccctggag    1800
gctgagatgg atggtgcaaa gggaaggctg tcctctggcc acttgaaatg tcgcttgaaa    1860
atggacaaac ttagattgaa gggcgtgtca tactccttat gtaccgcggc gttcacattc    1920
accaagatcc cggctgaaac gctgcatggg acagtcacag tggaggtaca gtatgcaggg    1980
acagatggac cctgcaaggt tccagctcag atggcggtgg atatgcaaac tctgacccca    2040
gttgggaggt tgataaccgc taaccctgtg atcactgaaa gcactgagaa ttcaaagatg    2100 atgttgaac ttgacccacc atttgggat tcttacattg tcataggagt tggggataag     2160
aagatcaccc accactggca caggagtggc agcaccatcg aaaagcatt tgaagccact    2220 gtgagaggcg ccaagagaat ggcagtcttg gagacacag cctgggactt tggatcagtc    2280
ggaggtgctc tcaactcatt gggcaagggc atccatcaaa tttttggagc agcttttcaaa   2340 tcattgtttg gaggaatgtc ctggttctca caaatcctca taggaacgtt gctggtgtgg    2400
ttgggtctga acacaaagaa tggaactatt tcccttacgt gcttggcctt aggggggagtg  2460 ttgatcttcc tatctacagc cgtctctgct gatgtggggt gttcggtgga cttctcaaag   2520
aaggaaacga gatgcggtac gggggtgttc gtctataacg acgttgaagc ctggagggac   2580
aggtacaagt accatcctga ctcccctcgt agattggcag cagcagtcaa gcaggcctgg   2640
gaagatggga tctgtgggat ctcctctgtt tcaagaatgg aaaacattat gtggagatca   2700
gtagaagggg agctcaacgc aattctggaa gagaatggag ttcaactgac ggtcgttgtg   2760
ggatctgtaa aaaaccccat gtggagaggt ccgcagaggt tgcctgtgcc tgtgaatgag   2820
ctgccccacg gttggaaggc ctgggggaaa tcgtactttg tcagggcagc aaagaccaac   2880
aacagctttg ttgtggatgg tgacacactg aaggaatgcc cgctcaaaca cagagcatgg   2940
aacagctttc ttgtgaggga tcacgggttc ggggtatttc acactagtgt ctggcttaaa    3000
gtcagagagg attactcatt agagtgtgat ccagccgtca taggaacagc tgctaaggga   3060
aaggaggccg tgcacagtga tctaggctac tggattgaga gtgaaaagaa cgacacatgg   3120
aggctgaaga gggctcacct gatcgagatg aaaacatgtg aatggccaaa gtcccacaca   3180
ctgtggacag atggaataga agaaagtgat ctgatcatac ctaagtcttt agctgggcca   3240
ctcagccacc acaacaccag agagggctac aggactcaag tgaaagggcc gtggcatagt   3300
gaagagcttg aaatccggtt tgaggaatgt ccaggcacca aggtccacgt ggaggaaaca   3360 tgtgaacga gaggaccgtc cctgagatca accactgcaa gcggaagggt gatcgaggaa   3420
tggtgctgca gggaatgcac aatgccccca ttgtcgttcc gggcaaaaga tggctgttgg   3480 tatgaatgg agataaggcc caggaaggaa ccagagagta acctagtaag gtcaatggtg   3540
actgcaggat caactgatca catggatcac ttctcccttg gagtgcttgt gattctgctc   3600
atggtgcagg aagggctgaa gaagagaatg accacaaaga tcatcataag cacatcaatg   3660
gcagtgttgg tagctatgat cctgggagga ttttcaatga gtgacttggc taagcttgca   3720
attctgatgg gtgccacctt cgcggaaatg aacactggag gagatgtagc tcatctggcg   3780
ctgatagcgg cattcaaagt cagacccgcg ttgctggtct ctttcatctt cagagccaat   3840
tggacacccc gtgagagcat gctgctggcc ttggcctcgt gccttctgca aactgtgatc   3900
```

```
tccgccctgg aaggcgacct gatggttctc atcaatggtt ttgctttggc ctggttggca      3960
atacgagcga tggctgttcc acgcactgac aacatcacct tggcaatcct ggctgctctg      4020
acaccactgg cccgaggcac actgcttgta gcgtggagag caggccttgc tacttgtggg      4080
gggttcatgc tcctctctct gaaggggaaa ggtagtgtga agaagaacct accatttgtc      4140
atggccttgg gactaaccgc tgtgaggctg gtttgacccca tcaacgtggt gggactgctg     4200
ttgctcacaa ggagtgggaa gcggagctgg cccctagtg aagtactcac agctgttggc      4260
ctgatatgtg cactggccgg agggttcgcc aaagcagata tagagatggc tgggcccatg      4320
gctgcagttg gcctgctaat tgttagttac gtggtctcag aaagagtgt ggacatgtac       4380 attgaaagag caggtgacat cacatgggaa aaagatgcgg aagttactgg aaacagcccc     4440
cggctcgatg tggcactaga tgagagtggt gatttctccc tggtggagga tgatggtccc     4500
cccatgagag agatcatact caaggtggtc ctgatgacca tctgtggcat gaacccaata     4560
gccataccct ttgcagctgg agcgtggtat gtgtatgtga agactggaaa gaggagtggt    4620
gctctatggg atgtgcctgc tcccaaggaa gtaaaaaagg gggagaccac agatggagtg     4680
tatagagtga tgactcgcag actgctaggt tcaacacaag ttggagtggg agtcatgcaa     4740 gaggggtct tccacactat gtggcacgtc acaaaaggat ccgcgctgag gagcggtgaa       4800
gggagacttg atccatactg gggagatgtt aagcaggatc tggtgtcata ctgtggcccg    4860
tggaagctag atgccgcttg ggacggacac agcgaggtgc agcttttggc cgtgcccccc     4920
ggagagagag cgaggaacat ccagactctg cccggaatat tcaagacaaa ggatggggac      4980
atcggagcag ttgctctgga ctacccagca ggaacttcag gatctccgat cctagacaag     5040
tgtgggagag tgataggact ctatggcaat ggggtcgtga tcaaaaatgg aagttatgtt      5100
agtgccatca cccaagggag gagggaggaa gagactcctg ttgaatgctt cgaaccttcg     5160
atgctgaaga agaagcagct aactgtcttg gatctgcatc ctggagctgg aaaaaccagg     5220
agagttcttc ctgaaatagt ccgtgaagcc ataaaaacaa gactccgcac ggtgatcctg     5280
gctccaacca gggttgtcgc tgctgaaatg gaggaagccc ttagagggct tccagtgcgt     5340
tacatgacaa cagcagttaa tgtcacccac tctgggacga aaatcgttga tttaatgtgc     5400
catgccacct tcacttcacg cctactacaa cccattagag tccccaacta caatctttac     5460
attatggatg aggcccactt cacagatccc tcaagtatag cagcaagagg atacatatca    5520
acaagggttg agatgggcga ggcggctgcc atcttcatga ccgccacacc accaggaacc    5580
cgcgacgcat ttccggactc taactcacca atcatggaca cagaagtgga agtcccagag     5640
agagcctgga gctcaggctt tgattgggtg acggatcatt ctggaaaaac agtttggttt      5700
gttccaagcg tgaggaacgg caacgagatc gcggcttgtc tgacaaaagc tggaaaacgg      5760
gtcatacagc tcagcagaaa gactttgag acagagttcc agaaaacaaa aaatcaagag      5820
tgggacttcg tcgtaacaac tgacatctca gagatgggcg ccaacttcaa agctgaccgg    5880
gtcatagatt ccaggagatg cctgaagccg gtcatacttg atggcgagag agtcattctg    5940
gctggaccca tgcctgtcac acatgccagc gctgcccaga ggaggggcg cataggcagg     6000 aatcccaaca aacctggaga tgagtatatg tatggaggtg ggtgcgcaga gactgatgaa     6060
gaccatgcac actggcttga agcaagaatg cttcttgata acatttacct ccaagatggc    6120
ctcatagcct cgctctatcg acctgaggcc gataaggtag cagccattga gggagagttc      6180
aagcttagga cggagcaaag gaagaccttt gtggaactga tgaaagagg agatcttcct     6240 gtttggctgg cctatcaggt tgcatctgcc ggaataacct acacagatag aagatggtgt     6300
```

```
tttgatggca cgaccaacaa caccataatg gaagacagtg tgccggcaga ggtgtggacc      6360
agatacggag agaaaagagt gctcaaaccg aggtggatgg acgccagagt ttgttcagat      6420
catgcggccc tgaagtcatt caaagaattt gccgctggga aaagaggagc ggcctttgga      6480
gtgatggaag ccctgggaac actgccagga cacatgacag agaggtttca ggaagccatt      6540
gacaacctcg ctgtgctcat gcgggcagag actggaagca ggccctacaa agccgcggcg      6600
gcccaattac cggagacctt agagaccatc atgcttttgg gtttgctggg aacagtctcg      6660
ctgggaatct tctttgtctt gatgcggaac aagggcatag ggaagatggg ctttggaatg      6720
gtgacccttg gggccagtgc atggcttatg tggctctcgg aaattgagcc agccagaatt      6780
gcatgtgtcc tcattgtcgt gtttctattg ctggtggtgc tcatacctga gccagaaaag      6840
cagagatctc cccaggacaa ccaaatggca attatcatca tggtagcagt gggtcttctg      6900
ggcttgataa ccgccaatga actcggatgg ttggagagaa caaaaagtga cctaggccat      6960
ctaatgggaa ggagagagga gggggcaacc atgggattct caatggacat tgacttgcgg      7020
ccagcctcag cttgggctat ctatgccgct ctgacaactc tcatcacccc agccgtccaa      7080
catgcggtaa ccacttcata caacaactac tccttaatgg cgatgccac gcaagccgga      7140 gtgttgtttg catgggcaa agggatgcca ttctatgcgt gggacttcgg agtcccgctg      7200
ctaatgatgg gttgctactc acaattaaca cccttgacct aatagtggc catcattctg      7260 ctcgtggcgc actacatgta cttgatccca ggtctacagg cagcagcggc gcgcgctgcc      7320
cagaagagaa cggcagctgg catcatgaag aaccctgttg tggatggaat agtggtgact      7380
gacattgaca caatgacaat tgaccccaa gtggagaaaa agatgggaca agtgctactc      7440
atagcagtag ccatctccag tgccgttctg ctgcgcaccg cctggggtg ggggaggct      7500 ggggccctga tcacagccgc aacttccact ttgtgggaag gctctccgaa taaatactgg      7560
aactcctcca cagccacttc actgtgtaac atttttaggg gaagttactt ggctggagct      7620
tctcttattt acacagtaac aagaaacgct ggcctggtca gagacgtgg aggtggaacg      7680 ggagagaccc tggggagaa atggaaggcc cgcctgaacc agatgtcggc cctggagttt      7740
tactcctaca aaaagtcagg catcaccgaa gtgtgcagag aagaagcccg ccgcgccctc      7800
aaggacggag tggcaacagg aggccatgct gtgtcccgag aagcgcaaa gcttagatgg      7860 ttggtggaga gaggataccct gcagccctat ggaaaggtca ttgatcttgg atgtggcaga      7920
gggggctgga gttactacgc cgccaccatc cgcaaagttc aagaggtgaa aggatacaca      7980
aagggaggcc ctggtcatga agaacccacg ttggtgcaaa gctatggatg aacatagtc      8040 cgtcttaaga gtggggtgga cgtctttcac atggcggcgg agtcgtgtga cactttgctg      8100
tgtgacatag gtgagtcatc atctagtcct gaagtggaag aagcacggac gctcagagta      8160
ctctccatgg tgggggattg gcttgaaaaa agaccagggg cctttttgtat aaaggtgttg      8220 tgcccataca ccagcaccat gatggaaacc ctagagcgac tgcagcgtag gtatgggga      8280 ggactggtca gagtgccact ctcccgcaac tctacacatg agatgtactg ggtctctgga      8340
gcgaaaagca acatcataaa aagtgtgtcc accacgagcc agctcctctt gggacgcatg      8400
gacgggccca ggaggccagt gaaatatgag gaggatgtga atctcggctc cggcacgcga      8460
gctgtggcaa gctgcgccga agctcccaac ctgaagatca ttggtaaccg cgttgagagg      8520
atccgcagtg agcatgcgga aacgtggttc tttgatgaga ccacccata caggacatgg      8580 gcttaccatg ggagctacga ggcccctaca caagggtcag cgtcttctct cataaacggg      8640
```

```
gttgtcaggc tcctgtcaaa gccctgggat gtggtgactg gagtcacagg aatagccatg    8700
accgacacca caccgtatgg ccagcaaaga gttttcaagg aaaaagtgga cactagggtg    8760
ccagaccccc aggaaggcac tcgtcaggtg atgaacatgg tctcttcctg gctatggaag    8820
gagctaggta aacacaaacg gccacgagtt tgcaccaaag aagagttcat caataaggtt    8880
cgcagcaatg cagcactggg ggcaatattt gaagaggaga agaatggaa gactgcagtg     8940
gaagctgtga acgatccaag gttctgggcc ctagtggaca aggaaagaga gcaccacttg    9000
agaggagagt gtcagagctg tgtgtacaac atgatgggaa aaagagaaaa gaagcaaggg    9060
gaatttggaa aggccaaggg cagccgcgcc atttggtaca tgtggctagg gctagatttg    9120
ctagagtttg aagcccttgg attcttgaac gaggatcact ggatggggag agagaattca    9180
ggaggtggtg ttgaagggct gggattacaa agacttggat atgttctaga gaaatgagc     9240
cgcacaccag gaggaaagat gtatgcagat gataccgctg gctgggacac ccgcatcagt    9300
aggtttgatc tggagaatga agctctgatc accaaccaaa tggagaaagg gcacagggcc    9360
ttggcgttgg ccataatcaa gtacacatac caaaacaaag tggtaaaggt ccttagacca    9420
gctgaaagag ggaagacagt tatggacatc atctcaagac aagaccaaag agggagcgga    9480
caagttgtta cttacgctct taatacattc accaacctgg tggtgcagct cattcggaac    9540
atggaggctg aggaagttct agagatgcaa gacttgtggc tgttgaggag gccagagaag    9600
gtgaccagct ggttgcagag caacggatgg atagggctca aacgaatggc agtcagtgga    9660
gatgattgtg ttgtgaaacc aattgatgat aggtttgcac atgccctcag gttttttgaat   9720
gacatgggga agttaggaa ggacacacag gagtggaaac cctcaactgg atggagcaac     9780
tgggaagaag ttccgttttg ctcccatcac ttcaacaagc tttacctcaa ggacgggagg    9840
tccattgtgt tcccctgtcg ccaccaagat gaactgattg gccgagcccg cgtctcacca    9900
ggggcgggat ggagcatccg ggagactgct tgcctagcaa aatcatatgc acaaatgtgg    9960
cagcttcttt atttccacag aagggacctc cgactgatgg ccaacgccat tgttcatct    10020
gtgccagttg actgggttcc aactgggaga accacctggt caatccatgg aaagggagaa   10080
tggatgacca ctgaggacat gcttgtggtg tggaacagag tgtggattga ggagaacgac   10140
cacatggagg acaagacccc agtcacgaaa tggacagaca ttccctattt gggaaaaagg   10200
gaagacttat ggtgtggatc tcttataggg cacagaccac gcactacttg gctgagaac    10260
attaaagaca cagtcaacat ggtgcgcagg atcataggtg atgaagaaaa gtacatggac   10320
tacctatcca ctcaagttcg ctacttgggt gaagaaggt ccacacctgg agtgttataa    10380
gcaccaattt tagtgttgtc aggcctgcta gtcagccaca gcttgggaa agctgtgcag    10440
cctgtgaccc ccccaggaga agctgggaaa ccaagcccat agtcaggccg agaacgccat   10500
ggcacggaag aagccatgct gcctgtgagc ccctcagagg acactgagtc aaaaaacccc   10560
acgcgcttgg aggcgcagga tgggaaaaga aggtggcgac cttccccacc ctccaatctg   10620
gggcctgaac tggagatcag ctgtggatct ccaggagagg gactagcggt tagaggagac   10680
ccccccggaaa acgcaaaaca gcatattgac gctgggaaag accagagact ccatgagttt   10740
ccaccacgct ggccgccagg cacagatcgc cgaatagcgg cggccggtgt ggggaaatcc    10800
atgggtctct agaacgtacg gaaggcgaca tacgcggccg ccctgcaggc atgccctcgt    10860
ccacgtggca tctcgagacc tttattccaa ggcgtcgaac cactgacgac taccctgtac    10920
tcagggctta agccatccaa cgaactcacc actgttgcta cccccctcat tatgctagtc    10980
ctactaaggg catggctagc ctcttttcgg ccttcgctga gagggatttg ttccctaggc   11040
```

```
ctaattatta tttttaattg cccaatacgt atacgagtgc cttttctaat tctcgtatac    11100
tatagtgagt cgtattatct agccgcccgg gccgtcgacc aattctcatg tttgacagct    11160
tatcatcgaa tttctgccat tcatccgctt attatcactt attcaggcgt agcaaccagg    11220
cgtttaaggg caccaataac tgccttaaaa aaattacgcc ccgccctgcc actcatcgca    11280
gtactgttgt aattcattaa gcattctgcc gacatggaag ccatcacaaa cggcatgatg    11340
aacctgaatc gccagcggca tcagcacctt gtcgccttgc gtataatatt tgcccatggt    11400
gaaaacgggg gcgaagaagt tgtccatatt ggccacgttt aaatcaaaac tggtgaaact    11460
cacccaggga ttggctgaga cgaaaaacat attctcaata aaccctttag ggaaataggc    11520
caggttttca ccgtaacacg ccacatcttg cgaatatatg tgtagaaact gccggaaatc    11580
gtcgtggtat tcactccaga gcgatgaaaa cgtttcagtt tgctcatgga aaacggtgta    11640
acaagggtga acactatccc atatcaccag ctcaccgtct ttcattgcca tacggaattc    11700
cggatgagca ttcatcaggc gggcaagaat gtgaataaag gccggataaa acttgtgctt    11760 attttttcttt acggtcttta aaaaggccgt aatatccagc tgaacggtct ggttataggt    11820
acattgagca actgactgaa atgcctcaaa atgttcttta cgatgccatt gggatatatc    11880
aacggtggta tatccagtga ttttttttctc cattttagct tccttagctc ctgaaaatct    11940
cgataactca aaaatacgcc cggtagtga tcttatttca ttatggtgaa agttggaacc    12000
tcttacgtgc cgatcaacgt ctcattttcg ccaaaagttg gcccagggct tcccggtatc    12060
aacagggaca ccaggattta tttattctgc gaagtgatct tccgtcacag gtatttattc    12120
gcgataagct catggagcgg cgtaaccgtc gcacaggaag gacagagaaa gcgcggatct    12180
gggaagtgac ggacagaacg gtcaggacct ggattgggga ggcggttgcc gccgctgctg    12240
ctgacggtgt gacgttctct gttccggtca caccacatac gttccgccat tcctatgcga    12300
tgcacatgct gtatgccggt ataccgctga aagttctgca aagcctgatg ggacataagt    12360
ccatcagttc aacggaagtc tacacgaagg ttttgcgct ggatgtggct gcccggcacc    12420
gggtgcagtt tgcgatgccg gagtctgatg cggttgcgat gctgaaacaa ttatcctgag    12480
aataaatgcc ttggccttta tatggaaatg tggaactgag tggatatgct gttttttgtct    12540 gttaaacaga gaagctggct gttatccact gagaagcgaa cgaaacagtc gggaaaatct    12600
cccattatcg tagagatccg cattattaat ctcaggagcc tgtgtagcgt ttataggaag    12660
tagtgttctg tcatgatgcc tgcaagcggt aacgaaaacg atttgaatat gccttcagga    12720
acaatagaaa tcttcgtgcg gtgttacgtt gaagtggagc ggattatgtc agcaatggac    12780
agaacaacct aatgaacaca gaaccatgat gtggtctgtc cttttacagc cagtagtgct    12840
cgccgcagtc gagcgacagg gcgaagccct cgagtgagcg aggaagcacc agggaacagc    12900
acttatatat tctgcttaca cacgatgcct gaaaaaactt cccttggggt tatccactta    12960
tccacgggga tattttttata attatttttt ttatagtttt tagatcttct tttttagagc    13020
gccttgtagg cctttatcca tgctggttct agagaaggtg ttgtgacaaa ttgcccttc    13080 agtgtgacaa atcaccctca aatgacagtc ctgtctgtga caaattgccc ttaaccctgt    13140
gacaaattgc cctcagaaga agctgttttt tcacaaagtt atccctgctt attgactctt    13200
ttttatttag tgtgacaatc taaaaacttg tcacacttca catggatctg tcatggcgga    13260
aacagcggtt atcaatcaca agaaacgtaa aaatagcccg cgaatcgtcc agtcaaacga    13320
cctcactgag gcggcatata gtctctcccg ggatcaaaaa cgtatgctgt atctgttcgt    13380
```

```
tgaccagatc agaaaatctg atggcaccct acaggaacat gacggtatct gcgagatcca  13440
tgttgctaaa tatgctgaaa tattcggatt gacctctgcg gaagccagta aggatatacg  13500
gcaggcattg aagagtttcg cggggaagga agtggttttt tatcgccctg aagaggatgc  13560
cggcgatgaa aaaggctatg aatcttttcc ttggtttatc aaacgtgcgc acagtccatc  13620
cagagggctt tacagtgtac atatcaaccc atatctcatt cccttcttta tcgggttaca  13680
gaaccggttt acgcagtttc ggcttagtga acaaaagaa atcaccaatc cgtatgccat  13740
gcgtttatac gaatccctgt gtcagtatcg taagccggat ggctcaggca tcgtctctct  13800
gaaaatcgac tggatcatag agcgttacca gctgcctcaa agttaccagc gtatgcctga  13860
cttccgccgc cgcttcctgc aggtctgtgt taatgagatc aacagcagaa ctccaatgcg  13920
cctctcatac attgagaaaa agaaaggccg ccagacgact catatcgtat tttccttccg  13980
cgatatcact tccatgacga caggatagtc tgagggttat ctgtcacaga tttgagggtg  14040
gttcgtcaca tttgttctga cctactgagg gtaatttgtc acagttttgc tgtttccttc  14100
agcctgcatg gattttctca tactttttga actgtaattt ttaaggaagc caaatttgag  14160
ggcagtttgt cacagttgat ttccttctct ttcccttcgt catgtgacct gatatcgggg  14220
gttagttcgt catcattgat gagggttgat tatcacagtt tattactctg aattggctat  14280
ccgcgtgtgt acctctacct ggagttttc ccacggtgga tatttcttct tgcgctgagc  14340
gtaagagcta tctgacagaa cagttcttct ttgcttcctc gccagttcgc tcgctatgct  14400
cggttacacg gctgcggcga gcgctagtga taataagtga ctgaggtatg tgctcttctt  14460
atctcctttt gtagtgttgc tcttattta aacaactttg cggttttttg atgactttgc  14520
gattttgttg ttgctttgca gtaaattgca agatttaata aaaaaacgca aagcaatgat  14580
taaaggatgt tcagaatgaa actcatggaa acacttaacc agtgcataaa cgctggtcat  14640
gaaatgacga aggctatcgc cattgcacag tttaatgatg acagcccgga agcgaggaaa  14700 ataaccggc gctggagaat aggtgaagca gcggatttag ttggggtttc ttctcaggct  14760
atcagagatg ccgagaaagc agggcgacta ccgcacccgg atatggaaat tcgaggacgg  14820
gttgagcaac gtgttggtta tacaattgaa caaattaatc atatgcgtga tgtgtttggt  14880
acgcgattgc gacgtgctga agacgtattt ccaccggtga tcggggttgc tgcccataaa  14940
ggtggcgttt acaaaacctc agtttctgtt catcttgctc aggatctggc tctgaagggg  15000
ctacgtgttt tgctcgtgga aggtaacgac ccccagggaa cagcctcaat gtatcacgga  15060
tgggtaccag atcttcatat tcatgcagaa gacactctcc tgccttcta tcttgggaa  15120 aaggacgatg tcacttatgc aataaagccc acttgctggc cggggcttga cattattcct  15180
tcctgtctgg ctctgcaccg tattgaaact gagttaatgg gcaaatttga tgaaggtaaa  15240
ctgcccaccg atccacacct gatgctccga ctggccattg aaactgttgc tcatgactat  15300
gatgtcatag ttattgacag cgcgcctaac ctgggtatcg gcacgattaa tgtcgtatgt  15360
gctgctgatg tgctgattgt tcccacgcct gctgagttgt ttgactacac ctccgcactg  15420 cagttttttcg atatgcttcg tgatctgctc aagaacgttg atcttaaagg gttcgagcct  15480
gatgtacgta ttttgcttac caaatacagc aatagtaatg gctctcagtc cccgtggatg  15540
gaggagcaaa ttcgggatgc ctggggaagc atggttctaa aaaatgttgt acgtgaaacg  15600
gatgaagttg gtaaaggtca gatccggatg agaactgttt ttgaacaggc cattgatcaa  15660
cgctcttcaa ctggtgcctg gagaaatgct ctttctattt gggaacctgt ctgcaatgaa  15720
attttcgatc gtctgattaa accacgctgg gagattagat aatgaagcgt gcgcctgtta  15780
```

```
ttccaaaaca tacgctcaat actcaaccgg ttgaagatac ttcgttatcg acaccagctg   15840
ccccgatggt ggattcgtta attgcgcgcg taggagtaat ggctcgcggt aatgccatta   15900
ctttgcctgt atgtggtcgg gatgtgaagt ttactcttga agtgctccgg ggtgatagtg   15960
ttgagaagac ctctcgggta tggtcaggta atgaacgtga ccaggagctg cttactgagg   16020
acgcactgga tgatctcatc ccttcttttc tactgactgg tcaacagaca ccggcgttcg   16080
gtcgaagagt atctggtgtc atagaaattg ccgatgggag tcgccgtcgt aaagctgctg   16140
cacttaccga aagtgattat cgtgttctgg ttggcgagct ggatgatgag cagatggctg   16200
cattatccag attgggtaac gattatcgcc caacaagtgc ttatgaacgt ggtcagcgtt   16260
atgcaagccg attgcagaat gaatttgctg gaaatatttc tgcgctggct gatgcggaaa   16320
atatttcacg taagattatt acccgctgta tcaacaccgc caaattgcct aaatcagttg   16380
ttgctctttt ttctcacccc ggtgaactat ctgcccggtc aggtgatgca cttcaaaaag   16440
cctttacaga taaagaggaa ttacttaagc agcaggcatc taaccttcat gagcagaaaa   16500 aagctgggt gatatttgaa gctgaagaag ttatcactct tttaacttct gtgcttaaaa   16560
cgtcatctgc atcaagaact agtttaagct cacgacatca gtttgctcct ggagcgacag   16620
tattgtataa gggcgataaa atggtgctta acctggacag gtctcgtgtt ccaactgagt   16680
gtatagagaa aattgaggcc attcttaagg aacttgaaaa gccagcaccc tgatgcgacc   16740
acgttttagt ctacgtttat ctgtctttac ttaatgtcct ttgttacagg ccagaaagca   16800
taactggcct gaatattctc tctgggccca ctgttccact tgtatcgtcg gtctgataat   16860
cagactggga ccacggtccc actcgtatcg tcggtctgat tattagtctg ggaccacggt   16920
cccactcgta tcgtcggtct gattattagt ctgggaccac ggtcccactc gtatcgtcgg   16980
tctgataatc agactgggac cacggtccca ctcgtatcgt cggtctgatt attagtctgg   17040
gaccatggtc ccactcgtat cgtcggtctg attattagtc tgggaccacg gtcccactcg   17100
tatcgtcggt ctgattatta gtctggaacc acggtcccac tcgtatcgtc ggtctgatta   17160
ttagtctggg accacggtcc cactcgtatc gtcggtctga ttattagtct gggaccacga   17220
tcccactcgt gttgtcggtc tgattatcgg tctgggacca cggtcccact tgtattgtcg   17280
atcagactat cagcgtgaga ctacgattcc atcaatgcct gtcaagggca agtattgaca   17340
tgtcgtcgta acctgtagaa cggagtaacc tcggtgtgcg gttgtatgcc tgctgtggat   17400
tgctgctgtg tcctgcttat ccacaacatt ttgcgcacgg ttatgtggac aaaatacctg   17460
gttacccagg ccgtgccggc acgttaaccg ggctgcatcc gatgcaagtg tgtcgctgtc   17520
gacgagctcg cgagctcgga catgaggttg ccccgtattc agtgtcgctg atttgtattg   17580
tctgaagttg ttttacgtt aagttgatgc agatcaatta atacgatacc tgcgtcataa   17640
ttgattattt gacgtggttt gatggcctcc acgcacgttg tgatatgtag atgataatca   17700
ttatcacttt acgggtcctt tccggtgatc cgacaggtta cggggcggcg acctcgcggg   17760
ttttcgctat ttatgaaaat tttccggttt aaggcgtttc cgttcttctt cgtcataact   17820
taatgttttt atttaaaata ccctctgaaa agaaaggaaa cgacaggtgc tgaaagcgag   17880 cttttttggcc tctgtcgttt cctttctctg tttttgtccg tggaatgaac aatggaagtc   17940
cgagctcatc gctaataact tcgtatagca tacattatac gaagttatat tcgatgcggc   18000
gctgaggtct gcctcgtgaa gaaggtgttg ctgactcata ccaggcctga atcgccccat   18060
catccagcca gaaagtgagg gagccacggt tgatgagagc tttgttgtag gtggaccagt   18120
```

| | |
|---|---|
| tggtgatttt gaacttttgc tttgccacgg aacggtctgc gttgtcggga agatgcgtga | 18180 |
| tctgatcctt caactcagca aaagttcgat ttattcaaca aagccacgtg tctcaaaatc | 18240 |
| tctgatgtta cattgcacaa gataaaaata tatcatcatg aacaataaaa ctgtctgctt | 18300 |
| acataaacag taatacaagg ggtgttatga gccatattca acgggaaacg tcttgctcga | 18360 |
| cgatgataag ctgtcaaaca tgagaattgg gtcgtcaata tgctaaaacg cggcataccc | 18420 |
| cgcgtattcc cactagttaa ttaacctgca ggggctgtt agaggtcttc cctagtccaa | 18480 |
| ctatagcgta tggacatatt gtcgttagaa cgcggctaca attaatacat aaccttatgt | 18540 |
| atcatacaca tacgatttag gggacactat a | 18571 |

<210> SEQ ID NO 3
<211> LENGTH: 18532
<212> TYPE: DNA
<213> ORGANISM: Artificial Sequence
<220> FEATURE:
<223> OTHER INFORMATION: Synthetic

<400> SEQUENCE: 3

| | |
|---|---|
| gagttgttga tctgtgtgaa tcagactgcg acagttcgag tttgaagcga aagctagcaa | 60 |
| cagtatcaac aggttttatt ttggatttgg aaacgagagt ttctggtcat gaaaaaccca | 120 |
| aaaagaaat ccggaggatt ccggattgtc aatatgctaa aacgcggagt agcccgtgtg | 180 |
| agccccttg ggggcttgaa gaggctgcca gccggacttc tgctgggtca tgggcccatc | 240 |
| aggatggtct tggcgattct agcctttttg agattcacgg caatcaagcc atcactgggt | 300 |
| ctcatcaata gatggggttc agtggggaaa aagaggcta tggaaacaat aaagaagttc | 360 |
| aagaaagatc tggctgccat gctgagaata atcaatgcta ggaaggagaa aagagacga | 420 |
| ggcgcagata ctagtgtcgg aattgttggc ctcctgctga ccacagctat ggcagcggag | 480 |
| gtcactagac gtgggagtgc atactatatg tacttggaca gaaacgatgc tggggaggcc | 540 |
| atatcttttc caaccacatt ggggatgaat aagtgttata tacagatcat ggatcttgga | 600 |
| cacatgtgtg atgccaccat gagctatgaa tgccctatgc tggatgaggg ggtggaacca | 660 |
| gatgacgtcg attgttggtg caacacgacg tcaacttggg ttgtgtacgg aacctgccat | 720 |
| cacaaaaaag gtgaagcacg gagatctaga agagctgtga cgctcccctc ccattccacc | 780 |
| aggaagctgc aaacgcggtc gcaaacctgg ttggaatcaa gagaatacac aaagcacttg | 840 |
| attagagtcg aaaattggat attcaggaac cctggcttcg cgttagcagc agctgccatc | 900 |
| gcttggcttt tgggaagctc aacgagccaa aaagtcatat acttggtcat gatactgctg | 960 |
| attgccccgg catacagcat caggtgcata ggagtcagca atagggactt tgtggaaggt | 1020 |
| atgtcaggtg ggacttgggt tgatgttgtc ttggaacatg gaggttgtgt caccgtaatg | 1080 |
| gcacaggaca accgactgt cgacatagag ctggttacaa caacagtcag caacatggcg | 1140 |
| gaggtaagat cctactgcta tgaggcatca atatcagaca tggcttctga cagccgctgc | 1200 |
| ccaacacaag gtgaagccta ccttgacaag caatcagaca ctcaatatgt ctgcaaaaga | 1260 |
| acgttagtgg acagaggctg gggaaatgga tgtggacttt ttggcaaagg gagcctggtg | 1320 |
| acatgcgcta gtttgcatg ctccaagaaa atgaccggga agagcatcca gccagagaat | 1380 |
| ctggagtacc ggataatgct gtcagttcat ggctcccagc acagtgggat gatcgttaat | 1440 |
| gacacaggac atgaaactga tgagaataga gcgaaagttg agataacgcc caattcaccg | 1500 |
| agagccgaag ccaccctggg gggttttgga agcctaggac ttgattgtga accgaggaca | 1560 |
| ggccttgact tttcagattt gtattacttg actatgaata acaagcactg gttggttcac | 1620 |

```
aaggagtggt tccacgacat tccattacct tggcacgctg gggcagacac cggaactcca    1680
cactggaaca acaaagaagc actggtagag ttcaaggacg cacatgccaa aaggcaaact    1740
gtcgtggttc tagggagtca agaaggagca gttcacacgg cccttgctgg agctctggag    1800
gctgagatgg atggtgcaaa gggaaggctg tcctctggcc acttgaaatg tcgcctgaaa    1860
atggataaac ttagattgaa gggcgtgtca tactccttgt gtactgcagc gttcacattc    1920
accaagatcc cggctgaaac actgcacggg acagtcacag tggaggtaca gtacgcaggg    1980
acagatggac cttgcaaggt tccagctcag atggcggtgg acatgcaaac tctgacccca    2040
gttgggaggt tgataaccgc taaccccgta atcactgaaa gcactgagaa ctctaagatg    2100
atgctggaac ttgatccacc atttggggac tcttacattg tcataggagt cggggagaag    2160
aagatcaccc accactggca caggagtggc agcaccattg gaaaagcatt tgaagccact    2220
gtgagaggtg ccaagagaat ggcagtcttg ggagacacag cctgggactt tggatcagtt    2280
ggaggcgctc tcaactcatt gggcaagggc atccatcaaa ttttttggagc agctttcaaa    2340
tcattgtttg gaggaatgtc ctggttctca caaattctca ttggaacgtt gctgatgtgg    2400
ttgggtctga acacaaagaa tggatctatt tcccttatgt gcttggcctt aggggggagtg    2460
ttgatcttct tatccacagc cgtctctgct gatgtggggt gctcggtgga cttctcaaag    2520
aaggagacga gatgcggtac aggggtgttc gtctataacg acgttgaagc ctggagggac    2580
aggtacaagt accatcctga ctcccccсcgt agattggcag cagcagtcaa gcaagcctgg    2640
gaagatggta tctgcgggat ctcctctgtt tcaagaatgg aaaacatcat gtggagatca    2700
gtagaagggg agctcaacgc aatcctggaa gagaatggag ttcaactgac ggtcgttgtg    2760
ggatctgtaa aaaaccccat ggggagaggt ccacagagat gccccgtgcc tgtgaacgag    2820
ctgccccacg gctggaaggc ttgggggaaa tcgtatttcg tcagagcagc aaagacaaat    2880
aacagctttg tcgtggatgg tgacacactg aaggaatgcc cactcaaaca tagagcatgg    2940
aacagctttc ttgtggagga tcatgggttc ggggtatttc acactagtgt ctggctcaag    3000
gttagagaag attattcatt agagtgtgat ccagccgtta ttggaacagc tgttaaggga    3060
aaggaggctg tacacagtga tctaggctac tggattgaga gtgagaagaa tgacacatgg    3120
aggctgaaga gggcccatct gatcgagatg aaaacatgtg aatggccaaa gtcccacaca    3180
ttgtggacag atggaataga agagagtgat ctgatcatac ccaagtcttt agctgggcca    3240
ctcagccatc acaataccag agagggctac aggacccaaa tgaaagggcc atggcacagt    3300
gaaagagctt gaaattcggtt tgaggaatgc ccaggcacta aggtccacgt ggaggaaaca    3360
tgtggaacaa gaggaccatc tctgagatca accactgcaa gcggaagggt gatcgaggaa    3420
tggtgctgca gggagtgcac aatgccccca ctgtcgttcc gggctaaaga tggctgttgg    3480
tatggaatgg agataaggcc caggaaagaa ccagaaagca acttagtaag gtcaatggtg    3540
actgcaggat caactgatca catggaccac ttctcccttg gagtgcttgt gatcctgctc    3600
atggtgcagg aagggctgaa gaagagaatg accacaaaga tcatcataag cacatcaatg    3660
gcagtgctgg tagctatgat cctgggagga tttttcaatga gtgacctggc taagcttgca    3720
attttgatgg gtgccacctt cgcggaaatg aacactggag gagatgtagc tcatctggcg    3780
ctgatagcgg cattcaaagt cagaccagcg ttgctggtat ctttcatctt cagagctaat    3840
tggacacccc gtgaaagcat gctgctggcc ttggcctcgt gtcttttgca aactgcgatc    3900
tccgccttgg aaggcgacct gatggttctc atcaatggtt ttgctttggc ctggttggca    3960
```

```
atacgagcga tggttgttcc acgcactgat aacatcacct tggcaatcct ggctgctctg    4020
acaccactgg cccggggcac actgcttgtg gcgtggagag caggccttgc tacttgcggg    4080
gggtttatgc tcctctctct aagggaaaa ggcagtgtga agaagaactt accatttgtc    4140
atggccctgg gactaaccgc tgtgaggctg gtcgacccca tcaacgtggt gggactgctg    4200
ttgctcacaa ggagtgggaa gcggagctgg cccctagcg aagtactcac agctgttggc    4260
ctgatatgcg cattggctgg agggttcgcc aaggcagata tagagatggc tgggcccatg    4320
gccgcggtcg gtctgctaat tgtcagttac gtggtctcag aaagagtgt ggacatgtac    4380 attgaaagag caggtgacat cacatgggaa aaagatgcgg aagtcactgg aaacagtccc    4440
cggctcgatg tggcgctaga tgagagtggt gatttctccc tggtggagga tgacggtccc    4500
cccatgagag agatcatact caaggtggtc ctgatgacca tctgtggcat gaacccaata    4560 gccatacccct ttgcagctgg agcgtggtac gtatacgtga agactggaaa aaggagtggt    4620
gctctatggg atgtgcctgc tcccaaggaa gtaaaaaagg gggagaccac agatggagtg    4680
tacagagtaa tgactcgtag actgctaggt tcaacacaag ttggagtggg agttatgcaa    4740
gagggggtct ttcacactat gtggcacgtc acaaaaggat ccgcgctgag aagcggtgaa    4800
gggagacttg atccatactg gggagatgtc aagcaggatc tggtgtcata ctgtggtcca    4860
tggaagctag atgccgcctg ggatgggcac agcgaggtgc agctcttggc cgtgcccccc    4920
ggagagagag cgaggaacat ccagactctg cccggaatat taagacaaa ggatggggac    4980 attggagcgg ttgcgctgga ttacccagca ggaacttcag gatctccaat cctagacaag    5040
tgtgggagag tgataggact ttatggcaat ggggtcgtga tcaaaaacgg gagttatgtt    5100
agtgccatca cccaagggag gagggaggaa gagactcctg ttgagtgctt cgagccctcg    5160
atgctgaaga agaagcagct aactgtctta gacttgcatc ctggagctgg aaaaccagg    5220 agagttcttc ctgaaatagt ccgtgaagcc ataaaaacaa gactccgtac tgtgatctta    5280
gctccaacca gggttgtcgc tgctgaaatg gaggaggccc ttagagggct tccagtgcgt    5340
tatatgacaa cagcagtcaa tgtcacccac tctggaacag aaatcgtcga cttaatgtgc    5400
catgccacct tcacttcacg tctactacag ccaatcagag tccccaacta taatctgtat    5460
attatggatg aggcccactt cacagatccc tcaagtatag cagcaagagg atacatttca    5520
acaagggttg agatgggcga ggcggctgcc atcttcatga ccgccacgcc accaggaacc    5580
cgtgacgcat ttccggactc caactcacca attatggaca ccgaagtgga agtcccagag    5640
agagcctgga gctcaggctt tgattgggtg acggatcatt ctggaaaaac agtttggttt    5700
gttccaagcg tgaggaacgg caatgagatc gcagcttgtc tgacaaaggc tggaaaacgg    5760
gtcatacagc tcagcagaaa gactttttgag acagagttcc agaaaacaaa acatcaagag    5820
tgggactttg tcgtgacaac tgacatttca gagatgggcg ccaactttaa agctgaccgt    5880
gtcatagatt ccaggagatg cctaaagccg gtcatacttg atggcgagag agtcattctg    5940
gctggaccca tgcctgtcac acatgccagc gctgcccaga ggaggggcg cataggcagg    6000 aatcccaaca aacctggaga tgagtatctg tatggaggtg ggtgcgcaga gactgacgaa    6060
gaccatgcac actggcttga agcaagaatg ctccttgaca atatttacct ccaagatggc    6120
ctcatagcct cgctctatcg acctgaggcc gacaaagtag cagccattga gggagagttc    6180
aagcttagga cggagcaaag gaagacctt gtggaactca tgaaaagagg agatcttcct    6240
gtttggctgg cctatcaggt tgcatctgcc ggaataacct acacagatag aagatggtgc    6300
tttgatggca cgaccaacaa caccataatg gaagacagtg tgccggcaga ggtgtggacc    6360
```

```
agacacggag agaaaagagt gctcaaaccg aggtggatgg acgccagagt ttgttcagat    6420
catgcggccc tgaagtcatt caaggagttt gccgctggga aaagaggagc ggcttttgga    6480
gtgatggaag ccctgggaac actgccagga cacatgacag agagattcca ggaagccatt    6540
gacaacctcg ctgtgctcat gcgggcagag actggaagca ggccttacaa agccgcggcg    6600
gcccaattgc cggagaccct agagaccata atgcttttgg ggttgctggg aacagtctcg    6660
ctgggaatct tcttcgtctt gatgaggaac aagggcatag gaagatggg ctttggaatg     6720 gtgactcttg gggccagcgc atggctcatg tggctctcgg aaattgagcc agccagaatt    6780
gcatgtgtcc tcattgttgt gttcctattg ctggtggtgc tcatacctga gccagaaaag    6840
caaagatctc cccaggacaa ccaaatggca atcatcatca tggtagcagt aggtcttctg    6900
ggcttgatta ccgccaatga actcggatgg ttggagagaa caagagtga  cctaagccat    6960 ctaatgggaa ggagagagga gggggcaacc ataggattct caatggacat tgacctgcgg    7020
ccagcctcag ctttgggccat ctatgctgcc ttgacaactt tcattacccc agccgtccaa    7080
catgcagtga ccacctcata caacaactac tccttaatgg cgatggccac gcaagctgga    7140
gtgttgtttg gcatgggcaa agggatgcca ttctacgcat gggactttgg agtcccgctg    7200
ctaatgatag gttgctactc acaattaaca ccccctgaccc taatagtggc catcattttg    7260
ctcgtggcgc actacatgta cttgatccca gggctgcagg cagcagctgc gcgtgctgcc    7320
cagaagagaa cggcagctgg catcatgaag aaccctgttg tggatggaat agtggtgact    7380
gacattgaca caatgacaat tgacccccaa gtggagaaaa agatgggaca ggtgctactc    7440
atagcagtag ccgtctccag cgccatactg tcgcggaccg cctgggggtg gggggaggct    7500
ggggctctga tcacagccgc aacttccact ttgtgggaag gctctccgaa caagtactgg    7560
aactcctcta cagccacttc actgtgtaac attttaggg gaagttactt ggctggagct    7620
tctctaatct acacagtaac aagaaacgct ggcttggtca agagacgtgg gggtggaaca    7680
ggagagaccc tgggagagaa atggaaggcc cgcttgaacc agatgtcggc cctggagttc    7740
tactcctaca aaaagtcagg catcaccgag gtgtgcagag aagaggcccg ccgcgccctc    7800
aaggacggtg tggcaacggg aggccatgct gtgtcccgag gaagtgcaaa gctgagatgg    7860
ttggtggagc ggggatacct gcagcccatt ggaaaggtca ttgatcttgg atgtggcaga    7920
gggggctgga gttactacgt cgccaccatc cgcaaagttc aagaagtgaa aggatacaca    7980
aaaggaggcc ctggtcatga agaacccgtg ttggtgcaaa gctatgggtg aacatagtc     8040 cgtcttaaga gtggggtgga cgtctttcat atggcggctg agccgtgtga cacgttgctg    8100
tgtgacatag gtgagtcatc atctagtcct gaagtggaag aagcacggac gctcagagtc    8160
ctctccatgt gggggattg gcttgaaaaa agaccaggag ccttttgtat aaaagtgttg     8220
tgcccataca ccagcactat gatggaaacc ctggagcgac tgcagcgtag gtatgggga     8280 ggattggtca gagtgccact ctcccgcaac tctacacatg agatgtactg ggtctctgga    8340
gcgaaaagca acaccataaa aagtgtgtcc accacgagcc agctcctctt ggggcgcatg    8400
gacgggccta ggaggccagt gaaatatgag gaggatgtga atctcggctc tggcacgcgg    8460
gctgtggtaa gctgcgctga agctcccaac atgaagatca ttggtaaccg cattgaaagg    8520
atccgcagtg agcacgcgga aacgtggttc tttgacgaga accacccata taggacatgg    8580
gcttaccatg gaagctatga ggccccccaca caagggtcag cgtcctctct aataaacggg    8640
gttgtcaggc tcctgtcaaa accctgggat gtggtgactg gagtcacagg aatagccatg    8700
```

```
accgacacca caccgtatgg tcagcaaaga gttttcaagg aaaaagtgga cactagggtg    8760
ccagaccccc aagaaggcac tcgtcaggtt atgagcatgg tctcttcctg gttgtggaaa    8820
gagctaggca aacacaaacg gccacgagtc tgcaccaaag aagagttcat caacaaggtt    8880
cgtagcaatg cagcattagg ggcaatattt gaagaggaaa aagagtggaa gactgcagtg    8940
gaagctgtga acgatccaag gttctgggct ctagtggaca aggaaagaga gcaccacctg    9000
agaggagagt gccagagctg tgtgtacaac atgatgggaa aaagagaaaa gaaacaaggg    9060
gaatttggaa aggccaaggg cagccgcgcc atctggtata tgtggctagg ggctagattt    9120
ctagagttcg aagcccttgg attcttgaac gaggatcact ggatggggag agagaactca    9180
ggaggtggtg ttgaagggct gggattacaa agactcggat atgtcctaga agagatgagt    9240
cgtataccag gaggaaggat gtatgcagat gacactgctg gctgggacac ccgcattagc    9300
aggtttgatc tggagaatga agctctaatc accaaccaaa tggagaaagg gcacagggcc    9360
ttggcattgg ccataatcaa gtacacatac caaaacaaag tggtaaaggt ccttagacca    9420
gctgaaaaag gaaaacagt tatggacatt atttcgagac aagaccaaag ggggagcgga    9480
caagttgtca cttacgctct taacacattt accaacctag tggtgcaact cattcggaat    9540
atggaggctg aggaagttct agagatgcaa acttgtggc tgctgcggag gtcagagaaa    9600
gtgaccaact ggttgcagag caacggatgg gataggctca aacgaatggc agtcagtgga    9660
gatgattgcg ttgtgaagcc aattgatgat aggtttgcac atgccctcag gttcttgaat    9720
gatatgggaa aagttaggaa ggacacacaa gagtggaaac cctcaactgg atgggacaac    9780
tgggaagaag ttccgttttg ctcccaccac ttcaacaagc tccatctcaa ggacgggagg    9840
tccattgtgg ttccctgccg ccaccaagat gaactgattg gccgggcccg cgtctctcca    9900
ggggcgggat ggagcatccg ggagactgct tgcctagcaa aatcatatgc gcaaatgtgg    9960
cagctccttt atttccacag aagggacctc cgactgatgg ccaatgccat tgttcatct    10020 gtgccagttg actgggttcc aactgggaga actacctggt caatccatgg aaagggagaa    10080
tggatgacca ctgaagacat gcttgtggtg tggaacagag tgtggattga ggagaacgac    10140
cacatggaag acaagacccc agttacgaaa tggacagaca ttccctattt gggaaaaagg    10200
gaagacttgt ggtgtggatc tctcataggg cacagaccgc gcaccacctg gctgagaac    10260 attaaaaaca cagtcaacat ggtgcgcagg atcataggtg atgaagaaaa gtacatggac    10320
tacctatcca cccaagttcg ctacttgggt gaagaagggt ctacacctgg agtgctgtaa    10380
gcaccaatct taatgttgtc aggcctgcta gtcagccaca gcttggggaa agctgtgcag    10440
cctgtgaccc cccaggaga agctgggaaa ccaagcctat agtcaggccg agaacgccat    10500
ggcacggaag aagccatgct gcctgtgagc ccctcagagg acactgagtc aaaaaacccc    10560
acgcgcttgg aggcgcagga tgggaaaaga aggtggcgac cttccccacc cttcaatctg    10620
gggcctgaac tggagatcag ctgtggatct ccagaagagg gactagtggt tagaggagac    10680
cccccggaaa acgcaaaaca gcatattgac gctgggaaag accagagact ccatgagttt    10740
ccaccacgct ggccgccagg cacagatcgc cgaatagcgg cggccggtgt ggggaaatcc    10800
atgggtctct agaacgtacg gaaggcgaca tacgcggccg ccctgcaggc atgcccgt    10860 ccacgtggca tctcgagacc tttattccaa ggcgtcgaac cactgacgac taccctgtac    10920
tcagggctta agccatccaa cgaactcacc actgttgcta cccccctcat tatgctagtc    10980
ctactaaggg catggctagg cctaattatt attttaatt gcccaatacg tatacgagtg    11040
ccttttctaa ttctcgtata ctatagtgag tcgtattatc tagccgcccg ggccgtcgac    11100
```

```
caattctcat gtttgacagc ttatcatcga atttctgcca ttcatccgct tattatcact   11160
tattcaggcg tagcaaccag gcgtttaagg gcaccaataa ctgccttaaa aaaattacgc   11220
cccgccctgc cactcatcgc agtactgttg taattcatta agcattctgc cgacatggaa   11280
gccatcacaa acggcatgat gaacctgaat cgccagcggc atcagcacct tgtcgccttg   11340
cgtataatat ttgcccatgg tgaaaacggg ggcgaagaag ttgtccatat tggccacgtt   11400
taaatcaaaa ctggtgaaac tcacccaggg attggctgag acgaaaaaca tattctcaat   11460
aaaccccttta gggaaatagg ccaggttttc accgtaacac gccacatctt gcgaatatat   11520
gtgtagaaac tgccggaaat cgtcgtggta ttcactccag agcgatgaaa acgtttcagt   11580
ttgctcatgg aaaacggtgt aacaagggtg aacactatcc catatcacca gctcaccgtc   11640
tttcattgcc atacggaatt ccggatgagc attcatcagg cgggcaagaa tgtgaataaa   11700
ggccggataa aacttgtgct tattttttctt tacggtcttt aaaaaggccg taatatccag   11760
ctgaacggtc tggttatagg tacattgagc aactgactga aatgcctcaa aatgttcttt   11820
acgatgccat tgggatatat caacggtggt atatccagtg attttttttct ccatttttagc   11880
ttccttagct cctgaaaatc tcgataactc aaaaaatacg cccggtagtg atcttatttc   11940
attatggtga aagttggaac ctcttacgtg ccgatcaacg tctcattttc gccaaaagtt   12000
ggcccagggc ttcccggtat caacagggac accaggattt atttattctg cgaagtgatc   12060
ttccgtcaca ggtatttatt cgcgataagc tcatggagcg gcgtaaccgt cgcacaggaa   12120
ggacagagaa agcgcggatc tgggaagtga cggacagaac ggtcaggacc tggattgggg   12180
aggcggttgc cgccgctgct gctgacggtg tgacgttctc tgttccggtc acaccacata   12240
cgttccgcca ttcctatgcg atgcacatgc tgtatgccgg tataccgctg aaagttctgc   12300
aaagcctgat gggacataag tccatcagtt caacggaagt ctacacgaag gttttgcgc   12360
tggatgtggc tgcccggcac cgggtgcagt ttgcgatgcc ggagtctgat gcggttgcga   12420
tgctgaaaca attatcctga gaataaatgc cttggccttt atatggaaat gtggaactga   12480
gtggatatgc tgttttttgtc tgttaaacag agaagctggc tgttatccac tgagaagcga   12540
acgaaacagt cgggaaaatc tcccattatc gtagagatcc gcattattaa tctcaggagc   12600
ctgtgtagcg tttataggaa gtagtgttct gtcatgatgc ctgcaagcgg taacgaaaac   12660
gatttgaata tgccttcagg aacaatagaa atcttcgtgc ggtgttacgt tgaagtggag   12720
cggattatgt cagcaatgga cagaacaacc taatgaacac agaaccatga tgtggtctgt   12780
cctttacag ccagtagtgc tcgccgcagt cgagcgacag ggcgaagccc tcgagtgagc   12840
gaggaagcac cagggaacag cacttatata ttctgcttac acacgatgcc tgaaaaaact   12900
tcccttgggg ttatccactt atccacgggg atattttttat aattattttt tttatagttt   12960
ttagatcttc ttttttagag cgccttgtag gcctttatcc atgctggttc tagagaaggt   13020
gttgtgacaa attgcccttt cagtgtgaca aatcaccctc aaatgacagt cctgtctgtg   13080
acaaattgcc cttaaccctg tgacaaattg ccctcagaag aagctgtttt tcacaaagt   13140
tatccctgct tattgactct tttttatttta gtgtgacaat ctaaaaactt gtcacacttc   13200
acatggatct gtcatggcgg aaacagcggt tatcaatcac aagaaacgta aaatagccc   13260
gcgaatcgtc cagtcaaacg acctcactga ggcggcatat agtctctccc gggatcaaaa   13320
acgtatgctg tatctgttcg ttgaccagat cagaaaatct gatggcaccc tacaggaaca   13380
tgacggtatc tgcgagatcc atgttgctaa atatgctgaa atattcggat tgacctctgc   13440
```

```
ggaagccagt aaggatatac ggcaggcatt gaagagtttc gcggggaagg aagtggtttt    13500
ttatcgccct gaagaggatg ccggcgatga aaaaggctat gaatcttttc cttggtttat    13560
caaacgtgcg cacagtccat ccagagggct ttacagtgta catatcaacc catatctcat    13620
tcccttcttt atcgggttac agaaccggtt tacgcagttt cggcttagtg aaacaaaaga    13680
aatcaccaat ccgtatgcca tgcgtttata cgaatccctg tgtcagtatc gtaagccgga    13740
tggctcaggc atcgtctctc tgaaaatcga ctggatcata gagcgttacc agctgcctca    13800
aagttaccag cgtatgcctg acttccgccg ccgcttcctg caggtctgtg ttaatgagat    13860
caacagcaga actccaatgc gcctctcata cattgagaaa aagaaaggcc gccagacgac    13920
tcatatcgta ttttccttcc gcgatatcac ttccatgacg acaggatagt ctgagggtta    13980
tctgtcacag atttgagggt ggttcgtcac atttgttctg acctactgag ggtaatttgt    14040
cacagttttg ctgtttcctt cagcctgcat ggattttctc atacttttg aactgtaatt     14100
tttaaggaag ccaaatttga gggcagtttg tcacagttga tttccttctc tttcccttcg    14160
tcatgtgacc tgatatcggg ggttagttcg tcatcattga tgagggttga ttatcacagt    14220
ttattactct gaattggcta tccgcgtgtg tacctctacc tggagttttt cccacggtgg    14280
atatttcttc ttgcgctgag cgtaagagct atctgacaga acagttcttc tttgcttcct    14340
cgccagttcg ctcgctatgc tcggttacac ggctgcggcg agcgctagtg ataataagtg    14400
actgaggtat gtgctcttct tatctccttt tgtagtgttg ctcttatttt aaacaacttt    14460
gcggttttt gatgactttg cgattttgtt gttgctttgc agtaaattgc aagatttaat      14520
aaaaaaacgc aaagcaatga ttaaaggatg ttcagaatga aactcatgga aacacttaac    14580
cagtgcataa acgctggtca tgaaatgacg aaggctatcg ccattgcaca gtttaatgat    14640
gacagcccgg aagcgaggaa aataacccgg cgctggagaa taggtgaagc agcggattta    14700
gttggggttt cttctcaggc tatcagagat gccgagaaag cagggcgact accgcacccg    14760
gatatggaaa ttcgaggacg ggttgagcaa cgtgttggtt atacaattga acaaattaat    14820
catatgcgtg atgtgtttgg tacgcgattg cgacgtgctg aagacgtatt tccaccggtg    14880
atcggggttg ctgcccataa aggtggcgtt tacaaaacct cagtttctgt tcatcttgct    14940
caggatctgg ctctgaaggg gctacgtgtt ttgctcgtgg aaggtaacga ccccaggga    15000
acagcctcaa tgtatcacgg atgggtacca gatcttcata ttcatgcaga agacactctc    15060
ctgcctttct atcttgggga aaaggacgat gtcacttatg caataaagcc cacttgctgg    15120
ccggggcttg acattattcc ttcctgtctg gctctgcacc gtattgaaac tgagttaatg    15180
ggcaaatttg atgaaggtaa actgcccacc gatccacacc tgatgctccg actggccatt    15240
gaaactgttg ctcatgacta tgatgtcata gttattgaca gcgcgcctaa cctgggtatc    15300
ggcacgatta atgtcgtatg tgctgctgat gtgctgattg ttcccacgcc tgctgagttg    15360
tttgactaca cctccgcact gcagtttttc gatatgcttc gtgatctgct caagaacgtt    15420
gatcttaaag ggttcgagcc tgatgtacgt atttttgctta ccaaatacag caatagtaat    15480
ggctctcagt ccccgtggat ggaggagcaa attcgggatg cctggggaag catggttcta    15540
aaaaatgttg tacgtgaaac ggatgaagtt ggtaaaggtc agatccggat gagaactgtt    15600
tttgaacagg ccattgatca acgctcttca actggtgcct ggagaaatgc tctttctatt    15660
tgggaacctg tctgcaatga aattttcgat cgtctgatta aaccacgctg ggagattaga    15720
taatgaagcg tgcgcctgtt attccaaaac atacgctcaa tactcaaccg gttgaagata    15780
cttcgttatc gacaccagct gccccgatgg tggattcgtt aattgcgcgc gtaggagtaa    15840
```

```
tggctcgcgg taatgccatt actttgcctg tatgtggtcg ggatgtgaag tttactcttg    15900
aagtgctccg gggtgatagt gttgagaaga cctctcgggt atggtcaggt aatgaacgtg    15960
accaggagct gcttactgag gacgcactgg atgatctcat cccttctttt ctactgactg    16020
gtcaacagac accggcgttc ggtcgaagag tatctggtgt catagaaatt gccgatggga    16080
gtcgccgtcg taaagctgct gcacttaccg aaagtgatta tcgtgttctg gttggcgagc    16140
tggatgatga gcagatggct gcattatcca gattgggtaa cgattatcgc ccaacaagtg    16200
cttatgaacg tggtcagcgt tatgcaagcc gattgcagaa tgaatttgct ggaaatattt    16260
ctgcgctggc tgatgcggaa aatatttcac gtaagattat tacccgctgt atcaacaccg    16320
ccaaattgcc taaatcagtt gttgctcttt tttctcaccc cggtgaacta tctgcccggt    16380
caggtgatgc acttcaaaaa gcctttacag ataaagagga attacttaag cagcaggcat    16440
ctaaccttca tgagcagaaa aaagctgggg tgatatttga agctgaagaa gttatcactc    16500
ttttaacttc tgtgcttaaa acgtcatctg catcaagaac tagtttaagc tcacgacatc    16560
agtttgctcc tggagcgaca gtattgtata agggcgataa aatggtgctt aacctggaca    16620
ggtctcgtgt tccaactgag tgtatagaga aaattgaggc cattcttaag gaacttgaaa    16680
agccagcacc ctgatgcgac cacgttttag tctacgttta tctgtcttta cttaatgtcc    16740
tttgttacag gccagaaagc ataactggcc tgaatattct ctctgggccc actgttccac    16800
ttgtatcgtc ggtctgataa tcagactggg accacggtcc cactcgtatc gtcggtctga    16860
ttattagtct gggaccacgg tcccactcgt atcgtcggtc tgattattag tctgggacca    16920
cggtcccact cgtatcgtcg gtctgataat cagactggga ccacggtccc actcgtatcg    16980
tcggtctgat tattagtctg gaccatggtc ccactcgta tcgtcggtct gattattagt     17040
ctgggaccac ggtcccactc gtatcgtcgg tctgattatt agtctggaac cacggtccca    17100
ctcgtatcgt cggtctgatt attagtctgg gaccacggtc ccactcgtat cgtcggtctg    17160
attattagtc tgggaccacg atcccactcg tgttgtcggt ctgattatcg gtctgggacc    17220
acggtcccac ttgtattgtc gatcagacta tcagcgtgag actacgattc catcaatgcc    17280
tgtcaagggc aagtattgac atgtcgtcgt aacctgtaga acgagtaac ctcggtgtgc     17340
ggttgtatgc ctgctgtgga ttgctgctgt gtcctgctta ccacaacat tttgcgcacg     17400
gttatgtgga caaaatacct ggttacccag gccgtgccgg cacgttaacc gggctgcatc    17460
cgatgcaagt gtgtcgctgt cgacgagctc gcgagctcgg acatgaggtt gccccgtatt    17520
cagtgtcgct gatttgtatt gtctgaagtt gtttttacgt taagttgatg cagatcaatt    17580
aatacgatac ctgcgtcata attgattatt tgacgtggtt tgatggcctc cacgcacgtt    17640
gtgatatgta gatgataatc attatcactt tacgggtcct ttccggtgat ccgacaggtt    17700
acggggcggc gacctcgcgg gttttcgcta tttatgaaaa ttttccggtt taaggcgttt    17760
ccgttcttct tcgtcataac ttaatgtttt tatttaaaat accctctgaa aagaaaggaa    17820
acgacaggtg ctgaaagcga gcttttggc ctctgtcgtt tcctttctct gttttgtcc     17880
gtggaatgaa caatggaagt ccgagctcat cgctaataac ttcgtatagc atacattata    17940
cgaagttata ttcgatgcgg cgctgaggtc tgcctcgtga agaaggtgtt gctgactcat    18000
accaggcctg aatcgcccca tcatccagcc agaaagtgag ggagccacgg ttgatgagag    18060
ctttgttgta ggtggaccag ttggtgattt tgaacttttg ctttgccacg gaacggtctg    18120
cgttgtcggg aagatgcgtg atctgatcct tcaactcagc aaaagttcga tttattcaac    18180
```

| | |
|---|---|
| aaagccacgt gtctcaaaat ctctgatgtt acattgcaca agataaaaat atatcatcat | 18240 |
| gaacaataaa actgtctgct tacataaaca gtaatacaag gggtgttatg agccatattc | 18300 |
| aacgggaaac gtcttgctcg acgatgataa gctgtcaaac atgagaattg ggtcgtcaat | 18360 |
| atgctaaaac gcggcatacc ccgcgtattc ccactagtta attaacctgc aggggggctgt | 18420 |
| tagaggtctt ccctagtcca actatagcgt atggacatat tgtcgttaga acgcggctac | 18480 |
| aattaataca taaccttatg tatcatacac atacgattta ggggacacta ta | 18532 |

<210> SEQ ID NO 4
<211> LENGTH: 10807
<212> TYPE: DNA
<213> ORGANISM: Artificial Sequence
<220> FEATURE:
<223> OTHER INFORMATION: Synthetic

<400> SEQUENCE: 4

| | |
|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaaacccaaa | 120 |
| gaagaaatcc ggaggattcc ggattgtcaa tatgctaaaa cgcggagtag cccgtgtaaa | 180 |
| ccccttggga ggtttgaaga ggttgccagc cggacttctg ctgggtcatg gacccatcag | 240 |
| aatggttttg gcgatactag cctttttgag atttacagca atcaagccat cactgggcct | 300 |
| tatcaacaga tgggggttccg tggggaaaaa agaggctatg gaaataataa agaagttcaa | 360 |
| gaaagatctt gctgccatgt tgagaataat caatgctagg aaagagagga agagacgtgg | 420 |
| cgcagacacc agcatcggaa tcattggcct cctgctgact acagccatgg cagcagagat | 480 |
| cactagacgc gggagtgcat actacatgta cttggatagg agcgatgccg ggaaggccat | 540 |
| ttcgtttgct accacattgg gagtgaacaa gtgccacgta cagatcatgg acctcgggca | 600 |
| catgtgtgac gccaccatga gttatgagtg ccctatgctg gatgagggag tggaaccaga | 660 |
| tgatgtcgat tgctggtgca acacgacatc aacttgggtt gtgtacggaa cctgtcatcg | 720 |
| caaaaaggt gaggcacggc gatctagaag agccgtgacg ctcccttctc actctacaag | 780 |
| gaagttgcaa acgcggtcgc agaccctggtt agaatcaaga gaatacacga agcacttgat | 840 |
| caaggttgaa aactggatat tcaggaaccc cgggtttgcg ctagtggccg ttgccattgc | 900 |
| ctggcttttg ggaagctcga cgagccaaaa agtcatatac ttggtcatga tactgctgat | 960 |
| tgccccggca tacagtatca ggtgcattgg agtcagcaat agagacttcg tggagggcat | 1020 |
| gtcaggtggg acctggggttg atgttgtctt ggaacatgga ggctgcgtta ccgtgatggc | 1080 |
| acaggacaag ccaacagttg acatagagtt ggtcacgacg acggttagta acatggccga | 1140 |
| ggtaagatcc tattgctacg aggcatcgat atcggacatg gcttcggaca gtcgttgccc | 1200 |
| aacacaaggt gaagcctacc ttgacaagca atcagacact caatatgtct gcaaaagaac | 1260 |
| attagtggac agaggttggg gaaacggttg tggactttttt ggcaaaggga gcttggtgac | 1320 |
| atgtgccaag tttacgtgtt ctaagaagat gaccgggaag agcattcaac cggaaaatct | 1380 |
| ggagtatcgg ataatgctat cagtgcatgg ctcccagcat agcgggatga ttgtcaatga | 1440 |
| tacaggatat gaaactgacg aaaatagagc gaaagtcgag gttacgccta attcaccaag | 1500 |
| agcggaagca accttgggag ctttggaag cttaggactt gactgtgaac caggacagg | 1560 |
| tcttgacttt tcagatctgt attacctgac catgaacaat aagcattggt tggtgcacaa | 1620 |
| agagtggttt catgacatcc cattgccttg gcatgctggg gcagacaccg gaactccaca | 1680 |
| ctggaacaac aaagaggcat tggtagaatt caaggatgcc cacgccaaga ggcaaaccgt | 1740 |

```
cgtcgttctg gggagccagg aaggagccgt tcacacggct ctcgctgag  ctctagaggc    1800
tgagatggat ggtgcaaagg gaaagctgtt ctctggccat ttgaaatgcc gcctaaaaat    1860
ggacaagctt agattgaagg gcgtgtcata ttccttgtgc actgcggcat tcacattcac    1920
caaggtccca gctgaaacac tgcatggaac agtcacagtg gaggtgcagt atgcagggac    1980
agatggaccc tgcaagatcc cagtccagat ggcggtggac atgcagaccc tgaccccagt    2040
tggaaggctg ataaccgcca accccgtgat tactgaaagc actgagaact caaagatgat    2100
gttggagctt gacccaccat ttggggattc ttacattgtc ataggagttg gggacaagaa    2160
aatcacccac cactggcata ggagtggtag caccatcgga aaggcatttg aggccactgt    2220
gagaggcgcc aagagaatgg cagtcctggg ggatacagcc tgggacttcg gatcagtcgg    2280
gggtgtgttc aactcactgg gtaagggcat tcaccagatt tttggagcag ccttcaaatc    2340
actgtttgga ggaatgtcct ggttctcaca gatcctcata ggcacgctgc tagtgtggtt    2400
aggtttgaac acaaagaatg gatctatctc cctcacatgc ttggccctgg ggggagtgat    2460
gatcttcctc tccacggctg tttctgctga cgtggggtgc tcagtggact tctcaaaaaa    2520
ggaaacgaga tgtggcacgg gggtattcat ctataatgat gttgaagcct ggagggaccg    2580
gtacaagtac catcctgact cccccccgcag attggcagca gcagtcaagc aggcctggga    2640
agaggggatc tgtgggatct catccgtttc aagaatggaa acatcatgt  ggaaatcagt    2700
agaaggggag ctcaatgcta tcctagagga gaatggagtt caactgacag ttgttgtggg    2760
atctgtaaaa aaccccatgt ggagaggtcc acaaagattg ccagtgcctg tgaatgagct    2820
gccccatggc tggaaagcct gggggaaatc gtattttgtt agggcggcaa agaccaacaa    2880
cagttttgtt gtcgacggtg acacactgaa ggaatgtccg cttgagcaca gagcatggaa    2940
tagttttctt gtggaggatc acgggtttgg agtcttccac accagtgtct ggcttaaggt    3000
cagagaagat tactcattag aatgtgaccc agccgtcata ggaacagctg ttaagggaag    3060
ggaagccgcg cacagtgatc tgggctattg gattgaaagt gaaaagaatg acacatggag    3120
gctgaagagg gccccacctga ttgagatgaa acatgtgaa tggccaaagt ctcacacatt    3180
gtggacagat ggagtagaag aaagtgatct tatcataccc aagtctttag ctggtccact    3240
cagccaccac aacaccagag agggttacag aacccaagtg aaagggccat ggcacagtga    3300
agagcttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggcca  ggaaagaacc agagagcaac ttagtgaggt caatggtgac    3540
agcgggtca  accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtctcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
```

-continued

```
gatcatgctc ctctccctga aagggaaagg tagtgtgaag aagaacctgc catttgtcat    4140
ggccctggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctgccggag  ggtttgccaa ggcagacatt gagatggctg acccatggc     4320 tgcagtaggc ttgctaattg tcagctatgt ggtctcggga aagagtgtgg acatgtacat    4380
tgaaagagca ggtgacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560 tataccttt  gctgcaggag cgtggtatgt gtatgtgaag actgggaaaa ggagtggcgc    4620
cctctgggac gtgcctgctc ccaaagaagt gaagaaagga gagaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc cagggaaaga gggaggagga gactccggtt gaatgtttcg aaccctcgat    5160
gctgaagaag aagcagttaa ctgtcttgga tctgcatcca ggagccggaa aaaccaggag    5220
agttcttcct gaaatagtcc gtgaagccat aaaaagaga  ctccggacag tgatcttggc    5280
accaactagg gttgtcgctg ctgagatgga ggaggcttg  agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctctacat    5460
catggatgaa gcccacttca cagacccctc aagtatagct gcaagaggat acatatcaac    5520
aagggttgaa atgggcgagg cggctgccat ttttatgact gccacaccac caggaaccgg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg gaaagcgggt    5760
catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taagtagcc  gccattgagg gagagtttaa    6180
gctgaggaca gagcaaagga agaccttcgt ggaactcatg aagagaggag accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
```

```
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagaccctag agaccattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccag ctgtccaaca    7080 tgcggtaacc acttcataca acaactactc cttaatggcg atgccacac aagctggagt    7140 gctgtttggc atgggcaaag gatgccatt ttatgcatgg gaccttggag tcccgctgct    7200
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccaggt ggagaagaag atgggacaag tgttactcat    7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accagggcc ttctgtataa aggtgctgtg    8220
cccatacacc agcactatga tggaaaccat ggagcgactg caacgtaggc atggggagg    8280 attagtcaga gtgccattgt ctcgcaactc cacacatgga atgtactggg tctctggggc    8340
aaagagcaac atcataaaaa gtgtgtccac cacaagtcag ctcctcctgg ggcgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760 agatcccaa gaaggcactc gccaggtaat gaacatagtc tcttcctggc tgtggaagga    8820
```

```
gctgggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga agcaaggaga    9060
gttcgggaaa gcaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc cagagaaagt    9600
gaccagatgg ttgcagagca atggatggga tagactcaaa cgaatggcgg tcagtggaga    9660
tgactgcgtt gtgaagccaa tcgatgatag gttttgcacat gccctcaggt tcttgaatga    9720
catgggaaaa gttaggaaag acacacagga gtggaaaccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960
gctcctttat ttccacagaa gagaccttcg actgatggct aatgccattt gctcggctgt   10020
gccagttgac tgggtaccaa ctgggagaac cacctggtca atccatggaa agggagaatg   10080
gatgaccact gaggacatgc tcatggtgtg gaatagagtg tggattgagg agaacgacca   10140
tatggaggac aagactcctg taacaaaatg gacagacatt ccctatctag gaaaaaggga   10200
ggacttatgg tgtggatccc ttatagggca cagaccccgc accactttggg ctgaaaacat   10260 caaagacaca gtcaacatgg tgcgcaggat cataggtgat gaagaaaagt acatggacta   10320
tctatccacc caagtccgct acttgggtga ggaagggtcc acacccgag tgttgtaagc   10380 accaattta gtgttgtcag gcctgctagt cagccacagt ttggggaaag ctgtgcagcc   10440
tgtaaccccc ccaggagaag ctgggaaacc aagctcatag tcaggccgag aacgccatgg   10500
cacggaagaa gccatgctgc ctgtgagccc ctcagaggac actgagtcaa aaacccac   10560 gcgcttggaa gcgcaggatg ggaaaagaag gtggcgacct tccccaccct tcaatctggg   10620
gcctgaactg gagactagct gtgaatctcc agcagaggga ctagtggtta gaggagaccc   10680
cccggaaaac gcaaaacagc atattgacgc tgggaaagac cagagactcc atgagtttcc   10740
accacgctgg ccgccaggca cagatcgccg aacagcggcg gccggtgtgg ggaaatccat   10800
ggtttct                                                             10807
```

<210> SEQ ID NO 5
<211> LENGTH: 10807
<212> TYPE: DNA
<213> ORGANISM: Artificial Sequence
<220> FEATURE:
<223> OTHER INFORMATION: Synthetic

<400> SEQUENCE: 5

```
agttgttgat ctgtgtgaat cagactgcga cagttcgagt ttgaagcgaa agctagcaac    60
agtatcaaca ggttttattt tggatttgga aacgagagtt tctggtcatg aaaaacccaa   120
aaaagaaatc cggaggattc cggattgtca atatgctaaa acgcggagta gcccgtgtga   180
gcccctttgg gggcttgaag aggctaccag ctggacttct gctgggtcat ggacccatca   240
ggatggtctt ggcgatacta gccttcttga gattcacggc aatcaagcca tcactgggtc   300
tcatcaatag atggggttcc gtggggaaaa agaggctat ggaataata aagaagttca    360
agaaagatct ggctgccatg ctgagaataa tcaatgctag gaaggagaag aagagacgtg   420
gcgcagacac cagtgtcgga attgttggcc tcctgctgac cacagccatg gcagtggagg   480
tcaccagacg tgggagtgca tactatatgt acttagacag aagcgatgct gggaaggcca   540
tatctttttcc aaccacactg ggggtgaata agtgttacat acagatcatg gatcttggac   600
acatgtgtga tgccacaatg agctatgaat gccctatgtt ggatgagggg gtagaaccag   660
atgacgtcga ttgctggtgc aacacgacat cgacttgggt tgtgtacgga acctgccatc   720
acaaaaaagg tgaggcacgg agatctagaa gagctgtgac gctcccctct cattccacta   780
ggaagctgca aacgcggtcg cagacctggt tggaatcaag agaatacaca aagcacttga   840
tcagagtcga aaattggata ttcaggaacc ctggctttgc gttggcagca gctgccattg   900
cttggctttt gggaagctca acgagccaaa aagtcatata cttggtcatg atactgttga   960
ttgccccggc atacagtatc aggtgcatag gagtcagcaa tagggatttt gtggaaggta  1020
tgtcaggtgg gacctgggtt gatgttgtct tggaacatgg aggttgtgtt accgtaatgg  1080
cacaggacaa gccaactgtt gatatagagt tggtcacaac aacggttagc aacatggcgg  1140
aggtaagatc ctactgctac gaggcatcaa tatcggacat ggcttcggac agccgctgcc  1200
caacacaagg tgaagcctac cttgacaagc agtcagacac tcaatatgtt tgcaaaagaa  1260
cgttagtgga cagaggttgg ggaaatggat gtggactctt tggcaaaggg agcctggtga  1320
catgcgccaa gtttgcatgc tccaagaaaa tgactgggaa gagcatccag ccagagaacc  1380
tggagtaccg gataatgctg tcagttcatg gctcccagca cagtgggatg attgttaatg  1440
acataggaca tgaaactgat gagaatagag cgaaggttga gataacgccc aattcaccaa  1500
gagccgaagc caccctggga ggttttggaa gcctaggact tgattgtgaa ccgaggacag  1560
gccttgactt ttcagatttg tattacttga ctatgaataa caagcattgg ttggtgcaca  1620
aggagtggtt ccatgacatt ccactacctt ggcatgctgg ggcagacacc ggaactccac  1680
attggaacaa caaagaagca ttggtagagt tcaaggacgc acatgccaaa aggcaaactg  1740
tcgtggttct agggagtcaa gaaggagccg ttcacacggc tcttgctgga gccctggagg  1800
ctgagatgga tggtgcaaag ggaaggctgt cctctggcca cttgaaatgt cgcttgaaaa  1860
tggacaaact tagattgaag ggcgtgtcat actccttatg taccgcggcg ttcacattca  1920
ccaagatccc ggctgaaacg ctgcatggga cagtcacagt ggaggtacag tatgcaggga  1980
cagatgacc ctgcaaggtt ccagctcaga tggcggtgga tatgcaaact ctgaccccag  2040
ttgggaggtt gataaccgct aaccctgtga tcactgaaag cactgagaat tcaaagatga  2100
tgttggaact tgacccacca tttggggatt cttacattgt cataggagtt ggggataagg  2160
agatcaccca ccactggcac aggagtggca gcaccatcgg aaaagcattt gaagccactg  2220
tgagaggcgc caagagaatg gcagtcttgg agacacagc ctgggacttt ggatcagtcg  2280
```

```
gaggtgctct caactcattg ggcaagggca tccatcaaat ttttggagca gctttcaaat    2340
cattgtttgg aggaatgtcc tggttctcac aaatcctcat aggaacgttg ctggtgtggt    2400
tgggtctgaa cacaaagaat ggaactattt cccttacgtg cttggcctta ggggagtgt     2460 tgatcttcct atctcagcc gtctctgcta tgtgggtg ttcggtggac ttctcaaaga       2520
aggaaacgag atgcggtacg ggggtgttcg tctataacga cgttgaagcc tggagggaca    2580
ggtacaagta ccatcctgac tcccctcgta gattggcagc agcagtcaag caggcctggg    2640
aagatgggat ctgtgggatc tcctctgttt caagaatgga aaacattatg tggagatcag    2700
tagaagggga gctcaacgca attctggaag agaatggagt tcaactgacg gtcgttgtgg    2760
gatctgtaaa aaaccccatg tggagaggtc cgcagaggtt gcctgtgcct gtgaatgagc    2820
tgccccacgg ttggaaggcc tgggggaaat cgtactttgt cagggcagca agaccaaca    2880 acagctttgt tgtggatggt gacacactga aggaatgccc gctcaaacac agagcatgga    2940
acagctttct tgtggaggat cacggttcg gggtatttca cactagtgtc tggcttaaag    3000
tcagagagga ttactcatta gagtgtgatc cagccgtcat aggaacagct gctaagggaa    3060
aggaggccgt gcacagtgat ctaggctact ggattgagag tgaaaagaac gacacatgga    3120
ggctgaagag ggctcacctg atcgagatga aacatgtga atggccaaag tcccacacac    3180
tgtggacaga tggaatagaa gaaagtgatc tgatcatacc taagtctta gctgggccac    3240 tcagccacca caacaccaga gagggctaca ggactcaagt gaaggggccg tggcatagtg    3300
aagagcttga atccggtttt gaggaatgtc caggcaccaa ggtccacgtg aggaaacat    3360 gtggaacgag aggaccgtcc ctgagatcaa ccactgcaag cggaagggtg atcgaggaat    3420
ggtgctgcag ggaatgcaca atgcccccat tgtcgttccg ggcaaaagat ggctgttggt    3480
atggaatgga gataaggccc aggaaggaac cagagagtaa cctagtaagg tcaatggtga    3540
ctgcaggatc aactgatcac atggatcact ctccccttgg agtgcttgtg attctgctca    3600
tggtgcagga agggctgaag aagagaatga ccacaaagat catcataagc acatcaatgg    3660
cagtgttggt agctatgatc ctgggaggat tttcaatgag tgacttggct aagcttgcaa    3720
ttctgatggg tgccaccttc gcggaaatga acactggagg agatgtagct catctggcgc    3780
tgatagcggc attcaaagtc agacccgcgt tgctggtctc tttcatcttc agagccaatt    3840
ggacaccccg tgagagcatg ctgctggcct tggcctcgtg ccttctgcaa actgtgatct    3900
ccgccctgga aggcgacctg atggttctca tcaatggttt tgctttggcc tggttggcaa    3960
tacgagcgat ggctgttcca cgcactgaca acatcacctt ggcaatcctg ctgctctga    4020 caccactggc ccgaggcaca ctgcttgtag cgtggagagc aggccttgct acttgtgggg    4080
ggttcatgct cctctctctg aaggggaaag gtagtgtgaa gaagaaccta ccatttgtca    4140
tggccttggg actaaccgct gtgaggctgg ttgaccccat caacgtggtg ggactgctgt    4200
tgctcacaag gagtgggaag cggagctggc cccctagtga agtactcaca gctgttggcc    4260
tgatatgtgc actggccgga gggttcgcca aagcagatat agagatggct gggcccatgg    4320
ctgcagttgg cctgctaatt gttagttacg tggtctcagg aaagagtgtg gacatgtaca    4380
ttgaaagagc aggtgacatc acatgggaaa agatgcggaa agttactgga aacagccccc    4440
ggctcgatgt ggcactagat gagagtggtg atttctccct ggtggaggat gatggtcccc    4500
ccatgagaga gatcatactc aaggtggtcc tgatgaccat ctgtggcatg aacccaatag    4560
ccataccctt tgcagctgga gcgtggtatg tgtatgtgaa gactgaaag aggagtggtg    4620 ctctatggga tgtgcctgct cccaaggaag taaaaaaggg ggagaccaca gatggagtgt    4680
```

```
atagagtgat gactcgcaga ctgctaggtt caacacaagt tggagtggga gtcatgcaag     4740
aggggtcttt ccacactatg tggcacgtca caaaaggatc cgcgctgagg agcggtgaag     4800
ggagacttga tccatactgg ggagatgtta agcaggatct ggtgtcatac tgtggcccgt     4860
ggaagctaga tgccgcttgg gacggacaca gcgaggtgca gcttttggcc gtgcccccg     4920 gagagagagc gaggaacatc cagactctgc ccggaatatt caagacaaag gatggggaca     4980
tcggagcagt tgctctggac tacccagcag gaacttcagg atctccgatc ctagacaagt     5040
gtgggagagt gataggactc tatggcaatg gggtcgtgat caaaaatgga agttatgtta     5100
gtgccatcac ccaagggagg agggaggaag agactcctgt tgaatgcttc gaaccttcga     5160
tgctgaagaa gaagcagcta actgtcttgg atctgcatcc tggagctggg aaaaccagga     5220
gagttcttcc tgaaatagtc cgtgaagcca taaaaacaag actccgcacg gtgatcctgg     5280
ctccaaccag ggttgtcgct gctgaaatgg aggaagccct tagagggctt ccagtgcgtt     5340
acatgacaac agcagttaat gtcacccact ctgggacaga aatcgttgat ttaatgtgcc     5400
atgccacctt cacttcacgc ctactacaac ccattagagt ccccaactac aatctttaca     5460
ttatggatga ggcccacttc acagatccct caagtatagc agcaagagga tacatatcaa     5520
caagggttga gatgggcgag gcggctgcca tcttcatgac cgccacacca ccaggaaccc     5580
gcgacgcatt tccggactct aactcaccaa tcatggacac agaagtggaa gtcccagaga     5640
gagcctggag ctcaggcttt gattgggtga cggatcattc tggaaaaaca gtttggtttg     5700
ttccaagcgt gaggaacggc aacgagatcg cggcttgtct gacaaaagct ggaaaacggg     5760
tcatacagct cagcagaaag actttgaga cagagttcca gaaaacaaaa aatcaagagt     5820
gggacttcgt cgtaacaact gacatctcag agatgggcgc caacttcaaa gctgaccggg     5880
tcatagattc caggagatgc ctgaagccgg tcatacttga tggcgagaga gtcattctgg     5940
ctggacccat gcctgtcaca catgccagcg ctgcccagag gaggggggcgc ataggcagga     6000 atcccaacaa acctggagat gagtatatgt atggaggtgg gtgcgcagag actgatgaag     6060
accatgcaca ctggcttgaa gcaagaatgc ttcttgataa catttacctc caagatggcc     6120
tcatagcctc gctctatcga cctgaggccg ataaggtagc agccattgag ggagagttca     6180
agcttaggac ggagcaaagg aagacctttg tggaactcat gaaaagagga gatcttcctg     6240
tttggctggc ctatcaggtt gcatctgccg gaataaccta cacagataga agatggtgtt     6300
ttgatggcac gaccaacaac accataatgg aagacagtgt gccggcagag gtgtggacca     6360 gatacgaga gaaaagagtg ctcaaaccga ggtggatgga cgccagagtt tgttcagatc     6420
atgcggccct gaagtcattc aaagaatttg ccgctgggaa agaggagcg gcctttggag     6480 tgatggaagc cctgggaaca ctgccaggac acatgacaga gaggtttcag gaagccattg     6540
acaacctcgc tgtgctcatg cgggcagaga ctggaagcag gccctacaaa gccgcggcgg     6600
cccaattacc ggagacctta gagaccatca tgctttgggg tttgctggga acagtctcgc     6660
tgggaatctt ctttgtcttg atgcggaaca agggcatagg gaagatgggc tttggaatgg     6720 tgaccctgg ggccagtgca tggcttatgt ggctctcgga aattgagcca gccagaattg     6780
catgtgtcct cattgtcgtg tttctattgc tggtggtgct cataccgag ccagaaaagc     6840 agagatctcc ccaggacaac caaatggcaa ttatcatcat ggtagcagtg ggtcttctgg     6900
gcttgataac cgccaatgaa ctcggatggt tggagagaac aaaaagtgac ctaggccatc     6960
taatgggaag gagagaggag ggggcaacca tgggattctc aatggacatt gacttgcggc     7020
```

```
cagcctcagc ttgggctatc tatgccgctc tgacaactct catcacccca gccgtccaac    7080
atgcggtaac cacttcatac aacaactact ccttaatggc gatggccacg caagccggag    7140
tgttgtttgg catgggcaaa gggatgccat tctatgcgtg ggacttcgga gtcccgctgc    7200
taatgatggg ttgctactca caattaacac ccttgacctt aatagtggcc atcattctgc    7260
tcgtggcgca ctacatgtac ttgatcccag gtctacaggc agcagcggcg cgcgctgccc    7320
agaagagaac ggcagctggc atcatgaaga accctgttgt ggatggaata gtggtgactg    7380
acattgacac aatgacaatt gaccccccaag tggagaaaaa gatgggacaa gtgctactca    7440
tagcagtagc catctccagt gccgttctgc tgcgcaccgc ctgggggtgg ggggaggctg    7500
gggccctgat cacagccgca acttccactt tgtgggaagg ctctccgaat aaatactgga    7560
actcctccac agccacttca ctgtgtaaca ttttaggggg aagttacttg gctggagctt    7620
ctcttattta cacagtaaca agaaacgctg gcctggtcaa gagacgtgga ggtggaacgg    7680
gagagaccct gggggagaaa tggaaggccc gcctgaacca gatgtcggcc ctggagtttt    7740
actcctacaa aaagtcaggc atcaccgaag tgtgcagaga agaagcccgc cgcgccctca    7800
aggacggagt ggcaacagga ggccatgctg tgtcccgagg aagcgcaaag cttagatggt    7860
tggtggagag aggataccta cagccctatg gaaaggtcat tgatcttgga tgtggcagag    7920
ggggctggag ttactacgcc gccaccatcc gcaaagttca gaggtgaaaa ggatacacaa    7980
agggaggccc tggtcatgaa gaacccacgt tggtgcaaag ctatggatgg aacatagtcc    8040
gtcttaagag tggggtggac gtctttcaca tggcggcgga gtcgtgtgac actttgctgt    8100
gtgacatagg tgagtcatca tctagtcctg aagtggaaga agcacggacg ctcagagtac    8160
tctccatggt gggggattgg cttgaaaaaa gaccaggggc ctttttgtata aggtgttgt    8220 gcccatacac cagcaccatg atggaaaccc tagagcgact gcagcgtagg tatgggggag    8280
gactggtcag agtgccactc tcccgcaact ctacacatga gatgtactgg gtctctggag    8340
cgaaaagcaa catcataaaa agtgtgtcca ccacgagcca gctcctcttg ggacgcatgg    8400
acgggcccag gaggccagtg aaatatgagg aggatgtgaa tctcggctcc ggcacgcgag    8460
ctgtggcaag ctgcgccgaa gctcccaacc tgaagatcat tggtaaccgc gttgagagga    8520
tccgcagtga gcatgcggaa acgtggttct ttgatgagaa ccacccatac aggacatggg    8580
cttaccatgg gagctacgag gcccctacac aagggtcagc gtcttctctc ataaacgggg    8640
ttgtcaggct cctgtcaaag ccctgggatg tggtgactgg agtcacagga atagccatga    8700
ccgacaccac accgtatggc cagcaaagag ttttcaagga aaaagtggac actagggtgc    8760 cagacccca ggaaggcact cgtcaggtga tgaacatggt ctcttcctgg ctatggaagg    8820
agctaggtaa acacaaacgg ccacgagttt gcaccaaaga agagttcatc aataaggttc    8880
gcagcaatgc agcactgggg gcaatatttg aagaggagaa agaatggaag actgcagtgg    8940
aagctgtgaa cgatccaagg ttctgggccc tagtggacaa ggaaagagag caccacttga    9000
gaggagagtg tcagagctgt gtgtacaaca tgatgggaaa aagagaaaag aagcaagggg    9060
aatttggaaa ggccaagggc agccgcgcca tttggtacat gtggctaggg gctagatttc    9120
tagagtttga agcccttgga ttcttgaacg aggatcactg gatggggaga gagaattcag    9180
gaggtggtgt tgaagggctg ggattacaaa gacttggata tgttctagaa gaaatgagcc    9240
gcacaccagg aggaaagatg tatgcagatg ataccgctgg ctgggacacc cgcatcagta    9300
ggtttgatct ggagaatgaa gctctgatca ccaaccaaat ggaaaagggg cacagggcct    9360
tggcgttggc cataatcaag tacacatacc aaaacaaagt ggtaaaggtc cttagaccag    9420
```

```
ctgaaagagg gaagacagtt atggacatca tctcaagaca agaccaaaga gggagcggac   9480
aagttgttac ttacgctctt aatacattca ccaacctggt ggtgcagctc attcggaaca   9540
tggaggctga ggaagttcta gagatgcaag acttgtggct gttgaggagg ccagagaagg   9600
tgaccagctg gttgcagagc aacgatggg ataggctcaa acgaatggca gtcagtggag    9660
atgattgtgt tgtgaaacca attgatgata ggtttgcaca tgccctcagg tttttgaatg   9720
acatggggaa agttaggaag gacacacagg agtggaaacc ctcaactgga tggagcaact   9780
gggaagaagt tccgttttgc tcccatcact tcaacaagct ttacctcaag gacgggaggt   9840
ccattgtggt ccctgtcgc caccaagatg aactgattgg ccgagcccgc gtctcaccag    9900
gggcgggatg gagcatccgg gagactgctt gcctagcaaa atcatatgca caaatgtggc   9960
agcttcttta tttccacaga agggacctcc gactgatggc caacgccatt tgttcatctg  10020
tgccagttga ctgggttcca actgggagaa ccacctggtc aatccatgga agggagaat   10080 ggatgaccac tgaggacatg cttgtggtgt ggaacagagt gtggattgag agaacgacc   10140 acatggagga caagacccca gtcacgaaat ggacagacat tccctatttg ggaaaaaggg  10200
aagacttatg gtgtggatct cttatagggc acagaccacg cactacttgg gctgagaaca  10260
ttaaagacac agtcaacatg gtgcgcagga tcataggtga tgaagaaaag tacatggact  10320
acctatccac tcaagttcgc tacttgggtg aagaagggtc cacacctgga gtgttataag  10380
caccaatttt agtgttgtca ggcctgctag tcagccacag cttggggaaa gctgtgcagc  10440
ctgtgacccc cccaggagaa gctgggaaac caagcccata gtcaggccga gaacgccatg  10500
gcacggaaga agccatgctg cctgtgagcc cctcagagga cactgagtca aaaaacccca  10560
cgcgcttgga ggcgcaggat gggaaaagaa ggtggcgacc ttccccaccc tccaatctgg  10620
ggcctgaact ggagatcagc tgtggatctc caggagaggg actagcggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtct                                                           10807
```

<210> SEQ ID NO 6
<211> LENGTH: 10807
<212> TYPE: DNA
<213> ORGANISM: Artificial Sequence
<220> FEATURE:
<223> OTHER INFORMATION: Synthetic

<400> SEQUENCE: 6

```
agttgttgat ctgtgtgaat cagactgcga cagttcgagt ttgaagcgaa agctagcaac     60
agtatcaaca ggttttattt tggatttgga acgagagtt tctggtcatg aaaaacccaa    120
aaaagaaatc cggaggattc cggattgtca atatgctaaa acgcggagta gcccgtgtga    180 gccccttttgg gggcttgaag aggctgccag ccggacttct gctgggtcat gggcccatca   240
ggatggtctt ggcgattcta gccttttga gattcacggc aatcaagcca tcactgggtc    300
tcatcaatag atgggggttca gtggggaaaa aagaggctat ggaaacaata aagaagttca   360
agaaagatct ggctgccatg ctgagaataa tcaatgctag gaaggagaag aagagacgag   420
gcgcagatac tagtgtcgga attgttggcc tcctgctgac cacagctatg gcagcggagg   480
tcactagacg tgggagtgca tactatatgt acttggacag aaacgatgct ggggaggcca   540
tatcttttcc aaccacattg gggatgaata agtgttatat acagatcatg gatcttggac    600
```

```
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacca    780
ggaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttctgac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaagggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaagttga gataacgccc aattcaccga   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg tactgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aacccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc aagagaatg gcagtcttgg agacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt cccttatgtg cttggcctta ggggagtgt   2460 tgatcttctt atccacagcc gtctctgctg atgtggggtg ctcggtggac ttctcaaaga   2520
aggagacgag atgcggtaca gggtgttcg tctataacga cgttgaagcc tgagggaca   2580 ggtacaagta ccatcctgac tccccccgta gattggcagc agcagtcaag caagcctggg   2640
aagatggtat ctgcgggatc tcctctgttt caagaatgga aaacatcatg tggagatcag   2700 tagaaggga gctcaacgca atcctggaag agaatgagt caactgacg gtcgttgtgg   2760 gatctgtaaa aaaccccatg gggagaggtc cacagagatt gccccgtgcct gtgaacgagc   2820 tgccccacgg ctgaaggct tggggaaat cgtatttcgt cagagcagca aagacaaata   2880
acagctttgt cgtggatggt gacacactga aggaatgccc actcaaacat agagcatgga   2940
acagctttct tgtggaggat catgggttcg gggtatttca cactagtgtc tggctcaagg   3000
```

```
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aacatgtga atggccaaag tcccacacat    3180
tgtggacaga tggaatagaa gagagtgatc tgatcatacc caagtctta gctgggccac    3240 tcagccatca caataccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagcaa cttagtaagg tcaatggtga   3540
ctgcaggatc aactgatcac atggaccact tctcccttgg agtgcttgtg atcctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga cactggagg agatgtagct catctggcgc    3780
tgatagcgga attcaaagtc agaccagcgt tgctggtatc tttcatcttc agagctaatt   3840
ggacaccccg tgaaagcatg ctgctggcct tggcctcgtg tctttttgcaa actgcgatct   3900 ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc ccctagcga agtactcaca gctgttggcc    4260
tgatatgcgc attggctgga gggttcgcca aggcagatat agagatggct gggcccatgg   4320
ccgcggtcgg tctgctaatt gtcagttacg tggtctcagg aaagagtgtg acatgtaca    4380 ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaagggg ggagaccaca gatggagtgt   4680
acagagtaat gactcgtaga ctgctaggtt caacacaagt tggagtggga gttatgcaag   4740 aggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gatgggcaca gcgaggtgca gctcttggcc gtgccccccg   4920
gagagagagc gaggaacatc cagactctgc ccggaatatt taagacaaag gatgggacat   4980 tggagcggt tgcgctggat tacccagcag gaacttcagg atctccaatc ctagacaagt   5040
gtgggagagt gataggactt tatggcaatg gggtcgtgat caaaaacggg agttatgtta   5100
gtgccatcac ccaagggag agggaggaag agactcctgt tgagtgcttc gagccctcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaggccct tagagggctt ccagtgcgtt   5340
```

```
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000
atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
tgatggcac gaccaacaac accataatgg aagacagtgt gccggcagag gtgtggacca    6360
gacacggaga gaaagagtg ctcaaaccga ggtggatgga cgccagagtt tgttcagatc    6420
atgcggccct gaagtcattc aaggagtttg ccgctgggaa aagaggagcg gcttttggag    6480
tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacccta gagaccataa tgcttttggg gttgctggga acagtctcgc    6660
tgggaatctt cttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct cataccctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaaagagtga ctaagccatc    6960
taatgggaag gagagaggag ggggcaacca taggattctc aatggacatt gacctgcggc    7020
cagcctcagc ttgggccatc tatgctgcct tgacaacttt cattacccca gccgtccaac    7080
atgcagtgac cacctcatac aacaactact ccttaatggc gatggccacg caagctggag    7140
tgttgtttgg catgggcaaa gggatgccat tctacgcatg gactttggaa gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gaccccccaag tggagaaaaa gatgggacag gtgctactca    7440
tagcagtagc cgtctccagc gccatactgt cgcggaccgc ctggggtgg ggggaggctg    7500
gggctctgat cacagccgca acttccactt tgtgggaagg ctctccgaac aagtactgga    7560
actcctctac agccacttca ctgtgtaaca tttttagggg aagttacttg gctggagctt    7620
ctctaatcta cacagtaaca agaaacgctg gcttggtcaa gagacgtggg ggtggaacag    7680
gagagaccct gggagagaaa tggaaggccc gcttgaacca gatgtcggcc ctggagttct    7740
```

```
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgtc gccaccatcc gcaaagttca agaagtgaaa ggatacacaa   7980
aaggaggccc tggtcatgaa gaacccgtgt tggtgcaaag ctatgggtgg aacatagtcc   8040
gtcttaagag tgggtggac gtctttcata tggcggctga gccgtgtgac acgttgctgt    8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatggggag    8280
gattggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gcaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gtataccagg aggaaggatg tatgcagatg acactgctgg ctgggacacc cgcattagca   9300
ggtttgatct ggagaatgaa gctctaatca ccaaccaaat ggaaaaggg cacagggcct    9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa cgaatggca gtcagtggag    9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctcccttta tttccacaga agggacctcc gactgatggc caatgccatt tgttcatctg  10020
tgccagttga ctgggttcca actgggagaa ctacctggtc aatccatgga aagggagaat  10080
```

```
ggatgaccac tgaagacatg cttgtggtgt ggaacagagt gtggattgag gagaacgacc    10140
acatggaaga caagcccca gttacgaaat ggacagacat tccctatttg ggaaaaaggg    10200
aagacttgtg gtgtggatct ctcatagggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctgtaag    10380
caccaatctt aatgttgtca ggcctgctag tcagccacag cttggggaaa gctgtgcagc    10440
ctgtgacccc cccaggagaa gctgggaaac caagcctata gtcaggccga gaacgccatg    10500
gcacggaaga agccatgctg cctgtgagcc cctcagagga cactgagtca aaaaccccca    10560
cgcgcttgga ggcgcaggat gggaaaagaa ggtggcgacc ttccccaccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg gccgccaggc acagatcgcc gaatagcggc ggccggtgtg gggaaatcca    10800
tgggtct                                                              10807

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7 atttaggga cactatag                                                   18

<210> SEQ ID NO 8
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(10)
<223> OTHER INFORMATION: n is a, c, g, t or u

<400> SEQUENCE: 8
gaacnnnnnn tac                                                       13

<210> SEQ ID NO 9
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(10)
<223> OTHER INFORMATION: n is a, c, g, t or u

<400> SEQUENCE: 9
gaagnnnnnn tac                                                       13

<210> SEQ ID NO 10
<211> LENGTH: 31
<212> TYPE: DNA
<213> ORGANISM: Artificial Sequence
<220> FEATURE:
<223> OTHER INFORMATION: Synthetic
```

<400> SEQUENCE: 10
gctattgggt tcatgccaca gatggtcatc a                                      31

<210> SEQ ID NO 11
<211> LENGTH: 41
<212> TYPE: DNA
<213> ORGANISM: Artificial Sequence
<220> FEATURE:
<223> OTHER INFORMATION: Synthetic

<400> SEQUENCE: 11
tatgtttaaa cagttgttga tctgtgtgaa tcagactgcg a                           41

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
tatggcgcgc caggaccacc ttgagtatga tctctctcat g                           41

<210> SEQ ID NO 13
<211> LENGTH: 31
<212> TYPE: DNA
<213> ORGANISM: Artificial Sequence
<220> FEATURE:
<223> OTHER INFORMATION: Synthetic

<400> SEQUENCE: 13
attgtcattg tgtcaatgtc agtcaccact a                                      31

<210> SEQ ID NO 14
<211> LENGTH: 41
<212> TYPE: DNA
<213> ORGANISM: Artificial Sequence
<220> FEATURE:
<223> OTHER INFORMATION: Synthetic

<400> SEQUENCE: 14
tatgtttaaa ctcattgttt ggaggaatgt cctggttctc a                           41

<210> SEQ ID NO 15
<211> LENGTH: 41
<212> TYPE: DNA
<213> ORGANISM: Artificial Sequence
<220> FEATURE:
<223> OTHER INFORMATION: Synthetic

<400> SEQUENCE: 15
tatggcgcgc ctcaatgtca gtcaccacta ttccatccac a                           41

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
ctccagttca ggccccagat tgaagggtgg gg                                     32

<210> SEQ ID NO 17
<211> LENGTH: 41
<212> TYPE: DNA
<213> ORGANISM: Artificial Sequence
<220> FEATURE:
<223> OTHER INFORMATION: Synthetic

<400> SEQUENCE: 17
tatgtttaaa cggaagtccc agagagagcc tggagctcag g          41

<210> SEQ ID NO 18
<211> LENGTH: 41
<212> TYPE: DNA
<213> ORGANISM: Artificial Sequence
<220> FEATURE:
<223> OTHER INFORMATION: Synthetic

<400> SEQUENCE: 18
tatggcgcgc caagggtggg gaaggtcgcc accttctttt c          41

<210> SEQ ID NO 19
<211> LENGTH: 34
<212> TYPE: DNA
<213> ORGANISM: Artificial Sequence
<220> FEATURE:
<223> OTHER INFORMATION: Synthetic

<400> SEQUENCE: 19
ctaggatcct taattaacct gcaggggggct gtta                 34

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
gatcaacaac tctatagtgt cccctaaatc                       30

<210> SEQ ID NO 21
<211> LENGTH: 32
<212> TYPE: DNA
<213> ORGANISM: Artificial Sequence
<220> FEATURE:
<223> OTHER INFORMATION: Synthetic

<400> SEQUENCE: 21
ggacactata gagttgttga tctgtgtgag tc                    32

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22
tatccgcggt agcgcaaacc cggggttcct gaat                  34

<210> SEQ ID NO 23
<211> LENGTH: 34
<212> TYPE: DNA
<213> ORGANISM: Artificial Sequence
<220> FEATURE:

<223> OTHER INFORMATION: Synthetic

<400> SEQUENCE: 23
tatccgcggg gaaaaaggga ggacttatgg tgtg          34

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24
agggcggccg cgtatgtcgc gttccgtacg ttctagagaa accatggatt tccccacacc          60

<210> SEQ ID NO 25
<211> LENGTH: 32
<212> TYPE: DNA
<213> ORGANISM: Artificial Sequence
<220> FEATURE:
<223> OTHER INFORMATION: Synthetic

<400> SEQUENCE: 25
ggacactata gagttgttga tctgtgtgaa tc          32

<210> SEQ ID NO 26
<211> LENGTH: 34
<212> TYPE: DNA
<213> ORGANISM: Artificial Sequence
<220> FEATURE:
<223> OTHER INFORMATION: Synthetic

<400> SEQUENCE: 26
tatccgcgga acgcaaagcc agggttcctg aata          34

<210> SEQ ID NO 27
<211> LENGTH: 34
<212> TYPE: DNA
<213> ORGANISM: Artificial Sequence
<220> FEATURE:
<223> OTHER INFORMATION: Synthetic

<400> SEQUENCE: 27
tatccgcggg ggaaaaaggg aagacttatg gtgt          34

<210> SEQ ID NO 28
<211> LENGTH: 60
<212> TYPE: DNA
<213> ORGANISM: Artificial Sequence
<220> FEATURE:
<223> OTHER INFORMATION: Synthetic

<400> SEQUENCE: 28
agggcggccg cgtatgtcgc cttccgtacg ttctagagac ccatggattt ccccacaccg          60

<210> SEQ ID NO 29
<211> LENGTH: 30
<212> TYPE: DNA
<213> ORGANISM: Artificial Sequence
<220> FEATURE:
<223> OTHER INFORMATION: Synthetic

<400> SEQUENCE: 29
tttgaattcg gtctcatcaa tagatggggt          30

```
<210> SEQ ID NO 30
<211> LENGTH: 36
<212> TYPE: DNA
<213> ORGANISM: Artificial Sequence
<220> FEATURE:
<223> OTHER INFORMATION: Synthetic

<400> SEQUENCE: 30
tttctcgagc tattatcgtc tcttcttctc cttcct                              36

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
tttgaattcg ctgtgacgct cccctcccat                                     30

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
tttctcgagc tattagactc taatcaagtg ctttgt                              36

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
tttgaattcc agcacagtgg gatgatcgtt                                     30

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
tttctcgagc tattatccta ggcttccaaa accccc                              36

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
tttgaattcg gagcggcttt tggagtgatg                                     30

<210> SEQ ID NO 36
<211> LENGTH: 36
<212> TYPE: DNA
<213> ORGANISM: Artificial Sequence
<220> FEATURE:
<223> OTHER INFORMATION: Synthetic
```

```
<400> SEQUENCE: 36
tttctcgagc tattaggtct ccggcaattg ggccgc                              36

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
tttgaattcg tgactgacat tgacacaatg                                    30

<210> SEQ ID NO 38
<211> LENGTH: 36
<212> TYPE: DNA
<213> ORGANISM: Artificial Sequence
<220> FEATURE:
<223> OTHER INFORMATION: Synthetic

<400> SEQUENCE: 38
tttctcgagc tattaggaag ttgcggctgt gatcag                              36

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gaagtggaag tcccagagag                                                20

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
tgctgagctg tatgacccg                                                 19

<210> SEQ ID NO 41
<211> LENGTH: 26
<212> TYPE: DNA
<213> ORGANISM: Artificial Sequence
<220> FEATURE:
<223> OTHER INFORMATION: Synthetic

<400> SEQUENCE: 41
tggagctcag gctttgattg ggtgac                                         26

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
agcgggaaat cgtgcgtgac                                                20

<210> SEQ ID NO 43
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 43
caatggtgat gacctggcca                                                    20

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
cacggcggct tctagctcct ccc                                                23

<210> SEQ ID NO 45
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Keyhole Limpet Hemocyanin (KLH) attached to
      residue 1

<400> SEQUENCE: 45

Asp Met Trp Leu Glu Arg Ala Ala Asp Ile Ser Trp
1               5                   10

<210> SEQ ID NO 46
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Keyhole Limpet Hemocyanin (KLH) attached to
      residue 1

<400> SEQUENCE: 46

Asn Pro Met Gly Arg Gly Pro Gln Arg Leu Pro Val Pro Val Asn Glu
1               5                   10                  15

Leu Pro His

<210> SEQ ID NO 47
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Keyhole Limpet Hemocyanin (KLH) attached to
      residue 1

<400> SEQUENCE: 47

Ser Gly Asp Phe Ser Leu Val Glu Asp Asp Gly Pro Pro Met Arg Glu
1               5                   10                  15

Ile Ile Leu
```

<210> SEQ ID NO 48
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: Majority

<400> SEQUENCE: 48
ggacccuuuu ccgcuugguc ugcuggugau guuccuggcc auccaggagg uccugaggaa    60
gagauggacg gccaagcuca                                               80

<210> SEQ ID NO 49
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: JEVSA14 (KU323483)

<400> SEQUENCE: 49
ugacccuuuu cagcugggcc uucuggugau guuucuggcc acccaggagg uccuucgcaa    60
gagguggacg gccagauuga                                               80

<210> SEQ ID NO 50
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: JEVSA14-14-2 (JN604986)

<400> SEQUENCE: 50
ugacccuuuu cagcugggcc uucuggugau guuucuggcc acccaggaag uccuucgcaa    60
gagguggacg gccagauuga                                               80

<210> SEQ ID NO 51
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: WNV NY99 (DQ211652)

<400> SEQUENCE: 51
ugacccuuuu caguugggcc uucuggucgu guucuuggcc acccaggagg uccuucgcaa    60
gagguggaca gccaagauca                                               80

<210> SEQ ID NO 52
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: WNV B956 (AY532665)

<400> SEQUENCE: 52
ugauccuuuu caguugggcc uucuggucgu guucuuggcc acccaggagg uccuucgcaa    60
gagguggacg gccaagauua                                                80

<210> SEQ ID NO 53
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: MVEV MVE-1-51 (AF161266)

<400> SEQUENCE: 53
ugauccuuuu caguuaggcc uucuggucgu guuucuggcc acccaggagg ucuugaggaa    60
gagguggacg gccagacuua                                                80

<210> SEQ ID NO 54
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: MVEV V11-10 (JX123032)

<400> SEQUENCE: 54
ugauccuuuu caguugggcc uucuggucgu guuucuggcc acccaggagg ucuugaggaa    60
gagguggacg gccagacuua                                                80

<210> SEQ ID NO 55
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: SLEV Hubbard (EU566860)

<400> SEQUENCE: 55
ggaaccauuc caacuugguc uccugguagc auucauagcc acccaagaag ugcugaaacg    60
cagauggacu gggaagcuga                                                80

<210> SEQ ID NO 56
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: SLEV Imperial Valley (JF460774)

-continued

<400> SEQUENCE: 56
ggaaccauuc caacuugguc ucuuggaugc auucauagcc acccaagaag ugcuaaaacg    60
cagauggacu gggaaguuga                                                80

<210> SEQ ID NO 57
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: DENV-1 16007 (AF180817)

<400> SEQUENCE: 57
ggacagcuuu ucacuaggac ugcuaugcau aucaauaaug auugaagaag ugaugagauc    60
cagauggagc aaaaaaaugc                                                80

<210> SEQ ID NO 58
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: DENV-2 16681 (U87411)

<400> SEQUENCE: 58
cgacaacuuu ucacuaggag ucuugggaau ggcauuguuc cuggaggaaa ugcuuaggac    60
ccgaguagga acgaaacaug                                                80

<210> SEQ ID NO 59
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: DENV-3 BID-V4782 (JN183884)

<400> SEQUENCE: 59
ggacaacuuc acaaggguug ucuugugcuu ggcauccuc uuugaagagg ugaugagagg    60
aaaauuuggg aagaaacaca                                                80

<210> SEQ ID NO 60
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: DENV-4 H780571 (JQ513344)

<400> SEQUENCE: 60
ggaaacuuuu ucuaugggguc uguugugccu gaccuuguuu guggaagaau gcuugaggag    60
aagagucacc aggaaacaca                                                80

<210> SEQ ID NO 61
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: YFV Asibi (AY640589)

<400> SEQUENCE: 61
acaugcuguc ccuuuugguu uggugagcau gaugauagca auggaagugg uccuaaggaa      60
aagacaggga ccaaagcaaa                                                 80

<210> SEQ ID NO 62
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: YFV 17D (X03700)

<400> SEQUENCE: 62
acaugcuguc ccuuuugguu uggugagcau gaugauagca auggaagugg uccuaaggaa      60
aagacaggga ccaaagcaaa                                                 80

<210> SEQ ID NO 63
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: ZIKV MR-766 (KX377335)

<400> SEQUENCE: 63
ggaccacuuc ucucuuggag ugcuugugau ucuacucaug gugcaggagg gguugaagaa      60
gagaaugacc acaaagauca                                                 80

<210> SEQ ID NO 64
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(80)
<223> OTHER INFORMATION: ZIKV P6-740 (KX377336)

<400> SEQUENCE: 64
ggaucacuuc ucccuuggag ugcuugugau ucugcucaug gugcaggaag ggcugaagaa      60
gagaaugacc acaaagauca                                                 80

<210> SEQ ID NO 65
<211> LENGTH: 80
<212> TYPE: DNA
<213> ORGANISM: Artificial Sequence
<220> FEATURE:
<223> OTHER INFORMATION: Synthetic

```
-continued

<220> FEATURE:
<221> NAME/KEY: misc_feature
<222> LOCATION: (1)..(80)
<223> OTHER INFORMATION: ZIKV PRVABC-59 (KX377337)

<400> SEQUENCE: 65
ggaccacuuc ucccuuggag ugcuugugau ccugcucaug gugcaggaag ggcugaagaa    60
gagaaugacc acaaagauca                                               80

<210> SEQ ID NO 66
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Amino acid sequence from pBac/P6-740

<400> SEQUENCE: 66

Gly Met Ile Val Asn Asp Ile Gly His Glu Thr
1               5                   10

<210> SEQ ID NO 67
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: pBac/P6-740/ENDT

<400> SEQUENCE: 67
gggatgattg ttaatgacac aggaccatga aact                               34

<210> SEQ ID NO 68
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: pBac/P6-740/EQDT

<400> SEQUENCE: 68
gggatgattg ttcaagacac aggaccatga aact                               34
```

COMPOSITIONS AND METHODS FOR ZIKA VIRUS CHARACTERIZATION AND VACCINE DEVELOPMENT

CROSS REFERENCE TO RELATED APPLICATION(S)

This application claims priority to U.S. Provisional Application No. 62/659,386, filed Apr. 18, 2018, which is hereby incorporated by reference in its entirety.

SEQUENCE LISTING

The instant application contains a Sequence Listing which has been submitted electronically and is hereby incorporated by reference in its entirety. The sequence listing text filed, created on Aug. 19, 2021, is named "P1802701-208159-9012-US02-REPLACEMENT-SEQUENCE ST25" and is 130,857 bytes in size.

FIELD

The present disclosure relates to compositions and methods for investigating Zika virus (ZIKV) biology and pathogenicity. In particular, the present disclosure provides full-length infectious cDNAs as bacterial artificial chromosomes (BACs) for three spatiotemporally distinct and genetically divergent ZIKVs. Also, the present disclosure uses these infectious ZIKV cDNAs to determine the genome-wide landscape of ZIKV gene products and to characterize genetic aspects of ZIKV replicability and pathogenicity. The full-length ZIKV cDNAs serve as the basis for establishing vaccine compositions for the prevention of ZIKV infection.

BACKGROUND

Discovered in Uganda in 1947 in a febrile rhesus macaque, ZIKV is a medically important flavivirus related to Japanese encephalitis (JEV), West Nile (WNV), dengue, and yellow fever viruses. Originally it was confined within an equatorial belt running from Africa to Asia, with only about a dozen cases of human illness reported. In 2007, however, it caused a major outbreak of mild illness characterized by fever, rash, arthralgia, and conjunctivitis on the western Pacific Island of Yap. Since then, it has spread eastward across the Pacific Ocean, invading French Polynesia and other Pacific Islands in 2013-2014, reaching the Americas and Caribbean in 2015-2016, and now threatening much of the world. ZIKV is spread to humans mainly through the bite of an infected *Aedes* species mosquito, e.g., *A. aegypti* or *A. albopictus*, but it can also be transmitted from a mother to her child during pregnancy or through sexual contact. Serious concerns have been raised over links to congenital neurological malformations (e.g., microcephaly) and severe neurological complications (e.g., Guillain-Barré syndrome). Despite its continuous rapid spread and high pandemic potential, no vaccine or drug is available to prevent or treat ZIKV infection.

ZIKV is an enveloped RNA virus with a nucleocapsid core comprising an ~11-kb plus-strand RNA genome and multiple copies of the C protein; this core is surrounded by a lipid bilayer bearing the anchored M and E proteins. To date, little information is available about the molecular events that occur during ZIKV infection, but current understanding of the molecular biology of closely related flaviviruses offers a promising starting point for ZIKV research. As the first step in flavivirus replication, the virion binds nonspecifically to the surface of a host cell and is then internalized via clathrin-mediated endocytosis in a viral glycoprotein E-dependent manner. Within endosomes, the E glycoprotein undergoes low pH-induced conformational changes, followed by fusion of the viral and host cell membranes. In the cytoplasm, the viral genomic RNA (vgRNA) functions initially as an mRNA for the translation of a single long open reading frame (ORF) flanked by 5' and 3' non-coding regions (NCRs); the resulting polyprotein is cleaved by viral and cellular proteases to generate at least 10 mature proteins: three structural (C, prM, and E) and seven nonstructural (NS1, 2A, 2B, 3, 4A, 4B, and 5). In JEV and WNV, ribosomal frameshifting is also used for the expression of NS1', a C-terminally extended form of NS1. A complex of the seven nonstructural proteins directs vgRNA replication on the distinct virus-induced membranous compartments derived from endoplasmic reticulum (ER). This replication process is catalyzed by two main viral components: (i) NS3, with serine protease (and its cofactor, NS2B) and RNA helicase/NTPase/RTPase activity, and (ii) NS5, with methyltransferase/guanylyltransferase and RNA-dependent RNA polymerase activity. Virus assembly begins with budding of the C proteins, complexed with a newly made vgRNA, into the ER lumen, and acquisition of the viral prM and E proteins. The prM-containing immature virions travel through the secretory pathway; in the trans-Golgi network, a cellular furin-like protease cleaves prM to yield the mature M protein, converting the immature particle to a mature virion.

The clinical presentation of ZIKV infection is highly variable, ranging from no apparent symptoms or mild self-limiting illness to severe neurological disorders such as microcephaly and Guillain-Barré syndrome. Fundamentally, the varied outcomes after infection with a pathogen depend on the specific combination of pathogen and host genotypes. On the virus side, a limited but significant number of ZIKVs have been isolated from Africa, Asia, and the Americas during the past 70 years. Recent phylogenetic analyses based on complete or near-complete viral genome sequences have revealed that the spatiotemporally distinct ZIKV strains are grouped into two major genetic lineages, African and Asian, with the 2015-2016 American epidemic strains originating from a common ancestor of the Asian lineage. Despite the continuous expansion of its genetic diversity, little is known about the effect of viral genetic variation on the pathogenicity of ZIKV between the two lineages or between different strains within a particular lineage. On the host side, much progress has recently been made in developing murine models for ZIKV infection, including mice genetically engineered to lack one or more components of the innate and adaptive immune systems that affect the development, severity, and progression of ZIKV-induced disease. However, the influence of host genetic variation on susceptibility to ZIKV infection is largely unknown.

SUMMARY

In one aspect disclosed is a genetically stable viral vector comprising: a Zika virus cDNA; a RNA polymerase promoter upstream of the 5' end of the Zika virus cDNA; and a restriction endonuclease site downstream of the 3' end of the Zika virus cDNA; wherein the Zika virus cDNA, the RNA polymerase promoter, and the restriction endonuclease site are cloned into a bacterial artificial chromosome vector, and wherein the Zika virus cDNA is capable of being transcribed into an RNA transcript that is functional.

In another aspect disclosed is a method of generating a genetically engineered attenuated Zika virus comprising: obtaining a genetically stable viral vector disclosed herein; and altering one or more nucleotides in the Zika virus cDNA to produce a synonymous or non-synonymous codon alteration; wherein the synonymous or non-synonymous codon alteration produces a Zika virus with compromised virulence.

In another aspect disclosed is a vaccine comprising a genetically engineered attenuated Zika virus made by the method disclosed herein.

Other aspects and embodiments of the disclosure will become apparent in light of the following description and drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A, FIG. 1B, FIG. 1C, and FIG. 1D are a trio of functional ZIKV cDNAs created for the rescue of three molecularly cloned genetically divergent strains: rMR-766, rP6-740, and rPRVABC-59. FIG. 1A is a phylogenetic tree based on the nucleotide sequence of 29 ZIKV genomes, including the 15 complete (MR-766, green; P6-740, orange; PRVABC-59, red; and 12 others, black) and 14 near-complete (gray) genomes, with JEV K87P39 included as an outgroup. Bootstrap values from 1000 replicates are shown at each node of the tree. The scale bar represents the number of nucleotide substitutions per site. Note that MR-766 has been fully sequenced in this study and by three other groups (designated MR-766/CDC, MR-766/NIID, and MR-766/USAMRIID) See also FIG. 8C for a detailed description of the strains used. FIG. 1B is the construction of three full-length ZIKV cDNAs as BACs for MR-766, P6-740, and PRVABC-59. In all three cases, each vgRNA (top panel) was first subcloned into five overlapping cDNAs (middle panel), which were then joined at four shared restriction sites as indicated to assemble its full-length cDNA (bottom panel). Presented below the three full-length cDNAs are the sequences corresponding to the 5' and 3' termini conserved in all three ZIKVs (black lowercase), an SP6 promoter placed just upstream of the viral genome (magenta uppercase), and a run-off site positioned immediately downstream of the viral genome (PsrI or BarI, blue uppercase). Marked below the sequences are the transcription start (white arrowhead) and run-off (black arrowhead) sites. FIG. 1C shows the functionality of the three full-length ZIKV cDNAs. After linearization with PsrI or BarI, as appropriate, each full-length cDNA was used as a template for in vitro transcription with SP6 RNA polymerase in the presence of the dinucleotide cap analog m$^7$GpppA. Capped RNA transcripts were transfected into ZIKV-susceptible African green monkey kidney (Vero) cells to determine the number of infectious centers (plaques) counterstained with crystal violet at 5 days after transfection (RNA infectivity). At 36 h post-transfection, culture supernatants from RNA-transfected cells were harvested to estimate the level of virus production by plaque assay on Vero cells (Virus yield). FIG. 1D are images of plaque morphology. The average plaque sizes were estimated by measuring 20 representative plaques.

FIG. 2A, FIG. 2B, and FIG. 2C are replicative and cytopathic properties of three cloned cDNA-derived ZIKVs (rMR-766, rP6-740, and rPRVABC-59) and their uncloned parental ZIKVs (MR-766, P6-740, and PRVABC-59) in Vero cells. Cells were infected at a multiplicity of infection (MOI) of 1 with each of the six ZIKVs. At the time points indicated after infection, cells were lysed to examine the accumulation levels of vgRNA by real-time RT-PCR with a ZIKV-specific fluorogenic probe (FIG. 2A), and supernatants were collected to analyze the production levels of progeny virions by plaque assay on Vero cells (FIG. 2B). At 5 days post-infection, cell monolayers maintained under a semisolid overlay medium were immunostained with rabbit anti-ZIKV NS1 (α-zNS1) antiserum to visualize the infectious plaques (FIG. 2C). FIG. 2D and FIG. 2E are graphs of the replicability and cytopathogenicity of the three cloned cDNA-derived ZIKVs in a wide range of animal cells (see also FIG. 12). Each virus was used to infect the cell lines (MOI=1) specified in the figure. At the indicated time points, cells were examined microscopically for the degrees of ZIKV-induced cytopathic effect (CPE) (−, 0%; +, 0-25%; ++, 25-50%; +++, 50-75%; ++++, 75-100% cell death), and supernatants were assayed for virus production by plaque assay on Vero cells. hpi, hour post-infection.

FIG. 4A is a schematic illustration showing the antigenic regions recognized by 15 JEV region-specific rabbit antisera. The 10,977-nt vgRNA of JEV SA$_{14}$ has a 95-nt 5'NCR, a 10,299-nt ORF, and a 583-nt 3'NCR (top panel). The ORF encodes a 3,432-aa polyprotein that is processed by viral and cellular proteases into at least 10 mature proteins (middle panel). Marked on the polyprotein are one or two transmembrane domains (vertical black bar) at the C-termini of three structural proteins (C, prM, and E) and at the junction of NS4A/NS4B, as well as four N-glycosylation sites (asterisk) in the pr portion of prM ($^{15}$NNT), E ($^{154}$NYS), and NS1 ($^{130}$NST and $^{207}$NDT). During viral morphogenesis, prM is cleaved by furin protease into a soluble pr peptide and a virion-associated M protein. NS1' is the product of a −1 ribosomal frameshift (F/S) event that occurs at codons 8-9 of NS2A, adding a 52-aa C-terminal extension to the NS1 protein. The bottom panel displays the antigenic regions (horizontal blue bar) recognized by 15 JEV region-specific rabbit antisera and the amino acid sequence identities (% in parentheses) between the corresponding JEV SA$_{14}$ and ZIKV PRVABC-59 regions. FIG. 4B, FIG. 4C, and FIG. 4D are immunoblots identifying viral proteins in ZIKV-infected cells. Vero cells were mock-infected or infected at MOI 1 with each of three ZIKVs (rMR-766, rP6-740, and rPRV-ABC-59) or two JEVs (SA$_{14}$ and SA$_{14}$-14-2, for reference). At 20 h post-infection, total cell lysates were separated by SDS-PAGE on a glycine (Gly) or tricine (Tri) gel and analyzed by immunoblotting with each of the 15 JEV region-specific rabbit antisera or α-GAPDH rabbit antiserum as a loading and transfer control. Molecular size markers are given on the left of each blot, and major JEV proteins for reference are labeled on the right. Provided below each blot are the estimated molecular sizes of the predicted ZIKV proteins, and marked on the blot are the predicted (yellow or pink dot) and unexpected (white circle) proteins. CHO, N-glycosylation.

Figure 5A:
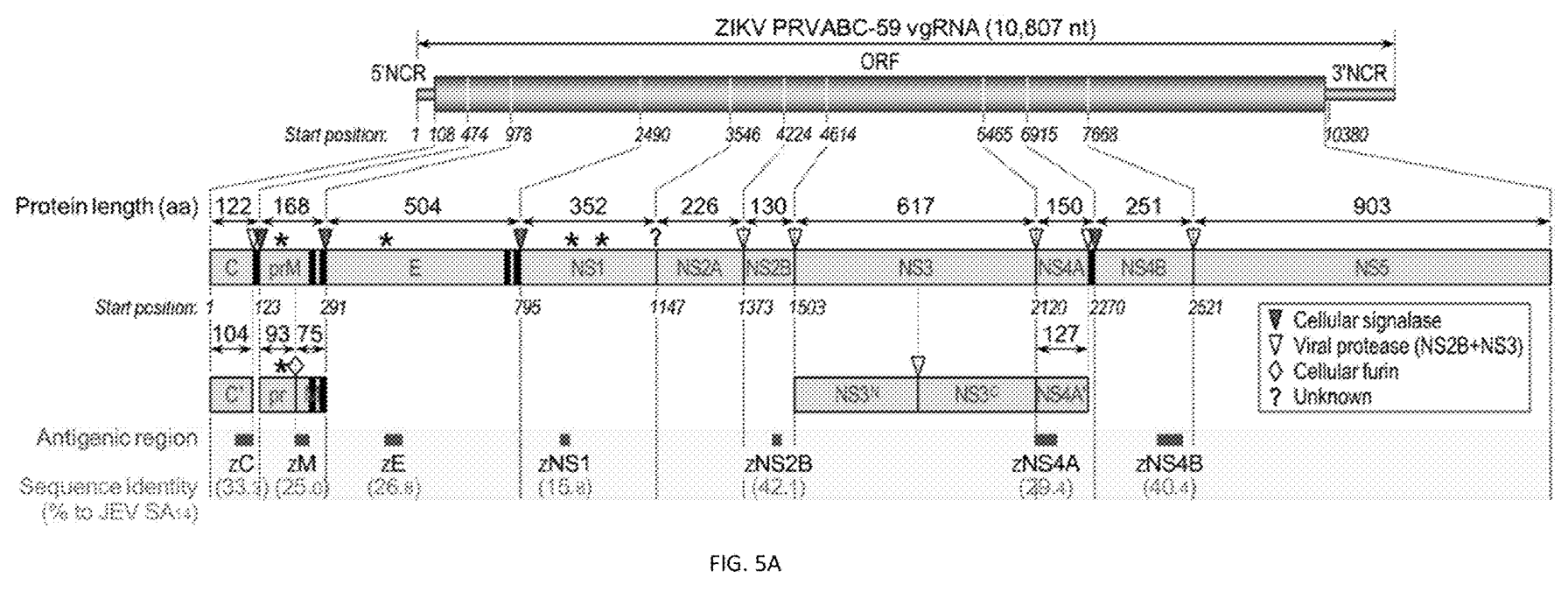
Figure 5B:
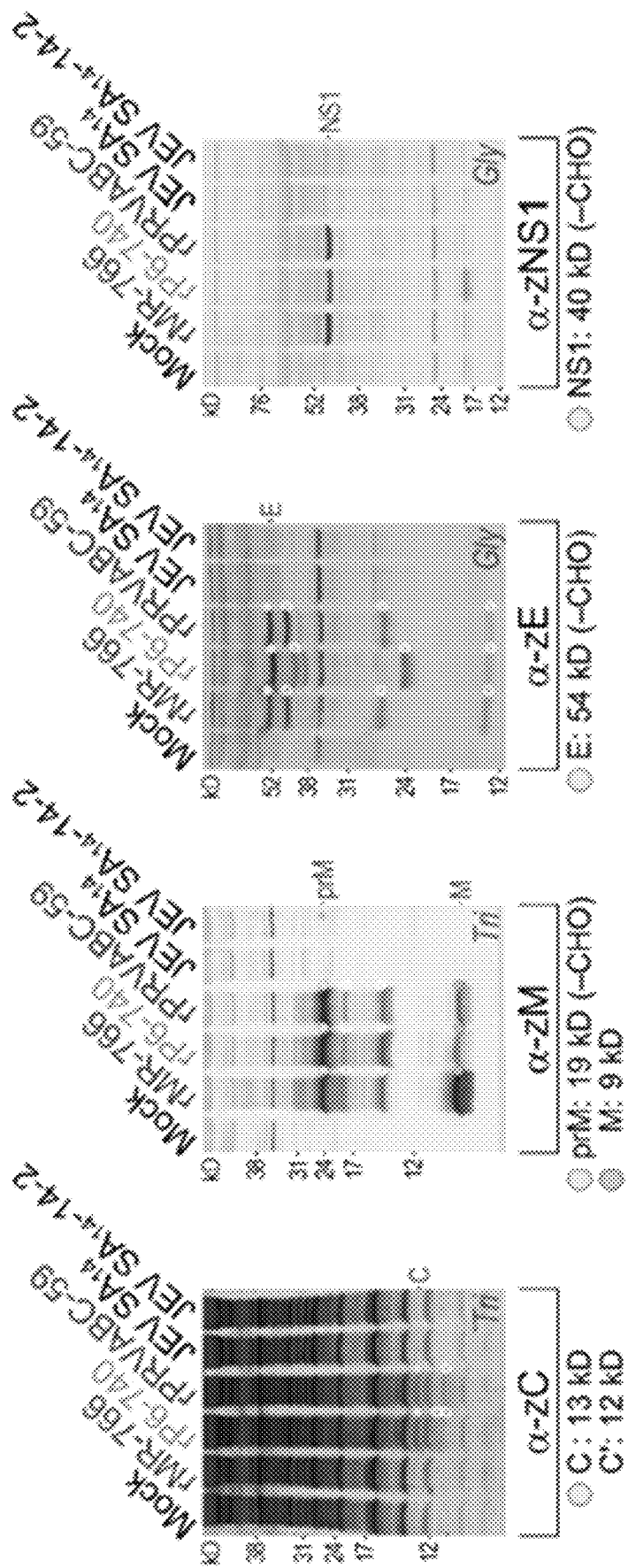
Figure 5C:
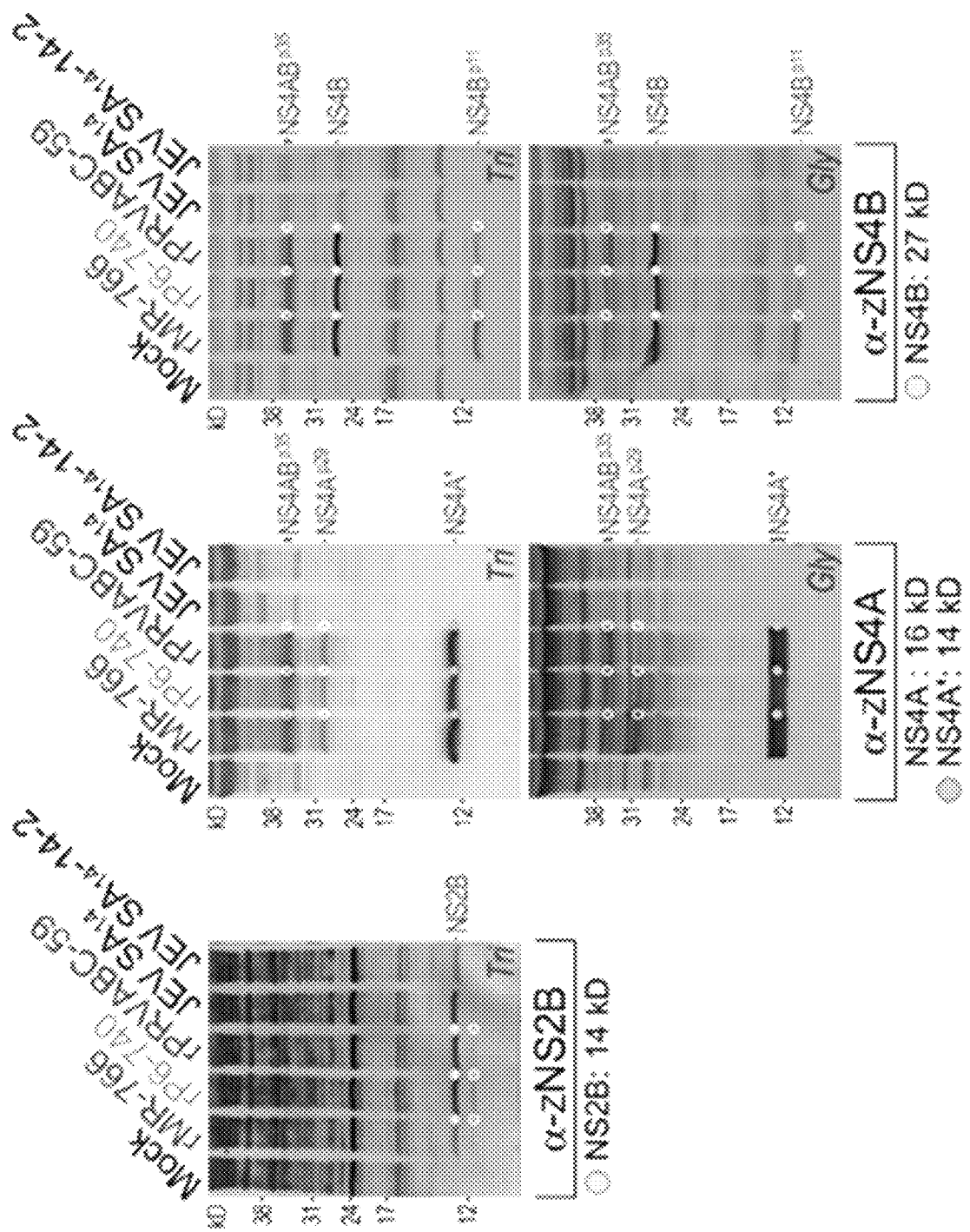

FIG. 5A, FIG. 5B, and FIG. 5C show that a panel of seven ZIKV region-specific polyclonal antibodies identifies ZIKV C, prM/M, E, NS1, NS2B, NS4A', NS4B, and their related species in ZIKV-infected cells. FIG. 5A is a schematic illustration showing the antigenic regions recognized by seven ZIKV region-specific rabbit antisera. The 10,807-nt vgRNA of ZIKV PRVABC-59 consists of a 107-nt 5'NCR, a 10,272-nt ORF, and a 428-nt 3'NCR (top panel). The ORF encodes a 3,423-aa polyprotein that is predicted to be cleaved by viral and cellular proteases into at least 10 mature proteins (middle panel). Marked on the polyprotein and its products are one or two transmembrane domains (vertical black bar) at the C-termini of three structural proteins (C, prM, and E) and at the junction of NS4A/NS4B, as well as four N-glycosylation sites (asterisk) in the pr portion of prM ($^{70}$NTT), E ($^{154}$NDT), and NS1 ($^{130}$NNS and $^{207}$NDT). The bottom panel shows the antigenic regions (horizontal magenta bar) recognized by seven ZIKV region-specific rabbit antisera and the amino acid sequence identities (% in parentheses) between the corresponding ZIKV PRVABC-59 and JEV SA$_{14}$ regions. FIG. 5B and FIG. 5C are immunoblots of the identification of viral proteins in ZIKV-infected cells. Vero cells were mock-infected or infected at MOI 1 with each of three ZIKVs (rMR-766, rP6-740, and rPRV-ABC-59) or two JEVs (SA$_{14}$ and SA$_{14}$-14-2, for comparison). At 20 h post-infection, total cell lysates were separated by SDS-PAGE on a glycine (Gly) or tricine (Tri) gel and analyzed by immunoblotting with each of the seven ZIKV region-specific rabbit antisera. Molecular size markers are given on the left of each blot, and major ZIKV proteins are labeled on the right. Provided below each blot are the estimated molecular sizes of predicted ZIKV proteins, and marked on the blot are the predicted (yellow or pink dot) and unexpected (white circle) proteins. CHO, N-glycosylation.

Figure 6A:
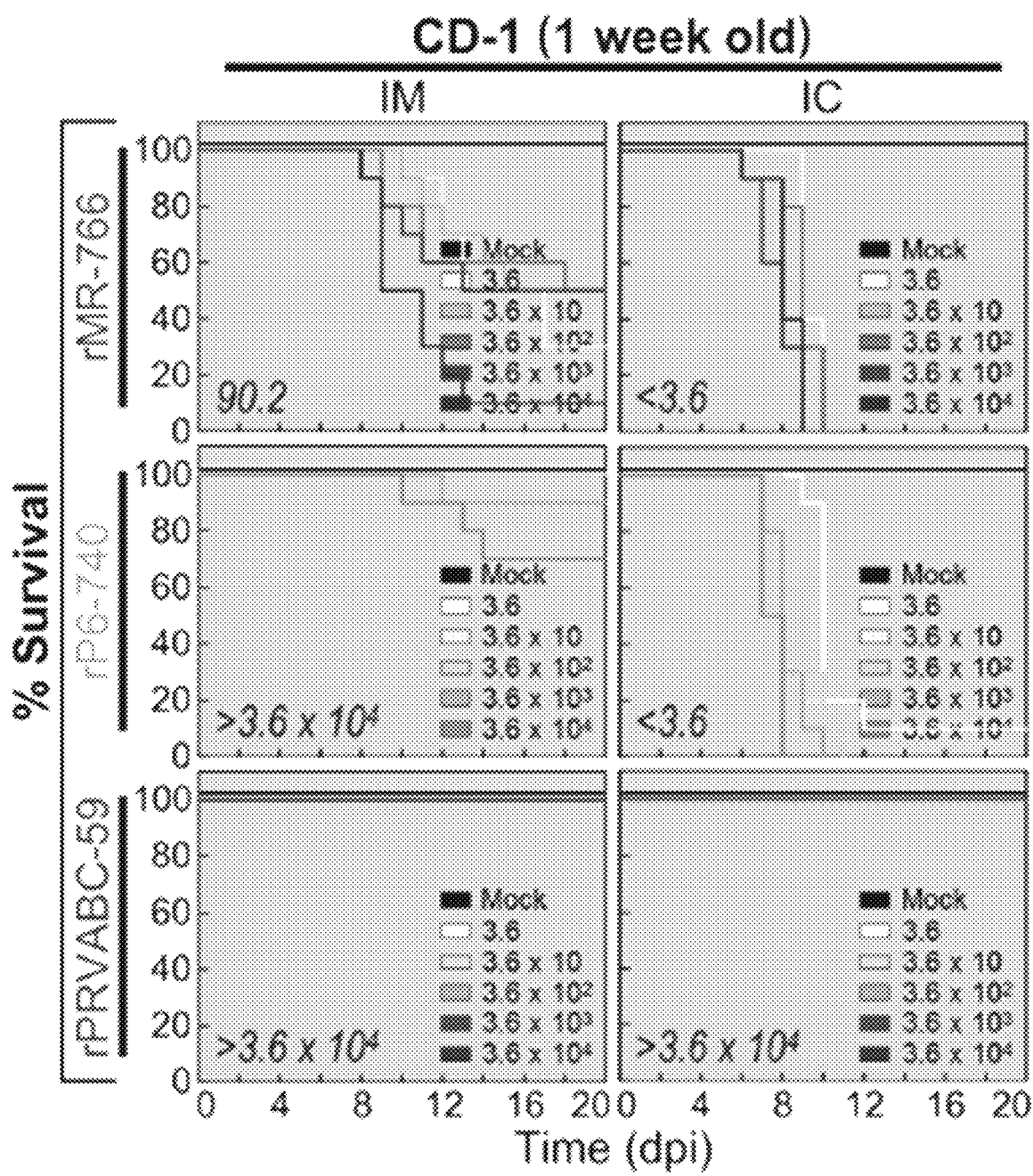
Figure 6B:
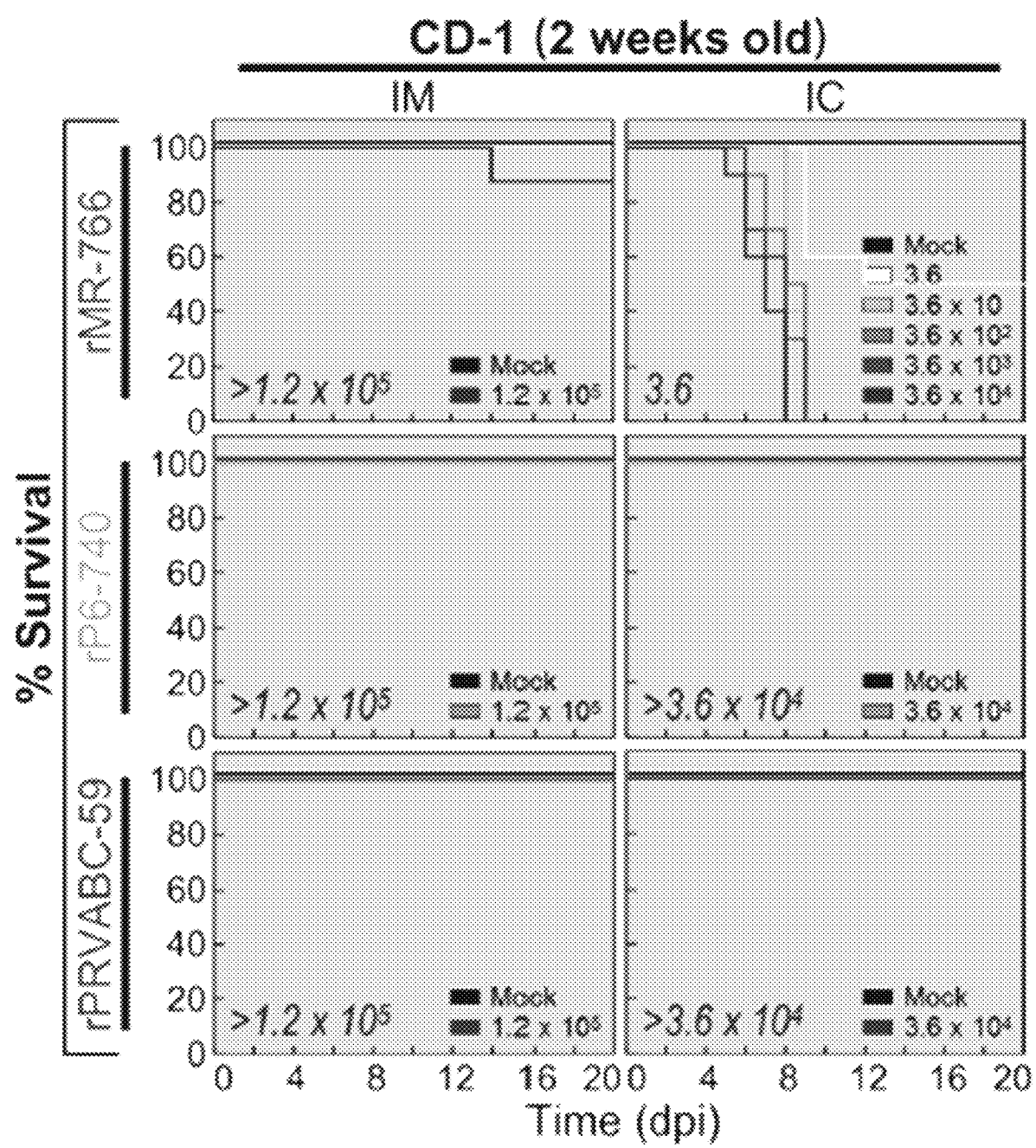
Figure 6C:
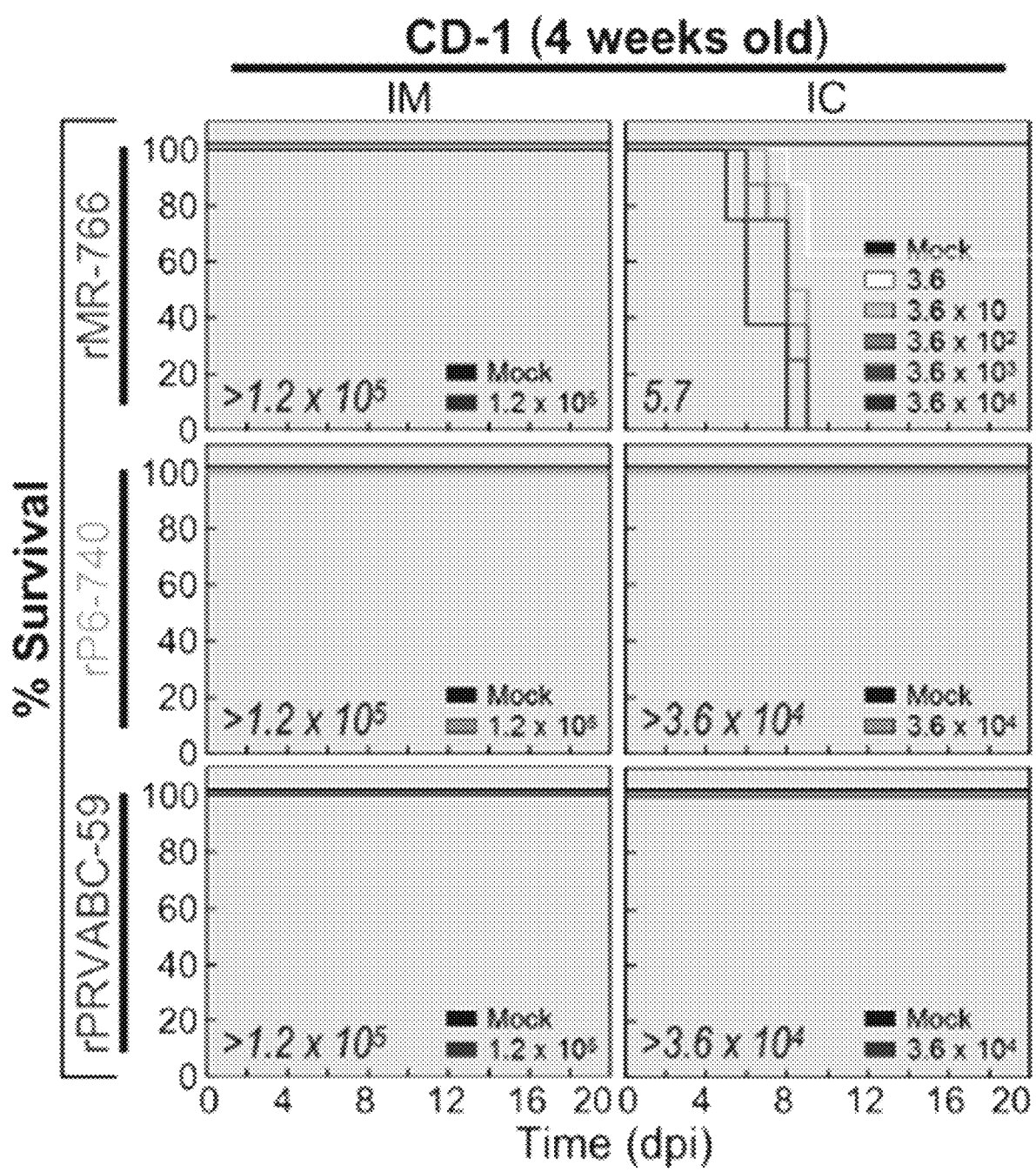
Figure 6D:
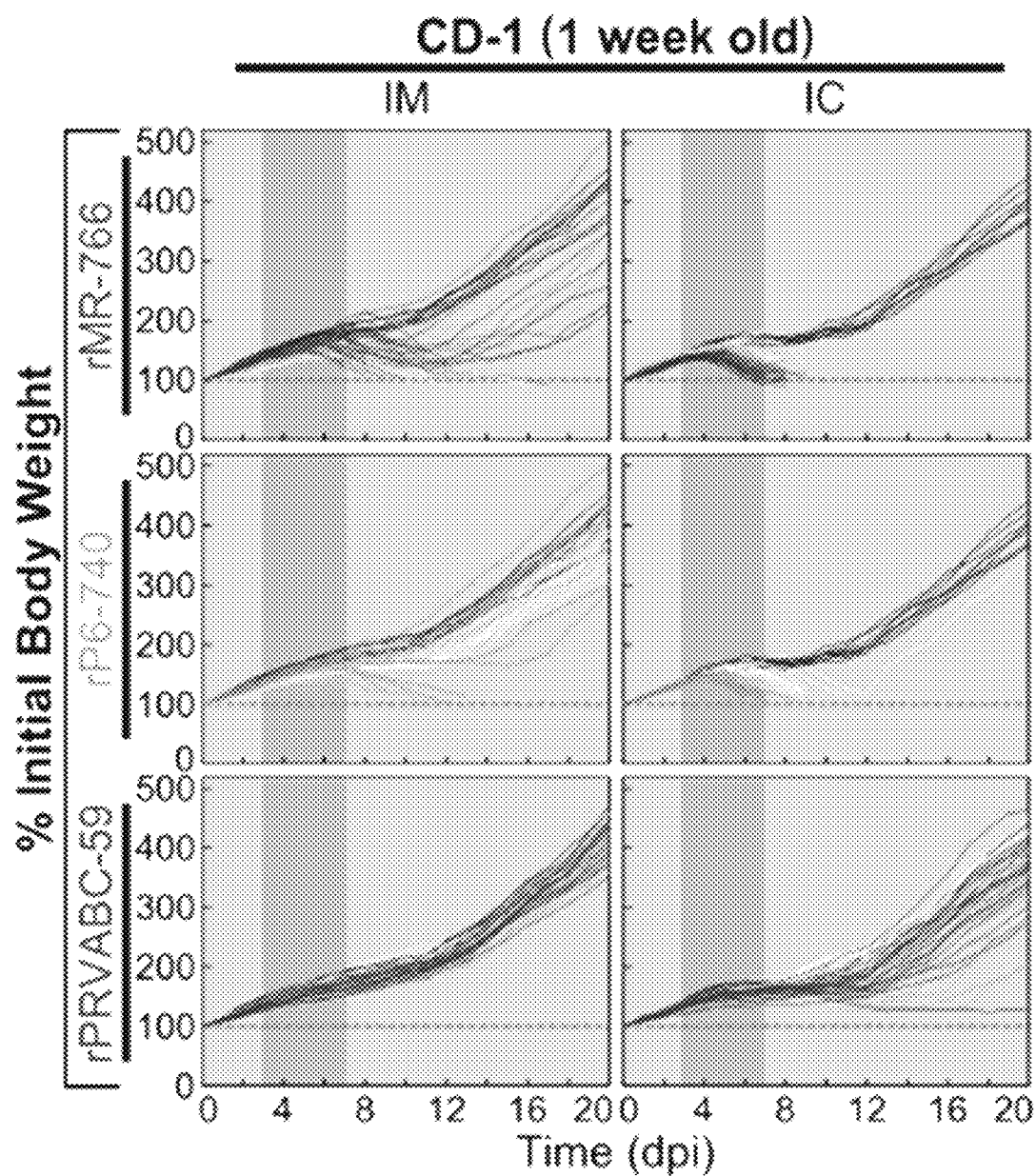
Figure 6E:
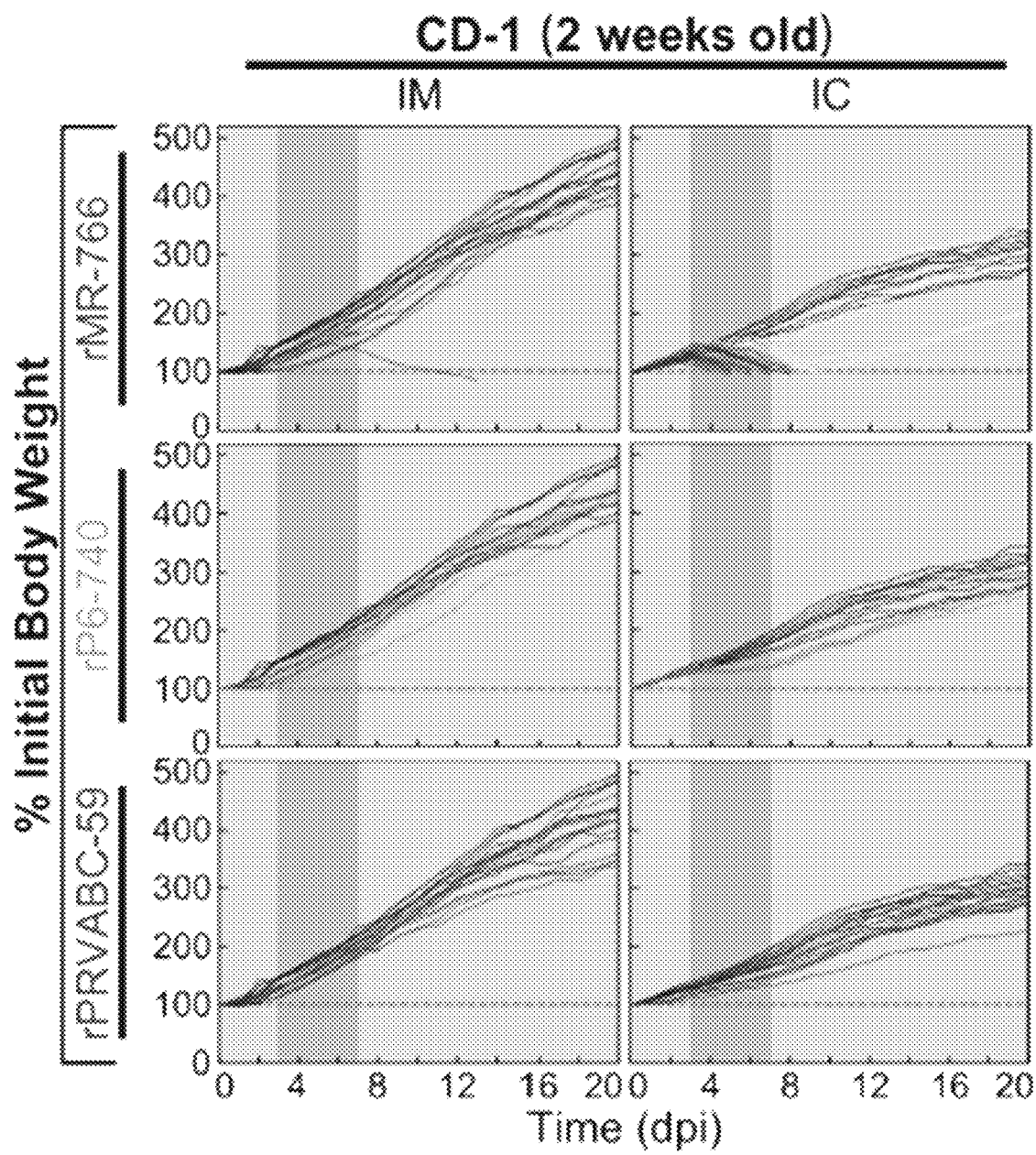
Figure 6F:
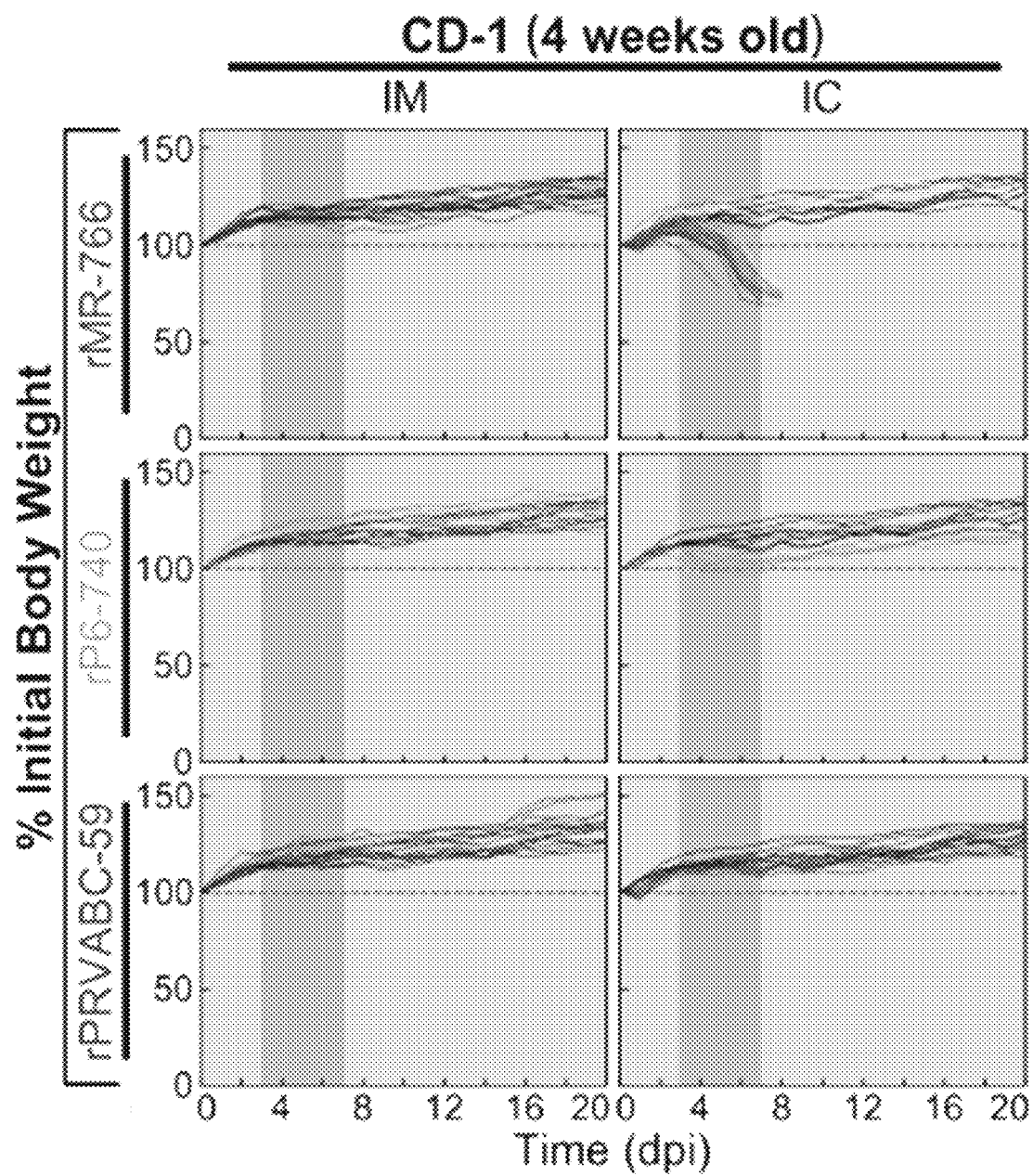

FIG. 6A, FIG. 6B, FIG. 6C, FIG. 6D, FIG. 6E, and FIG. 6F show that three molecularly cloned ZIKVs display a full range of variation in neuropathogenicity for outbred CD-1 mice in an age-dependent manner. Groups of CD-1 mice (n=8-10, half male, half female) were mock-inoculated or inoculated at 1, 2, and 4 weeks of age via the intramuscular (IM) or intracerebral (IC) route with a maximum dose of 3.6×10$^4$ or 1.2×10$^5$ plaque-forming unit (PFU), or serial 10-fold dilutions of rMR-766, rP6-740, or rPRVABC-59. FIGS. 6A-6C are survival curves generated by the Kaplan-Meier method. The lethal dose 50% (LD$_{50}$) values were determined by the Reed-Muench method and are presented in the bottom left corner of each curve. FIGS. 6D-6F are graphs of weight changes with each mouse represented by one color-coded line. dpi, days post-infection.

Figure 7A:
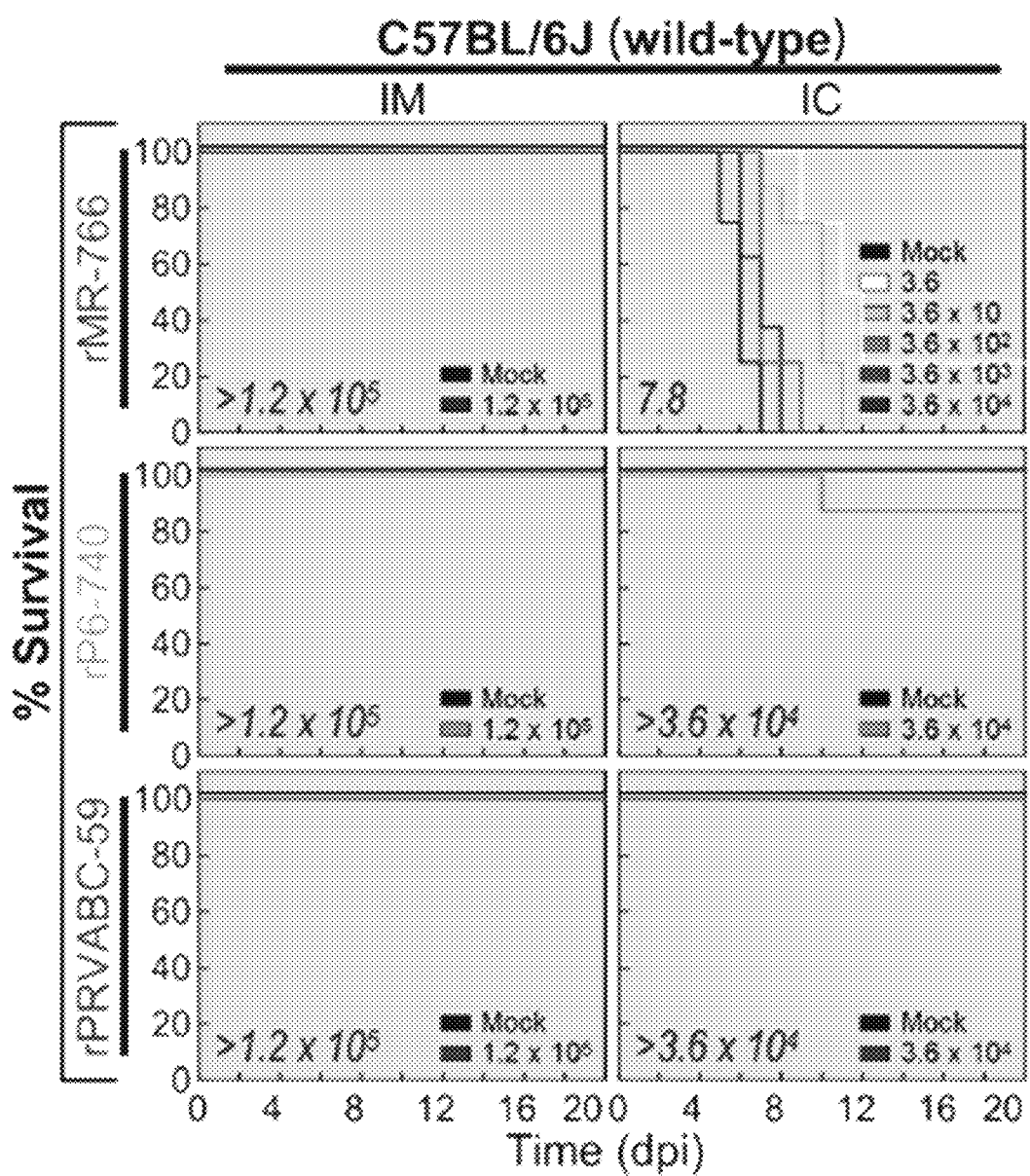
Figure 7B:
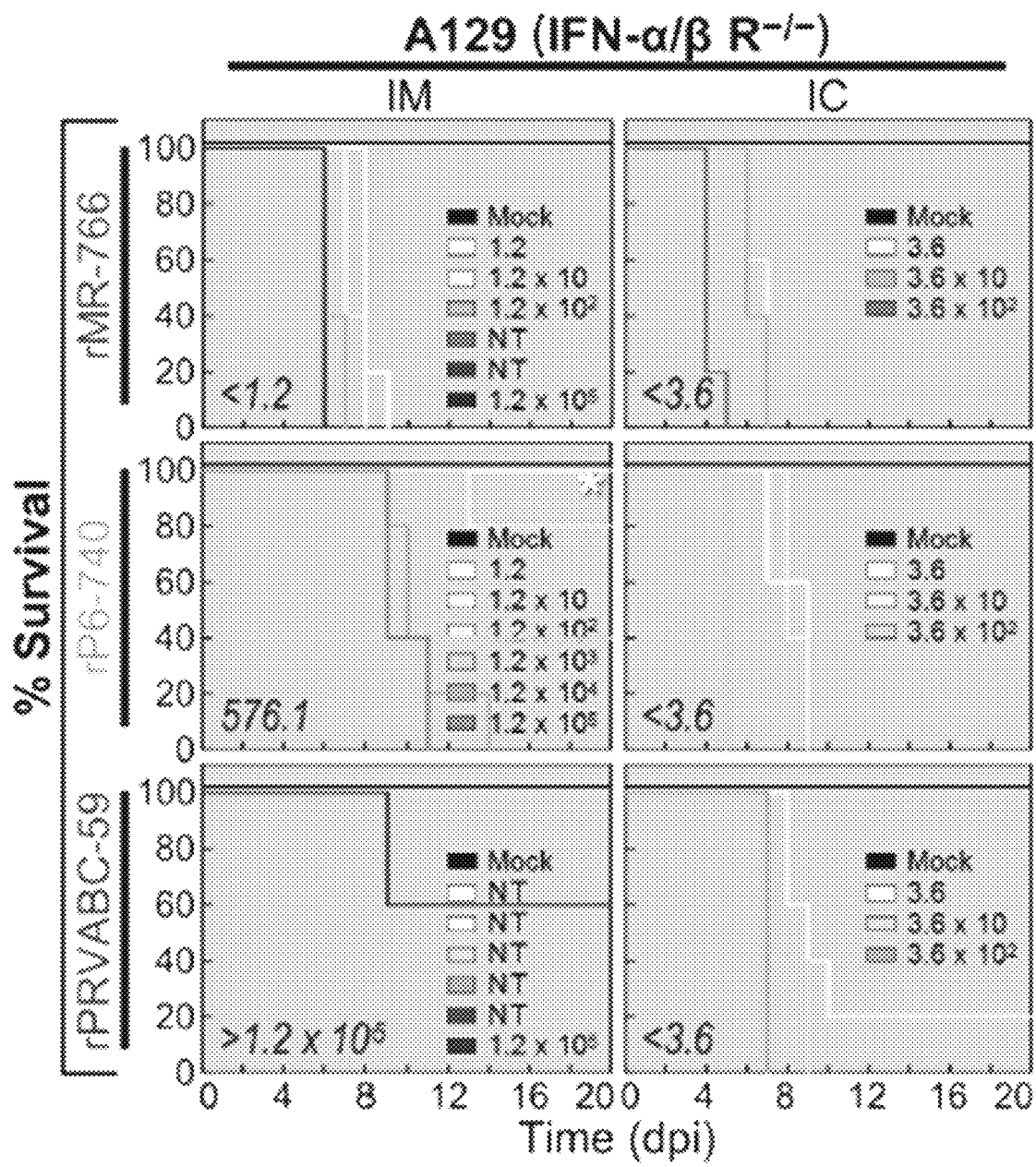
Figure 7C:
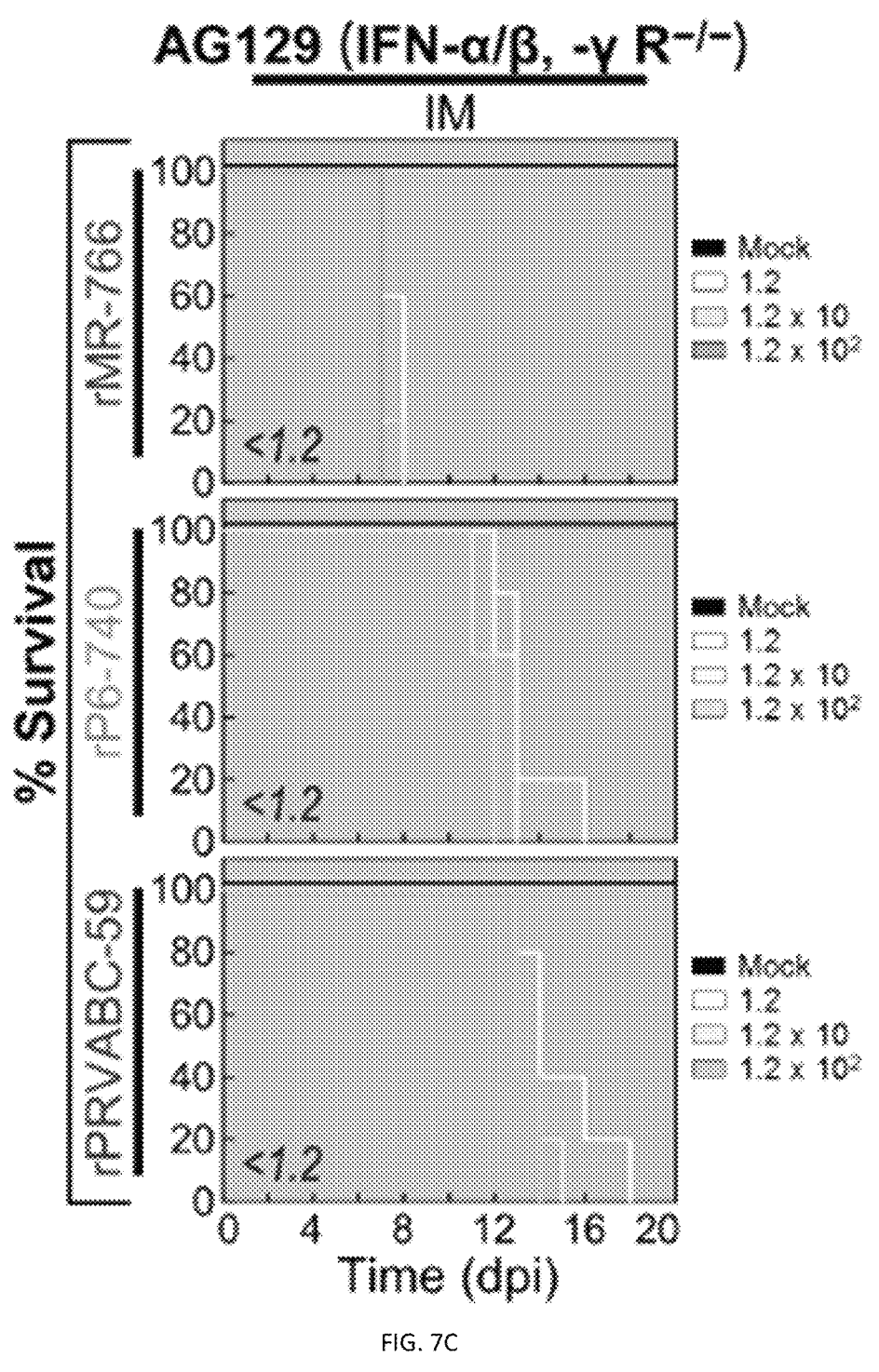
Figure 7D:
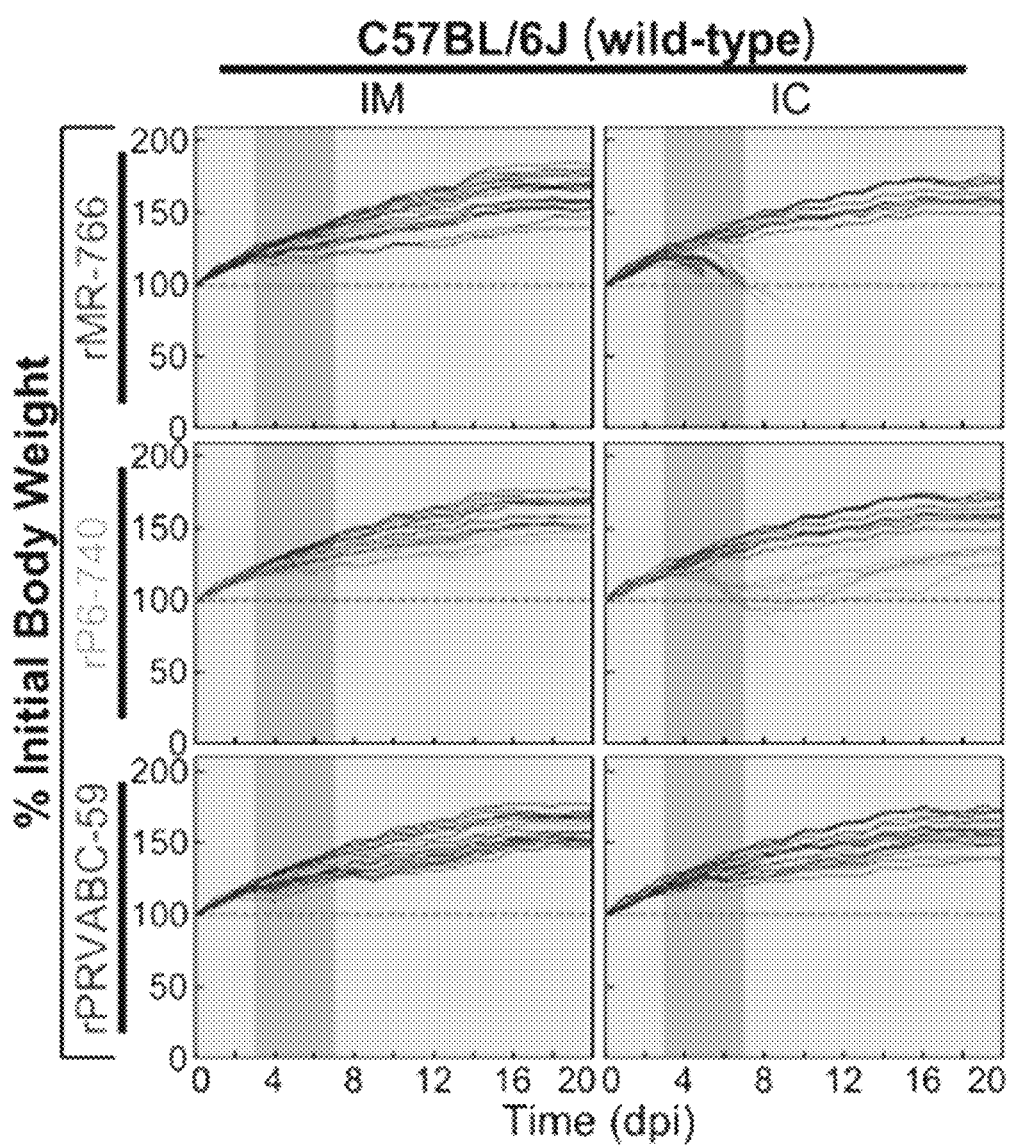
Figure 7E:
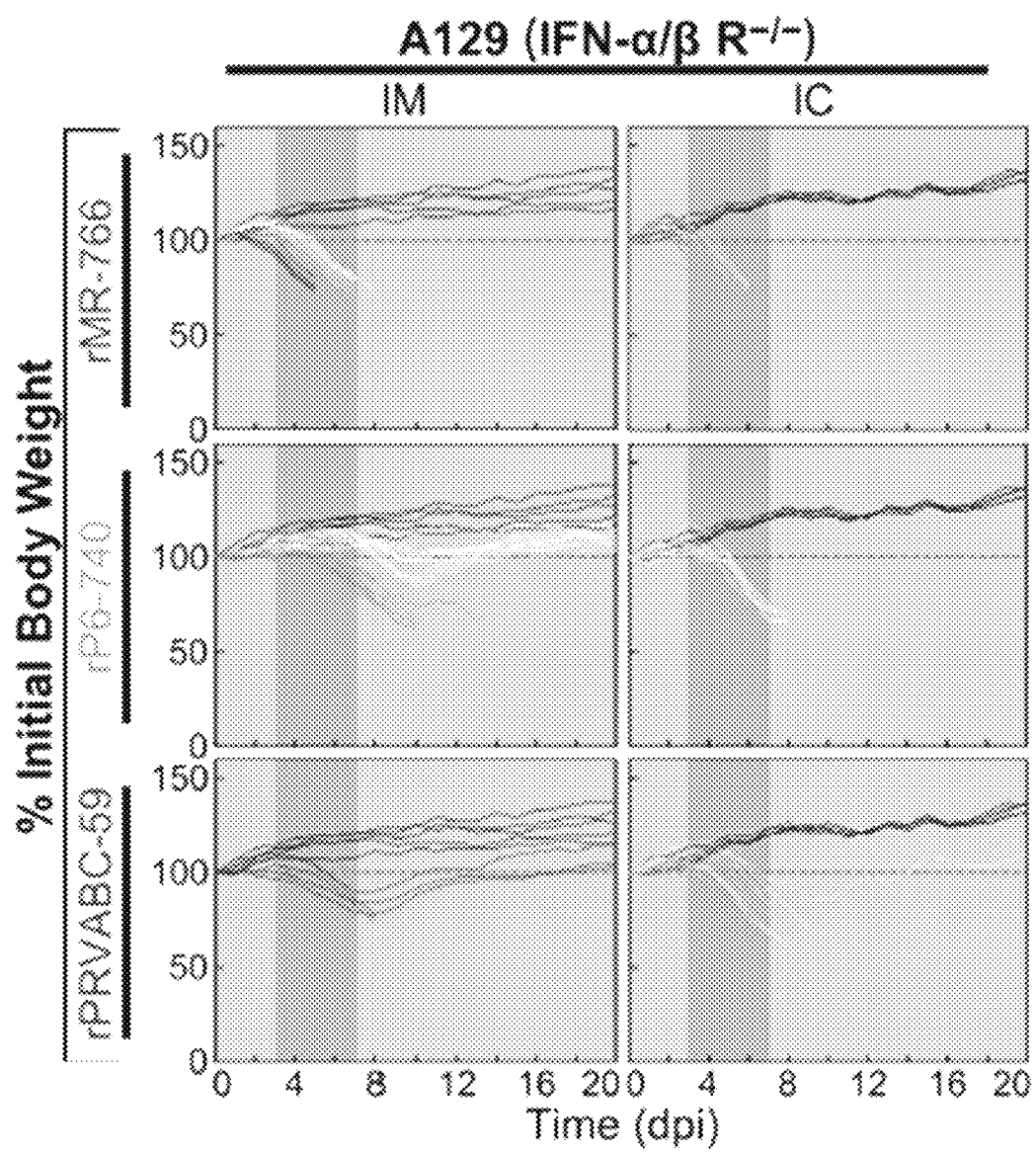
Figure 7F:
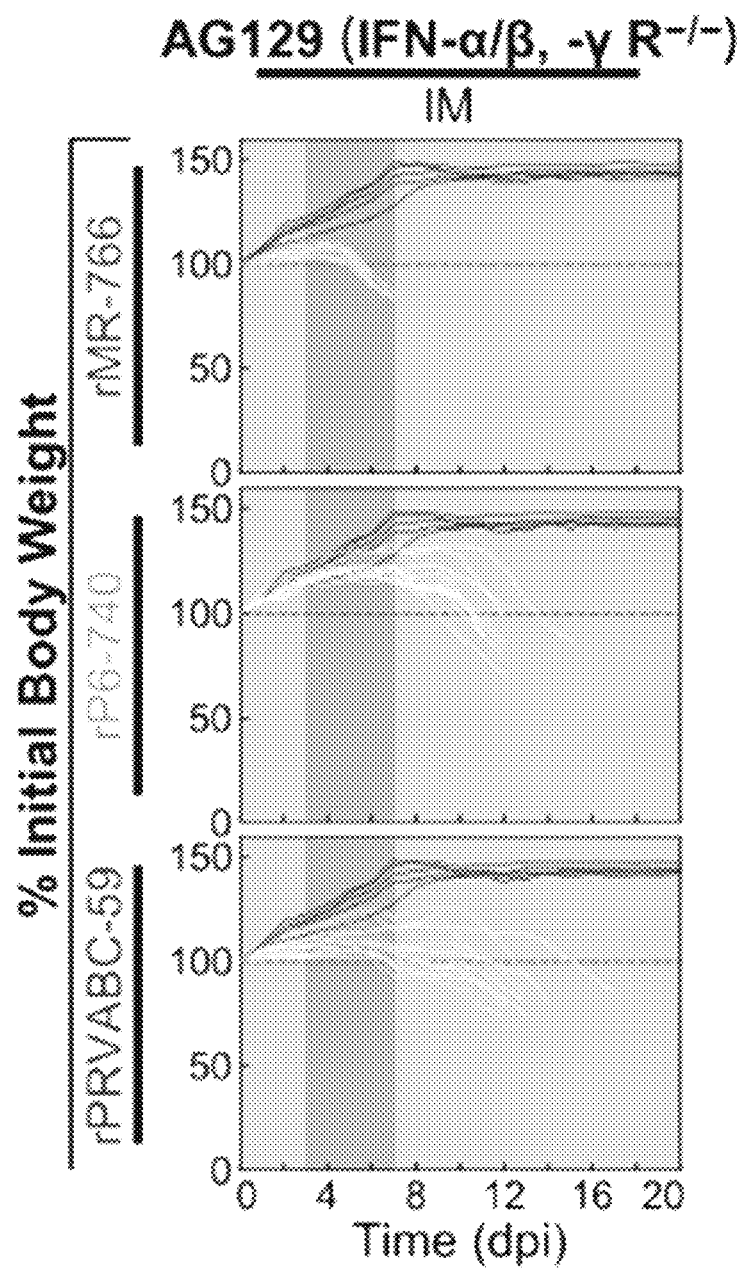

FIG. 7A, FIG. 7B, FIG. 7C, FIG. 7D, FIG. 7E, and FIG. 7F show a full spectrum of variation in interferon (IFN) sensitivity in mice lacking type I or both type I and II IFN receptors for the three molecularly cloned ZIKVs. Groups of 4-week-old C57BL/6J (n=8), A129 (n=5), or AG129 (n=5) mice, approximately half of each sex, were mock-inoculated or inoculated through the intramuscular (IM) or intracerebral (IC) route with a maximum dose of 3.6×10$^4$ or 1.2×10$^5$ PFU, or serial 10-fold dilutions of rMR-766, rP6-740, or rPRV-ABC-59. FIGS. 7A-7C are survival curves created by the Kaplan-Meier method. The LD$_{50}$ values were calculated by the Reed-Muench method and are given in the bottom left corner of each curve. FIGS. 7D-7F are graphs of weight changes with each mouse indicated by one color-coded line. NT, not tested; dpi, days post-infection.

Figure 8C:
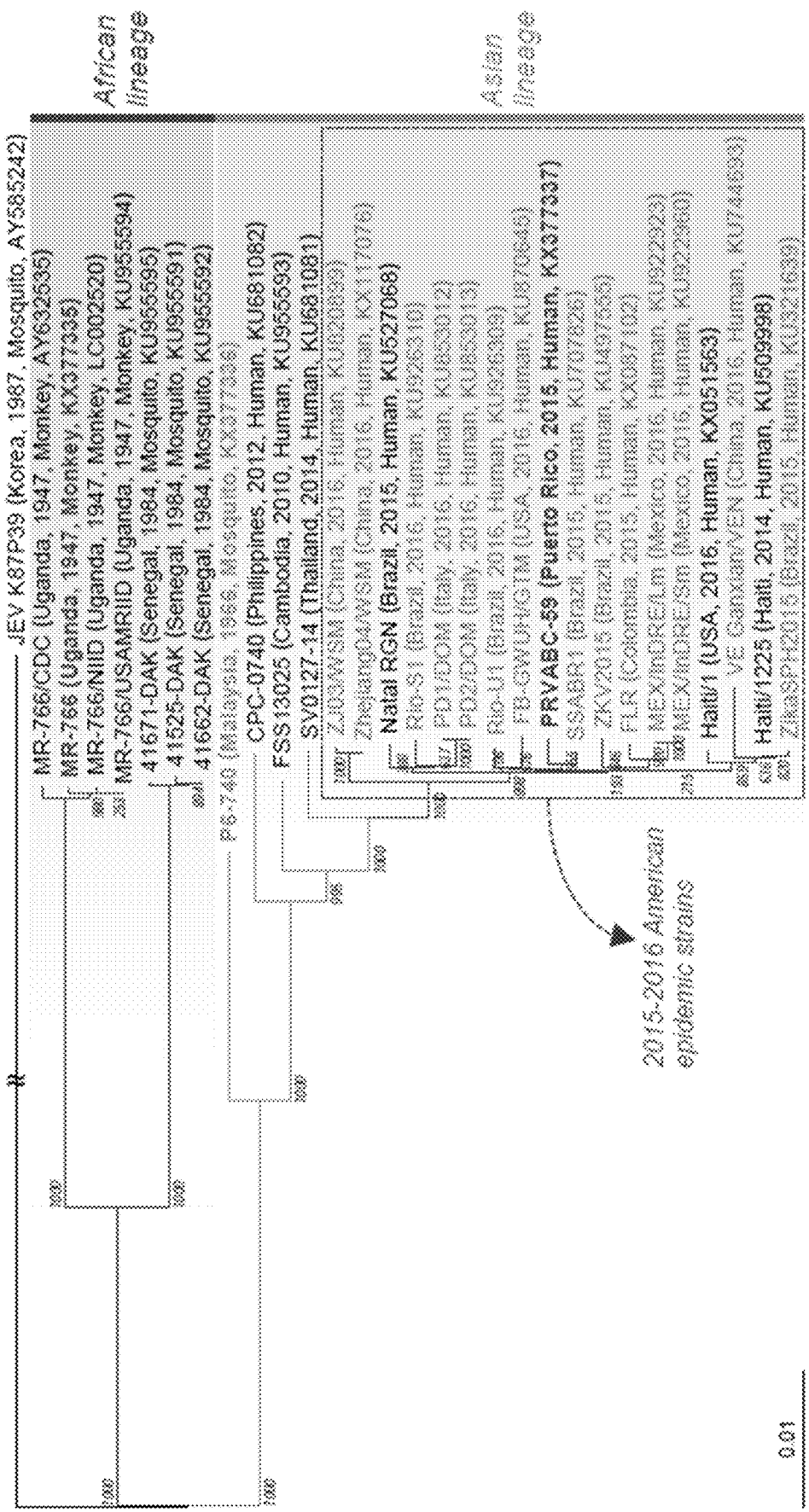

FIG. 8A, FIG. 8B, and FIG. 8C show the spectrum of ZIKV genetic diversity that is represented by three historically important and spatiotemporally distinct strains: MR-766, P6-740, and PRVABC-59. The consensus nucleotide sequence for each of their full-length vgRNAs was determined by sequencing three overlapping uncloned cDNA amplicons collectively representing the entire vgRNA except for the 5' and 3' termini, which were subsequently defined by performing both 5'- and 3'-rapid amplification of cDNA ends (RACEs); each of these RACEs was followed by cDNA cloning and sequencing of ~20 randomly picked clones. FIG. 8A is a chart of the genomic organization of the three ZIKV strains. FIG. 8B is a chart of the pairwise comparison of the complete nucleotide (nt) and deduced amino acid (aa) sequences of the three ZIKV genomes. FIG. 8C is a phylogenetic tree based on the nucleotide sequence of 29 ZIKV genomes, including the 15 complete (MR-766, green; P6-740, orange; PRVABC-59, red; and 12 others, black) and 14 near-complete (gray) genomes, with JEV K87P39 included as an outgroup. Bootstrap values from 1000 replicates are shown at each node of the tree. The scale bar represents the number of nucleotide substitutions per site. The strain name is followed by a description in parenthesis of the country, year, and host of isolation and the GenBank accession numbers. Note that MR-766 has been fully sequenced in this study and by three other groups (designated MR-766/CDC, MR-766/NIID, and MR-766/USAMRIID).

Figure 9:
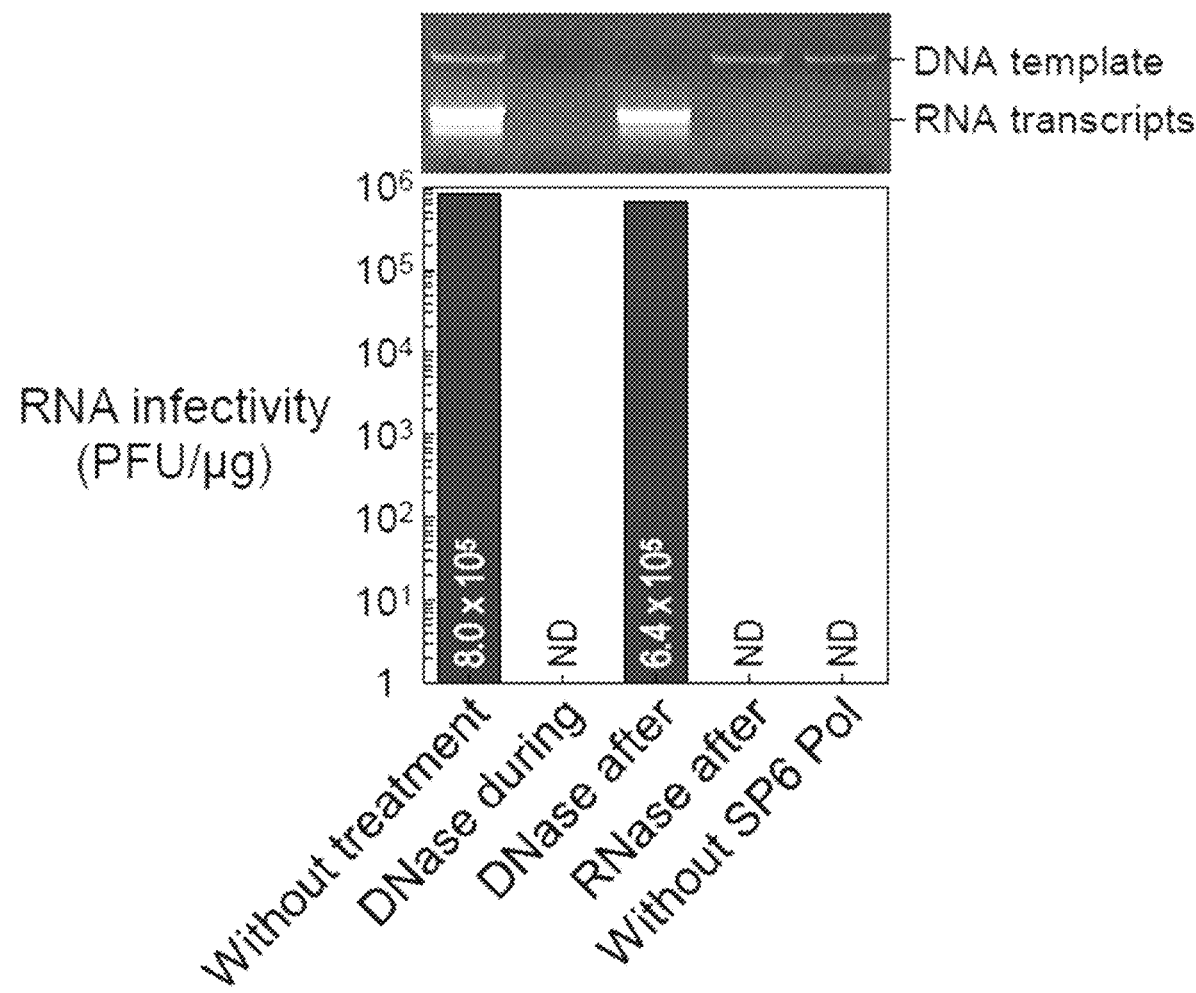

FIG. 9 shows that infectious RNA is derived by transcription from a full-length ZIKV cDNA clone. The BarI-linearized pBac/PRVABC-59 (250 ng) was used as the template DNA in a 25-µl transcription reaction with SP6 RNA polymerase to synthesize capped RNA in the absence (without treatment) or presence (DNase during) of DNase I. After completion of the transcription, some reaction mixtures were treated with DNase I (DNase after) or RNase A (RNase after) for 30 min at 37° C. A control reaction was carried out in parallel in the absence of SP6 RNA polymerase (without SP6 Pol). A 2-µl aliquot of each reaction mixture was separated on a 0.6% agarose gel containing ethidium bromide to visualize the integrity of the DNA template and RNA transcripts (Top). A 20-µl portion of each reaction mixture was transfected directly into Vero cells, and infectious centers (plaques) were counted after counterstaining with crystal violet at 5 days post-transfection. ND, not detected (Bottom).

Figure 10:
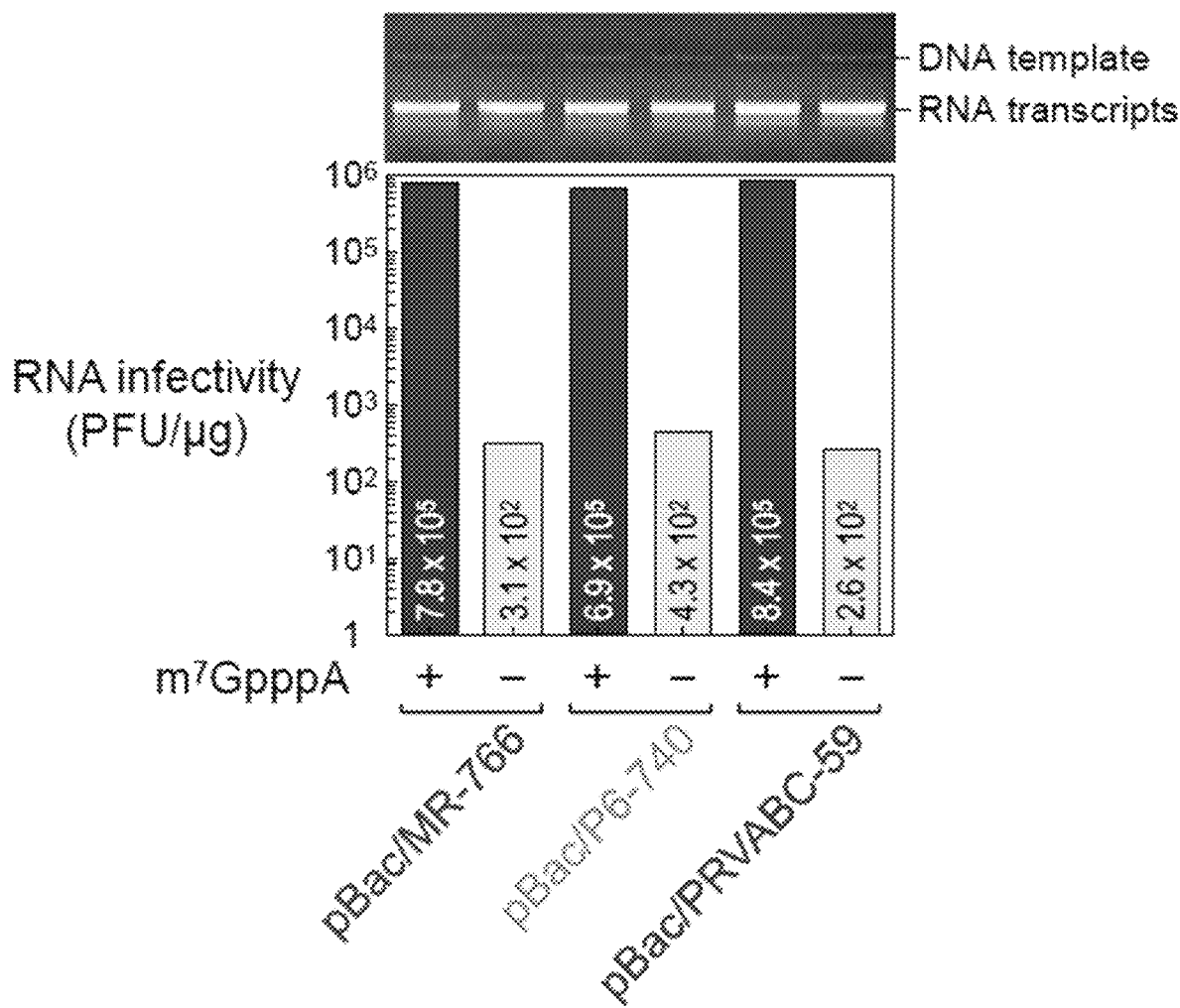

FIG. 10 shows that a 5' cap on the in vitro transcribed ZIKV RNA maximizes its specific infectivity. Each of the three PsrI/BarI-linearized full-length ZIKV cDNAs (250 ng), as indicated, was used as a DNA template in a 25-µl transcription reaction with SP6 RNA polymerase in the presence or absence of the dinucleotide cap analog m$^7$GpppA. A 2-µl aliquot of the reaction mixtures was run on a 0.6% agarose gel containing ethidium bromide to visualize the integrity of the DNA template and RNA transcripts (Top). A 20-µl portion of the reaction mixtures was transfected into Vero cells, and infectious centers (plaques) were counted after counterstaining with crystal violet at 5 days post-transfection (Bottom).

Figure 11:
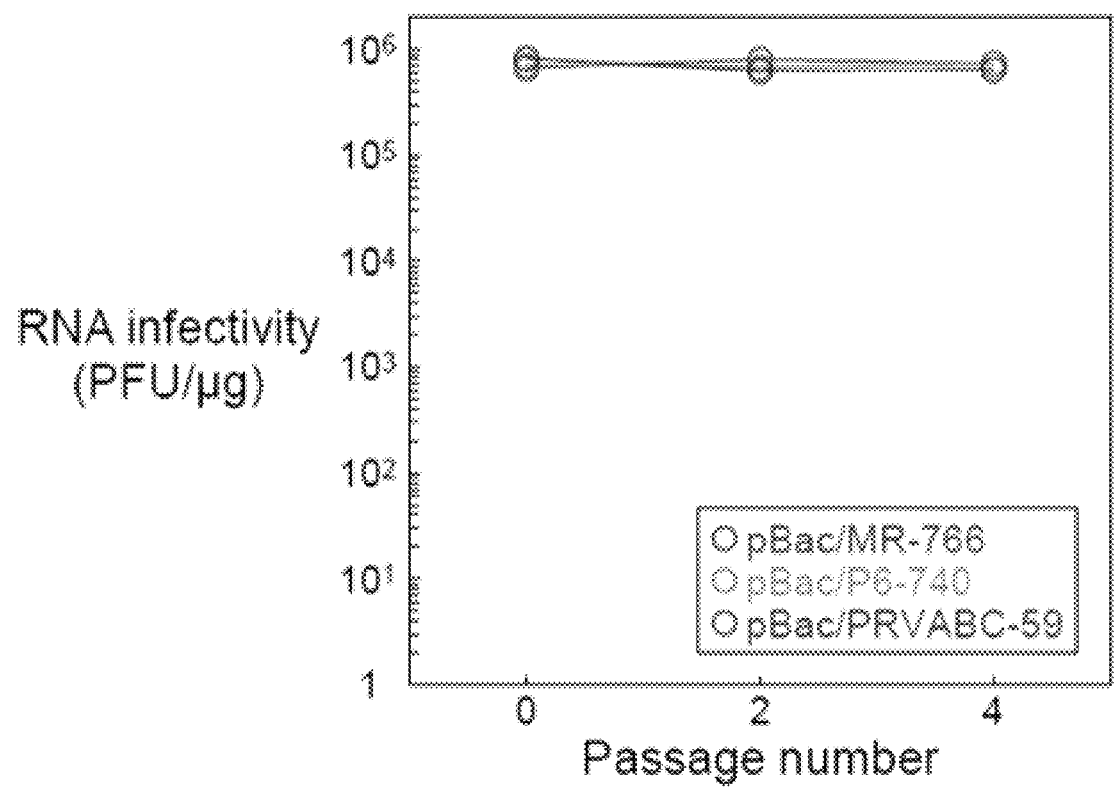

FIG. 11 is a graph of the three functional ZIKV cDNAs as BACs stably propagated in bacteria. A colony of E. coli DH10B cells transformed with each of three functional ZIKV BACs (pBac/MR-766 (SEQ ID NO:1), pBac/P6-740 (SEQ ID NO:2), and pBac/PRVABC-59 (SEQ ID NO:3)) was picked randomly and grown at 35° C. overnight in 2×YT medium with chloramphenicol (passage 0). Cells from these initial cultures were then passaged four times by diluting them $10^6$-fold daily. At passages 0, 2, and 4, the ZIKV BACs were purified, linearized, and transcribed in vitro for the synthesis of capped RNAs. The transcribed RNAs were subsequently transfected into Vero cells to determine their specific infectivity.

Figure 12:
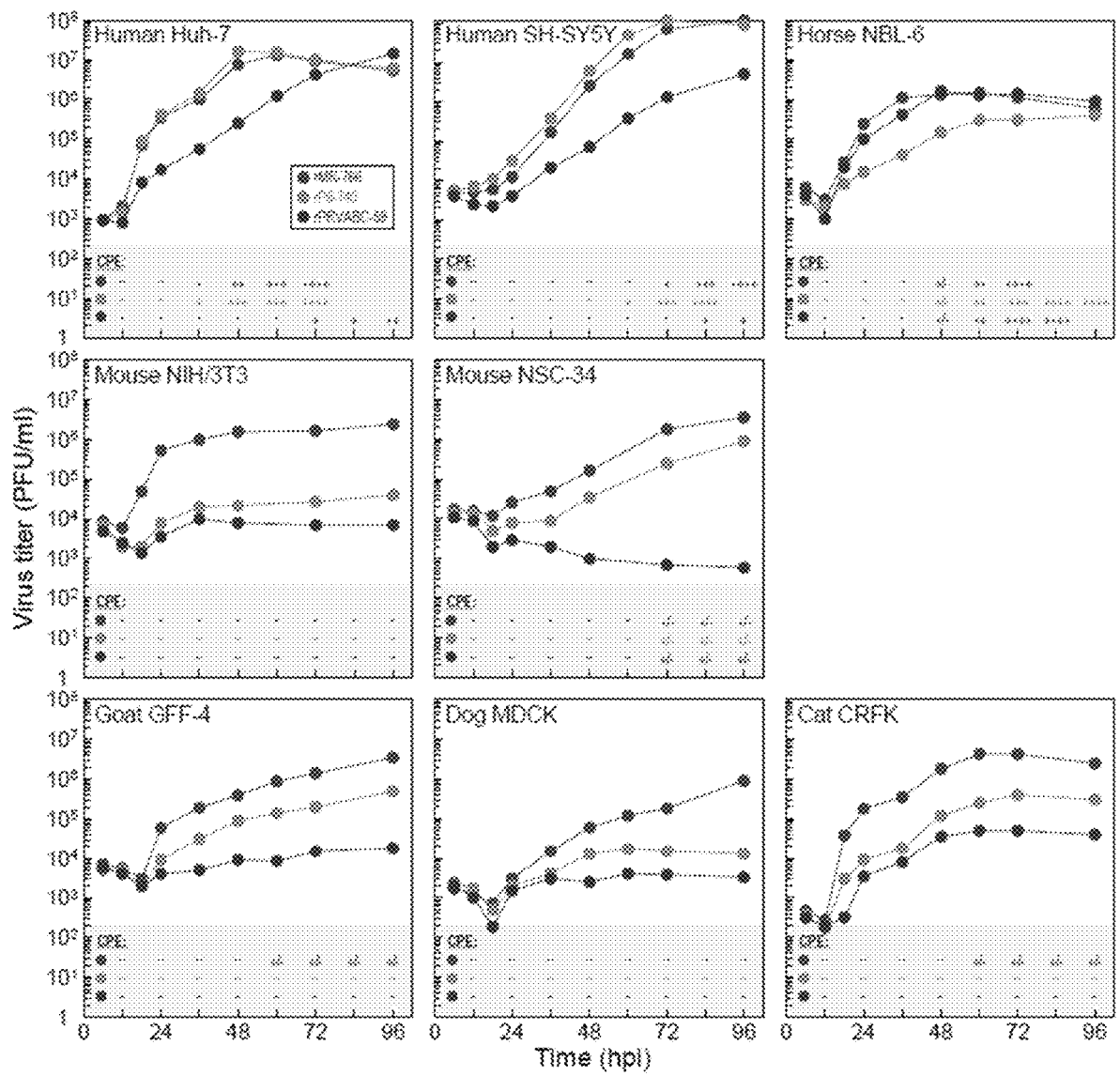

FIG. 12 is graphs of ZIKV replicability and cytopathogenicity in cell cultures that depends on the particular combination of virus strain and host cells. Each of three molecularly cloned ZIKVs (rMR-766, rP6-740, and rPRV-ABC-59) was used to infect the indicated cells at an MOI of 1. At the time points marked in the figure, cells were examined microscopically to determine the degrees of ZIKV-induced CPE (−, 0%; +, 0-25%; ++, 25-50%; +++, 50-75%; ++++, 75-100% cell death), and supernatants were harvested to evaluate the levels of virus production by plaque assay on Vero cells. hpi, hour post-infection.

Figures 13A, 13B:
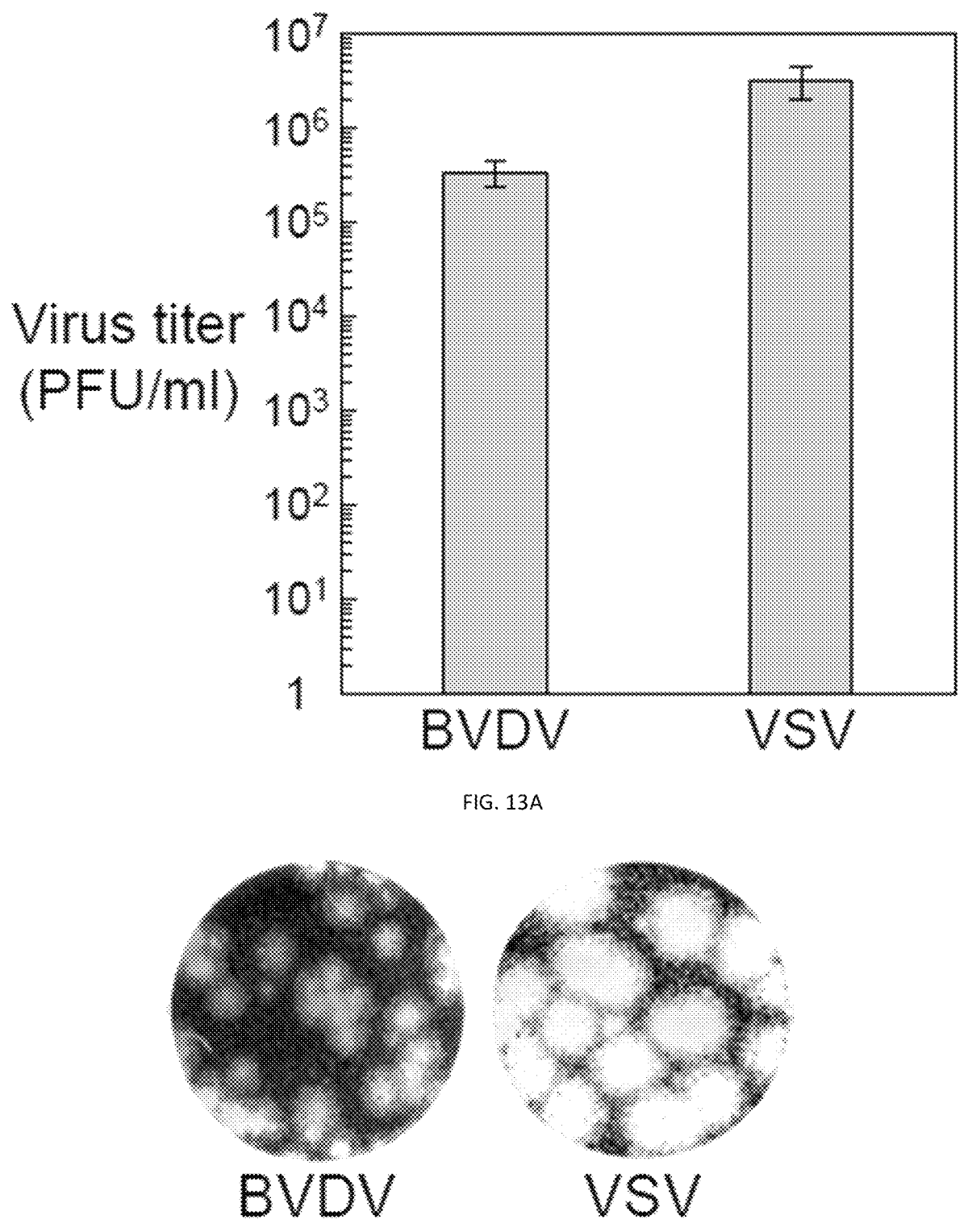

FIG. 13A and FIG. 13B show that MDBK cells are highly susceptible to infection with both bovine viral diarrhea virus (BVDV) and vesicular stomatitis virus (VSV). MDBK cells were infected at an MOI of 1 with BVDV (strain NADL) or VSV (strain Indiana). FIG. 13A is a graph of viral replication. At 36 h post-infection, culture supernatants were tested to measure the infectious virus yields by plaque assay on MDBK cells. FIG. 13B shows representative plaques. At 3 days post-infection, cell monolayers maintained under a semisolid overlay medium were counterstained with crystal violet to visualize the infectious plaques.

FIG. 14 is a chart showing the details of the 15 JEV region-specific rabbit antisera used to detect their antigenically cross-reactive ZIKV counterparts. A collection of 15 rabbit antisera covering nearly all parts of the JEV protein-coding regions were raised by immunization with 14 E. coli-expressed glutathione-S-transferase (GST) fusion proteins ($\alpha$-jC, $\alpha$-jPr, $\alpha$-jM, $\alpha$-jE$^{N\text{-}term}$, $\alpha$-jE$^{C\text{-}term}$, $\alpha$-jNS1$^{N\text{-}term}$, $\alpha$-jNS1$^{C\text{-}term}$, $\alpha$-jNS1$^{\prime FS}$, $\alpha$-jNS3$^{N\text{-}term}$, $\alpha$-jNS3$^{C\text{-}term}$, $\alpha$- jNS4A, $\alpha$-jNS4B, $\alpha$-jNS5$^{N\text{-}term}$, and $\alpha$-jNS5$^{C\text{-}term}$) or with a keyhole limpet hemocyanin (KLH)-conjugated synthetic oligopeptide ($\alpha$-jNS2B). The nucleotide (nt) and amino acid (aa) positions of the viral antigenic regions (blue) are based on the complete genomic sequence of JEV SA$_{14}$ (GenBank accession no. KU323483; see also FIG. 4A). The working dilutions of the rabbit antisera used herein are provided.

Figure 15B:
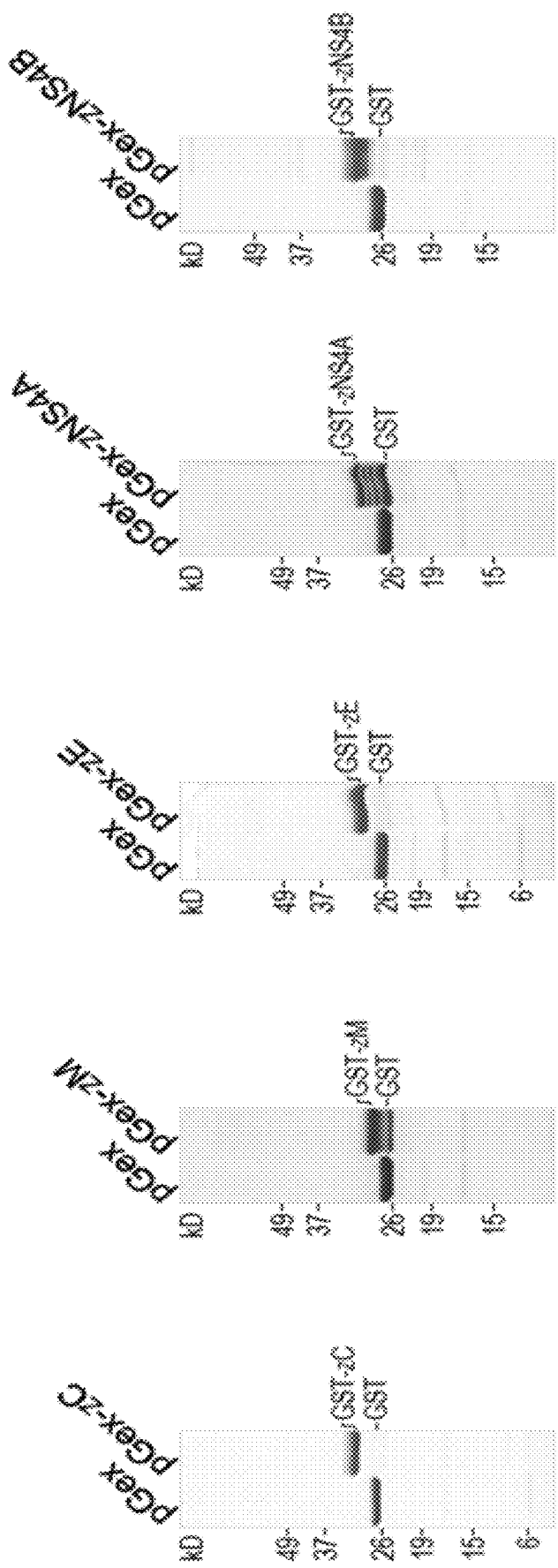

FIG. 15A and FIG. 15B show the details of the seven ZIKV region-specific rabbit antisera used to identify ZIKV gene products and their related species. FIG. 15A is a chart of seven rabbit antisera, each recognizing a 19- to 51-aa region defined in the ZIKV protein-coding sequences, were generated using five E. coli-expressed GST fusion proteins ($\alpha$-zC, $\alpha$-zM, $\alpha$-zE, $\alpha$-zNS4A, and $\alpha$-zNS4B) or two keyhole limpet hemocyanin (KLH)-conjugated synthetic oligopeptides ($\alpha$-zNS1 and $\alpha$-zNS2B) as antigens. The nucleotide (nt) and amino acid (aa) positions of the viral antigenic regions (magenta) are based on the complete genomic sequence of ZIKV PRVABC-59 (GenBank accession no. KX377337; see also FIG. 5A). The working dilutions of the rabbit antisera used in this study are presented. FIG. 15B are images of SDS-PAGE gels showing production of five GST-tagged recombinant proteins. GST fusion proteins were expressed from pGex-4T-1 vector in E. coli BL21 and purified from bacterial lysates by affinity chromatography using glutathione-Sepharose. Purified proteins were resolved by SDS-PAGE on a glycine gel and stained with Coomassie blue.

Figure 16A:
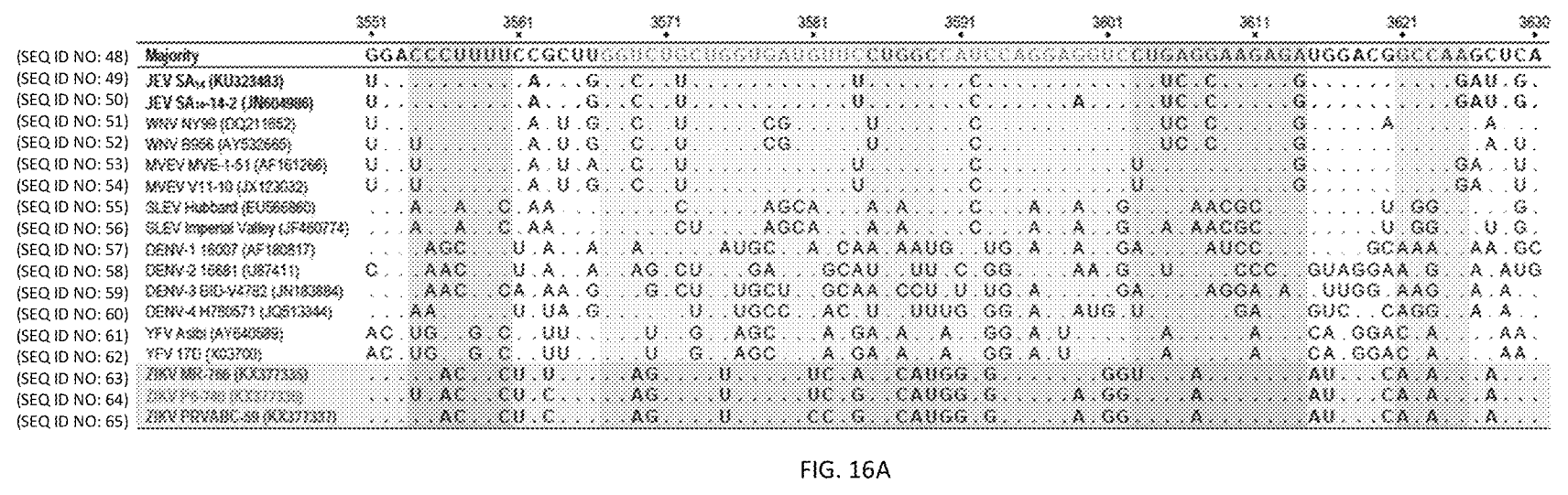
Figure 16B:
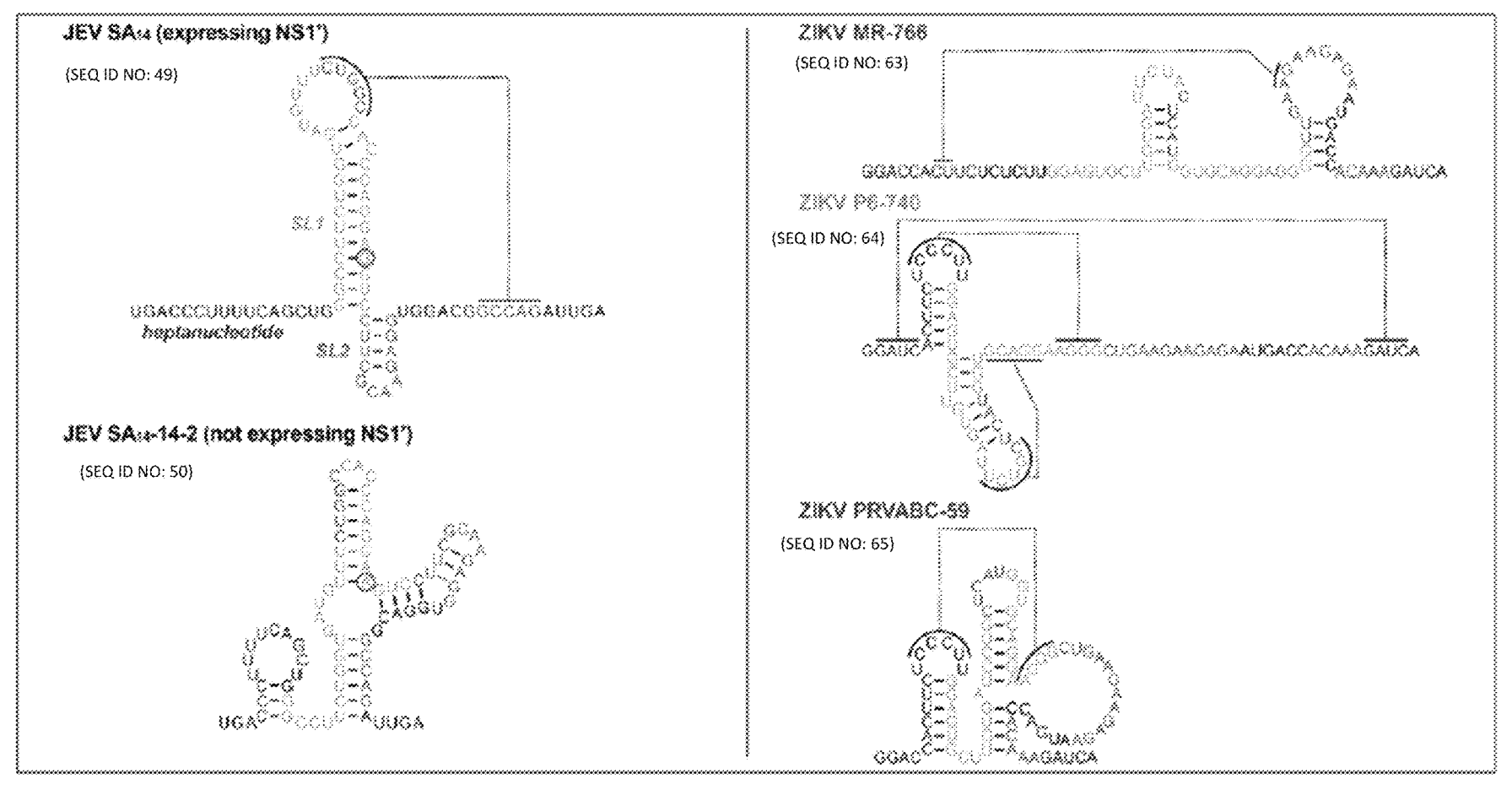

FIG. 16A and FIG. 16B show that ZIKV lacks the ribosomal frameshift signal directing the expression of NS1'. FIG. 16A is a nucleotide sequence alignment for seven major mosquito-borne flaviviruses (17 strains total). The consensus sequence is shown on top, and residues that match the consensus are hidden as dots to emphasize residues that differ from the consensus. FIG. 16B are schematics showing the predicted RNA folding involved in JEV NS1' frameshifting and its ZIKV counterpart. RNA secondary structures with pseudoknots are predicted using the IPknot program. Highlighted are the primary sequences and secondary structures important for the expression of JEV NS1': the heptanucleotide slippery sequence (blue), stem-loop 1 (SL1, orange), stem-loop 2 (SL2, magenta) and pseudoknot base-pairing (green). Also, indicated is the silent point mutation $G^{3599}A$ (red circle) that is sufficient to abolish the synthesis of JEV SA$_{14}$ NS1'.

Figure 17A:
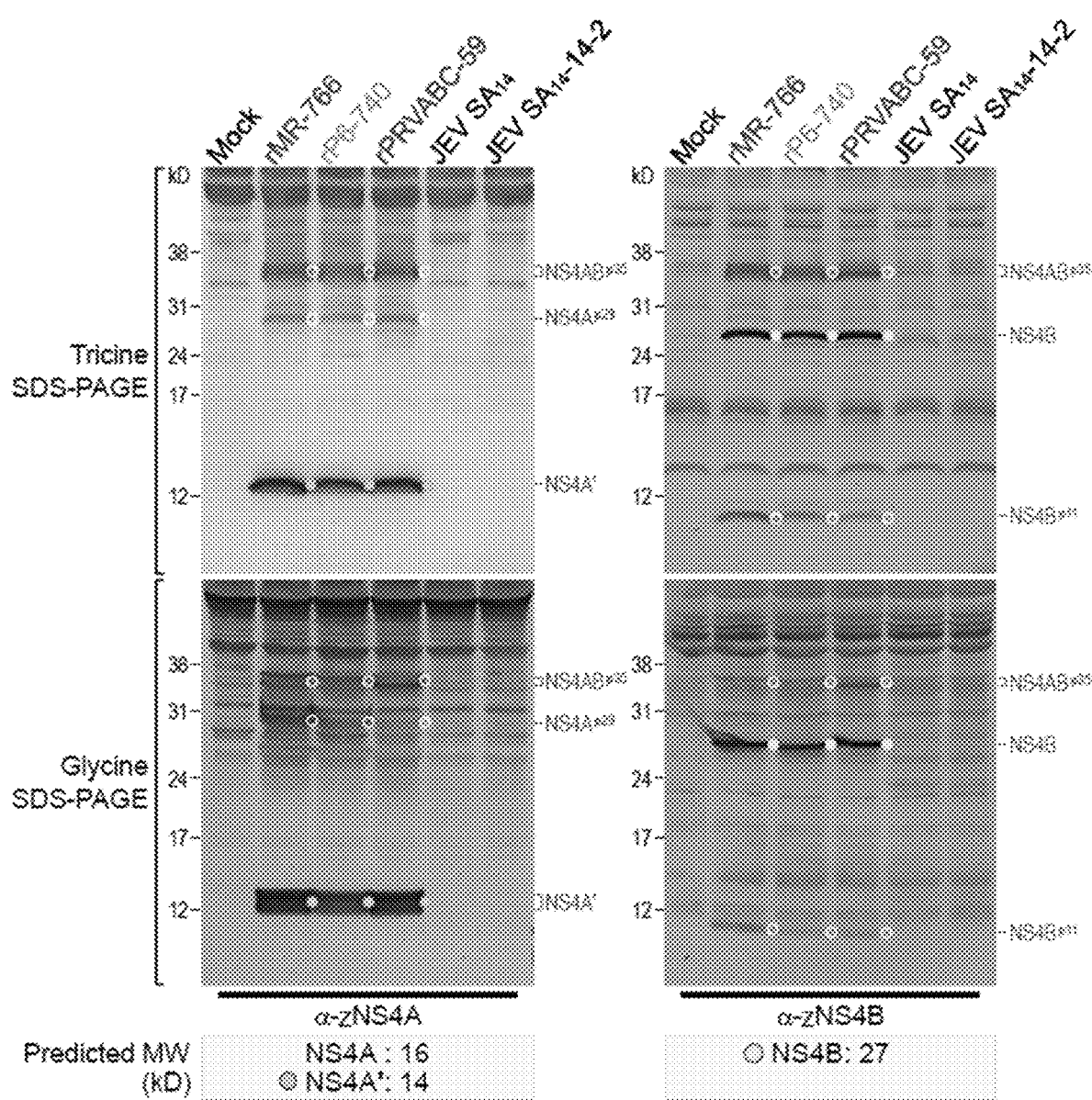
Figure 17B:
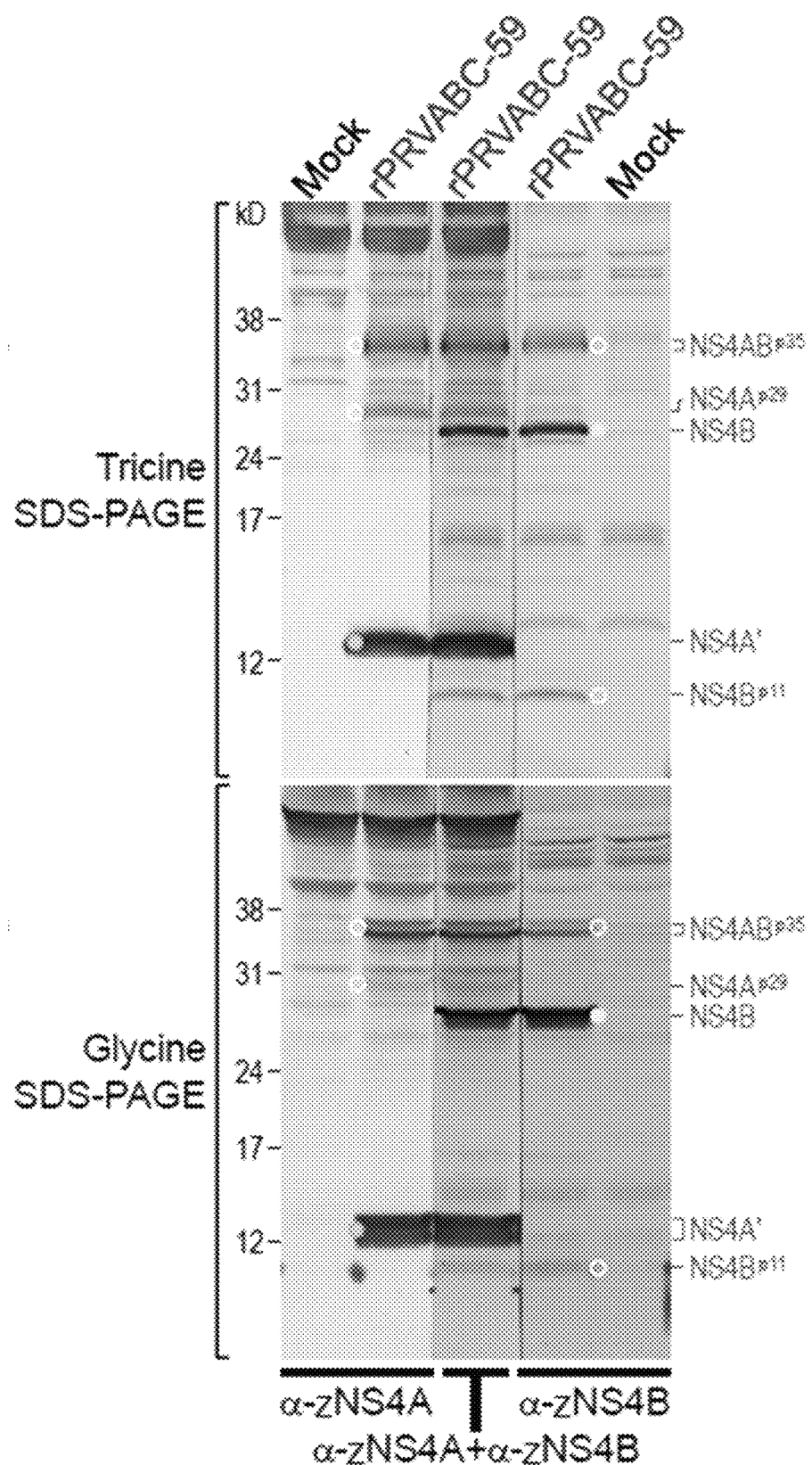

FIG. 17A and FIG. 17B are immunoblots of multiple NS4A- and NS4B-related proteins that are accumulated in ZIKV-infected cells. Vero cells were mock-infected or infected at an MOI of 1 with each of three ZIKVs (rMR-766, rP6-740, and rPRVABC-59) or two JEVs (SA$_{14}$ and SA$_{14}$-14-2). FIG. 17A are immunoblots at 20 h post-infection. Total cell lysates were separated by glycine- or tricine-SDS-PAGE and analyzed by immunoblotting with $\alpha$-zNS4A or $\alpha$-zNS4B. FIG. 17B are immunoblots for two sets of the same lysates from mock- and rPRVABC-59-infected Vero cells that were run side-by-side in a glycine or tricine gel and transferred to a single membrane. The membrane was split into two parts, each stained with either $\alpha$-zNS4A or $\alpha$-zNS4B. In parallel, an aliquot of the same rPRVABC-59-infected cell lysate was also included in between the two sample sets, and the corresponding membrane strip was probed with a mixture of both $\alpha$-zNS4A and $\alpha$-zNS4B to serve as a reference for all the immunoreactive proteins. Provided below the blot are the molecular weights of predicted ZIKV NS4A, NS4A' and NS4B proteins, and marked on the blot are the predicted (yellow or pink dot) and unexpected (white circle) proteins.

Figure 18:
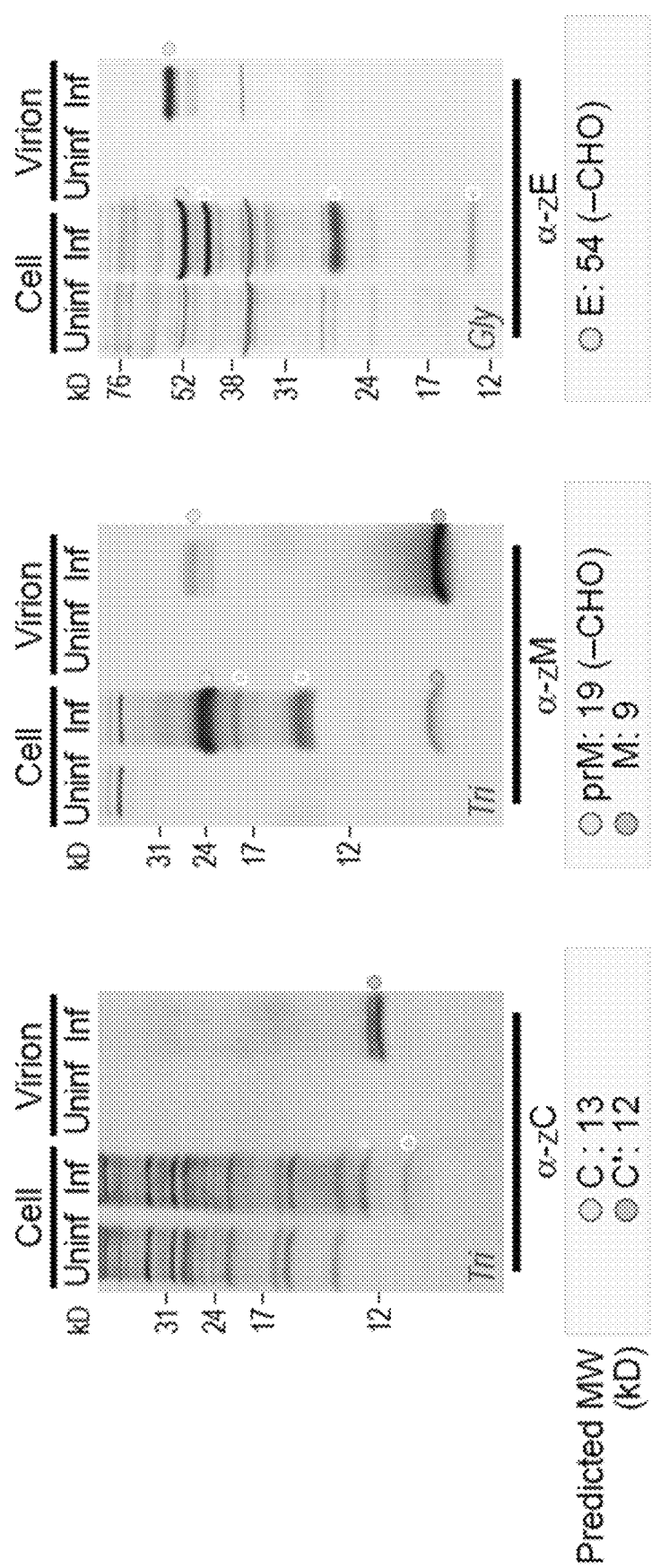

FIG. 18 is the profiling of virion-associated ZIKV proteins compared to their cell-associated counterparts. Vero cells were left uninfected (Uninf) or infected (Inf) with ZIKV rPRVABC-59 at an MOI of 1. For cell-associated viral proteins, total cell lysates were prepared by lysing the cell monolayers at 20 h post-infection. For virion-associated viral proteins, cell culture supernatants were collected at the same time point, and extracellular virions were pelleted by ultracentrifugation through a 20% sucrose cushion. Equivalent portions of total cell lysates and pelleted virions were resolved by SDS-PAGE on a glycine (Gly) or tricine (Tri) gel and analyzed by immunoblotting with $\alpha$-zC, $\alpha$-zM, or $\alpha$-zE. Molecular weight markers are shown on the left of each blot. The molecular weights of predicted C, C', prM, M, and E proteins are indicated below each blot. Marked on each blot are the predicted (yellow or pink dot) and unexpected (white circle) proteins. CHO, N-glycosylation.

Figure 19B:
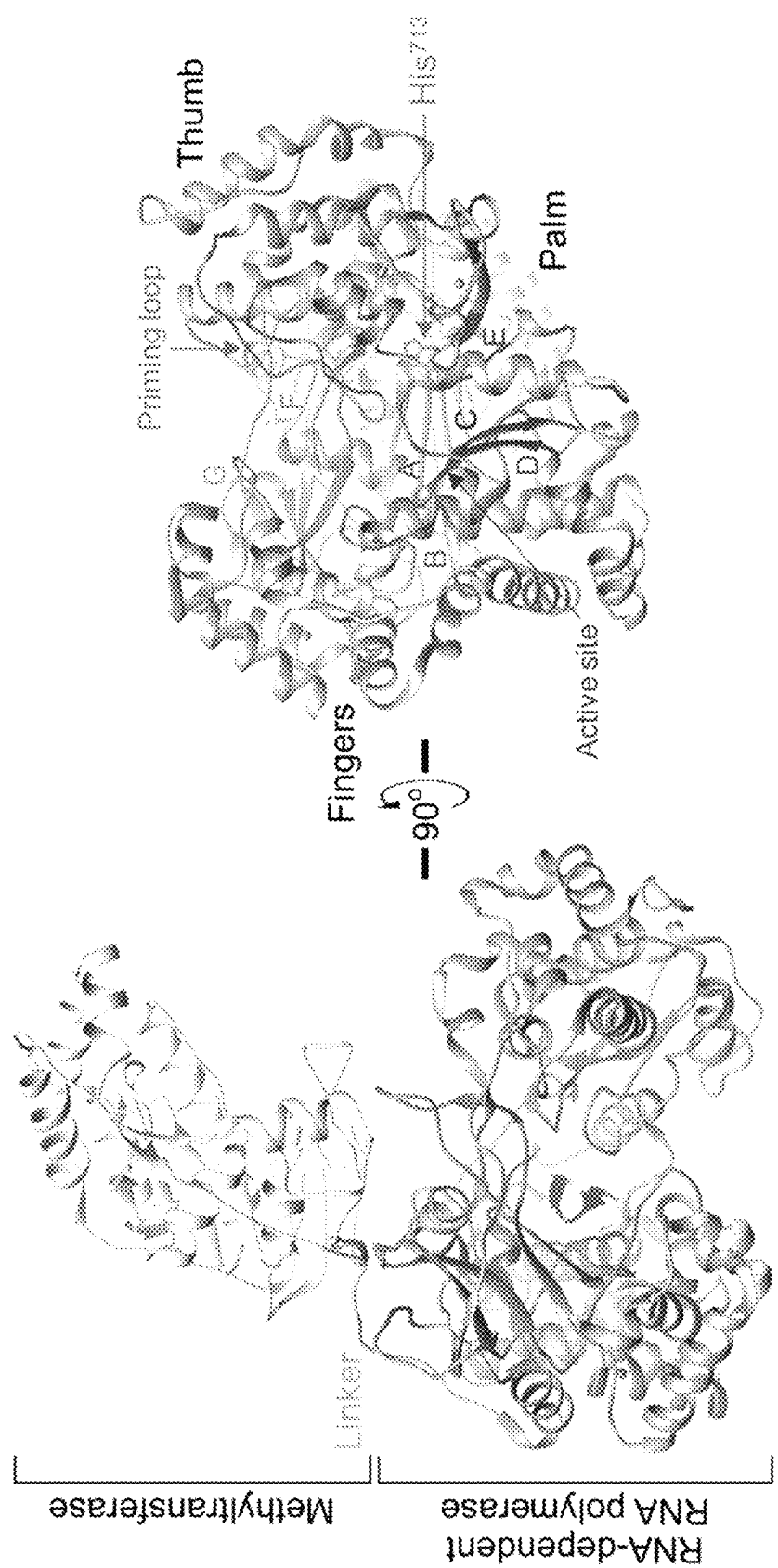

FIG. 19A and FIG. 19B show that a single $C^{9804} \rightarrow U$ substitution essentially eliminates the specific infectivity of RNA transcripts derived from a full-length infectious cDNA clone of ZIKV P6-740. FIG. 19A is a schematic representation showing the locus of the $C^{9804} \rightarrow U$ substitution (pBac/P6-740/NS5$^{H713Y}$) replacing a His with Tyr at position 713 of the viral NS5 protein in the context of the full-length infectious cDNA clone of ZIKV P6-740 (pBac/P6-740), and includes a is a chart of RNA infectivity. After linearization with BarI, each full-length cDNA was used as a template for in vitro run-off transcription with SP6 RNA polymerase in the presence of the dinucleotide cap analog m$^7$GpppA. Capped RNA transcripts were then transfected into Vero cells to determine the number of infectious centers (plaques) counterstained with crystal violet at 5 days after transfection. Means and standard deviations from two independent experiments are shown. FIG. 19B shows the location of His$^{713}$ on the crystal structure of ZIKV NS5. Ribbon representation shows the arrangement of the methyltransferase and RNA-dependent RNA polymerase domains of ZIKV NS5 (PDB accession code 5U0B). Highlighted in color around the catalytic active site of the RNA-dependent RNA polymerase domain are the seven structural motifs (A to G), priming loop, and His$^{713}$ residue.

Figure 20A:
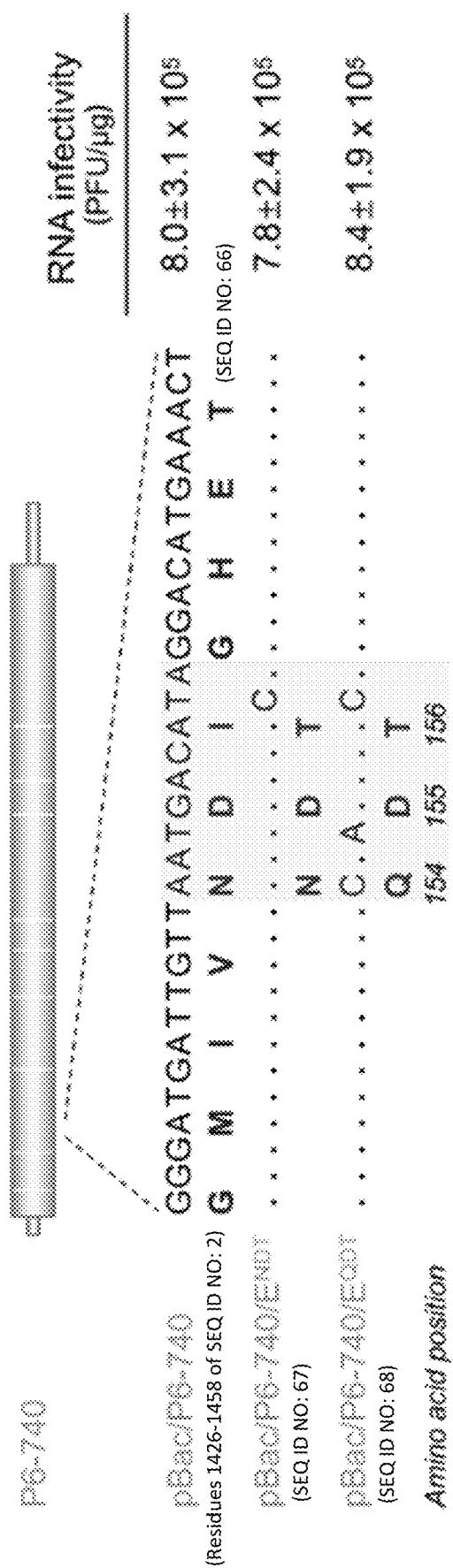
Figure 20B:
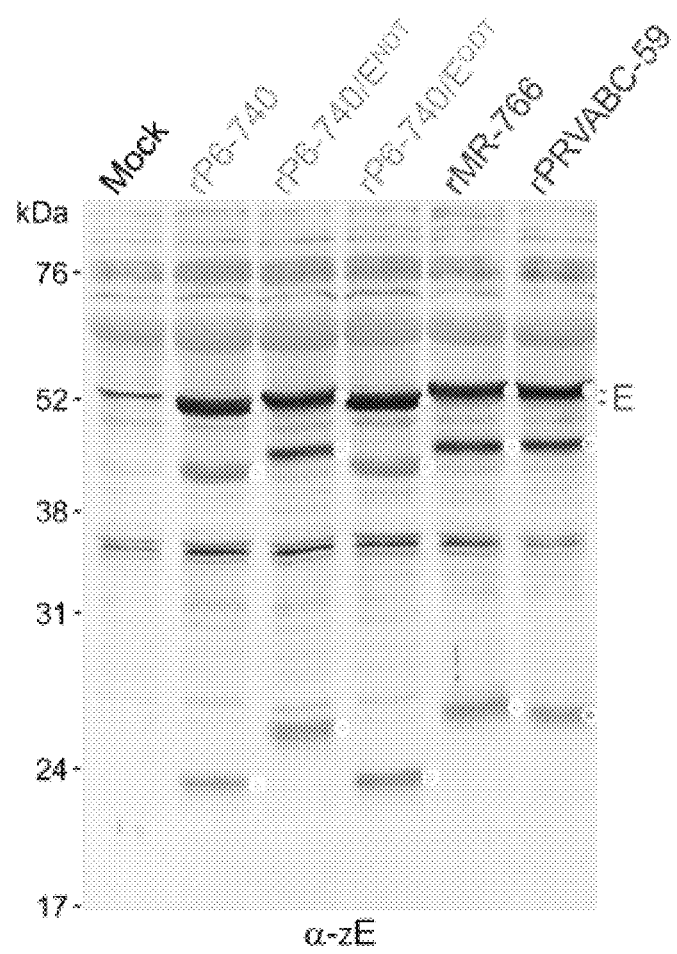

FIG. 20A and FIG. 20B show that a missense mutation eliminating the N-glycosylation site at Asn-154 in the viral protein E of rP6-740 is responsible for the observed lower molecular weights of the E and its two related proteins. FIG. 20A is a schematic representation illustrating the parental full-length cDNA clone (pBac/P6-740) and two E N-glycosylation mutants (pBac/P6-740/E$^{NDT}$ and pBac/P6-740/E$^{QDT}$). The genomic RNA of ZIKV P6-740 is depicted at the top. Below the diagram of the viral genome, the nucleotide and amino acid sequences corresponding to positions 154 to 156 of the parental and its two mutants are shown. Dots indicate identical nucleotides. A chart of RNA infectivity is shown on the right. Once linearized with BarI, each full-length cDNA was used as a template for in vitro run-off transcription with SP6 RNA polymerase in the presence of the dinucleotide cap analog m$^7$GpppA. Capped RNA transcripts were then transfected into Vero cells to estimate the number of infectious centers (plaques) that were counterstained with crystal violet at 5 days post-transfection. Means and standard deviations from two independent experiments are shown. FIG. 20B is the identification of viral E protein and its related species in ZIKV-infected cells. Vero cells were mock-infected or infected at an MOI of 1 with each of three rP6-740 derivatives (rP6-740, rP6-740/E$^{NDT}$, and rP6-740/E$^{QDT}$) and two other ZIKVs (rMR-766 and rPRVABC-59, for comparison). At 20 hours post-infection, total cell lysates were resolved by SDS-PAGE on a glycine gel and analyzed by immunoblotting with α-zE rabbit antiserum. Molecular size markers are shown on the left side of the blot, and the full-length E (yellow dot) and its two related proteins (white circle) are indicated on the blot.

FIG. 21 is a table of oligonucleotides used for cloning. ZIKV-specific sequences are indicated in uppercase normal letters, and Vero β-actin-specific sequences are shown in uppercase italic letters. Other nonviral sequences are indicated in lowercase letters. Restriction enzyme sites used for cDNA cloning are underlined. FAM, 6-Carboxyfluorescein; HEX, Hexachlorofluorescein; BHQ, Black hole quencher. Nucleotide position refers to the complete genome sequence of ZIKV PRVABC-59 (GenBank accession number KX377337) or to the mRNA sequence of Vero β-actin (GenBank accession number AB004047).

FIG. 22 is a table of the various cells and conditions of cell culture. MEM, minimum essential medium; α-MEM, alpha minimum essential medium; DMEM, Dulbecco's modified eagle medium; EMEM, Eagle's minimum essential medium; EBSS, Earle's balanced salt solution; FBS, fetal bovine serum; HS, horse serum; NEAA, nonessential amino acids; SP, sodium pyruvate; PS, penicillin-streptomycin. ATCC, American Type Culture Collection; RU, Rockefeller University; USU, Utah State University; KNIAS, Korea National Institute of Animal Science.

DETAILED DESCRIPTION

The present disclosure relates to the development of a reverse genetics system for the study of ZIKV biology. In particular, the present disclosure provides full-length infectious cDNAs as BACs for three spatiotemporally distinct and genetically divergent ZIKVs. Also, the present disclosure uses these infectious ZIKV cDNAs to determine the genome-wide landscape of ZIKV gene products and to characterize genetic aspects of ZIKV replicability and pathogenicity. The full-length ZIKV cDNAs serve as the basis for establishing vaccine compositions for the prevention of ZIKV infection.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

"Functional" as used herein referring to an RNA transcript indicated that the transcript is replication competent and infectious.

"Identical" or "identity," as used herein in the context of two or more polypeptide or polynucleotide sequences, can mean that the amino acid or nucleotide sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Sample," "test sample," "specimen," "sample from a subject," and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find in the context of the present disclosure.

The term "attenuated virus" as used herein, refers to a virus with compromised virulence in the intended recipient (e.g., human or animal recipient). More specifically, an attenuated virus has a decreased or weakened ability to produce disease while retaining the ability to stimulate an immune response similar to the wild-type (non-attenuated) virus.

As used herein, the terms "synonymous nucleotide codon(s)" or "synonymous codon(s)" refer to two or more nucleotide codons encoding the same amino acid. As recognized by one of ordinary skill in the art, most amino acids are encoded by more than one codon. Synonymous codons are codons that encode the same amino acid. As used herein, the expressions "synonymous mutation or "synonymous substitution" refer to the substitution of a nucleotide codon by another nucleotide codon which encodes the same amino acid (i.e. a synonymous codon). By contrast "non-synonymous mutations" are nucleotide substitutions in a codon that do result in the alteration of an amino acid.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Development of Comparative Functional Genomics and Immunologic Tools for ZIKV Embodiments of the present disclosure represent the first development of three full-length infectious ZIKV cDNAs as BACs for each of three spatiotemporally distinct and genetically divergent ZIKV strains: MR-766 (Uganda, 1947), P6-740 (Malaysia, 1966), and PRVABC-59 (Puerto Rico, 2015). The present disclosure also provides 13 ZIKV region-specific polyclonal rabbit antisera capable of identifying all the viral structural and nonstructural proteins and their related species, except for NS2A. Using the functional cDNAs and antibodies disclosed herein in combination with various cell culture and murine infection model systems, results of the present disclosure have demonstrated that the three molecularly cloned cDNA-derived ZIKVs have the nearly same genome-wide viral protein expression profile but differ dramatically in their replicability and neuropathogenicity (neuroinvasiveness and neurovirulence), depending on the particular combination of viral and host genetic backgrounds, as well as in the presence or absence of type I/II IFN signaling. In particular, these data demonstrate that type I IFN regulates ZIKV neuroinvasiveness in a virus strain-dependent manner. In all, these reagents offer a new toolbox for viral genome engineering and protein analysis. Together with a roster of in vitro and in vivo infection models, these tools will not only provide an ideal platform for defining the viral and host genetic factors that contribute to ZIKV replication and pathogenesis at the cellular and organismic levels but also offer promising new avenues for developing and testing an effective, critically needed vaccine against ZIKV, including the generation of a genetically engineered attenuated ZIKV.

The advent of functional cDNA-based reverse genetics has revamped the field of RNA viruses. For flaviviruses, however, the cloned cDNAs are commonly unstable because of the toxicity of their prM-E genes in host cells, posing a major technical challenge to functional cDNA construction. The present disclosure demonstrated that a complete cDNA copy of the ZIKV vgRNA could be cloned into a BAC vector that is capable of stably housing a DNA fragment of >300 kb in bacteria. In the case of all three ZIKVs (MR-766, P6-740, and PRVABC-59), these results showed that the structural and functional integrity of their full-length cDNA BACs remained stable for at least 80 generations of growth in $E.$ $coli$. To date, the BAC cloning technology has been applied to constructing full-length infectious cDNAs for ~10 members of three plus-strand RNA virus families (Flaviviridae, Arteriviridae, and Coronaviridae), all of which have a large genome size of 11-31 kb. Moreover, site-directed mutagenesis was performed to introduce a point mutation(s) into each of the three infectious ZIKV cDNAs, indicating that targeted mutations can be engineered by manipulating the infectious ZIKV BACs in $E.$ $coli$. Thus, the BAC-based reverse genetics for ZIKV will facilitate genetic studies of both viral RNA elements and gene products associated with all aspects of ZIKV biology.

Several functional cDNAs for ZIKV have hitherto been made using two different strategies, depending on the vector adopted to clone its full-length cDNA and the method applied to create the viral 5' and 3' ends: (i) The low-copy plasmid pACYC177 (~15 copies/cell) has been utilized to house a complete cDNA flanked by a 5' bacteriophage T7 promoter and a 3' hepatitis delta virus ribozyme (HDVr). This T7-HDVr system, analogous to the SP6-PsrI/BarI system used in the present disclosure, requires an in vitro transcription and transfection of transcribed RNAs into cells for virus recovery. This "RNA-initiated" approach has been implemented to clone the vgRNA of the 2010 Cambodian FSS13025 strain. To circumvent the need for a single plasmid containing a full-length cDNA, in vitro ligation of two or four cDNA fragments pre-cloned individually into the low-copy pACYC177 or high-copy pUC57 (500-700 copies/cell) plasmid, although relatively inefficient, has been done to generate a full-length cDNA template prior to in vitro transcription using the T7-HDVr system for the Ugandan MR-766 (1947), French Polynesian H/PF/2013 (2013), Puerto Rican PRVABC-59 (2015), and Brazilian SPH2015 (2015) and BeH819015 (2015) strains. (ii) The low-copy pACNR1811 (10-20 copies/cell) or high-copy pcDNA6.2 (500-700 copies/cell) plasmid is used to house a full-length cDNA containing one or two artificial introns to restrict its instability during propagation in $E.$ $coli$. In this case, a eukaryotic RNA polymerase (RNAP) II-dependent cytomegalovirus (CMV) promoter is positioned before the viral 5' end, and a pair of HDVr and an SV40 poly(A) signal/RNAP II terminator are placed after the viral 3' end. Unlike the SP6-PsrI/BarI system used in the present disclosure, the CMV-HDVr system requires transfection of cells with a plasmid carrying the intron-bearing full-length cDNA. This "DNA-initiated" approach has been applied to clone the vgRNA of the Ugandan MR-766 (1947) and Brazilian Paraiba (2015) strains. Alternatively, a circular form of the intronless full-length cDNA for the 2015 Brazilian Natal strain has been generated by PCR-mediated joining of eight overlapping cDNA fragments that are pre-cloned individually into the high-copy pUC plasmid. Although far less efficient, a similar PCR-based method has also been reported to use three overlapping cDNA fragments covering the vgRNA with no joining of these fragments into a circular cDNA. In the present disclosure, a single plasmid-based RNA-initiated reverse genetics system was developed for ZIKV, in order to not only maximize the stability of its cloned cDNA, but also simplify the synthesis of infectious RNAs in vitro.

ZIKV circulates in a sylvatic cycle between nonhuman primates (NHPs) and forest-dwelling mosquitoes, as well as in an urban cycle between humans and town-dwelling mosquitoes. Apart from NHPs, however, information is scarce on any potential animal hosts or reservoirs for ZIKV transmission. The three cDNA-derived genetically distinct ZIKVs were herein used to evaluate the ability to infect and replicate in 17 animal cell lines from 12 different species (monkeys, humans, mosquitoes, mice, cows, pigs, sheep, goats, horses, dogs, cats, and chickens). These data showed that ZIKV has a broad cell tropism in vitro, being capable of establishing productive infection in 16 of the 17 cell lines tested, although its growth rate and ability to induce CPE varied widely depending on both the specific virus strain and host cell line.

The present disclosure also provides a large panel of 13 ZIKV region-specific antibodies that can identify nearly all the viral gene products and their related species in infected Vero cells and define all three structural proteins associated with extracellular virions. These data revealed the following unexpected findings: (1) While the full-length 13-kDa C and its one or two processed 10- to 11-kDa proteins were accumulated intracellularly, the extracellular virion-associated C' protein appeared as a tightly spaced 12-kDa doublet. (2) For each of the two viral surface glycoproteins (24-kDa prM and 54/56-kDa E), two or three smaller products were also cell-associated but not virion-associated. (3) Only the 45-kDa NS1, but not its theoretically frameshift-derived product NS1', was expressed. (4) In addition to the intact 14-kDa NS2B, its processed 11-kDa product was also stained, although weakly. (5) The full-length 69-kDa NS3 was processed to yield multiple truncated species of 33-60 kDa, of which the C-terminal 34-kDa fragment was the most prominent species. (6) The predicted 16-kDa NS4A was completely undetectable, but three unexpected NS4A-related proteins were readily identified (i.e., a major doublet at 14 kDa (NS4A') and two minor protein clusters at 29 kDa ($NS4A^{p29}$) and 35 kDa ($NS4AB^{p35}$)). (7) Not only the predicted 27-kDa NS4B but also two unexpected NS4B-related proteins were observed, one at 11 kDa ($NS4B^{p11}$) and the other at 35 kDa ($NS4AB^{p35}$). Although the importance of these findings for ZIKV biology requires further investigation, the results of the present disclosure provides a solid foundation for the study of viral replication and pathogenesis, virus-host interactions, and host responses to viral infection at both the cellular and organismic levels, and for the generation of attenuated viruses for vaccine development.

Much progress has been made developing animal models (i.e., mice and NHPs) for ZIKV. To date, the mouse is the most feasible small animal that mimics aspects of ZIKV infection in humans, albeit with some limitations resulting from species differences in innate immunity, reproductive system, and fetal development. Previously, no productive infection was detected when several strains of immunocompetent adult mice were inoculated peripherally with diverse ZIKVs, but robust peripheral ZIKV infection causing substantial morbidity and mortality was observed in both immunocompromised adult and immunocompetent neonatal mice. Additionally, there is large variation in ZIKV pathogenicity among previous studies, which were conducted by inoculating a variety of ZIKVs into different strains of mice via various routes. In the present disclosure, results have shown in immunocompetent CD-1 mice at 1, 2, and 4 weeks of age that ZIKV neuropathogenicity can only be defined in the context of a virus-host combination, as evidenced by comparison of the neuroinvasiveness and neurovirulence of the three molecularly cloned, genetically distinct ZIKVs: (i) rMR-766 exhibited neonate-specific age-dependent neuroinvasiveness but displayed a high level of neurovirulence at all three ages. (ii) rP6-740 had little-to-no neuroinvasiveness at all three ages but possessed neonate-specific age-dependent neurovirulence. (iii) rPRVABC-59 was non-neuroinvasive and non-neurovirulent at all three ages. Also, results of the present disclosure showed marked differences in IFN sensitivity among the three ZIKVs: In 4-week-old A129 mice lacking type I IFN receptor ($IFNAR^{-/-}$), the three ZIKVs were uniformly neurovirulent but varied in neuroinvasiveness (rMR-766, neuroinvasive; rP6-740, intermediate; and rPRVABC-59, almost non-neuroinvasive); however, all three ZIKVs, including rPRVABC-59, were neuroinvasive in age-matched AG129 mice lacking both type I and II IFN receptors ($IFNAR^{-/-}/IFNGR^{-/-}$). Consistent with previous work, a greater susceptibility and more severe disease was seen in AG129 mice than in A129 mice. In all fatal cases, the mortality was related to the productive infection in the brain, coupled with tremors, ataxia, and hind limb paralysis.

a) Genetically Stable Viral Vector

Provided herein is a genetically stable viral vector comprising a ZIKV cDNA, an RNA polymerase promoter upstream of the 5' end of the ZIKV cDNA, and a restriction endonuclease site downstream of the 3' end of the ZIKV cDNA, wherein the ZIKV cDNA, the RNA polymerase promoter, and the restriction endonuclease site are cloned into a BAC vector, and wherein the ZIKV cDNA is capable of being transcribed into an RNA transcript that is functional. In some embodiments, the RNA polymerase promoter is immediately upstream of the 5' end of the ZIKV cDNA. In some embodiments, the restriction endonuclease site is immediately downstream of the 3' end of the ZIKV cDNA. Functional RNA transcripts of the ZIKV virus includes those that are replication competent and infectious.

The ZIKV cDNA may comprise the viral genome sequence of any ZIKV strain from either of the two genetic lineages: African and Asian. In some embodiments, the ZIKV cDNA is from three ZIKV strains: MR-766 (Uganda, 1947), P6-740 (Malaysia, 1966), and PRVABC-59 (Puerto Rico, 2015).

In some embodiments, the ZIKV cDNA comprises a nucleotide sequence selected from the group consisting of SEQ ID NO: 4, SEQ ID NO: 5, and SEQ ID NO: 6. The ZIKV cDNA may comprise a nucleotide sequence with at least partial sequence identity to a nucleotide sequence selected from the group consisting of SEQ ID NO: 4, SEQ ID NO: 5, or SEQ ID NO: 6. In some embodiments, the ZIKV cDNA may be at least 75%, at least 80%, at least 85%, at least 90%, at least 95%, at least 96%, at least 97%, at least 98%, or at least 99% identical to a nucleotide sequence selected from the group consisting of SEQ ID NO: 4, SEQ ID NO: 5, or SEQ ID NO: 6.

The genetically stable viral vector may comprise an RNA polymerase promoter upstream of the 5' end of the ZIKV cDNA. The promoter can be selected from the group consisting of an eukaryotic promoter, yeast promoter, plant promoter, bacterial or bacteriophage promoter, or viral promoter. The RNA polymerase promoter may be any bacterial promoter, including but not limited to a promoter recognized by T7 RNA polymerase, SP6 RNA polymerase, or T3 RNA polymerase.

In some embodiments, the RNA polymerase promoter is an SP6 promoter. In some embodiments, the SP6 promoter comprises the nucleotide sequence of SEQ ID NO: 7 (5'-ATTTAGGGGACACTATA<u>G</u>-3'). The bacteriophage SP6 RNA polymerase is poised such that in vitro transcription results in the inclusion of only a single non-viral G nucleotide, as underlined, upstream of the first adenine nucleotide of the viral genome, which corresponds to the authentic ZIKV 5' end.

The genetically stable viral vector may comprise a restriction endonuclease site downstream of the 3' end of the ZIKV cDNA. In some embodiments, the restriction endonuclease site does not interfere with the 3' end of the ZIKV cDNA. As such, the restriction endonuclease site is downstream of the last thymine nucleotide of the viral genome, maintaining the authentic 3' end for the production of infectious ZIKV RNAs. RNA transcripts with 11 ZIKV-unrelated nucleotides hanging on their 3' ends were found to be about 1-log less infectious than those with authentic 3' ends, indicating the importance of the authentic 3' end for the production of infectious ZIKV RNAs.

In some embodiments, the restriction endonuclease site is capable of being cleaved by PsrI or BarI. In some embodiments, the restriction endonuclease site comprises a nucleotide sequence of SEQ ID NO: 8 GAACNNNNNNNTAC, wherein N is any nucleotide, or SEQ ID NO: 9 GAAGNNNNNNTAC, wherein N is any nucleotide. The use of PsrI or BarI is advantageous because both are extremely rare-cutting endonucleases that cut out their recognition sequences after any nucleotide, which makes this approach applicable for all plus-strand RNA viruses, regardless of the identity of the nucleotide at the 3' end of the viral genome.

The genetically stable viral vector may comprise the ZIKV cDNA, the RNA polymerase promoter and the restriction endonuclease site cloned into a BAC vector. A BAC vector is a DNA sequence which comprises the sequence of the fertility factor or F factor, which allows stable propagation of the plasmids containing this sequence. BACs are capable of stably maintaining an extremely long DNA fragment, when compared to any traditional plasmid vectors.

The bacterial artificial chromosome may be single, low or high copy number. In some embodiments, the bacterial artificial chromosome is a single- or low-copy number bacterial artificial chromosome.

The genetically stable viral vector may allow the ZIKV cDNA to be transcribed into an RNA transcript. The RNA transcript may comprise a 5' cap or a modified nucleotide at the 5' end. The 5' cap includes a guanine nucleobase connected to the RNA via an unusual 5' to 5' triphosphate linkage, for example $m^7G(5')ppp(5')N$- or $m^7G(5')ppp(5')Nm$, in which N is any nucleotide and Nm is a ribose 2'-O methylated nucleotide. In some embodiments, the cap is an $m^7G(5')ppp(5')A$ cap. Uncapped RNAs derived from the ZIKV cDNA may have lower infectivity than capped RNAs.

In some embodiments, the genetically stable vector comprises a complete cDNA copy of ZIKV strain MR-766 cloned into a BAC, wherein the sequence of the vector is represented by SEQ ID NO:1.

In some embodiments, the genetically stable vector comprises a complete cDNA copy of ZIKV strain P6-740 cloned into a BAC, wherein the sequence of the vector is represented by SEQ ID NO:2.

In some embodiments, the genetically stable vector comprises a complete cDNA copy of ZIKV strain PRVABC-59 cloned into a BAC, wherein the sequence of the vector is represented by SEQ ID NO:3.

b) Method of Generating a Genetically Engineered Attenuated ZIKV

Provided herein is methods of generating a genetically engineered attenuated ZIKV, obtaining a genetically stable viral vector, and altering one or more nucleotides in the ZIKV cDNA to produce a synonymous or non-synonymous codon alteration, wherein the synonymous or non-synonymous codon alteration produces a ZIKV with compromised virulence.

Any method of altering one or more nucleotides may be used. For example, a mutation can be introduced randomly during propagation, purposefully by PCR, site-directed mutagenesis, or any other method known in the art.

The one or more nucleotides may be in a protein-coding region of the ZIKV cDNA such that the alteration of one or more nucleotides may cause synonymous of non-synonymous codon alteration. In synonymous codon alteration, the amino acid sequence remains unaltered. In non-synonymous codon alteration, the amino acid sequence is changed.

The nucleotides may be altered in any location within the ZIKV cDNA. In some embodiments, the alteration is located in a nucleotide sequence of the ZIKV cDNA corresponding to the RNA-dependent RNA polymerase domain of the ZIKV NS5 protein. In some embodiments, altering one or more nucleotides in the ZIKV cDNA replaces a His with Tyr at position 713 of the ZIKV NS5 protein.

In some embodiments, the alteration is located in a nucleotide sequence of the ZIKV cDNA corresponding to the ZIKV E protein.

The ZIKV with compromised virulence may include any ZIKV having decreased virulence as compared to the non-altered ZIKV. The virulence may be decreased by at least 1 log, at least 2 logs, at least 3 logs, at least 4 logs, or at least 5 logs. The virulence may be determined from the value of $LD_{50}$ following infection into mice.

c) Methods of Use

The infectious ZIKV cDNAs disclosed herein may be used to determine the genome-wide landscape of ZIKV gene products and to characterize genetic aspects of ZIKV replicability and pathogenicity.

The full-length ZIKV cDNAs may also serve as the basis for establishing vaccine compositions for the prevention of ZIKV infection. Provided herein is a vaccine comprising a genetically engineered attenuated ZIKV made by the methods disclosed herein.

For vaccine use, genetically engineered attenuated ZIKV produced according to the present invention can be used directly in vaccine construction, as desired, using mutagenesis procedures well known in the art.

ZIKV vaccines of the invention contain as an active ingredient as described herein. The genetically modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI Immuno-Chem Research, Inc., Hamilton, Mont.) and IL-12 (Genetics Institute, Cambridge Mass.), among many other suitable adjuvants well known in the art.

The vaccine compositions may be formulated for any appropriate manner of administration, and thus administered, including for example, oral, nasal, intravenous, intravaginal, epicutaneous, sublingual, intracranial, intradermal, intraperitoneal, subcutaneous, intramuscular administration, or via inhalation. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed.

Upon immunization with a ZIKV vaccine composition as described herein, the host responds to the vaccine by producing antibodies specific for ZIKV viral proteins (e.g., prM/M and E proteins). As a result of the vaccination with an immunogenically effective amount of ZIKV produced as described herein, the host may become at least partially or completely immune to ZIKV infection, or resistant to developing moderate or severe ZIKV infection.

The host to which the vaccines are administered can be any vertebrates which are susceptible to infection by ZIKV or a closely related virus and which host is capable of generating a protective immune response to the antigens of the strain used for vaccination. Accordingly, the invention provides methods for creating vaccines for a variety of human and veterinary uses.

The vaccine compositions containing the attenuated ZIKV of the invention are administered to a host susceptible to or otherwise at risk for ZIKV infection to enhance the host's own immune response capabilities. Such an amount is defined to be an "immunogenically effective dose." In this use, the precise amount of attenuated ZIKV to be administered within an effective dose will depend on the host's state of health and weight, the mode of administration, the nature of the formulation, etc.

3. Materials and Methods

Figure 1A:
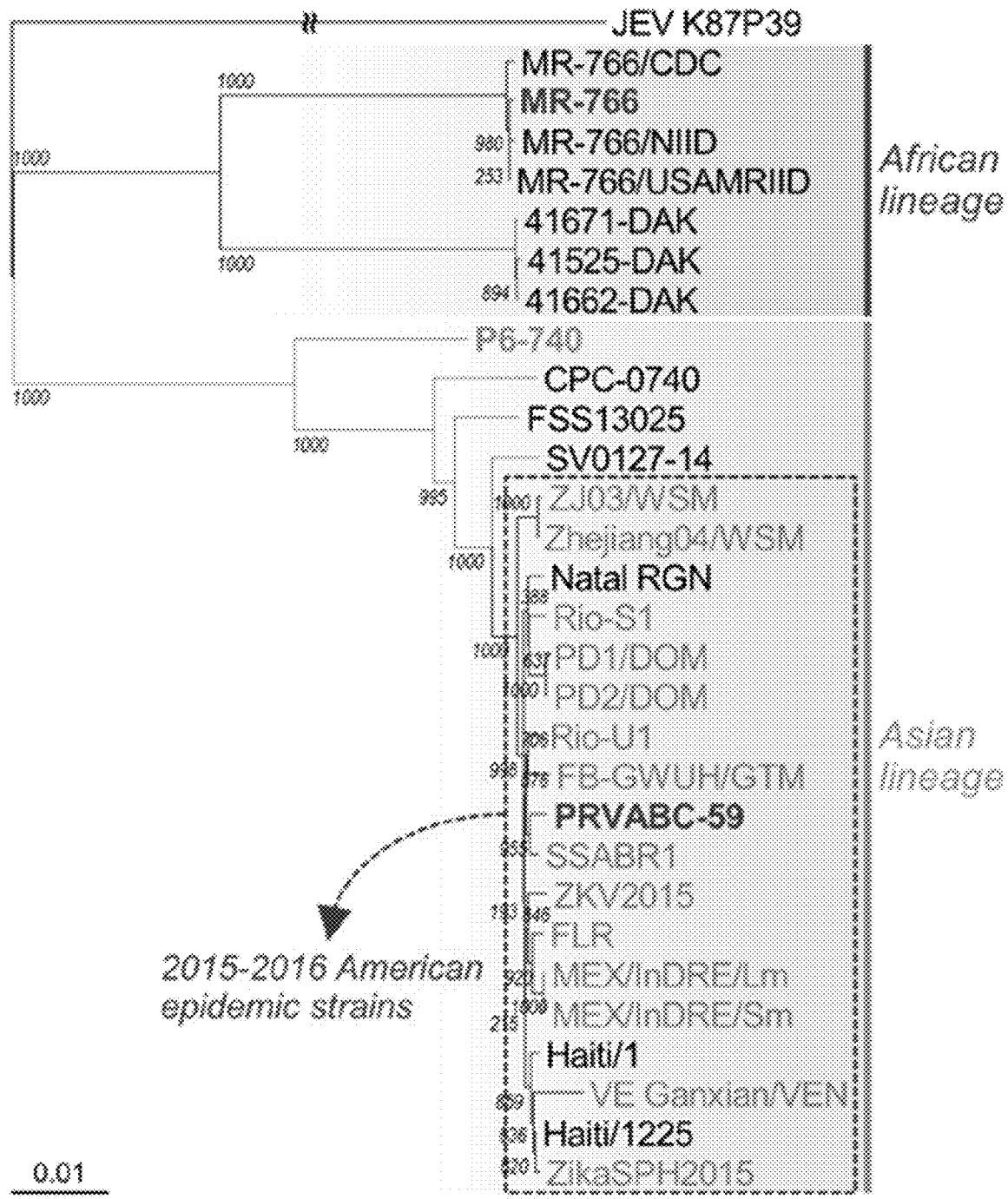
Figure 1B:
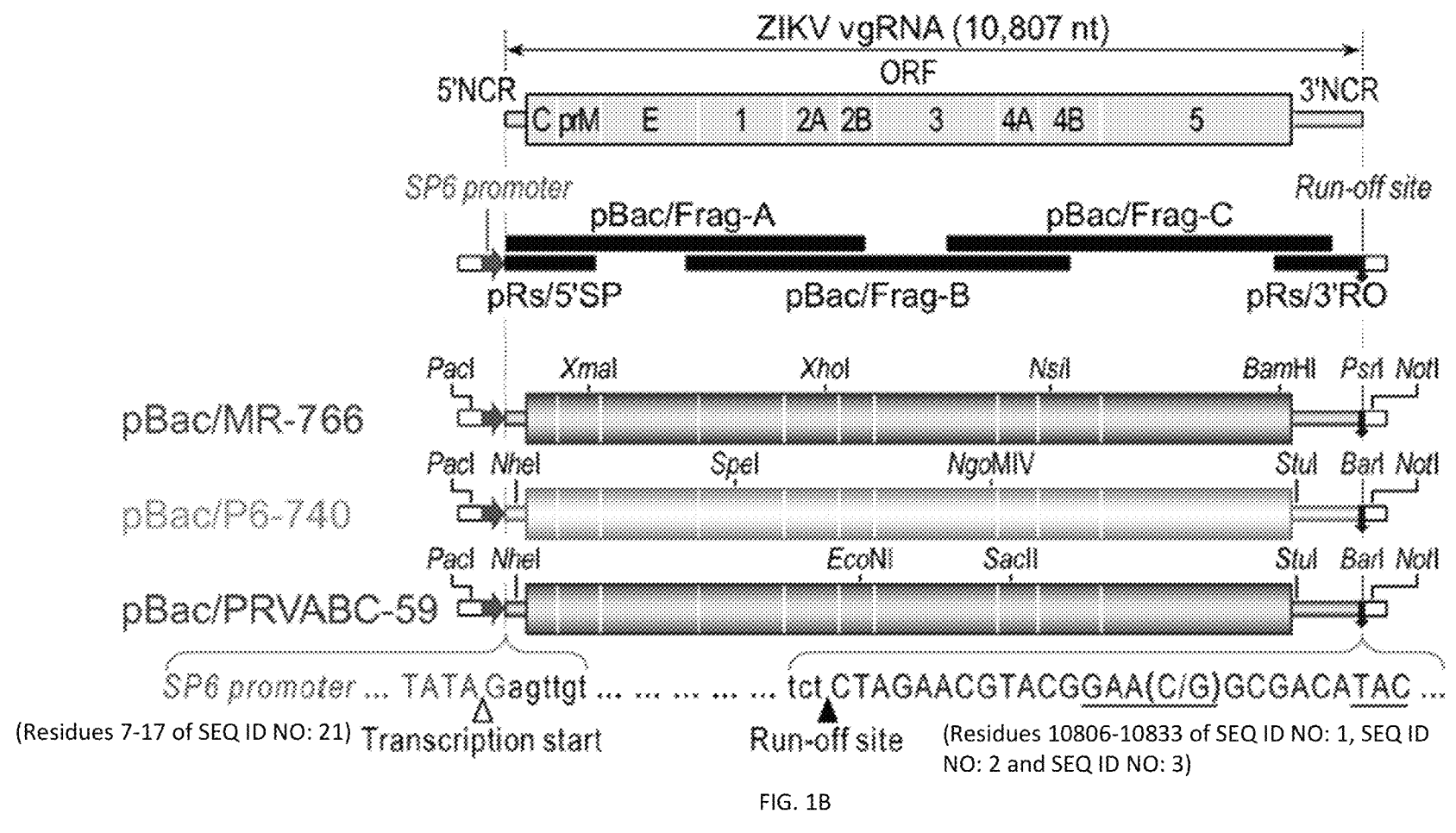

Construction of three full-length infectious ZIKV cDNA clones, one each for MR-766, P6-740, and PRVABC-59 in the BAC plasmid pBeloBAC11, designated pBac/MR-766, pBac/P6-740, and pBac/PRVABC-59. All DNA manipulations were performed according to standard cloning techniques. The oligonucleotides used in this study are listed in FIG. 21. The same cloning strategy was used to construct three full-length ZIKV cDNAs, one each for the MR-766, P6-740, and PRVABC-59 strains (FIG. 1B). Essentially, each full-length ZIKV cDNA flanked by the 5' SP6 promoter and the 3' PsrI/BarI restriction enzyme site was created by joining five overlapping RT-PCR-generated cDNA fragments at four natural restriction enzyme sites found in the viral genome (see below for detailed description of cloning strategy). The cloned cDNAs were checked by restriction enzyme mapping and sequencing.

(1) pBac/MR-766 (SEQ ID NO:1): The genomic RNA of ZIKV MR-766 (GenBank accession no. KX377335) was used as a template for the synthesis of three overlapping cDNA fragments by RT-PCR with the following primer sets: Frag-$A^{MR-766}$ (4552 bp), Z1RT and Z1F+Z1R; Frag-$B^{MR-766}$ (5070 bp), Z2RT and Z2F+Z2R; and Frag-$C^{MR-766}$ (5008 bp), Z3RT and Z3F+Z3R. Each of the three cDNA amplicons was subcloned into pBAC$^{SP6}$/JVFLx/XbaI, a derivative of the pBeloBAC11 plasmid, by ligating the 8381-bp PmeI-MluI fragment of pBAC$^{SP6}$/JVFLx/XbaI with the 4538-, 5056-, and 4994-bp PmeI-AscI fragments of the Frag-$A^{MR-766}$, Frag-$B^{MR-766}$, and Frag-$C^{MR-766}$ amplicons, respectively. This generated pBac/Frag-$A^{MR-766}$ to -$C^{MR-766}$. To introduce an SP6 promoter immediately upstream of the first adenine residue of the viral genome, two cDNA fragments were first amplified individually by (i) PCR of pBAC$^{SP6}$/JVFLx/XbaI with a pair of primers, S123-5sp1F+ S123-5sp1R (S123-5sp1R contains the antisense sequence of the SP6 promoter) and (ii) PCR of pRs/5'NCR$^{MR-766}$ with another pair of primers, S1-5sp2F+S1-5sp2R. Subsequently, these two fragments were fused by a second round of PCR with the outer forward and reverse primers S123-5sp1F+ S1-5sp2R. The 1025-bp BamHI-SacII fragment of the fused PCR amplicons was ligated with the 2718-bp BamHI-SacII fragment of pRs2, creating pRs/5'SP$^{MR-766}$. To engineer a unique PsrI run-off site just downstream of the last thymine residue of the viral genome, one cDNA fragment was amplified by PCR of pRs/3'NCR$^{MR-766}$ with primers S1-3roF+S1-3roR (S1-3roR contains the antisense sequence of the PsrI and NotI recognition sites in a row). The 649-bp SacII-NotI fragment of the resulting amplicons was ligated with the 2667-bp SacII-NotI fragment of pRs2, creating pRs/3'RO$^{MR-766}$. The full-length MR-766 cDNA clone pBac/MR-766 was then assembled by sequentially joining the 7456-bp PacI-NotI fragment of pBAC$^{SP6}$/JVFLx/XbaI with the following five DNA fragments: (i) the 1004-bp PacI-XmaI fragment of pRs/5'SP$^{MR-766}$, (ii) the 3160-bp XmaI-XhoI fragment of pBac/Frag-$A^{MR-766}$, (iii) the 3144-bp XhoI-NsiI fragment of pBac/Frag-$B^{MR-766}$, (iv) the 3041-bp NsiI-BamHI fragment of pBac/Frag-$C^{MR-766}$, and (v) the 619-bp BamHI-NotI fragment of pRs/3'RO$^{MR-766}$.

(2) pBac/P6-740 (SEQ ID NO:2): The genomic RNA of ZIKV P6-740 (GenBank accession no. KX377336) was used as a template for the synthesis of three overlapping cDNA fragments by RT-PCR with the following primer sets: Frag-$A^{P6-740}$ (4553 bp), Z1RT and Z1F+Z1R; Frag-$B^{P6-740}$ (5070 bp), Z2RT and Z2F+Z2R; and Frag-$C^{P6-740}$ (5008 bp), Z3RT and Z3F+Z3R. Each of the three cDNA amplicons was subcloned into pBAC$^{SP6}$/JVFLx/XbaI, by ligating the 8381-bp PmeI-MluI fragment of pBAC$^{SP6}$/JVFLx/XbaI with the 4539-, 5056-, and 4994-bp PmeI-AscI fragments of the Frag-$A^{P6-740}$, Frag-$B^{P6-740}$, and Frag-$C^{P6-740}$ amplicons, respectively. This generated pBac/Frag-$A^{P6-740}$ to -$C^{P6-740}$. To introduce an SP6 promoter immediately upstream of the first adenine residue of the viral genome, two cDNA fragments were first amplified individually by (i) PCR of pBAC$^{SP6}$/JVFLx/XbaI with a pair of primers, S123-5sp1F+ S123-5sp1R (S123-5sp1R contains the antisense sequence of the SP6 promoter) and (ii) PCR of pRs/5'NCR$^{P6-740}$ with another pair of primers, S23-5sp2F+S23-5sp2R. Subsequently, these two fragments were fused by a second round of PCR with the outer forward and reverse primers S123-5sp1F+S23-5sp2R. The 1025-bp BamHI-SacII fragment of the fused PCR amplicons was ligated with the 2718-bp BamHI-SacII fragment of pRs2, creating pRs/5' SP$^{P6-740}$. To engineer a unique BarI run-off site just downstream of the last thymine residue of the viral genome, one cDNA fragment was amplified by PCR of pRs/3'NCR$^{P6-740}$ with primers S23-3roF+S23-3roR (S23-3roR contains the antisense sequence of the BarI and NotI recognition sites in a row). The 649-bp SacII-NotI fragment of the resulting amplicons was ligated with the 2667-bp SacII-NotI fragment of pRs2, creating pRs/3'RO$^{P6-740}$. The full-length P6-740 cDNA clone pBac/P6-740 was then assembled by sequentially joining the 7456-bp PacI-NotI fragment of pBAC$^{SP6}$/JVFLx/XbaI with the following five DNA fragments: (i) the 187-bp PacI-NheI fragment of pRs/5' SP$^{P6-740}$, (ii) the 2930-bp NheI-SpeI fragment of pBac/Frag-$A^{P6-740}$, (iii) the 3359-bp SpeI-NgoMIV fragment of pBac/Frag-$B^{P6-740}$, (iv) the 4059-bp NgoMIV-StuI fragment of pBac/Frag-$C^{P6-740}$, and (v) the 433-bp StuI-NotI fragment of pRs/3'RO$^{P6-740}$.

(3) pBac/PRVABC-59 (SEQ ID NO:3): The genomic RNA of ZIKV PRVABC-59 (GenBank accession no. KX377337) was used as a template for the synthesis of three overlapping cDNA fragments by RT-PCR with the following primer sets: Frag-$A^{PRVABC-59}$ (4553 bp), Z1RT and Z1F+ Z1R; Frag-$B^{PRVABC-59}$ (5070 bp), Z2RT and Z2F+Z2R; and Frag-$C^{PRVABC-59}$ (5008 bp), Z3RT and Z3F+Z3R. Each of the three cDNA amplicons was subcloned into pBAC$^{SP6}$/JVFLx/XbaI, by ligating the 8381-bp PmeI-MluI fragment of pBAC$^{SP6}$/JVFLx/XbaI with the 4539-, 5056-, and 4994-bp PmeI-AscI fragments of the Frag-$A^{PRVABC-59}$ Frag-$B^{PRVABC-59}$, and Frag-$C^{PRVABC-59}$ amplicons, respectively. This generated pBac/Frag-$A^{PRVABC-59}$ to -$C^{PRVABC-59}$. To introduce an SP6 promoter immediately upstream of the first adenine residue of the viral genome, two cDNA fragments were first amplified individually by (i) PCR of pBAC$^{SP6}$/JVFLx/XbaI with a pair of primers, S123-5sp1F+S123-5sp1R (S123-5sp1R contains the antisense sequence of the SP6 promoter) and (ii) PCR of pRs/5'NCR$^{PRVABC-59}$ with another pair of primers, S23-5sp2F+S23-5sp2R. Subsequently, these two fragments were fused by a second round of PCR with the outer forward and reverse primers S123-5sp1F+S23-5sp2R. The 1025-bp BamHI-SacII fragment of the fused PCR amplicons was ligated with the 2718-bp BamHI-SacII fragment of pRs2, creating pRs/5' SP$^{PRVABC-59}$. To engineer a unique BarI run-off site just downstream of the last thymine residue of the viral genome, one cDNA fragment was amplified by PCR of pRs/3'NCR$^{PRVABC-59}$ with primers S23-3roF+S23-3roR (S23-3roR contains the antisense sequence of the BarI and NotI recognition sites in a row). The 649-bp SacII-NotI fragment of the resulting amplicons was ligated with the 2667-bp SacII-NotI fragment of pRs2, creating pRs/3'RO$^{PRVABC-59}$. The full-length PRV-ABC-59 cDNA clone pBac/PRVABC-59 was then assembled by sequentially joining the 7456-bp PacI-NotI fragment of pBAC$^{SP6}$/JVFLx/XbaI with the following five DNA fragments: (i) the 187-bp PacI-NheI fragment of pRs/5' SP$^{PRVABC-59}$, (ii) the 4426-bp NheI-EcoNI fragment of pBac/Frag-A$^{PRVABC-59}$, (iii) the 2114-bp EcoNI-SacII fragment of pBac/Frag-B$^{PRVABC-59}$, (iv) the 3808-bp SacII-StuI fragment of pBac/Frag-C$^{PRVABC-59}$, and (v) the 433-bp StuI-NotI fragment of pRs/3'RO$^{PRVABC-59}$.

Construction of five GST-tagged recombinant protein expression vectors. A total of five bacterial expression plasmids were constructed, each of which was used to express a 32- to 51-aa non-hydrophobic region of the ZIKV polyprotein as a GST fusion protein. In all cases, a defined region of the ZIKV ORF was amplified by PCR using pBac/PRVABC-59 as a template and the appropriate pair of primers listed in FIG. 21: (i) Frag-zC (147 bp), ZikaC-F+ZikaC-R; (ii) Frag-zM (120 bp), ZikaM-F+ZikaM-R; (iii) Frag-zE (147 bp), ZikaE-F+ZikaE-R; (iv) Frag-zNS4A (177 bp), ZikaNS4A-F+ZikaNS4A-R; and (v) Frag-zNS4B (177 bp), ZikaNS4B-F+ZikaNS4B-R. Each of the resulting amplicons was cloned into pGex-4T-1 (GE Healthcare) by ligating the 4954-bp EcoRI-XhoI fragment of the pGex-4T-1 vector with 135-, 108-, 135-, 165-, and 165-bp EcoRI-XhoI fragments of the Frag-zC, -zM, -zE, -zNS4A, and -zNS4B amplicons, respectively. This created pGex-zC, -zM, -zE, -zNS4A, and -zNS4B (FIG. 15A).

Cells and viruses. Details of the 17 cell lines used in this invention, including their growth medium and culture conditions, are presented in FIG. 22. ZIKV MR-766 and P6-740 were obtained from the World Reference Center for Emerging Viruses and Arboviruses, University of Texas Medical Branch (Galveston, Tex.), and ZIKV PRVABC-59 was provided by the Centers for Disease Control and Prevention (Fort Collins, Colo.). In all three ZIKVs, viral stocks were amplified once in Vero cells at an MOI of 1.

Sequence alignment and phylogenetic analysis. Multiple sequence alignments were performed via ClustalX, and the phylogenetic tree was constructed using MEGA and visualized via TreeView. Sequence identities between aligned nucleotide and amino acid sequences were calculated using ClustalX.

Transcription and transfection. Infectious transcripts were synthesized from P BarI-linearized BAC plasmid DNA with SP6 RNA polymerase in reactions containing m$^7$GpppA (New England Biolabs). RNA integrity was examined by agarose gel electrophoresis. RNA was transfected into Vero cells by electroporation under optimized conditions (980 V, 99-μs pulse length, and 3 pulses); RNA infectivity was quantified by infectious center assay. The infectious centers of plaques were visualized either nonspecifically by counterstaining of uninfected cells with crystal violet or specifically by immunostaining of ZIKV-infected cells with rabbit α-zNS1 antiserum and horseradish peroxidase-conjugated goat α-rabbit IgG (Jackson ImmunoResearch), followed by developing with 3,3'-diaminobenzidine.

Real-time RT-PCR. ZIKV vgRNA levels in infected Vero cells were quantified by real-time RT-PCR with the primer pairs and fluorogenic probes listed in FIG. 21: the ZikaF+ZikaR and ZikaProbe specific for the ZIKV NS3-coding region that has the identical sequences in all three ZIKVs, and the VeroF+VeroR and VeroProbe specific for the Vero β-actin-coding region. Each ZIKV vgRNA level was normalized to the corresponding β-actin mRNA level as an internal control.

Immunoblotting, confocal microscopy, and flow cytometry. Individual ZIKV proteins were identified by immunoblotting using each of the 15 previously characterized JEV region-specific rabbit antisera (FIG. 14) that have the potential to cross-react with their ZIKV counterparts, or seven newly generated ZIKV region-specific rabbit antisera (FIGS. 15A-15B). The rabbit antibody was detected using alkaline phosphatase (AP)-conjugated goat α-rabbit IgG (Jackson ImmunoResearch), and the AP enzyme was visualized using colorimetric detection with 5-bromo-4-chloro-3-indolyl phosphate and nitro blue tetrazolium (Sigma). ZIKV E proteins were visualized by confocal microscopy with rabbit α-zE antiserum, followed by secondary labeling with fluorescein isothiocyanate-conjugated goat α-rabbit IgG (Jackson ImmunoResearch). ZIKV NS4A proteins were detected by flow cytometry with rabbit α-zNS4A antiserum, followed by secondary labeling with Alexa 488-conjugated goat α-rabbit IgG (Invitrogen).

Mouse studies and ethics statements. ZIKV neuropathogenicity was examined in male and female mice of four strains: CD-1 (1, 2, and 4 weeks, Charles River), C57BL/6J (4 weeks, the Jackson Laboratory), A129 (4 weeks, bred in-house), and AG129 (4 weeks, bred in-house). Groups of mice were inoculated intramuscularly (IM, 50 μl) or intracerebrally (IC, 20 μl) with 10-fold serial dilutions of virus stock in α-minimal essential medium and monitored for any ZIKV-induced clinical signs, weight loss, or death daily for 20 days. The IM and IC LD$_{50}$ values for each virus were calculated from the respective dose-dependent survival curves of the infected mice. All mouse studies were conducted in strict accordance with the Guide for the Care and Use of Laboratory Animals of the National Institutes of Health. The animal protocol was approved by the Institutional Animal Care and Use Committee of Utah State University (protocol #2505). Discomfort, distress, pain and injury were minimized as much as possible through limited handling and euthanization of mice when they were moribund.

4. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Characterization of Three Spatiotemporally Distinct and Genetically Divergent ZIKV Strains As an initial step in examining the genetic diversity of ZIKV and its biological significance for viral replication and pathogenesis, three historically important strains of distinct geographical and temporal origins were selected: (i) MR-766, the first ZIKV identified from the blood of a rhesus macaque monkey in Uganda in 1947; (ii) P6-740, the first non-African strain, isolated from a pool of *A. aegypti* mosquitoes in Malaysia in 1966; and (iii) PRVABC-59, the recent American strain recovered from the blood of a human patient in Puerto Rico in 2015. To compare the genome sequence and composition of these three ZIKVs, the consensus nucleotide sequence for each of their full-length vgRNAs was determined. In all three ZIKVs, it was found that the vgRNA is 10,807 nucleotides long, with a single ORF of 10,272 nucleotides flanked by a 106- or 107-nt 5'NCR and a 428- or 429-nt 3'NCR (FIG. 8A). Also, the three vgRNAs all begin with the dinucleotide 5'-AG and end with the dinucleotide CU-3', both of which are conserved among all mosquito- and tick-borne flaviviruses. However, pairwise sequence comparisons of the three complete genomes showed a considerable degree of genetic diversity, with a range in sequence identity of 89.1-95.6% at the nucleotide level and 96.8-98.8% at the amino acid level over the 3,423-aa polyprotein encoded by the single ORF of the vgRNA (FIG. 8B).

To examine the genetic relationship between the three spatiotemporally distinct ZIKVs and their associations with other strains, multiple sequence alignments were performed for phylogenetic analysis using the nucleotide sequence of all 29 ZIKV genomes (15 complete, 14 near-complete) available in GenBank at the time of analysis, including the complete nucleotide sequence of the genomes of MR-766, P6-740, and PRVABC-59. Construction of a genome-based rooted phylogenetic tree using JEV K87P39 as an outgroup revealed two distinct phylogenetic groups (FIGS. 1A and 8C), in agreement with previous ORF-based phylogenetic studies that classified 10-40 ZIKV isolates into two major genetic lineages, African and Asian. The African lineage branches into two clusters, one including four different versions of the Ugandan MR-766 strain (1947) that are not identical in genome sequence, and the other including the three Senegalese isolates 41671-DAK, 41525-DAK, and 41662-DAK, all isolated in 1984. On the other hand, the Asian lineage contains a single cluster of the Malaysian P6-740 (1966), Cambodian FSS13025 (2010), Philippine CPC-0740 (2012), and Thai SV0127-14 (2014) strains, as well as 18 other isolates collected during the 2015-2016 American epidemic, including the Puerto Rican PRVABC-59 strain (2015). Notably, the four pre-epidemic Asian strains (P6-740, FSS13025, CPC-0740, and SV0127-14) are closely related to the 2015-2016 American epidemic strains, but each forms a single minor branch. Overall, these data indicate that MR-766 belongs to the African lineage, whereas both P6-740 and PRVABC-59 belong to the Asian lineage, with PRVABC-59 being derived from an ancestor of the Asian lineage.

Example 2

Development of Genetically Stable Full-Length Infectious cDNA Clones for the Three ZIKV Strains Three full-length infectious ZIKV cDNAs were constructed for the MR-766, P6-740, and PRVABC-59 strains, each capable of serving as a template for the rescue of molecularly cloned ZIKVs (FIG. 1B). In each strain, the 10,807-nt vgRNA, excluding the 5' and 3' termini, was cloned as three overlapping cDNAs of 4.5-5.0 kb into the single-copy BAC vector pBeloBAC11 to ensure the stable maintenance of cloned cDNAs during propagation in *E. coli*. Each of the 5'- and 3'-terminal regions (0.9 and 0.6 kb, respectively) was cloned into the high-copy vector pRS2 to facilitate the introduction of a bacteriophage SP6 promoter immediately upstream of the viral 5'-end and a unique restriction endonuclease recognition site (PsrI for MR-766, BarI for P6-740 and PRVABC-59) just downstream of the viral 3'-end. Both the SP6 promoter and the unique restriction site were engineered so that in vitro run-off transcription could be used to produce $m^7G$-capped synthetic RNAs bearing authentic 5' and 3' ends of the vgRNA. In the last cloning step, a set of the five overlapping ZIKV cDNAs was sequentially assembled by joining at four natural pre-existing restriction sites in the viral genome to generate the full-length ZIKV cDNA without introducing any point mutations for cloning. Using this BAC-based cloning strategy, a panel of three full-length ZIKV cDNAs was created, and designated pBac/MR-766 (SEQ ID NO:1), pBac/P6-740 (SEQ ID NO:2), and pBac/PRVABC-59 (SEQ ID NO:3).

Figure 1C:
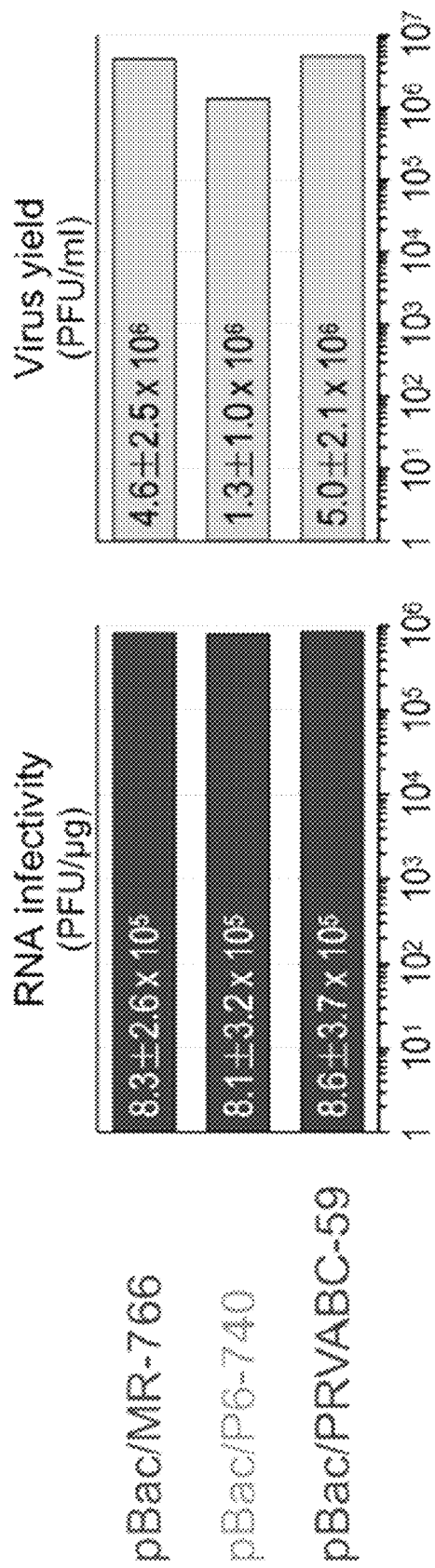
Figure 1D:
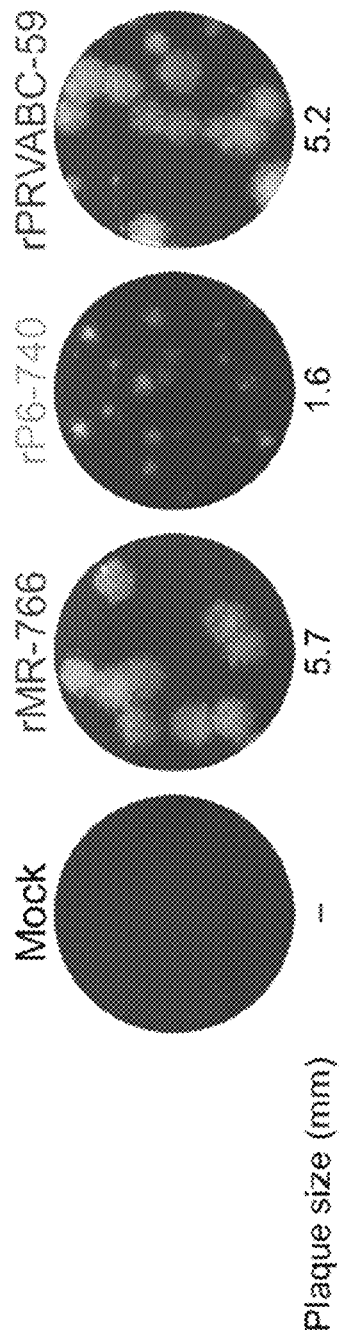

To evaluate the functionality of the three full-length ZIKV BACs, the viability of the synthetic RNAs transcribed in vitro from each BAC was determined by measuring their specific infectivity after RNA transfection into ZIKV-susceptible Vero cells. To prepare a DNA template for in vitro run-off transcription, the three full-length ZIKV BACs were first linearized by digestion with PsrI (for pBac/MR-766) or BarI (for pBac/P6-740 and pBac/PRVABC-59). Each was then used as a template for a run-off transcription reaction using SP6 RNA polymerase in the presence of the $m^7$GpppA cap structure analog. After removal of the DNA template by DNase I digestion, Vero cells were transfected with the RNA transcripts, quantifying their infectivity as the number of PFU per μg of transfected RNA. In all three BACs, the RNA transcripts invariably had a high infectivity of $8.1$-$8.6 \times 10^5$ PFU/μg and were capable of producing a high-titer stock of infectious ZIKVs in culture medium that reached $1.3$-$5.0 \times 10^6$ PFU/ml at 36 h after transfection (FIG. 1C). Each of the three recombinant BAC-derived ZIKVs (designated by the prefix "r") formed a homogeneous population of plaques that differed from the others in size, with mean diameters of 5.7 mm (rMR-766), 1.6 mm (rP6-740), and 5.2 mm (rPRV-ABC-59) (FIG. 1D). It was demonstrated that using pBac/P6-740, the infectivity of its RNA transcripts was decreased by ~4 logs to a barely detectable level (55-105 PFU/μg), with a single $C^{9804} \rightarrow U$ substitution (an unintended mutation introduced during the overlapping cDNA synthesis by RT-PCR) replacing a His with Tyr at position 713 of the viral NS5 protein (FIG. 19A). On the crystal structure of ZIKV NS5, the His-713 residue is located within the conserved structural motif E region near the priming loop in the RNA-dependent RNA polymerase domain (FIG. 19B), suggesting this domain may play a role for His-713 in the polymerase function of ZIKV NS5.)

Next, the system was fully characterized by addressing the three key aspects that are important for reliable and efficient recovery of infectious viruses from the cloned cDNAs: (1) Specific infectivity requires the in vitro run-off transcription of RNA from a full-length ZIKV cDNA (FIG. 9). Using pBac/PRVABC-59, it was demonstrated that the full-length cDNA itself was not infectious but was required as the template for transcription, since the presence of DNase I in the transcription reaction eliminated infectivity. After transcription, DNase I treatment had no effect on infectivity, when compared to the intact reaction mixture, but RNase A treatment abolished infectivity. (2) An RNA cap structure is necessary for the full infectivity of in vitro-generated RNAs (FIG. 10). It was found that the uncapped RNA transcripts synthesized in the absence of the $m^7$GpppA cap structure analog from each of the three full-length ZIKV cDNAs always had an infectivity of 2.6-4.3×$10^2$ PFU/μg, >3 logs lower than those of their $m^7$G-capped RNA counterparts (6.9-8.4×$10^5$ PFU/μg). (3) Full-length ZIKV BACs are stable during propagation in bacteria (FIG. 11). Experimentally, a single colony of E. coli DH10B carrying each of the three full-length ZIKV BACs was grown in liquid 2×YT medium overnight and then serially passaged for 4 days by diluting it $10^6$-fold daily, such that each passage represented ~20 generations. In all three cases, it was found no differences in specific infectivity of the RNA transcripts made from the BAC plasmids extracted from passages 0, 2, or 4. These data demonstrate the establishment of genetically stable BAC-based reverse genetics platforms for the recovery of three molecularly cloned, genetically distinct ZIKVs.

Example 3

Figure 2A:
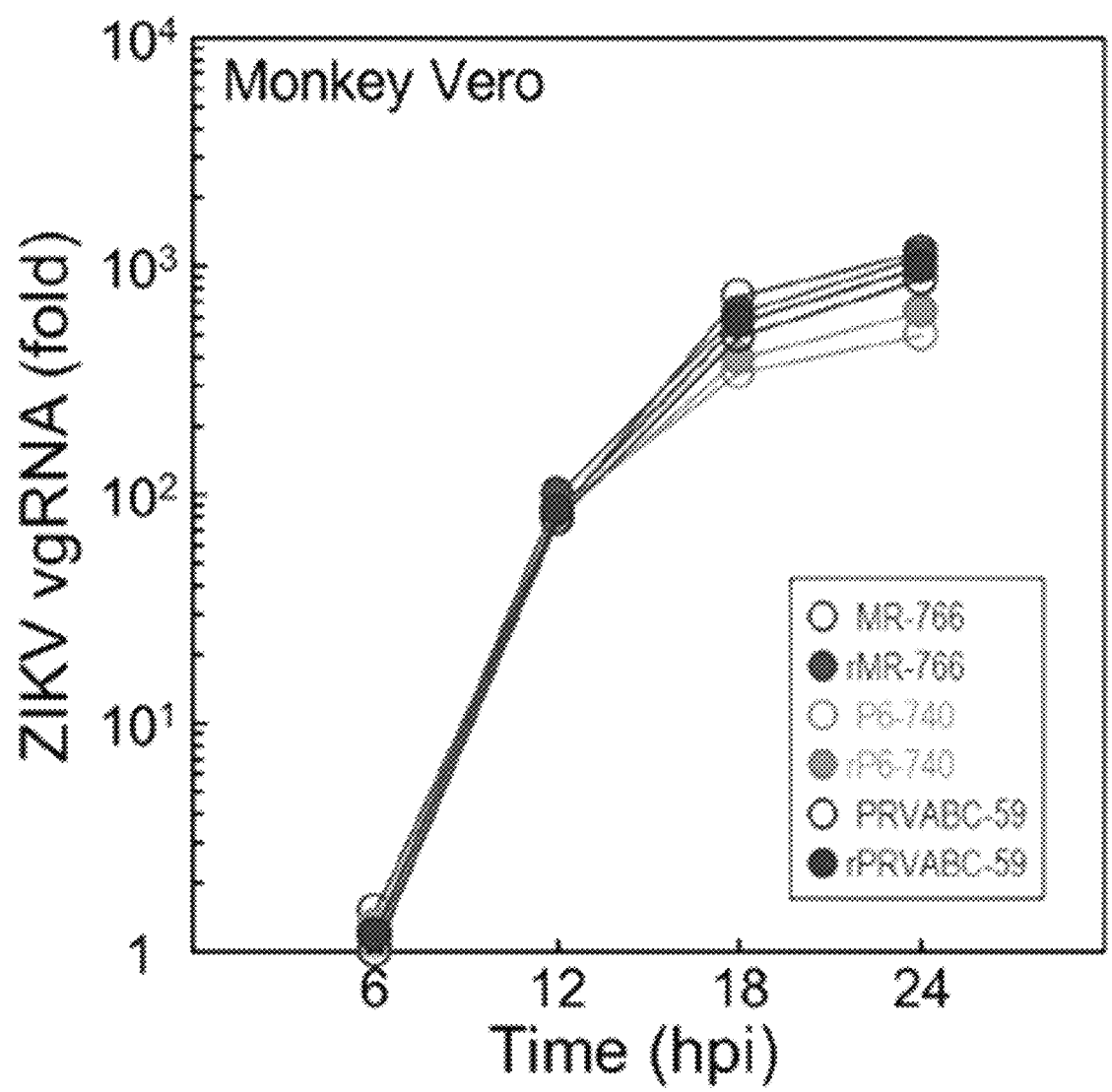
FIG. 2A, FIG. 2B, FIG. 2C, FIG. 2D, and FIG. 2E are graphs and images of ZIKV replicability and cytopathogenicity in cell cultures that depends on the particular combination of virus strain and host cells.
Figure 2B:
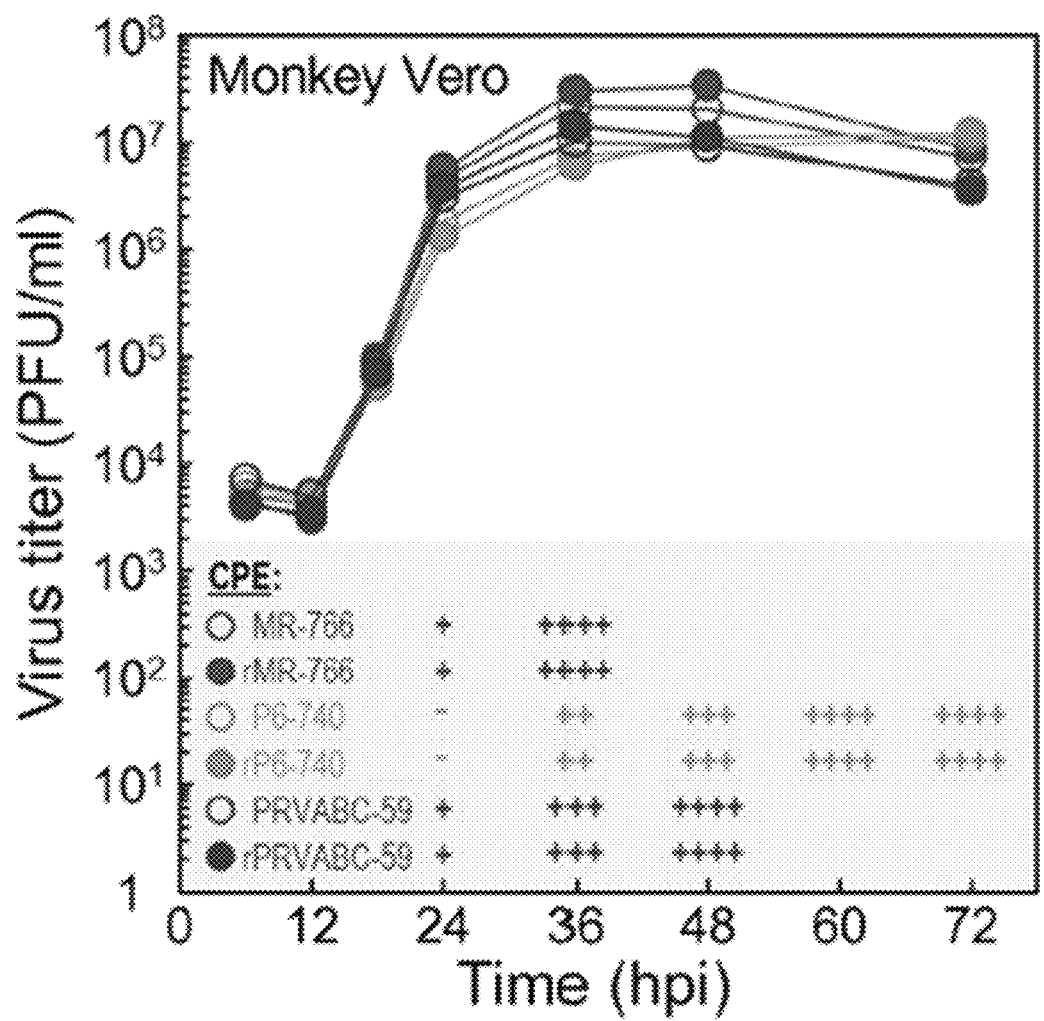
Figure 2C:
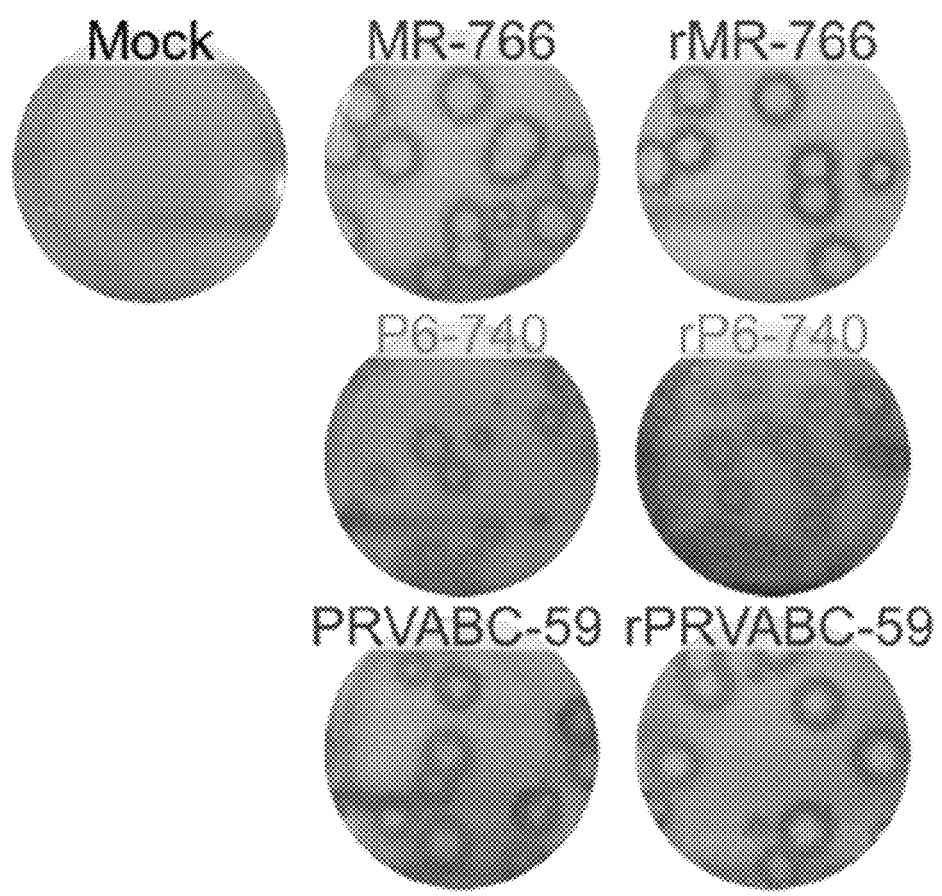

Differential Replicability and Cytopathogenicity Among Three Molecularly Cloned ZIKVs in Human, Mosquito, and Animal Cell Lines To test whether the genetic variation in ZIKV can have differential effects on its replicability and cytopathogenicity, monkey kidney-derived Vero cells were infected at an MOI of 1, then examined the replicative and cytopathic properties of the three cloned cDNA-derived ZIKVs (rMR-766, rP6-740, and rPRVABC-59) as compared to those of the uncloned parental ZIKVs (MR-766, P6-740, and PRVABC-59) used for cDNA construction. In all three strains, no noticeable differences were found between the cloned and uncloned viruses in the accumulation of vgRNA over the first 24 h post-infection (hpi) (FIG. 2A), paralleling the kinetics of viral growth and CPE of the first 3 days post-infection (dpi) (FIG. 2B) and the average sizes of the α-zNS1 antibody-reactive plaques stained at 4 dpi (FIG. 2C). However, clear differences were observed among the three strains, for both the cloned and uncloned viruses, in their replicability and cytopathogenicity (FIGS. 2A-2C): (i) rMR-766/MR-766 displayed the fastest rate of RNA replication, induced complete lysis of the infected cells by 36 hpi, achieved the highest virus titer of 2.0-3.3×$10^7$ PFU/ml at 36-48 hpi, and formed the largest plaques of 6.3-mm diameter. (ii) rP6-740/P6-740 had the slowest rate of RNA replication, did not cause complete CPE until 72 hpi, reached its maximal virus titer of 1.1-1.2×$10^7$ PFU/ml at 60-72 hpi, and generated the smallest plaques of 2.4-mm diameter. (iii) rPRVABC-59/PRVABC-59 had a rate of RNA replication slightly slower than rMR-766/MR-766 but much faster than that of rP6-740/P6-740; it caused complete CPE by 48 hpi, with a peak virus titer of 0.9-1.4×$10^7$ PFU/ml at 36-48 hpi, and produced plaques of 5.9-mm diameter.

Figure 2D:
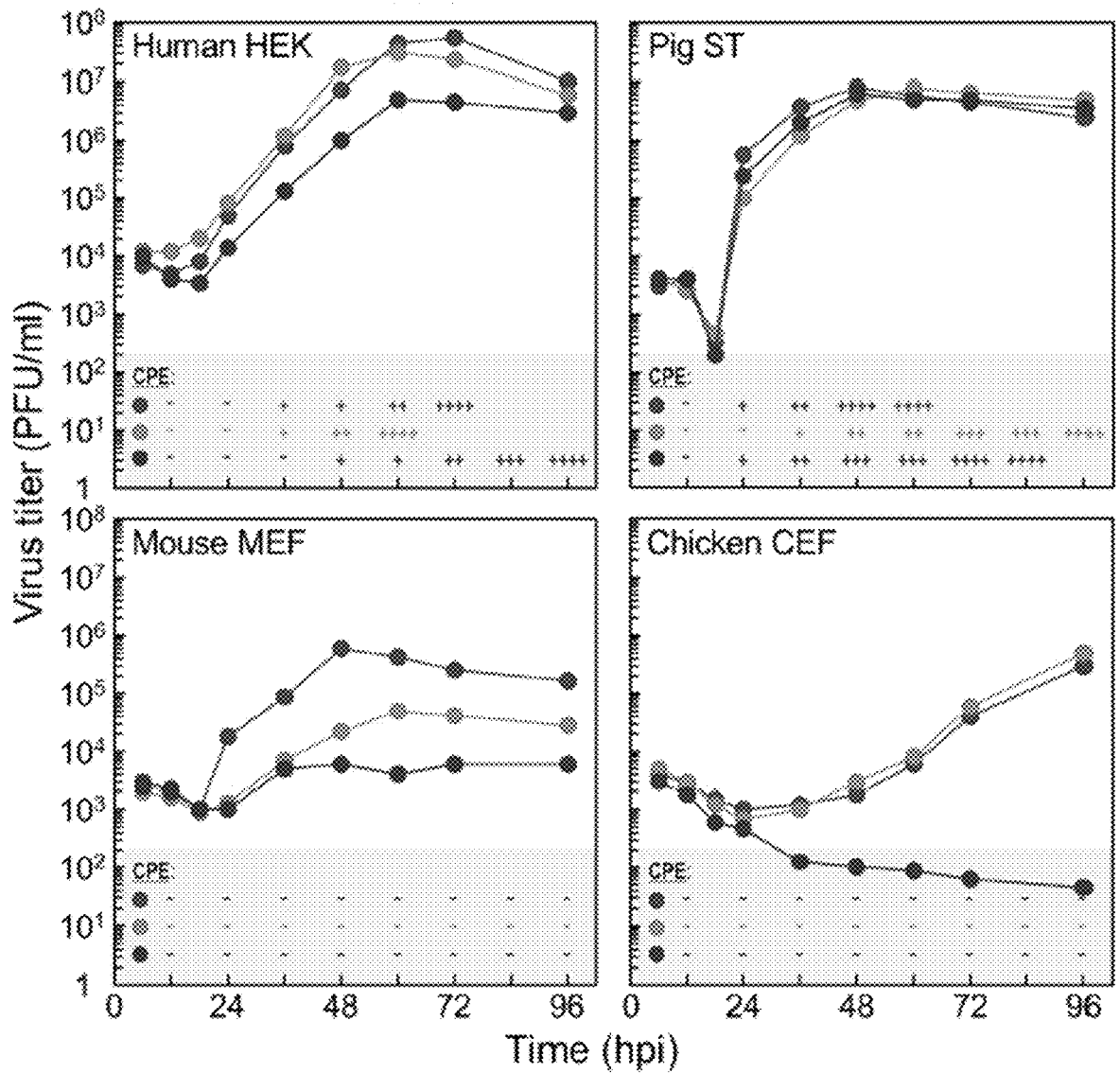
Figure 2E:
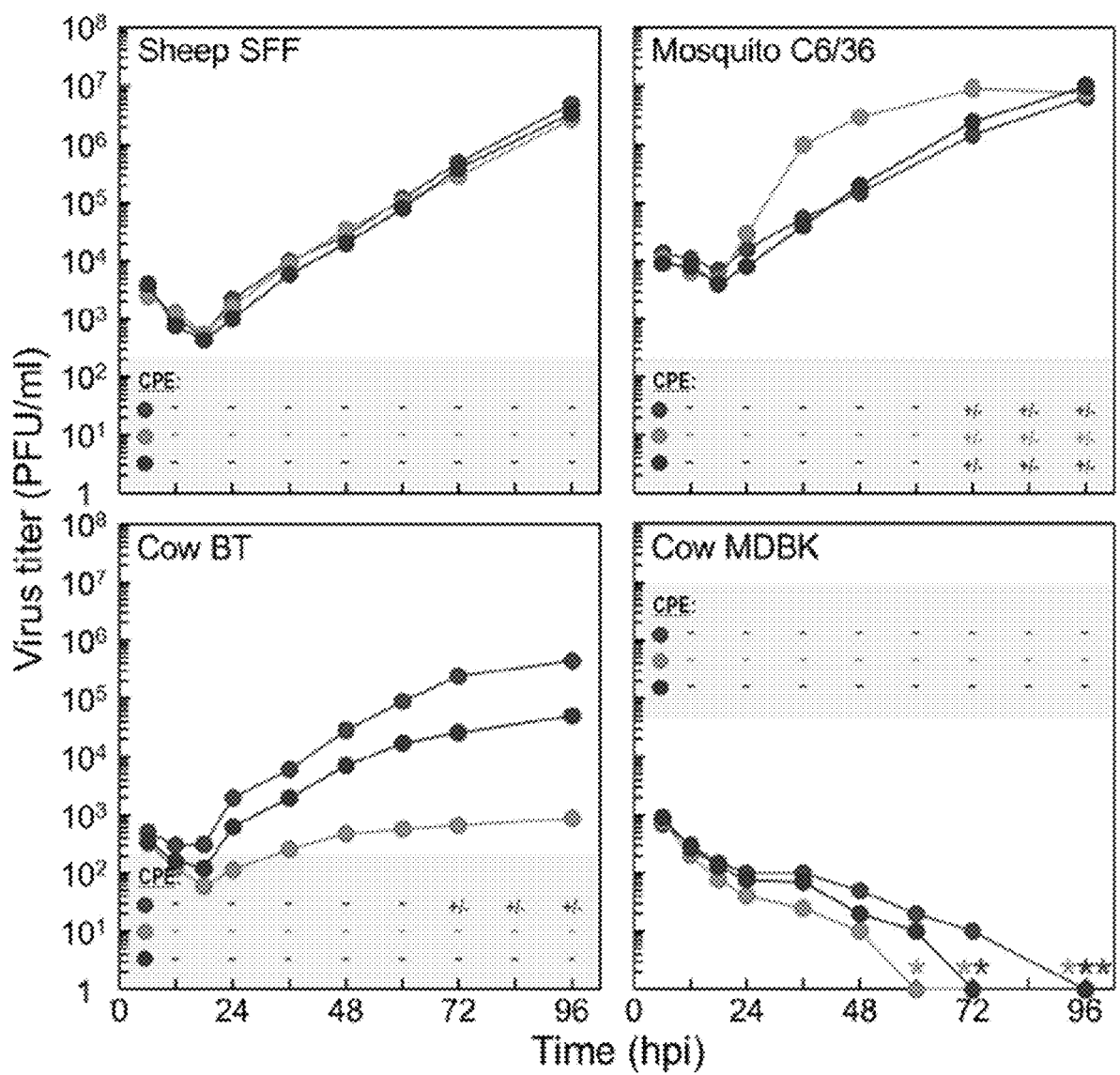

The replicative and cytopathic potential of the three cDNA-derived ZIKVs was further analyzed in 16 other animal cell lines from 11 different species that are potentially relevant to ZIKV pathogenesis and transmission, over the first 4 days after infection of the cells with each virus at an MOI of 1. These data revealed seven distinct patterns of viral growth kinetics and cytopathogenesis, depending on a combination of the viral strain and host cell line (FIGS. 2D, 2E, and 12): (1) In all three human cell types (embryonic kidney HEK, hepatocarcinoma Huh-7, and neuroblastoma SH-SY5Y), rMR-766 and rP6-740 grew equally well, to maximum titers of $10^7$-$10^8$ PFU/ml at 48-72 hpi, but rPRVABC-59 always grew at a slower rate, attaining a peak titer 1-2 logs lower than that of the other two strains at 72-96 hpi (HEK and SH-SY5Y) or reaching a peak titer similar to that of the other two strains only at 96 hpi (Huh-7); all three ZIKVs induced cell death, with a correlation between the degree of CPE and the magnitude of viral replication. (2) In swine testis (ST) and equine skin (NBL-6) cells, the three ZIKVs replicated to their peak titers of $10^6$-$10^7$ PFU/ml at 48 hpi, with differential growth rates similar to those seen in Vero cells (rMR-766, fastest; rP6-740, slowest; rPRVABC-59, intermediate) that paralleled the kinetics of CPE development. (3) In sheep fetal fibroblast (SFF) and A. albopictus (C6/36) cells, the three ZIKVs shared a superimposable growth curve, characterized by a steady increase in virus titers up to ~$10^7$ PFU/ml by 96 hpi, except for rP6-740, which had an exponential growth during 24-48 hpi in C6/36, but not SFF cells. None of the three ZIKVs produced any visible CPE. (4) In goat fetal fibroblast (GFF), canine kidney (MDCK), and feline kidney (CRFK) cells and in all three mouse cell types (C57BL/6-derived embryonic fibroblast MEF, NIH/Swiss-derived embryonic fibroblast NIH/3T3, and motor neuron-like hybrid NSC-34), rMR-766 was the fastest-growing, reaching its highest titer of $10^6$-$10^7$ PFU/ml at 48-96 hpi; rPRVABC-59 was the slowest-growing, gaining a maximum titer of only $10^3$-$10^4$ PFU/ml during the same period; and rP6-740 was intermediate in growth rate. However, none of these viruses produced visible CPE. (5) In chicken embryo fibroblast (CEF) cells, both rMR-766 and rP6-740 had a relatively long lag period of 36 h, followed by a gradual increase in virus titer up to $10^5$-$10^6$ PFU/ml by 96 hpi; in contrast, rPRVABC-59 grew extremely poorly, resulting in a slow decrease in virus titer to 45 PFU/ml by 96 hpi. No CPE was observed for any of the three ZIKV-infected cell types. (6) In bovine turbinate (BT) cells, the three ZIKVs showed substantial differences in growth kinetics, reaching a plateau at 96 hpi, with peak titers of 4.4×$10^5$ PFU/ml (rMR-766), 5.0×$10^4$ PFU/ml (rPRVABC-59), and 8.8×$10^2$ PFU/ml (rP6-740). However, no visible CPE was induced in any of the ZIKV-infected cells. (7) In bovine kidney (MDBK) cells, the titers of all three ZIKVs declined to undetectable levels at 60-96 hpi, with no overt signs of viral replication.

Figure 3A:
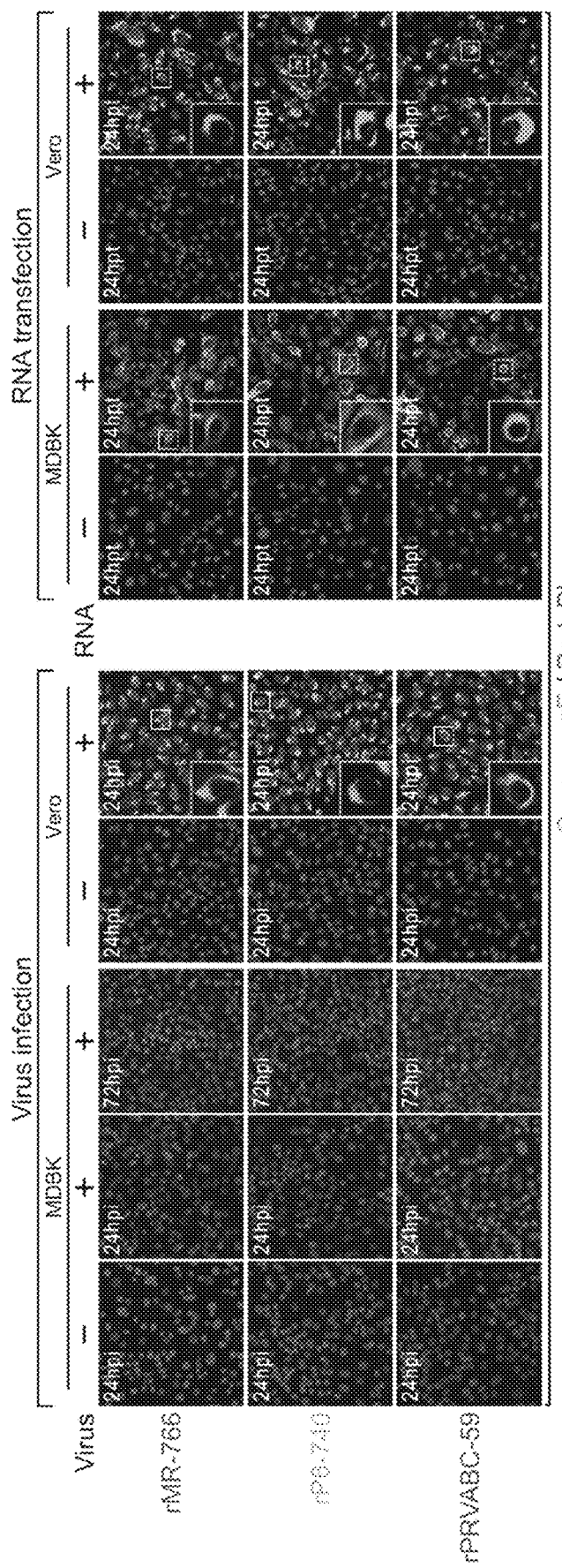
FIG. 3A, FIG. 3B, and FIG. 3C show that MDBK cells are permissive for ZIKV RNA replication but are not susceptible to infection with the virus. MDBK cells were mock-infected or infected with rMR-766, rP6-740, or rPRVABC-59 at an MOI of 3 (for virus infection experiments), or mock-transfected or transfected with 3 μg of synthetic RNAs transcribed in vitro from their respective infectious cDNAs (for RNA transfection experiments). At the indicated time points, the expression of three ZIKV proteins (E, NS1, and NS4A) within the cells was analyzed by confocal microscopy for E (FIG. 3A), flow cytometry for NS4A (FIG. 3B), and immunoblotting for NS1 (FIG. 3C). The insets in panel A show enlarged views of the boxed areas with the fluorescence of propidium iodide (PI)-stained nuclei excluded. In all experiments, ZIKV-susceptible Vero cells were included in parallel. hpi, hour post-infection; hpt, hour post-transfection.
Figure 3B:
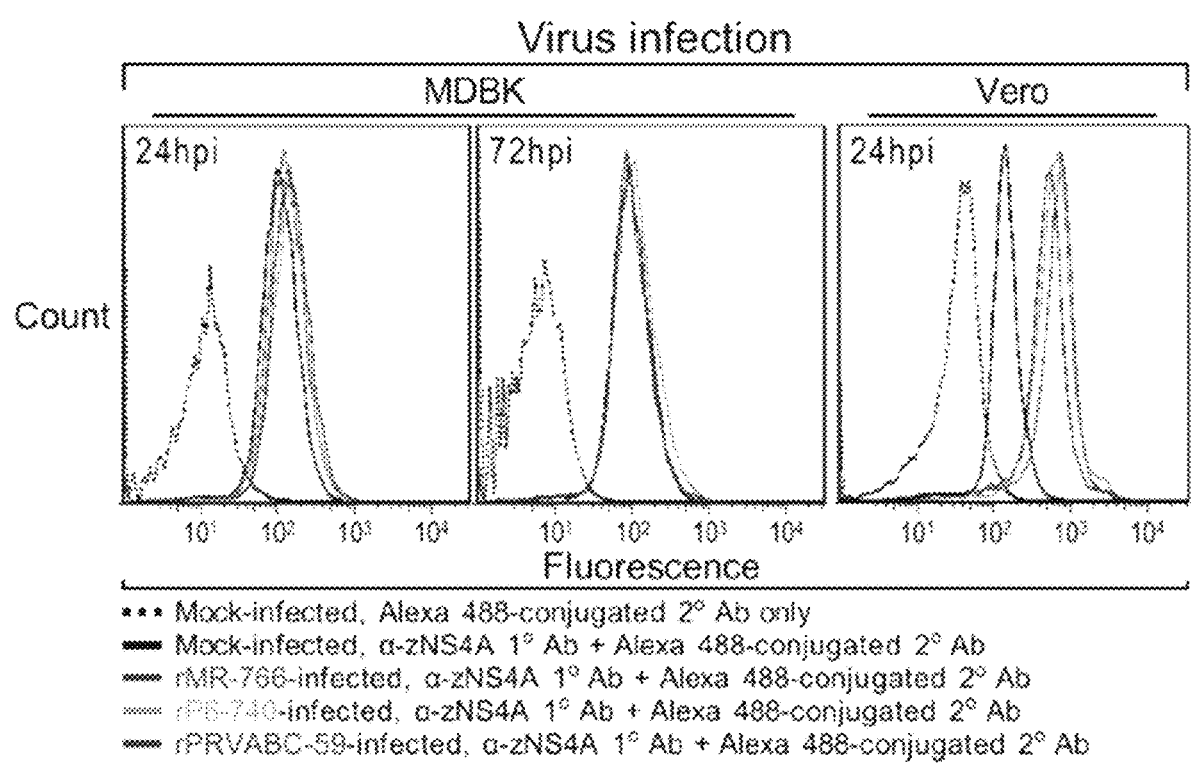
Figure 3C:
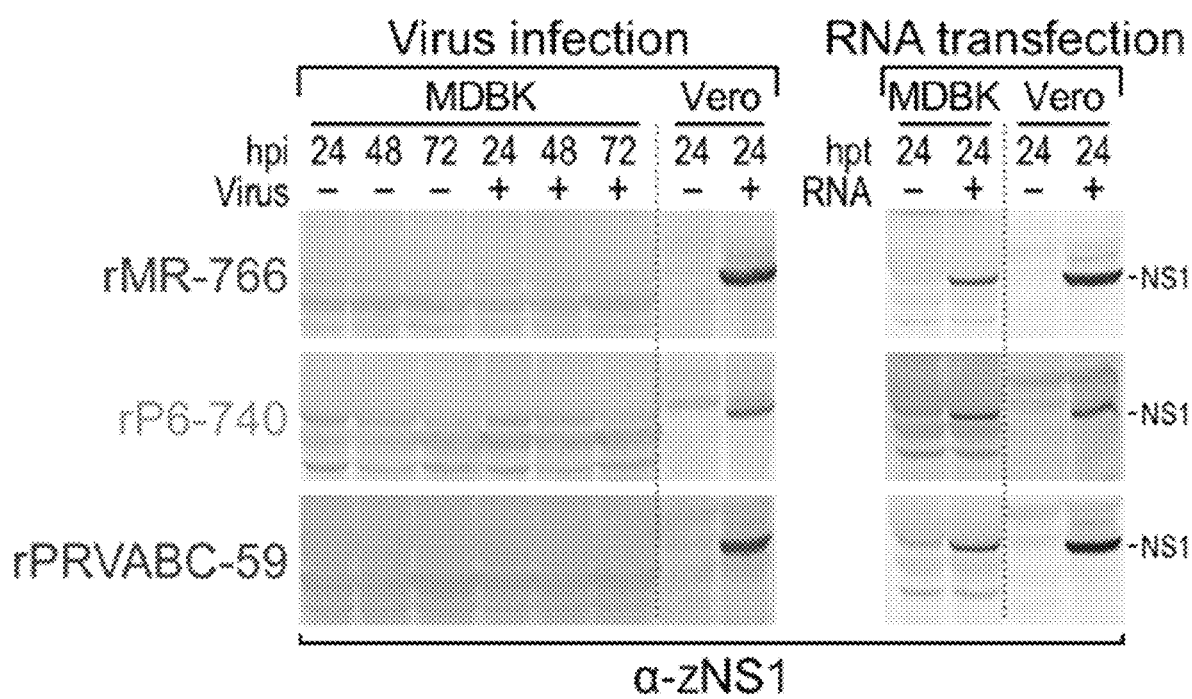

Subsequently, it was demonstrated that MDBK cells are not susceptible to ZIKV infection, but instead are permissive for ZIKV RNA replication, by using (i) single cell-based immunofluorescence (FIG. 3A) and flow cytometry (FIG. 3B) assays to determine the number of cells expressing ZIKV proteins (E or NS4A), when MDBK cells were either infected with each of the three cDNA-derived ZIKVs or transfected with each of the three infectious RNAs transcribed in vitro from their corresponding cDNAs; and (ii)

total cell lysate-based immunoblot analyses to assess the accumulation levels of ZIKV NS1 protein in the virus-infected vs. RNA-transfected MDBK cells (FIG. 3C). In all these experiments, Vero cells, a ZIKV-susceptible cell line, was used as a control. These results led to the proposition that MDBK cells might lack one or more host factors required for ZIKV entry; alternatively, they might have a general defect in the clathrin-dependent endocytic pathway that ZIKV utilizes for internalization. Thus, the functional integrity of the clathrin-dependent endocytic pathway in MDBK cells was investigated, by analyzing the susceptibility of these cells to infection by two other enveloped RNA viruses whose entry depends on clathrin-mediated endocytosis: BVDV and VSV. In contrast to their resistance to ZIKV infection, it was found that MDBK cells were highly susceptible to infection with both BVDV and VSV, as demonstrated by their plaque formation and high level of progeny virion production (FIGS. 13A-13B). These results indicate that the cellular machinery associated with the clathrin-dependent endocytic pathway is functional in MDBK cells, and they support the hypothesis that MDBK cells lack a host factor(s) promoting ZIKV entry.

Example 4

Figure 4A:
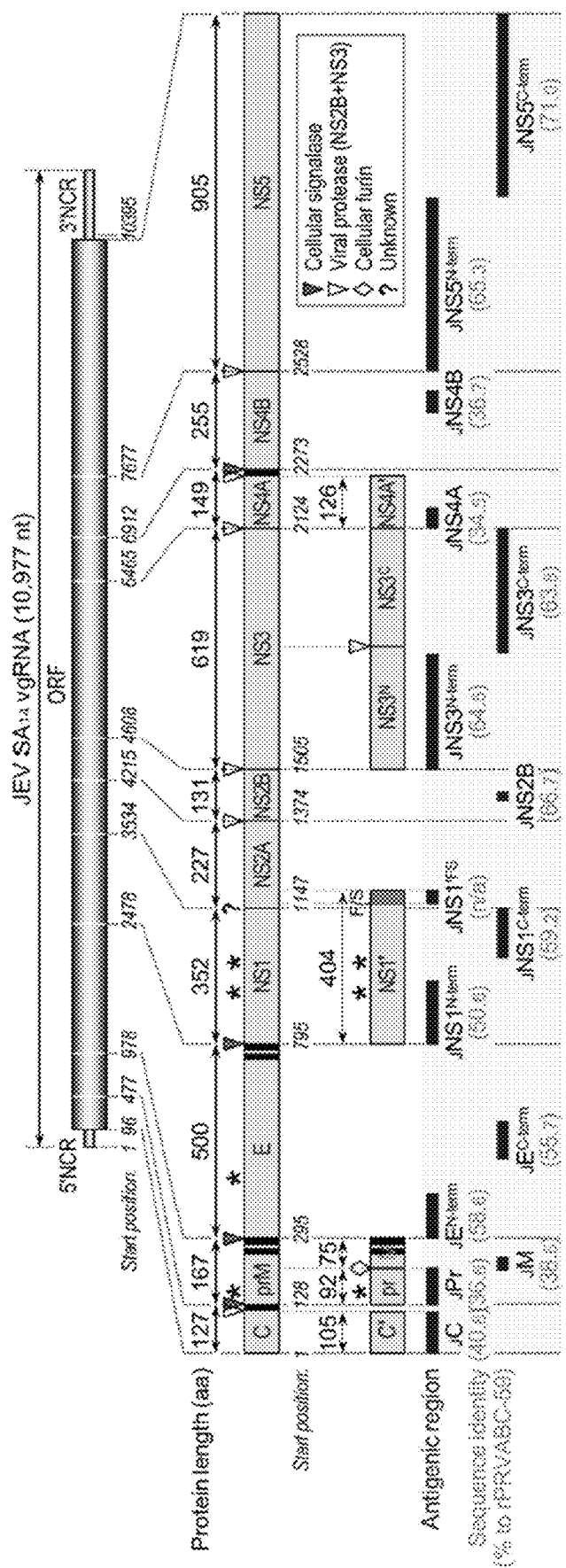
FIG. 4A, FIG. 4B, FIG. 4C, and FIG. 4D show that a subset of 15 JEV region-specific polyclonal antibodies detects the cross-reactive ZIKV E, NS1, NS2B, NS3, NS5, and their related species in ZIKV-infected cells.
Figure 4B:
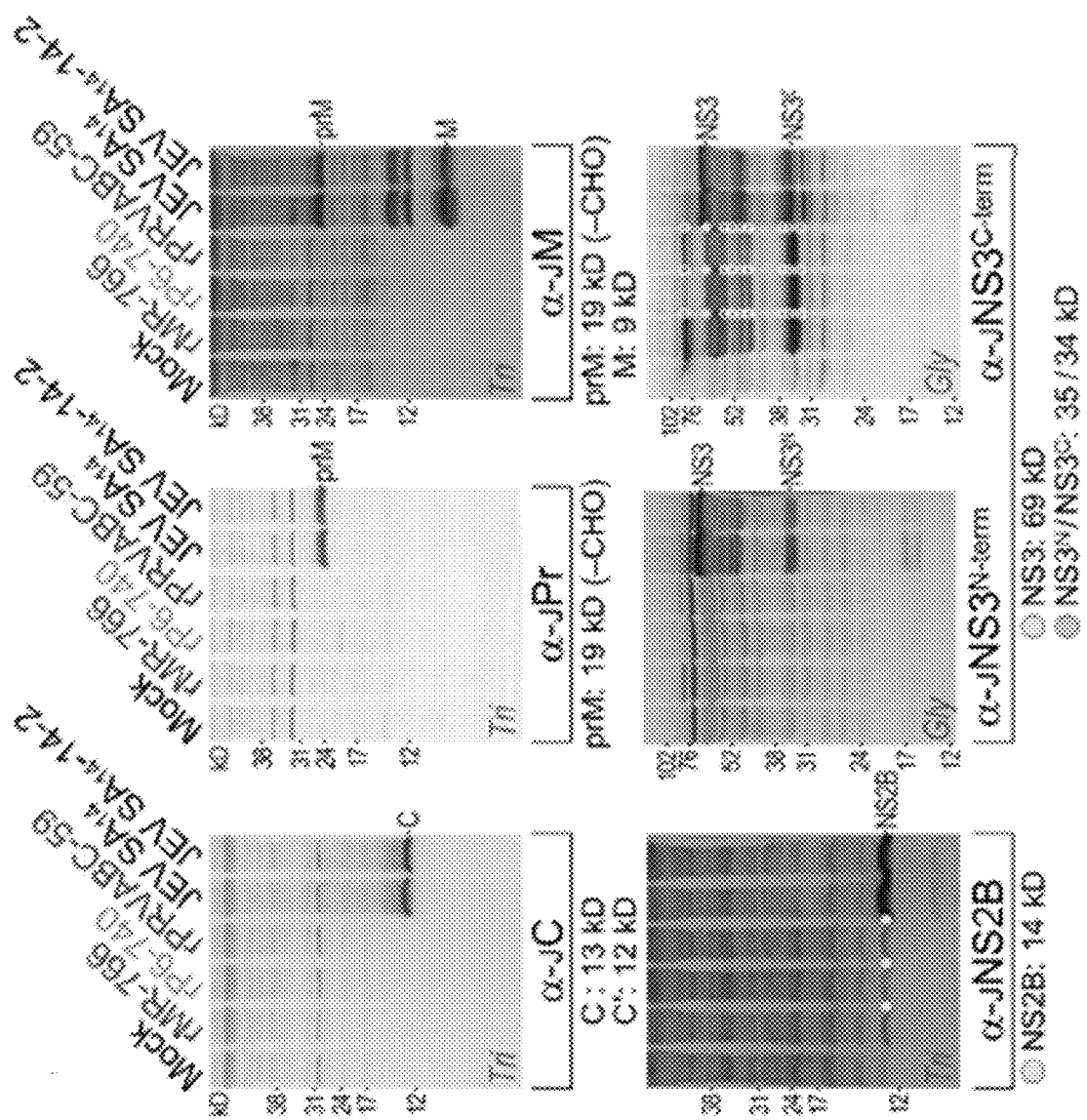
Figure 4C:
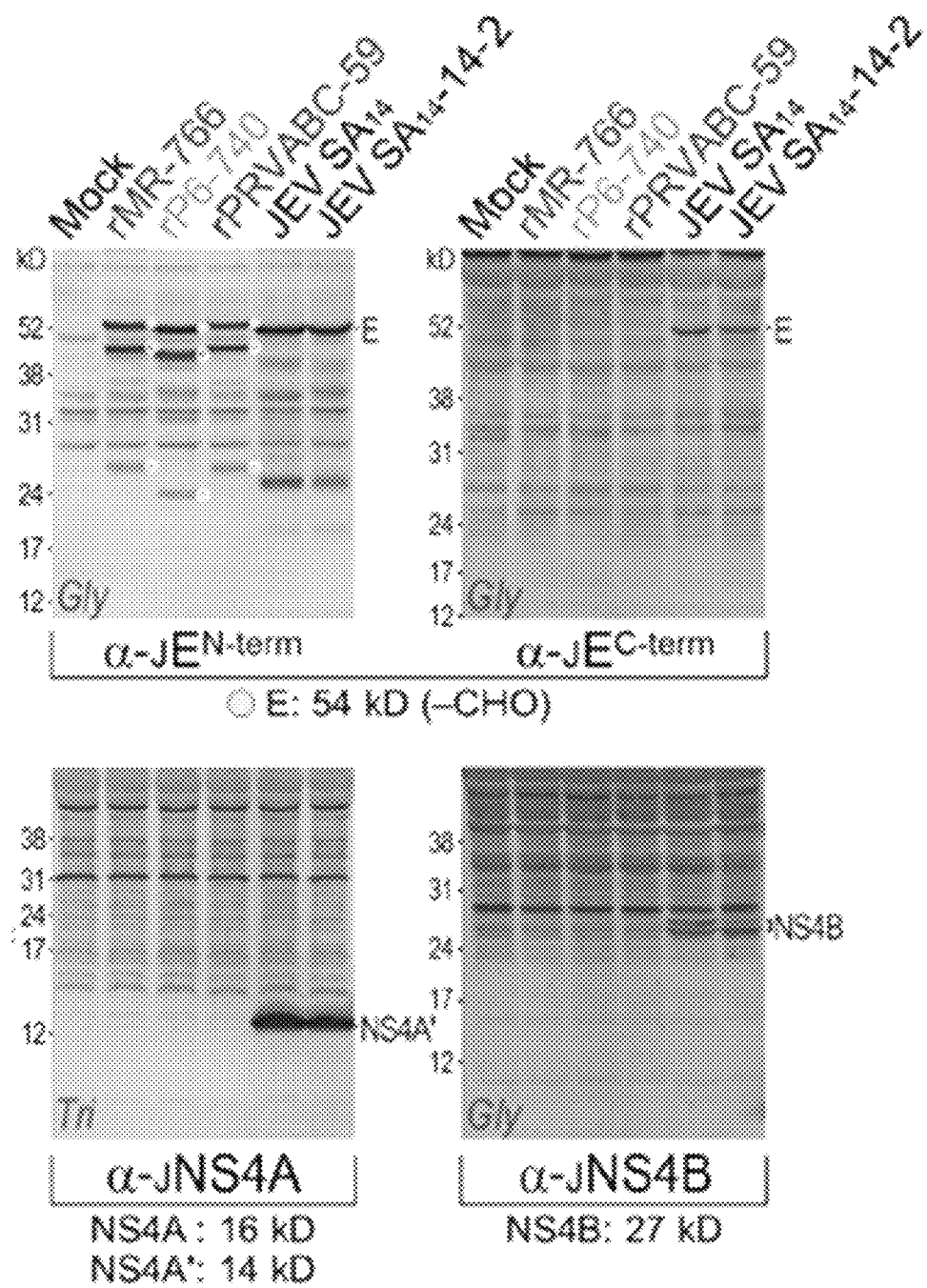
Figure 4D:
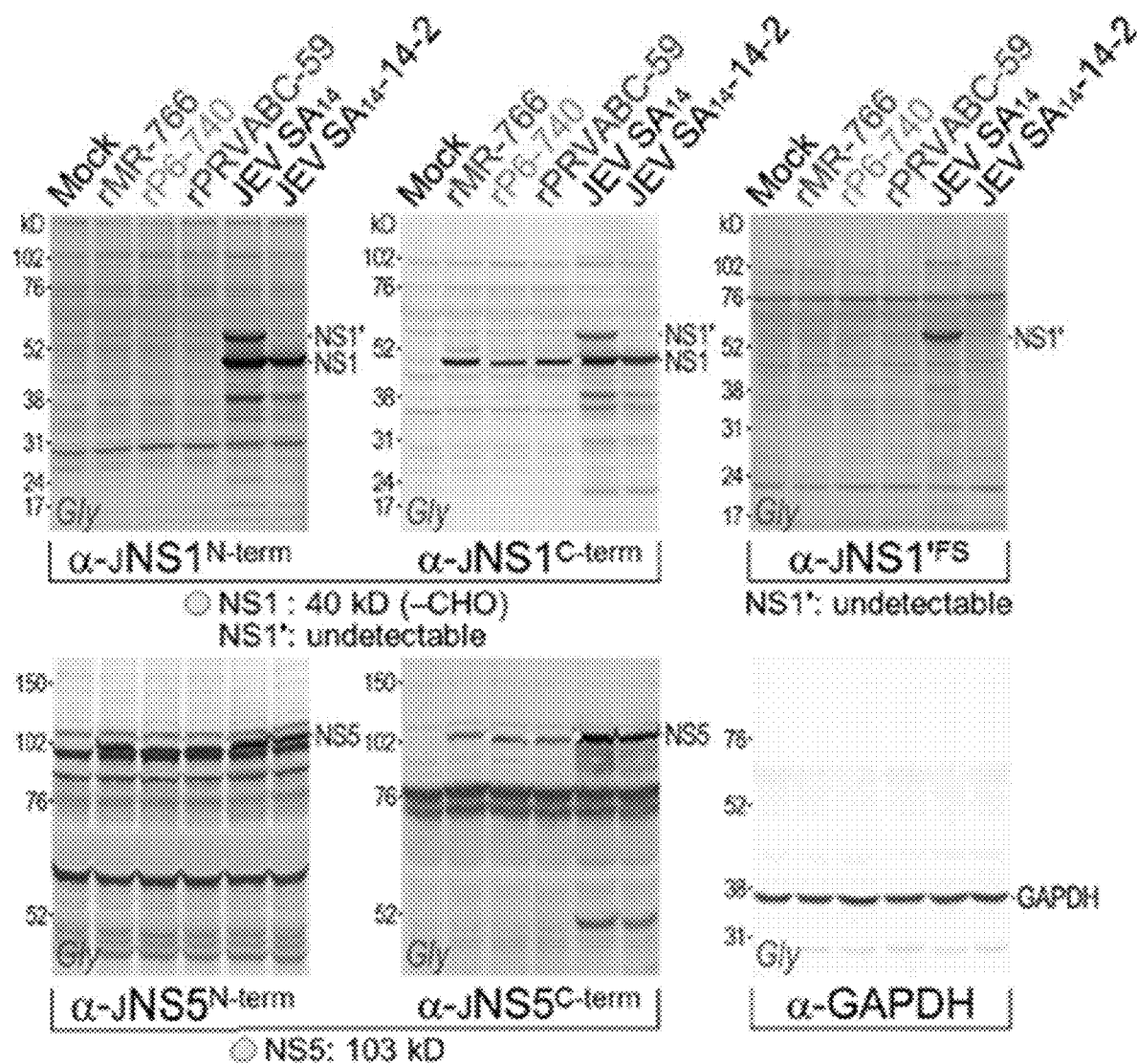

Genome-Wide Landscape of the Viral Gene Products and their Related Species Produced by the Molecularly Cloned ZIKVs To identify all the viral proteins produced by rMR-766, rP6-740, and rPRVABC-59, total cell lysates of mock- and ZIKV-infected Vero cells were examined in two series of immunoblotting experiments. In the first series, each of the 15 JEV region-specific rabbit antisera was used (FIG. 14), with each originally produced to detect all JEV gene products, which were estimated to have the potential for cross-reactivity with their ZIKV counterparts, given the significantly high levels (35-71%) of amino acid sequence identity between their antigenic regions (FIG. 4A). Indeed, six ($\alpha$-jE$^{N\text{-}term}$, $\alpha$-jNS1$^{C\text{-}term}$, $\alpha$-jNS2B, $\alpha$-jNS3$^{C\text{-}term}$, $\alpha$-jNS5$^{N\text{-}term}$, and $\alpha$-jNS5$^{C\text{-}term}$) of the 15 antisera showed moderate-to-strong cross-reactivity with their respective ZIKV gene products, but the remaining nine had no reactivity (FIGS. 4B-4C). To cover the remaining undetected parts of ZIKV ORF, seven ZIKV region-specific rabbit antisera were generated, using rPRVABC-59 as the viral strain of choice (FIGS. 15A-15B), immunizing the rabbits with five bacterially expressed GST fusion proteins ($\alpha$-zC, $\alpha$-zM, $\alpha$-zE, $\alpha$-zNS4A, and $\alpha$-zNS4B) or two chemically synthesized oligopeptides ($\alpha$-zNS1 and $\alpha$-zNS2B). In all cases, the 19- to 51-aa antigenic regions of ZIKV were selected to have relatively low levels (16-42%) of amino acid sequence identity with those of JEV (FIG. 5A). The resulting seven ZIKV region-specific antisera were used for a second series of immunoblots, in which their respective ZIKV gene products were detected (FIGS. 5B-5C). In all immunoblots, two additional cell lysates (as a reference for JEV proteins) were included, which were extracted from Vero cells infected with the virulent JEV strain SA$_{14}$ or its attenuated strain SA$_{14}$-14-2; both JEVs share the same genome-wide viral protein expression profile, except that the NS1' protein is expressed only by SA$_{14}$.

The immunoblot analysis using a battery of 13 ZIKV antigen-reactive region-specific rabbit antisera created a full catalog of viral gene products and their related species, except for the predicted 24-kDa NS2A (FIGS. 4-5): (1) $\alpha$-zC recognized the 13-kDa C protein, with no accumulation of the further-processed 12-kDa C' (see below for description of virion-associated proteins), but with appearance of one or two cleavage products of 10-11 kDa in rPRVABC-59- or rP6-740-infected cells, respectively; however, this antiserum did not react with any of the C-related proteins of rMR-766. (2) $\alpha$-zM reacted strongly with the 9-kDa M protein and its 24-kDa precursor prM, with the ratio of M:prM varying, depending on the viral strain; the observed size of prM was 5 kDa larger than its predicted size, consistent with an addition of N-glycans at Asn-70 ($^{70}$NTT) to its pr domain that is conserved in all three ZIKVs. Also, the $\alpha$-zM reacted weakly with at least two minor proteins of 15 and 19 kDa. (3) $\alpha$-jE$^{N\text{-}term}$/$\alpha$-zE detected four E-related proteins (of 54/56, 43/45, 24/26, and 14 kDa). Among these, the first three proteins from rP6-740 were all 2 kDa smaller than those from rMR-766 and rPRVABC-59, in agreement with a missense mutation of the N-glycosylation site at Asn-154 ($^{154}$NDT→NDI) in the E protein of rP6-740 relative to that of rMR-766 and rPRVABC-59. The three 2 kDa smaller proteins from rP6-740 became similar in size to those from rMR-766 and rPRVABC-59, when the mutated N-glycosylation motif in rP6-740 was restored by changing $^{154}$NDI into $^{154}$NDT, but not by changing $^{154}$NDI into $^{154}$QDT (FIGS. 20A-20C). Notably, the full-length 54/56-kDa E protein on the gel was pushed down by a large amount of cellular protein migrating just above it, forcing it to run faster than its actual size. (4) Both $\alpha$-jNS1$^{C\text{-}term}$ and $\alpha$-zNS1 identified the 45-kDa NS1 exclusively. This protein was 5 kDa larger than predicted by its amino acid sequence because of the addition of N-glycans at Asn-130 ($^{130}$NNS) and Asn-207 ($^{207}$NDT), both of which are conserved in all three ZIKVs. These data also showed that only NS1, but not its frameshift product NS1', was produced by all three ZIKVs. The lack of NS1' expression corroborated the finding that ZIKV lacks the two-component ribosomal frameshift signal found in JEV and WNV (FIGS. 16A-16B). (5) $\alpha$-jNS2B/$\alpha$-zNS2B revealed the 14-kDa NS2B, together with an unexpected protein of 11 kDa at a barely detectable level. (6) $\alpha$-jNS3$^{C\text{-}term}$ recognized the 69-kDa NS3; it also reacted more strongly with a major cleavage product of 34 kDa, representing the C-terminal half of the full-length NS3, and less intensely with at least seven minor proteins of 33-60 kDa. Intriguingly, $\alpha$-jNS3$^{C\text{-}term}$ detected a species with a mass of 85 kDa, corresponding to the calculated size of an NS2B-3 or NS3-4A/4A' processing intermediate. (7) $\alpha$-zNS4A did not detect the predicted 16-kDa NS4A but did predominantly recognize its further-processed 14-kDa NS4A', which ran as a single species in tricine-SDS-PAGE but migrated as a doublet in glycine-SDS-PAGE. Unexpectedly, this antiserum also identified two clusters of multiple protein bands, one at 29 kDa (NS4A$^{p29}$) and the other at 35 kDa (NS4AB$^{p35}$, which also reacted with $\alpha$-zNS4B; FIGS. 17A-17B). (8) $\alpha$-zNS4B stained the predicted major 27-kDa NS4B, along with two unexpected minor proteins at 11 kDa (NS4B$^{p11}$) and 35 kDa (NS4AB$^{p35}$, which again reacted with $\alpha$-zNS4A; FIGS. 17A-17B). (9) $\alpha$-jNS5$^{N\text{-}term}$ and $\alpha$-jNS5$^{C\text{-}term}$ reacted with the predicted 103-kDa NS5.

In addition to the three full-length structural proteins (C, prM/M, and E) of ZIKV, their multiple smaller products were accumulated to lower but still significant amounts in Vero cells infected with each of the three ZIKVs, with nearly the same protein expression profile (FIGS. 5A-5C). To define the actual viral structural proteins incorporated into ZIKV particles, rPRVABC-59 was used to profile all the structural proteins associated with extracellular virions, which were purified by pelleting through a 20% sucrose cushion. They were then compared with their cell-associated counterparts by immunoblotting with α-zC, α-zM, and α-zE (FIG. 18). The purified ZIKV particles were shown to contain (i) the 12-kDa C' protein, which appeared as a closely spaced doublet with the lower band being more prominent than the upper band and migrating in a gel marginally faster than one cell-associated major 13-kDa C protein, but slower than the other cell-associated minor 10-kDa C-derived cleavage product; (ii) the 9-kDa M protein and a trace amount of its glycosylated precursor prM, which appeared as two bands, the slightly less intense and faster one migrating with a mass of 23-24 kDa and the slightly more intense and slower one at 25-26 kDa, reflecting the trimming of high mannose and the addition of more complex sugars to the cell-associated 24-kDa prM protein during virus release through the cellular secretory pathway; and (iii) the glycosylated 58-kDa E protein, which ran slightly slower than the cell-associated 56-kDa E protein, again reflecting the difference in its glycosylation status. Collectively, these data demonstrate that the extracellular ZIKVs are composed of three post-translationally modified full-length structural proteins, excluding their smaller species.

Example 5

Wide Range of Differences in Age-Dependent Neuropathogenicity Among Three Molecularly Cloned ZIKVs in Outbred CD-1 Mice The virulence of rMR-766, rP6-740, and rPRVABC-59 were compared in CD-1 mice at three different ages (1, 2, and 4 weeks) by examining two neuropathogenic properties: (i) neuroinvasiveness (the ability to penetrate the central nervous system from a peripheral site), quantified by generating the dose-dependent survival curve and determining the $LD_{50}$ after an intramuscular (IM) inoculation; and (ii) neurovirulence (the ability to establish a lethal infection within the central nervous system), quantified by creating the dose-dependent survival curve and measuring the $LD_{50}$ after an intracerebral (IC) inoculation. For both IM and IC inoculations, the appropriate dose ranges for calculating the $LD_{50}$ values were first determined, and study designs were optimized prior to the performance of full-scale experiments. For these pilot experiments, all three age groups of the mice were injected with a maximum dose of each virus: $1.2 \times 10^5$ PFU/mouse for IM inoculations and $3.6 \times 10^4$ PFU/mouse for IC inoculations. If necessary, a series of large-scale dose-response studies was performed, inoculating groups of the mice at 1, 2, and 4 weeks of age via the IM or IC route with serial 10-fold dilutions of the virus. Following infection, the mice were monitored daily for mortality, weight loss, and other clinical signs of illness over 20 days.

The comparative assessments of the dose-dependent survival curves and $LD_{50}$ values revealed the following (FIGS. 6A-6C): (i) rMR-766 exhibited age-dependent neuroinvasiveness, as evidenced by an IM $LD_{50}$ of 90.2 PFU for 1-week-old mice and $>1.2 \times 10^5$ PFU for 2- and 4-week-old mice, yet it displayed a high level of neurovirulence at all three ages, as evidenced by an IC $LD_{50}$ of <3.6, 3.6, and 5.7 PFU for 1-, 2-, and 4-week-old mice, respectively. (ii) rP6-740 showed barely detectable neuroinvasiveness in 1-week-old mice, with only 1 or 3 of 10 infected mice dying when inoculated with the two highest doses, $3.6 \times 10^3$ or $3.6 \times 10^4$ PFU/mouse, respectively (IM $LD_{50}$, $>3.6 \times 10^4$ PFU). Similarly, it had no detectable neuroinvasiveness in 2- and 4-week-old mice, with no infected mice dying even when inoculated with the highest dose, $1.2 \times 10^5$ PFU/mouse ($LD_{50}$, $>1.2 \times 10^5$ PFU). However, rP6-740 showed age-dependent neurovirulence, as it was highly neurovirulent in 1-week-old mice (IC $LD_{50}$, <3.6 PFU) but non-neurovirulent in 2- and 4-week-old mice (IC $LD_{50}$, $>3.6 \times 10^4$ PFU). (iii) rPRVABC-59 was essentially non-neuroinvasive and non-neurovirulent, regardless of the mouse age, with its IM and IC $LD_{50}$ values estimated to be greater than the highest dose used for each route of infection, without a single death. Of the three ZIKVs, therefore, rMR-766 was the most virulent, rPRVABC-59 was the least virulent, and rP6-740 showed intermediate virulence.

Moreover, not only was the lethal virulence displayed by rMR-766 and rP6-740, but also the non-lethal virulence exhibited by all of the three ZIKVs, including rPRVABC-59. This effect was most prominent in 1-week-old mice (FIGS. 6D-6F). The lethal virulence was invariably associated with a sharp drop in the body weight of infected mice that began ~3 days prior to death, in conjunction with clinical signs. It began with decreased activity, ruffled fur, and hunched posture, and often progressed to tremors and hind limb paralysis. Various viral loads were detected postmortem in the brains of all mice that died ($8.0 \times 10^3$-$3.9 \times 10^8$ PFU/brain). Non-lethal virulence, in contrast, was characterized by an initial weight loss of various degrees, albeit without obvious clinical signs, and a subsequent recovery to some extent that was not complete. At the end of the study, no infectious ZIKV was detected in the brains of any of the mice that survived. In both the lethal and non-lethal virulent cases, no changes in body temperature were observed. Altogether, it was found that in CD-1 mice, the three ZIKVs had a wide range of virulence, depending on the virus strain, mouse age, and route of infection.

Example 6

High Degree of Variation in IFN Sensitivity Among Three Molecularly Cloned ZIKVs in Mice Lacking Type I IFN (IFNAR$^{-/-}$) or Both Type I and II IFN (IFNAR$^{-/-}$/IFNGR$^{-/-}$) Receptors To compare the contributions of the host IFN response to the virulence of rMR-766, rP6-740, and rPRVABC-59, their neuroinvasiveness and neurovirulence were examined by using groups of 4-week-old A129 (IFNAR$^{-/-}$) mice and groups of age-matched wild-type inbred C57BL/6J mice as a control (FIGS. 7A-7B). In the control mice, rMR-766 was non-neuroinvasive (IM $LD_{50}$, $>1.2 \times 10^5$ PFU) but neurovirulent (IC $LD_{50}$, 7.8 PFU). In contrast, both rP6-740 and rPRVABC-59 were non-neuroinvasive (IM $LD_{50}$, $>1.2 \times 10^5$ PFU) as well as non-neurovirulent (IC $LD_{50}$, $>3.6 \times 10^4$ PFU), in agreement with the data obtained in age-matched outbred CD-1 mice (FIG. 6C). In A129 mice, however, the neurovirulence of all three ZIKVs was increased dramatically, and they became highly neurovirulent (IC $LD_{50}$, <3.6 PFU), with median survival times estimated to be 4 days (rMR-766), 5 days (rP6-740), and 7 days (rPRVABC-59), with a lethal dose of $3.6 \times 10^2$ PFU/mouse. Similarly, the neuroinvasiveness of the three ZIKVs was also elevated but to different degrees, as evidenced by the estimated IM $LD_{50}$ of <1.2 PFU (rMR-766), 576.1 PFU (rP6-740), and $>1.2 \times 10^5$ PFU (rPRVABC-59). Noticeably, rPRVABC-59 was nearly non-neuroinvasive in A129 mice. This finding prompted further testing of the neuroinvasiveness of rPRVABC-59, as compared to that of the other two ZIKVs, in 4-week-old AG129 (IFNAR$^{-/-}$/IFNGR$^{-/-}$) mice (FIG. 7C). In AG129 mice, all three ZIKVs were highly neuroinvasive (IM $LD_{50}$, <1.2 PFU), although the median survival times for the three viruses varied from 7 days (rMR-766) to 12 days (rP6-740) and 13 days (rPRVABC-59), with a lethal dose of $1.2 \times 10^2$ PFU/mouse. Furthermore, in all three mouse strains (C57BL/6J, A129, and AG129), the two $LD_{50}$-based neuropathogenic properties of the three ZIKVs were always corroborated by the decreases in body weight (FIGS. 7D-7F), accompanied by the typical clinical signs seen in CD-1 mice. In all the mice that died, various viral loads were detected in their brains postmortem, with higher loads being found in the absence of IFN signaling, i.e., $4.7 \times 10^4$-$2.0 \times 10^8$ PFU/brain for C57BL/6J, $1.3 \times 10^6$-$1.0 \times 10^9$ PFU/brain for A129, and $8.5 \times 10^6$-$3.6 \times 10^9$ PFU/brain for AG129. In the case of all mice that survived, however, no infectious ZIKV was detected in the brain at the end of the study. Taken together, these data show a full range of variation in IFN sensitivity among the three cloned ZIKVs in mice.

Herein a strategy was formulated to generate three full-length ZIKV cDNAs, each capable of generating $m^7G$-capped in vitro-transcribed RNAs identical in nucleotide sequence to their respective genomic RNAs, particularly regarding the 5'- and 3'-end sequences. On the 5' side, an SP6 promoter sequence (5'-ATTTAGGGGACACTATAG, with transcription starting at the underlined G) was positioned upstream of the first adenine nucleotide of the viral genome to incorporate the dinucleotide cap analog $m^7GpppA$ in SP6 RNA polymerase-driven in vitro transcription reactions. The $m^7G$ cap at the 5'-end of transcribed RNAs was shown to be important in maximizing RNA infectivity when compared with uncapped RNAs derived from each of the three functional ZIKV cDNAs that always had an infectivity >3-logs lower than that of their $m^7G$-capped counterparts. On the 3' side, a unique restriction endonuclease recognition site, PsrI $GAACN_6TAC$ (SEQ ID NO: 8 or BarI [$GAAGN_6TAC$ (SEQ ID NO: 9), was placed downstream of the last thymine nucleotide of the viral genome. The use of PsrI/BarI for cDNA linearization was particularly advantageous because both are extremely rare-cutting endonucleases that cut out their recognition sequences after any nucleotide, which makes this approach applicable for all plus-strand RNA viruses, regardless of the identity of the nucleotide at the 3' end of the viral genome. RNA transcripts with 11 ZIKV-unrelated nucleotides hanging on their 3' ends were surprisingly found to be ~1-log less infectious than those with authentic 3' ends, indicating the importance of the authentic 3' end for the production of infectious ZIKV RNAs.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the invention are set out in the following numbered clauses:

Clause 1. A genetically stable viral vector comprising:
a Zika virus cDNA;
a RNA polymerase promoter upstream of the 5' end of the Zika virus cDNA; and
a restriction endonuclease site downstream of the 3' end of the Zika virus cDNA;
wherein the Zika virus cDNA, the RNA polymerase promoter, and the restriction endonuclease site are cloned into a bacterial artificial chromosome vector, and wherein the Zika virus cDNA is capable of being transcribed into an RNA transcript that is functional.

Clause 2. The vector of clause 1, wherein the Zika virus cDNA comprises a nucleotide sequence selected from the group consisting of SEQ ID NO: 4, SEQ ID NO: 5, and SEQ ID NO: 6.

Clause 3. The vector of clause 1, wherein the Zika virus cDNA comprises a nucleotide sequence with at least 85% sequence identity to a nucleotide sequence selected from the group consisting of SEQ ID NO: 4, SEQ ID NO: 5, or SEQ ID NO: 6.

Clause 4. The vector of clause 1, wherein the Zika virus cDNA comprises a nucleotide sequence with at least 90% sequence identity to a nucleotide sequence selected from the group consisting of SEQ ID NO: 4, SEQ ID NO: 5, or SEQ ID NO: 6.

Clause 5. The vector of clause 1, wherein the Zika virus cDNA comprises a nucleotide sequence with at least 95% sequence identity to a nucleotide sequence selected from the group consisting of SEQ ID NO: 4, SEQ ID NO: 5, or SEQ ID NO: 6.

Clause 6. The vector of clause 1, wherein the Zika virus cDNA comprises a nucleotide sequence with at least 99% sequence identity to a nucleotide sequence selected from the group consisting of SEQ ID NO: 4, SEQ ID NO: 5, or SEQ ID NO: 6.

Clause 7 The vector of any of clauses 1-6, wherein the RNA polymerase promoter is an SP6 promoter.

Clause 8. The vector of any of clauses 1-7, wherein the RNA polymerase promoter comprises a nucleotide sequence of SEQ ID NO: 7.

Clause 9. The vector of any of clause 1-8, wherein the restriction endonuclease site does not interfere with the 3' end of the Zika virus cDNA.

Clause 10. The vector of any of clause 1-9, wherein the restriction endonuclease site is capable of being cleaved by PsrI or BarI endonucleases.

Clause 11. The vector of any of clauses 1-10, wherein the restriction endonuclease site comprises a nucleotide sequence of SEQ ID NO: 8 or SEQ ID NO: 9.

Clause 12. The vector of any of clauses 1-11, wherein the bacterial artificial chromosome vector is a single- or low-copy number bacterial artificial chromosome vector.

Clause 13. The vector of any of clauses 1-12, wherein the bacterial artificial chromosome is pBeloBac11.

Clause 14. The vector of any of clauses 1-13, wherein the RNA transcript has a $N^7$-methyl-guanosine-5'-triphosphate-5'-adenosine ($m^7GpppA$) cap.

Clause 15. The vector of clause 1, comprising a Zika virus cDNA of strain MR-766 cloned into a bacterial artificial chromosome vector, wherein the sequence of the vector is represented by SEQ ID NO:1.

Clause 16. The vector of clause 1, comprising a Zika virus cDNA of strain P6-740 cloned into a bacterial artificial chromosome vector, wherein the sequence of the vector is represented by SEQ ID NO:2.

Clause 17. The vector of clause 1, comprising a Zika virus cDNA of strain PRVABC-59 cloned into a bacterial artificial chromosome vector, wherein the sequence of the vector is represented by SEQ ID NO:3.

Clause 18. A method of generating a genetically engineered attenuated Zika virus comprising:
obtaining a genetically stable viral vector of any of clauses 1-17; and altering one or more nucleotides in the Zika virus cDNA to produce a synonymous or non-synonymous codon alteration;

wherein the synonymous or non-synonymous codon alteration produces a Zika virus with compromised virulence.

Clause 19. The method of clause 18, wherein the one or more nucleotides are located in a nucleotide sequence of the Zika virus cDNA corresponding to the RNA-dependent RNA polymerase domain of Zika virus NS5 protein.

Clause 20. The method of clause 18 or clause 19, wherein the Zika virus cDNA is SEQ ID NO: 2 and wherein the one or more nucleotides comprises cytidine at nucleotide position 9804 altered to uridine.

Clause 21. The method of any of clauses 18-20, wherein altering one or more nucleotides in the Zika virus cDNA replaces a His with Tyr at amino acid position 713 of the Zika virus NS5 protein.

Clause 22. The method of any of clauses 18-21, wherein the Zika virus with compromised virulence has decreased virulence compared to a Zika virus without any altered nucleotide sequences.

Clause 23. The method of any of clauses 18-22, wherein the virulence of the Zika virus with compromised virulence is decreased by at least 1 log.

Clause 24. A vaccine comprising a genetically engineered attenuated Zika virus made by the method of clauses 18-23.

What is claimed is:

1. A genetically stable viral vector comprising:
a Zika virus cDNA of strain PRVABC-59;
a RNA polymerase promoter upstream of the 5' end of the Zika virus cDNA; and
a restriction endonuclease site downstream of the 3' end of the Zika virus cDNA;
wherein the Zika virus cDNA, the RNA polymerase promoter, and the restriction endonuclease site are cloned into a bacterial artificial chromosome vector,
wherein the Zika virus cDNA is capable of being transcribed into an RNA transcript that is functional, and
wherein the sequence of the vector is represented by SEQ ID NO:3.

* * * * *